United States Patent
van Duzer et al.

(10) Patent No.: US 9,765,066 B2
(45) Date of Patent: Sep. 19, 2017

(54) SELECTIVE HDAC1 AND HDAC2 INHIBITORS

(71) Applicant: Acetylon Pharmaceuticals, Inc., Boston, MA (US)

(72) Inventors: John H. van Duzer, Georgetown, MA (US); Ralph Mazitschek, Belmont, MA (US)

(73) Assignee: REGENACY PHARMACEUTICALS, LLC, Boston, MA (US)

(*) Notice: Subject to any disclaimer, the term of this patent is extended or adjusted under 35 U.S.C. 154(b) by 0 days.

(21) Appl. No.: 15/214,061

(22) Filed: Jul. 19, 2016

(65) Prior Publication Data

US 2017/0044144 A1   Feb. 16, 2017

Related U.S. Application Data

(62) Division of application No. 14/824,831, filed on Aug. 12, 2015, now Pat. No. 9,421,212, which is a division of application No. 14/069,741, filed on Nov. 1, 2013, now Pat. No. 9,145,412.

(60) Provisional application No. 61/889,276, filed on Oct. 10, 2013, provisional application No. 61/778,231, filed on Mar. 12, 2013, provisional application No. 61/721,881, filed on Nov. 2, 2012.

(51) Int. Cl.

| | | |
|---|---|---|
| C07D 409/12 | (2006.01) |
| C07D 401/12 | (2006.01) |
| C07D 471/04 | (2006.01) |
| C07D 231/56 | (2006.01) |
| C07D 333/20 | (2006.01) |
| C07D 215/48 | (2006.01) |
| C07D 215/54 | (2006.01) |
| C07D 209/08 | (2006.01) |
| C07D 209/34 | (2006.01) |
| A61K 31/4045 | (2006.01) |
| A61K 31/4709 | (2006.01) |
| A61K 31/496 | (2006.01) |
| A61K 31/498 | (2006.01) |
| A61K 31/5377 | (2006.01) |

(52) U.S. Cl.
CPC ........ *C07D 409/12* (2013.01); *A61K 31/4045* (2013.01); *A61K 31/4709* (2013.01); *A61K 31/496* (2013.01); *A61K 31/498* (2013.01); *A61K 31/5377* (2013.01); *C07D 209/08* (2013.01); *C07D 209/34* (2013.01); *C07D 215/48* (2013.01); *C07D 215/54* (2013.01); *C07D 231/56* (2013.01); *C07D 333/20* (2013.01); *C07D 401/12* (2013.01); *C07D 471/04* (2013.01)

(58) Field of Classification Search
CPC .. C07D 409/12; C07D 401/12; C07D 471/04; C07D 231/56; C07D 333/20; C07D 215/48; C07D 215/54; C07D 209/08; C07D 209/34

See application file for complete search history.

(56) References Cited

U.S. PATENT DOCUMENTS

| | | |
|---|---|---|
| 7,868,205 B2 | 1/2011 | Moradei et al. |
| 8,119,685 B2 | 2/2012 | Heidebrecht et al. |
| 8,148,526 B1 | 4/2012 | van Duzer et al. |
| 8,394,810 B2 | 3/2013 | van Duzer et al. |
| 8,598,168 B2 | 12/2013 | Moradei et al. |
| 8,609,678 B2 | 12/2013 | van Duzer et al. |
| 8,614,223 B2 | 12/2013 | van Duzer et al. |
| 9,096,549 B2 | 8/2015 | van Duzer et al. |
| 9,139,583 B2 | 9/2015 | van Duzer et al. |
| 9,145,412 B2 | 9/2015 | van Duzer et al. |
| 9,249,087 B2 | 2/2016 | Kozikowski et al. |
| 9,278,963 B2 | 3/2016 | van Duzer et al. |
| 9,421,212 B2 | 8/2016 | van Duzer et al. |
| 2009/0124631 A1 | 5/2009 | Li et al. |
| 2013/0225543 A1 | 8/2013 | Jones et al. |
| 2014/0011767 A1 | 1/2014 | Yang et al. |
| 2014/0142104 A1 | 5/2014 | van Duzer et al. |
| 2014/0142117 A1 | 5/2014 | van Duzer et al. |
| 2014/0243345 A1 | 8/2014 | van Duzer et al. |
| 2014/0249148 A1 | 9/2014 | van Duzer et al. |
| 2014/0357512 A1 | 12/2014 | Yang et al. |
| 2015/0045380 A1 | 2/2015 | van Duzer et al. |
| 2015/0099744 A1 | 4/2015 | Yang et al. |
| 2015/0105358 A1 | 4/2015 | Quayle et al. |
| 2015/0105383 A1 | 4/2015 | Quayle et al. |
| 2015/0105384 A1 | 4/2015 | Jones et al. |
| 2015/0105409 A1 | 4/2015 | Quayle et al. |
| 2015/0150871 A1 | 6/2015 | Quayle et al. |
| 2015/0176076 A1 | 6/2015 | Yang et al. |
| 2015/0239869 A1 | 8/2015 | Mazitschek et al. |
| 2015/0299130 A1 | 10/2015 | van Duzer et al. |
| 2016/0030458 A1 | 2/2016 | Jones et al. |
| 2016/0067259 A1 | 3/2016 | van Duzer et al. |
| 2016/0137630 A1 | 5/2016 | Shearstone et al. |
| 2016/0168093 A1 | 6/2016 | van Duzer et al. |

FOREIGN PATENT DOCUMENTS

| | | |
|---|---|---|
| WO | 2005/030704 A1 | 4/2005 |
| WO | 2005/030705 A1 | 4/2005 |
| WO | 2008/111299 A1 | 9/2008 |

*Primary Examiner* — Rebecca Anderson
(74) *Attorney, Agent, or Firm* — Lathrop & Gage LLP; Brian C. Trinque

(57) ABSTRACT

Provided herein are compounds, pharmaceutical compositions comprising such compounds and methods of using such compounds to treat or prevent diseases or disorders associated with HDAC activity, particularly diseases or disorders that involve activity of HDAC1 and/or HDAC2. Such diseases include cancer, sickle-cell anemia, beta-thalassemia, and HIV.

14 Claims, 3 Drawing Sheets

SELECTIVE HDAC1 AND HDAC2 INHIBITORS

RELATED APPLICATIONS

This application is a Division of U.S. application Ser. No. 14/824,831, filed Aug. 12, 2015, which is a Division of U.S. application Ser. No. 14/069,741, filed Nov. 1, 2013, now issued as U.S. Pat. No. 9,145,412, which claims the benefit of U.S. Provisional Patent Application No. 61/721,881, filed Nov. 2, 2012, U.S. Provisional Patent Application No. 61/778,231, filed Mar. 12, 2013, and U.S. Provisional Patent Application No. 61/889,276, filed Oct. 10, 2013, the entire contents of which are incorporated herein by reference in their entirety.

BACKGROUND OF THE INVENTION

A biological target of recent interest is histone deacetylase (HDAC) (see, for example, a discussion of the use of inhibitors of histone deacetylases for the treatment of cancer: Marks et al. *Nature Reviews Cancer* 2001, 7, 194; Johnstone et al. *Nature Reviews Drug Discovery* 2002, 287). Post-translational modification of proteins through acetylation and deacetylation of lysine residues plays a critical role in regulating their cellular functions. HDACs are zinc hydrolases that modulate gene expression through deacetylation of the N-acetyl-lysine residues of histone proteins and other transcriptional regulators (Hassig et al. *Curr. Opin. Chem. Biol.* 1997, 1, 300-308). HDACs participate in cellular pathways that control cell shape and differentiation, and an HDAC inhibitor has been shown effective in treating an otherwise recalcitrant cancer (Warrell et al. *J. Natl. Cancer Inst.* 1998, 90, 1621-1625).

At this time, eleven human HDACs, which use Zn as a cofactor, have been identified (Taunton et al. *Science* 1996, 272, 408-411; Yang et al. *J. Biol. Chem.* 1997, 272, 28001-28007. Grozinger et al. *Proc. Natl. Acad. Sci. U.S.A.* 1999, 96, 4868-4873; Kao et al. *Genes Dev.* 2000, 14, 55-66; Hu et al. *J. Biol. Chem.* 2000, 275, 15254-15264; Zhou et al. *Proc. Natl. Acad. Sci U.S.A.* 2001, 98, 10572-10577; Venter et al. *Science* 2001, 291, 1304-1351) and these members fall into three classes (class I, II, and IV) based on sequence homology to their yeast orthologues (O. Witt et al. *Cancer Letters*, 2009, 277, 8-21). Class I HDACs include HDAC1, HDAC2, HDAC3, and HDAC8, and are referred to as "classical" HDACs, which implies a catalytic pocket with a $Zn^{2+}$ ion at its base.

There remains a need for preparing structurally diverse HDAC inhibitors, particularly ones that are potent and/or selective inhibitors of particular classes of HDACs and individual HDACs.

SUMMARY OF THE INVENTION

Provided herein are compounds, pharmaceutical compositions comprising such compounds and methods of using such compounds to treat or prevent diseases or disorders associated with HDAC activity, particularly diseases or disorders that involve any type of HDAC1 and/or HDAC2 expression. Such diseases include cancer, sickle-cell anemia, beta-thalassemia and HIV.

Thus, in one aspect, provided herein is a compound of Formula I:

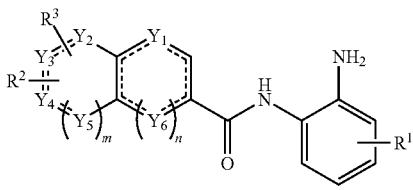

or a pharmaceutically acceptable salt thereof.

In another aspect, provided herein is a compound of Formula II:

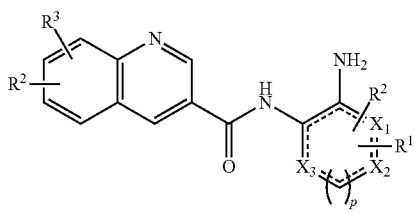

or a pharmaceutically acceptable salt thereof.

In another aspect, provided herein is a pharmaceutical composition comprising a compound of Formula I, Formula II, Formula III, or any of the compounds presented in Table 1, or a pharmaceutically acceptable salt thereof, together with a pharmaceutically acceptable carrier.

In another aspect, provided herein is a method of inhibiting the activity of HDAC1 or HDAC2 in a subject, comprising administering a compound of Formula I, Formula II, Formula III, or any of the compounds presented in Table 1 or a pharmaceutically acceptable salt thereof.

In another aspect, provided herein is a method of selectively inhibiting the activity of HDAC1 or HDAC2 over other HDACs in a subject, comprising administering to the subject a compound of Formula I, Formula II, Formula III, or any of the compounds presented in Table 1, or a pharmaceutically acceptable salt thereof. In some embodiments, the compound has a selectivity for HDAC1 and/or HDAC2 that is 5 to 1000 fold greater than for other HDACs. In other embodiments, the compound has a selectivity for HDAC1 and/or HDAC2, when tested in a HDAC enzyme assay, of about 5 to 1000 fold greater than for other HDACs. In some embodiments, the compound has a selectivity for HDAC1 over HDAC2. In other embodiments, the compound has a selectivity for HDAC2 over HDAC1. In some embodiments, the compound has a balanced HDAC1 and HDAC2 selectivity. The term "balanced" means that the selectivity for HDAC1 and HDAC2 is approximately equal, i.e., that the selectivities for HDAC1 and HDAC2 are within about ±10% of each other.

In another aspect, provided herein is a method of activating latent HIV in a subject comprising administering to the subject a compound of Formula I, Formula II, Formula III, or any of the compounds presented in Table 1, or a pharmaceutically acceptable salt thereof.

In another aspect, provided herein is a method of treating HIV infection in a subject comprising administering to the subject a compound of Formula I, Formula II, Formula III, or any of the compounds presented in Table 1, or a pharmaceutically acceptable salt thereof.

In another aspect, provided herein is a method of treating HIV infection in a subject comprising administering to the subject a compound of Formula I, Formula II, Formula III, or any of the compounds presented in Table 1, or a pharmaceutically acceptable salt thereof, and one or more anti-retroviral agents. The anti-retroviral agent can be selected from the group consisting of nucleoside reverse transcriptase inhibitors, non-nucleoside reverse transcriptase inhibitors, protease inhibitors, virus uptake/adsorption inhibitors, virus receptor antagonists, viral fusion inhibitors, viral integrase inhibitors, entry inhibitor, co-receptor antagonist, cyclin dependent kinase inhibitor, and transcription inhibitors. The anti-retroviral agent can also be selected from the group consisting of efavirenz, indinavir sulfate, and raltegravir potassium. In an embodiment, HIV is HIV-1.

In another aspect, provided herein is a method of treating a disease mediated by HDAC1 or HDAC2 in a subject comprising administering to the subject a compound of Formula I, Formula II, Formula III, or any of the compounds presented in Table 1, or a pharmaceutically acceptable salt thereof.

In another aspect, provided herein is a method of treating a disease in a subject comprising administering to the subject a compound of Formula I, Formula II, Formula III, or any of the compounds presented in Table 1, or a pharmaceutically acceptable salt thereof. In an embodiment, the disease is a hemoglobinopathy. In another embodiment, the disease is sickle-cell disease. In still another embodiment, the disease is beta-thalassemia.

In yet another embodiment, the disease is a cancer or a proliferation disease. The cancer can be selected from a group consisting of lung cancer, colon and rectal cancer, breast cancer, prostate cancer, liver cancer, pancreatic cancer, brain cancer, kidney cancer, ovarian cancer, stomach cancer, skin cancer, bone cancer, gastric cancer, breast cancer, glioma, gliobastoma, hepatocellular carcinoma, papillary renal carcinoma, head and neck squamous cell carcinoma, leukemia, lymphomas, myelomas, retinoblastoma, cervical cancer, melanoma and/or skin cancer, bladder cancer, uterine cancer, testicular cancer, esophageal cancer, and solid tumors. In another embodiment, the cancer is lung cancer, colon cancer, breast cancer, leukemia, or lymphomas. In still another embodiment, the cancer is non-small cell lung cancer (NSCLC). In another embodiment, the cancer is a hematologic cancer. In a further embodiment, the hematologic cancer is a leukemia. In a further embodiment, the hematologic cancer is a lymphoma. The lymphoma can be Hodgkin's lymphoma.

In another aspect, provided herein is a method of treating a subject suffering from or susceptible to Hodgkin's lymphoma comprising administering to a subject in need thereof a therapeutically effective amount of a compound of Formula I, Formula II, Formula III, or any of the compounds presented in Table 1, to thereby treat the subject suffering from or susceptible to Hodgkin's lymphoma.

In an embodiment, the methods provided herein can further comprise co-administering one or more of a chemotherapeutic agent, radiation agent, hormonal agent, biological agent or an anti-inflammatory agent to the subject. The chemotherapeutic agent can be selected from the group consisting of azacitidine, clofarabine, erlotinib, bortezomib, tamoxifen, trastuzumab, raloxifene, doxorubicin, fluorouracil/5-fu, pamidronate disodium, anastrozole, exemestane, cyclophosphamide, epirubicin, letrozole, toremifene, fulvestrant, fluoxymesterone, methotrexate, megastrol acetate, docetaxel, paclitaxel, testolactone, aziridine, vinblastine, capecitabine, goselerin acetate, zoledronic acid, taxol, vinblastine, or vincristine. The chemotherapeutic agent can be an aromatase inhibitor.

In a further embodiment of the methods of treatment described herein, the subject to be treated is a human.

BRIEF DESCRIPTION OF THE FIGURES

FIG. 1C, lower row, is a graph that shows the results of an experiment in which cells from CS2 were differentiated for 2 days in the presence of vehicle (DMSO), or 1 µM each of MS-275 (entinostat), Compound 001, Compound 002, or Compound 003. After 2 days, media was exchanged and cells were differentiated for an additional 2 days in the absence of compound. Hemoglobin protein levels within each cell were determined at day 4 of differentiation.

DETAILED DESCRIPTION OF THE INVENTION

Figure 1A:
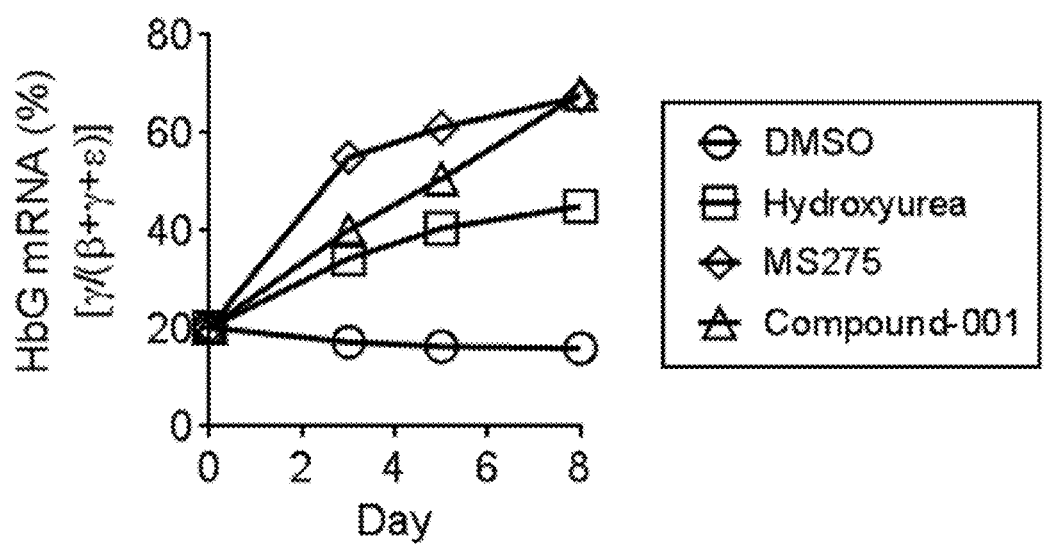
FIG. 1A is a graph that shows the results of an experiment in which cells from CS1 were differentiated in the presence of vehicle (DMSO), 30 µM hydroxyurea, 1 µM MS-275 (entinostat), or 1 µM Compound 001. Globin mRNA levels were determined in cells at day 0, 3, 5, and 8 of differentiation.

Inhibition of HDAC1 and HDAC2 has been shown to derepress fetal globin. Fetal hemoglobin (HbF) derepression, or induction, is an established therapeutic strategy in sickle cell disease (SCD), and could also be effective in treating beta-thalassemia. Hydroxyurea is currently the only drug with proven efficacy in sickle cell disease. This therapy is cytotoxic, poorly tolerated, and only reduces the frequency and severity of sickle cell crises in a subset of patients. There are no approved drugs for treatment of beta-thalassemia. Fetal (γ) globin expression is silenced in adults partly through the action of a complex containing BCL11A and HDACs 1 and 2. Genetic ablation and chemical inhibition of HDAC1 or HDAC2 result in the derepression of γ globin in adult bone marrow derived erythroid cells (Bradner, *Proc. Natl. Acad. Sci.* 2010). While a variety of non-specific HDAC inhibitors have been used successfully to induce HbF, further clinical development has been limited by their variable efficacy and concerns over off target side-effects observed in small clinical trials. Therefore, development of selective and potent HDAC1 and HDAC2 inhibitors leading to HbF reactivation represents a refined and more targeted therapeutic approach for the treatment of SCD and beta-thalassemia.

It has also been shown that deregulated HDAC1 expression is particularly common in advanced cancers of the gastrointestinal system, such as, for example, pancreatic, colorectal, and liver (hepatocellular) carcinomas as well as in prostate and breast cancer. HDAC2 and HDAC3 expression are also associated with advanced stage disease and poor prognosis in gastric, prostate and colorectal cancers.

HDAC2 is also over expressed in cervical cancer. Clinical trials for the treatment of patients with advanced solid tumors, lymphomas, and leukemias utilizing class I selective HDAC inhibitors such as MS275, depsipeptide, and MGCD0103 have been published (O. Witt et al., *Cancer Letters*, 2009, 277, 8-21 and H-J. Kim and S.-C. Bae, *Am. J. Transl. Res.* 2011; 3(2): 166-179).

HDACs have also been found to repress HIV-1 (Human Immunodeficiency Virus) transcription through deacetylation events, particularly in latently infected resting CD4+ T cells.

As such, it is known that HDAC inhibitors can induce the transcriptional activation of the HIV-1 promoter, or re-activate latent HIV-1 from the patient viral reservoir. It is generally accepted that the use of HDAC inhibitors in the treatment of HIV infection can be valuable in purging the latently infected reservoirs in patients, particularly patients undergoing Highly Active Antiretroviral Therapy (HAAT). For examples of HDAC inhibitors used alone or in combination with one or more anti-retroviral agents for the treatment of HIV latency and/or infection, please see US 2010/0166806, US 2010/0324034, and US 2012/0203014, which are hereby incorporated in their entirety.

Provided herein are compounds, pharmaceutical compositions comprising such compounds and methods of using such compounds to treat or prevent diseases or disorders associated with HDAC activity. The compounds are, in particular, able to inhibit HDAC1 and HDAC2 activity.

The compounds described herein may have HDAC1 $IC_{50}$ values ranging from 5 to 100 nM and HDAC2 $IC_{50}$ values ranging from 10 to 300 nM, demonstrating approximately 10- to 100-fold selectivity over HDAC3, respectively. Certain compounds also have good oral bioavailability in rat and monkey, with area under curve values (AUC) exceeding 10000 ng*hr/mL following a 4-5 mg/kg dose. Furthermore, the half-life was found to range between 6 and 10 hours.

Definitions

Listed below are definitions of various terms used to describe this invention. These definitions apply to the terms as they are used throughout this specification and claims, unless otherwise limited in specific instances, either individually or as part of a larger group.

The number of carbon atoms in a hydrocarbyl substituent can be indicated by the prefix "$C_{x-y}$," where x is the minimum and y is the maximum number of carbon atoms in the substituent. Likewise, a $C_x$ chain means a hydrocarbyl chain containing x carbon atoms.

The term "alkyl," as used herein, refers to saturated, straight- or branched-chain hydrocarbon moieties containing, in certain embodiments, between one and six, or one and eight carbon atoms, respectively. Examples of $C_{1-6}$ alkyl moieties include, but are not limited to, methyl, ethyl, propyl, isopropyl, n-butyl, tert-butyl, neopentyl, n-hexyl moieties; and examples of $C_{1-8}$ alkyl moieties include, but are not limited to, methyl, ethyl, propyl, isopropyl, n-butyl, tert-butyl, neopentyl, n-hexyl, heptyl, and octyl moieties.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, idenyl and the like. In some embodiments, aryl groups have 6 carbon atoms. In some embodiments, aryl groups have from six to ten carbon atoms. In some embodiments, aryl groups have from six to sixteen carbon atoms.

The term "cycloalkyl," as used herein, denotes a monovalent group derived from a monocyclic or polycyclic saturated or partially unsaturated carbocyclic ring compound. Examples of $C_{3-8}$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but are not limited to, cyclopropyl, cyclobutyl, cyclopentyl, cyclohexyl, bicyclo [2.2.1] heptyl, and bicyclo [2.2.2] octyl. Also contemplated are monovalent groups derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like. In some embodiments, cycloalkyl groups have from three to six carbon atoms. In some embodiments, cycloalkyl groups have from three to eight carbon atoms.

The term "heteroaryl," as used herein, refers to a mono- or poly-cyclic (e.g., bi-, or tri-cyclic or more) fused or non-fused, moieties or ring system having at least one aromatic ring, having from five to ten ring atoms of which one ring atom is selected from oxygen, sulfur, and nitrogen; zero, one or two ring atoms are additional heteroatoms independently selected from oxygen, sulfur, and nitrogen; and the remaining ring atoms are carbon. In some embodiments, the heteroaryl group has from about one to six carbon atoms, and in further embodiments from one to fifteen carbon atoms. In some embodiments, the heteroaryl group contains five to sixteen ring atoms of which one ring atom is selected from oxygen, sulfur, and nitrogen; zero, one, two, or three ring atoms are additional heteroatoms independently selected from oxygen, sulfur, and nitrogen; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur, and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In an embodiment, the heterocycloalkyl group is a 4-7, e.g., 4-6, membered ring.

In accordance with the invention, any of the aryls, substituted aryls, heteroaryls and substituted heteroaryls described herein, can be any aromatic group. Aromatic groups can be substituted or unsubstituted.

The terms "halo" and "halogen," as used herein, refer to an atom selected from fluorine, chlorine, bromine and iodine.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted" and any other optionally substituted group as used herein, refer to groups that are substituted or unsubstituted by independent replacement of one, two, or three or more of the hydrogen atoms thereon with substituents including, but not limited to:

alkyl, alkenyl, alkynyl, cycloalkyl, aryl, heterocycloalkyl, heteroaryl,
—F, —Cl, —Br, —I,
—OH,
—NO$_2$, —CN,
—NH$_2$, —NH—C$_{1-12}$-alkyl, —NH-aryl, -dialkylamino,
—O—C$_1$-C$_{12}$-alkyl, —O-aryl,
—C(O)—, —C(O)O—, —C(O)NH—, —OC(O)—, —OC(O)O—, —OC(O)NH—, —NHC(O)—, —NHC(O)O—,
—C(O)—C$_{1-12}$-alkyl, —C(O)—C$_{3-12}$-cycloalkyl, —C(O)-aryl, —C(O)-heteroaryl, —C(O)— heterocycloalkyl,
—C(O)O—C$_{1-12}$-alkyl, —C(O)O—C$_{3-12}$-cycloalkyl, —C(O)O-aryl, —C(O)O-heteroaryl, —C(O)O— heterocycloalkyl,
—CONH$_2$, —CONH—C$_1$-C$_{12}$-alkyl, —CONH-aryl, OCO$_2$—C$_{1-12}$-alkyl, —OCO$_2$-aryl, —OCONH$_2$, —OCONH—C$_{1-12}$-alkyl, —OCONH-aryl,
—NHC(O)—C$_{1-12}$-alkyl, —NHC(O)-aryl, —NHCO$_2$—C$_{1-12}$-alkyl, —NHCO$_2$-aryl,
—S(O)—C$_{1-12}$-alkyl, —S(O)-aryl, —SO$_2$NH—C$_{1-12}$-alkyl, —SO$_2$NH-aryl,
—NHSO$_2$—C$_{1-12}$-alkyl, —NHSO$_2$-aryl,
—SH, —S—C$_{1-12}$-alkyl, or —S-aryl.

In certain embodiments, the optionally substituted groups include the following: C$_{1-12}$-alkyl, C$_{2-12}$-alkenyl, C$_{2-12}$-alkynyl, C$_{3-12}$-cycloalkyl, C$_{3-12}$-aryl, C$_{3-12}$-heterocycloalkyl, or C$_{3-12}$-heteroaryl.

It is understood that the aryls, heteroaryls, alkyls, and the like can be further substituted.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hdal gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "inhibitor" is synonymous with the term antagonist.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977).

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

Compounds of the Invention

In one aspect, the invention provides a compound of Formula I:

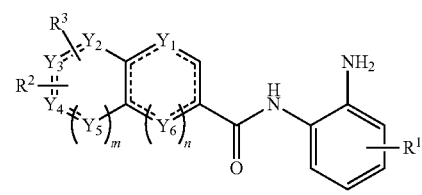

or a pharmaceutically acceptable salt thereof,
wherein
Y$_1$ is CR$^7$ or NR$^7$;
Y$_2$, Y$_3$, Y$_4$, Y$_5$, and Y$_6$ are each independently CH, CH$_2$, N, or C(O), wherein at least one of Y$_2$, Y$_3$, Y$_4$, and Y$_5$ are CH;
R$^1$ is mono-, bi-, or tri-cyclic aryl or heteroaryl, wherein the mono-, bi-, or tri-cyclic aryl or heteroaryl is optionally substituted;
R$^2$ and R$^3$ are each independently selected from C$_{2-6}$-alkenyl, C$_{2-6}$-alkynyl, C$_{3-6}$-cycloalkyl, C$_{1-6}$-alkyl-C$_{3-6}$-cycloalkyl, heterocyclo alkyl, C$_{1-6}$-alkyl-heterocycloalkyl, NR$^4$R$^5$, O—C$_{1-6}$-alkyl-OR$^6$, C$_{1-6}$-alkyl-OR$^6$, aryl, heteroaryl, C(O)N(H)-heteroaryl, C(O)-heteroaryl, C(O)-heterocycloalkyl, C(O)-aryl, C(O)—C$_{1-6}$-alkyl, CO$_2$—C$_{1-6}$-alkyl, or C(O)—C$_{1-6}$-alkyl-heterocycloalkyl, wherein the cycloalkyl, heterocycloalkyl, aryl, or heteroaryl is optionally substituted;
R$^4$ is H, C$_{1-6}$-alkyl, or C$_{1-6}$-alkyl-OR$^6$;

$R^5$ is $CO_2R^6$, $C_1$-$C_6$-alkyl-aryl, or $C_{1-6}$-alkyl-$OR^6$;

$R^6$ is H or $C_{1-6}$-alkyl;

$R^7$ is null, H, $C_{1-6}$-alkyl, $C_{3-6}$-cycloalkyl, $C_{1-6}$-alkyl-$C_{3-6}$-cycloalkyl, heterocycloalkyl, or $C_{1-6}$-alkyl-heterocycloalkyl;

a ---- line denotes an optionally double bond;

m is 0 or 1; and n is 0 or 1, provided at least one of m or n is 1.

In one embodiment of the compound of Formula I, $R^1$ is mono-, bi-, or tri-cyclic aryl or heteroaryl, wherein the mono-, bi-, or tri-cyclic aryl or heteroaryl is optionally substituted with halo, $C_{1-4}$-alkyl, $CO_2R^6$, $C(O)R^6$, or $C_{1-6}$-alkyl-$OR^6$;

and $R^2$ and $R^3$ are each independently selected from $C_{2-6}$-alkenyl, $C_{2-6}$-alkynyl, $C_{3-6}$-cycloalkyl, $C_{1-6}$-alkyl-$C_{3-6}$-cycloalkyl, heterocycloalkyl, $C_{1-6}$-alkyl-heterocycloalkyl, $NR^4R^5$, O—$C_{1-6}$-alkyl-$OR^6$, $C_{1-6}$-alkyl-$OR^6$, aryl, heteroaryl, C(O)N(H)-heteroaryl, C(O)-heteroaryl, C(O)-heteroacycloalkyl, C(O)-aryl, C(O)—$C_{1-6}$-alkyl, $CO_2$—$C_{1-6}$-alkyl, and C(O)—$C_{1-6}$-alkyl-heterocycloalkyl, wherein the cycloalkyl, heterocycloalkyl, aryl, or heteroaryl is optionally substituted with $C_{1-4}$-alkyl, $CO_2R^6$, $C(O)R^6$, or $C_{1-6}$-alkyl-$OR^6$.

In another embodiment of the compound of Formula I, $R^1$ is monocyclic aryl or heteroaryl, wherein the aryl or heteroaryl is optionally substituted with halo;

$R^2$ and $R^3$ are each independently selected from $C_{2-6}$-alkenyl, $C_{3-6}$-cycloalkyl, $C_{1-6}$-alkyl-$C_{3-6}$-cycloalkyl, heterocycloalkyl, $C_{1-6}$-alkyl-heterocycloalkyl, $NR^4R^5$, O—$C_{1-6}$-alkyl-$OR^6$, or $C_{1-6}$-alkyl-$OR^6$;

$R^4$ is H or $C_{1-6}$-alkyl;

$R^5$ is $CO_2R^6$ or $C_{1-6}$-alkyl-$OR^6$; and $R^6$ is $C_{1-6}$-alkyl.

In one embodiment of the compound of Formula I, m is 1; n is 1; $Y_1$ is N; and $Y_2$, $Y_3$, $Y_4$, $Y_5$, and $Y_6$ are each CH.

In another embodiment of the compound of Formula I, m is 0; n is 1; $Y_2$ is N; $Y_1$ is $CR^7$; and $Y_3$, $Y_4$, and $Y_6$ are each CH.

In another embodiment of the compound of Formula I, m is 0; n is 1; $Y_1$ is $CR^7$; $Y_2$ is N; $Y_3$ is C(O); $Y_4$ is $CH_2$; and $Y_6$ is CH.

In another embodiment of the compound of Formula I m is 1; n is 1; $Y_1$ is $CR^7$; $Y_2$ is N, and $Y_3$, $Y_4$, $Y_5$, and $Y_6$ are each CH.

In another embodiment of the compound of Formula I, m is 0; n is 1; $Y_1$ is $CR^7$; $Y_2$ and $Y_3$ are each N; and $Y_4$ and $Y_6$ are each CH.

In another embodiment of the compound of Formula I, m is 0; n is 1; $Y_1$ and $Y_2$ are N; $Y_3$, $Y_4$, and $Y_6$ are each CH.

In yet another embodiment of the compound of Formula I, m is 1; n is 1; and Y1, $Y_2$, $Y_3$, $Y_4$, $Y_5$, and $Y_6$ are each CH.

In another embodiment of the compound of Formula I, $R^1$ is a monocyclic aryl or heteroaryl.

In yet a further embodiment of the compound of Formula I, $R^1$ is phenyl. $R^1$ can also be phenyl, wherein phenyl is optionally substituted with halo.

In another embodiment, $R^1$ is thienyl.

In a further embodiment, $R^1$ is pyridinyl.

In another embodiment of the compound of Formula I, $R^1$ is para to $NH_2$ in the compound of Formula I.

In one embodiment of the compound of Formula I, $R^2$ is $C_{3-6}$-cycloalkyl.

In another embodiment of the compound of Formula I, $R^2$ is cyclopropyl. In another embodiment, $R^2$ is cyclopentyl.

In a further embodiment of the compound of Formula I $R^2$ is $C_{1-6}$-alkyl-$C_{3-6}$-cycloalkyl. $R^2$ can be $CH_2$-cyclopropyl.

In a further embodiment of the compound of Formula I, $R^2$ is $C_{2-6}$-alkenyl. For example, $R^2$ can be $CH_2CH=CH_2$.

In an embodiment of the compound of Formula I, $R^3$ is heterocycloalkyl.

In a further embodiment of the compound of Formula I, $R^3$ is morpholinyl or piperazinyl.

In another embodiment of the compound of Formula I, $R^3$ is $C_{1-6}$-alkyl-heterocycloalkyl. For example, $R^3$ can be $CH_2CH_2$-morpholinyl, $CH_2$-morpholinyl, $CH_2CH_2$-piperazinyl, or $CH_2$-piperazinyl.

In another embodiment of the compound of Formula I, $R^3$ is O—$C_{1-6}$-alkyl-$OR^6$. For example, $R^3$ can be $OCH_2CH_2OCH_3$ or $OCH_2OCH_3$.

In another embodiment of the compound of Formula I, $R^3$ is $C_{1-6}$-alkyl-$OR^6$. For example, $R^3$ can be $CH_2CH_2OCH_3$.

In a further embodiment of the compound of Formula I, $R^3$ is $NR^4R^5$. For example, $R^3$ can be $NHCO_2CH_2CH_3$.

In an embodiment of the compound of Formula I, $R^7$ is H or $C_{3-6}$-cycloalkyl. For example, $R^7$ can be cyclopropyl.

In another embodiment of Formula I, m is 0; n is 1; $Y_2$ is N; $Y_1$ is $CR^7$; and $Y_3$, $Y_4$, and $Y_6$ are each CH, and Formula I is of the Formula III:

III or a pharmaceutically acceptable salt thereof, wherein $R^1$, $R^2$, $R^3$ and $R^7$ have the definitions provided above. In an embodiment of Formula III, $R^2$ and $R^3$ are each independently selected from $C_{3-6}$-cyclo alkyl, $C_{1-6}$-alkyl-$C_{3-6}$-cycloalkyl, heterocycloalkyl, or $C_{1-6}$-alkyl-heterocycloalkyl. In another embodiment of Formula III, $R^7$ can be H or $C_{1-6}$-alkyl. In still another embodiment of Formula III, $R^1$ is $R^1$ is mono- or bi-cyclic aryl or heteroaryl, wherein the aryl or heteroaryl groups are optionally substituted with halogen. In yet another embodiment of Formula III, $R^1$ is para to the $NH_2$ group.

In another embodiment of Formula III, $R^2$ and $R^3$ are each independently selected from $C_{3-6}$-cycloalkyl, $C_{1-6}$-alkyl-$C_{3-6}$-cycloalkyl, heterocycloalkyl, or $C_{1-6}$-alkyl-heterocycloalkyl; $R^7$ can be H or $C_{1-6}$-alkyl; and $R^1$ is $R^1$ is mono- or bi-cyclic aryl or heteroaryl, wherein the aryl or heteroaryl groups are optionally substituted with halogen.

In another aspect, the invention provides a compound of Formula II:

II or a pharmaceutically acceptable salt thereof;

wherein

R$^1$ and R$^2$ are independently H, mono-, bi-, or tri-cyclic aryl or heteroaryl, wherein the mono-, bi-, or tri-cyclic aryl or heteroaryl is optionally substituted;

or R$^1$ and R$^2$ are linked together to form a group of Formula:

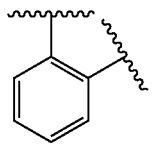 [SMILES: *c1ccccc1*]

R$^3$ and R$^4$ are independently selected from H, C$_{1-6}$-alkyl, C$_{2-6}$-alkenyl, C$_{2-6}$-alkynyl, C$_{3-6}$-cycloalkyl, C$_{1-6}$-alkyl-C$_{3-6}$-cycloalkyl, heterocyclo alkyl, C$_{1-6}$-alkyl-heterocycloalkyl, NR$^5$R$^6$, O—C$_{1-6}$-alkyl-OR$^7$, aryl, heteroaryl, C(O)N(H)-heteroaryl, C(O)-heteroaryl, C(O)-heterocycloalkyl, C(O)-aryl, C(O)—C$_{1-6}$-alkyl, CO$_2$—C$_{1-6}$-alkyl, or C(O)—C$_{1-6}$-alkyl-heterocycloalkyl, wherein the cycloalkyl, heterocycloalkyl, aryl, or heteroaryl is optionally substituted;

R$^5$ is H, C$_{1-6}$-alkyl, CO$_2$R$^7$ or C$_{1-6}$-alkyl-OR$^7$;

R$^6$ is H, C$_{1-6}$-alkyl, CO$_2$R$^7$ or C$_{1-6}$-alkyl-OR$^7$;

R$^7$ is H or C$_{1-6}$-alkyl;

X$_1$, X$_2$, and X$_3$ are each independently CH, N, or S, wherein at least one of X$_1$ or X$_2$ is N or S;

a ---- line denotes an optionally double bond; and p is 0 or 1.

In one embodiment of the compound of Formula II, R$^1$ is mono-, bi-, or tri-cyclic aryl or heteroaryl, wherein the mono-, bi-, or tri-cyclic aryl or heteroaryl is optionally substituted with halo, C$_{1-4}$-alkyl, CO$_2$R$^7$, C(O)R$^7$, or C$_{1-6}$-alkyl-OR$^7$;

R$^2$ is H;

or R$^1$ and R$^2$ are linked together to form the following fused ring:

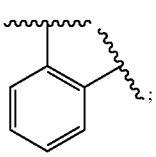 [SMILES: *c1ccccc1*]

and

R$^3$ and R$^4$ are independently selected from H, C$_{2-6}$-alkenyl, C$_{2-6}$-alkynyl, C$_{3-6}$-cycloalkyl, heterocyclo alkyl, C$_{1-6}$-alkyl-heterocycloalkyl, NR$^5$R$^6$, C$_{1-6}$-alkyl-OR$^7$, aryl, heteroaryl, C(O)N(H)-heteroaryl, C(O)-heteroaryl, C(O)-heterocycloalkyl, C(O)-aryl, C(O)—C$_{1-6}$-alkyl, CO$_2$—C$_{1-6}$-alkyl, or C(O)—C$_{1-6}$-alkyl-heterocycloalkyl In another embodiment of the compound of Formula II, R$^1$ is monocyclic aryl or heteroaryl, wherein aryl or heteroaryl is optionally substituted with halo;

R$^2$ is H;

or R$^1$ and R$^2$ are linked together to form the following fused ring:

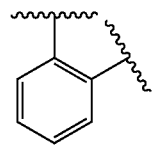

R$^3$ is H; and

R$^4$ is heterocycloalkyl, wherein the heterocycloalkyl is optionally substituted with C$_{1-4}$-alkyl, CO$_2$R$^7$, C(O)R$^7$, C$_{1-6}$-alkyl-OR$^7$.

In another embodiment of the compound of Formula II, p is 1; X$_1$ is N; and X$_2$ and X$_3$ are CH.

In another embodiment of the compound of Formula II, p is 1; X$_1$ and X$_2$ are CH; and X$_3$ is N.

In yet another embodiment of the compound of Formula II, p is 1; X$_1$ and X$_3$ are CH; and X$_2$ is N.

In still another embodiment of the compound of Formula II, p is 0; X$_1$ is S; and X$_2$ and X$_3$ are CH.

In still another embodiment of the compound of Formula II p is 0; X$_1$ and X$_2$ are CH; and X$_3$ is S.

In another embodiment of the compound of Formula II, R$^1$ is monocyclic aryl or heteroaryl, and the aryl or heteroaryl can be optionally substituted with halo. In another embodiment, R$^1$ can be phenyl.

R$^1$ can also be thienyl.

In another embodiment of the compound of Formula II, R$^2$ is H. In yet another embodiment of the compound of Formula II, R$^1$ and R$^2$ are each H.

In another embodiment of the compound of Formula II, R$^1$ and R$^2$ are linked together to form the following fused ring:

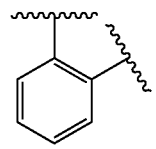

In another embodiment of the compound of Formula II, R$^3$ is H.

In another embodiment of the compound of Formula II R$^4$ is heterocycloalkyl. R$^4$ can be piperazinyl.

In another aspect, provided herein is a compound selected from the group consisting of:

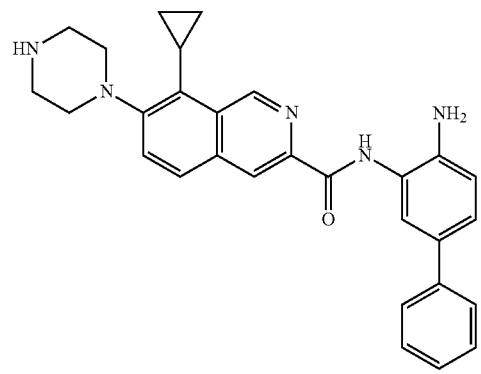

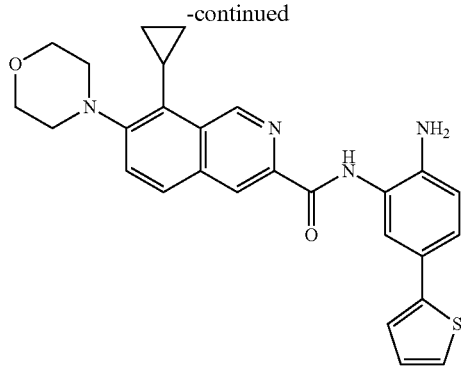
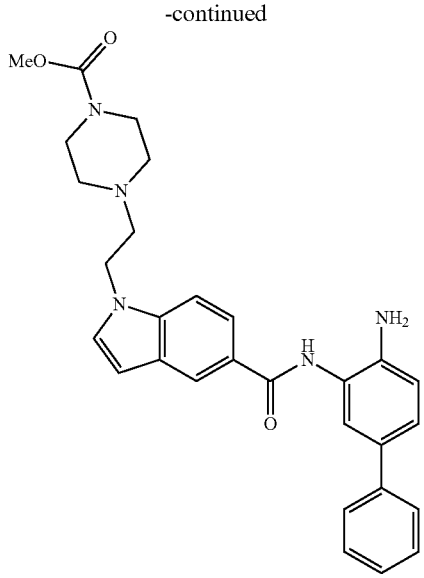
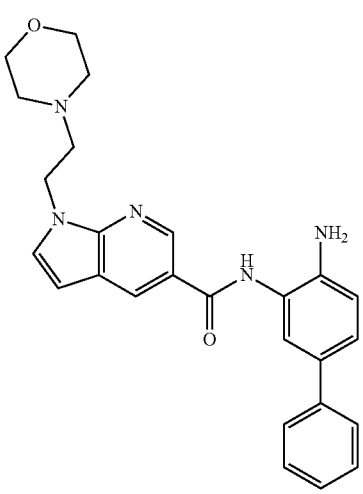
or pharmaceutically acceptable salts thereof.
In one aspect, provided herein is a compound selected from the group consisting of:
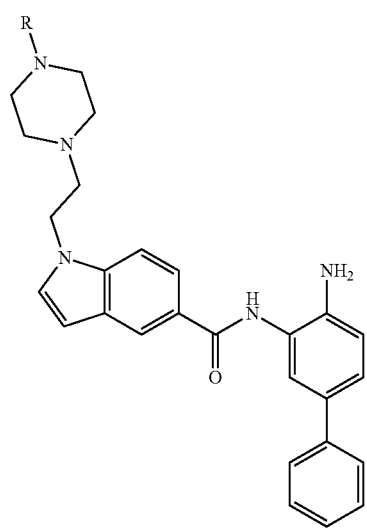
R = H, CH₃
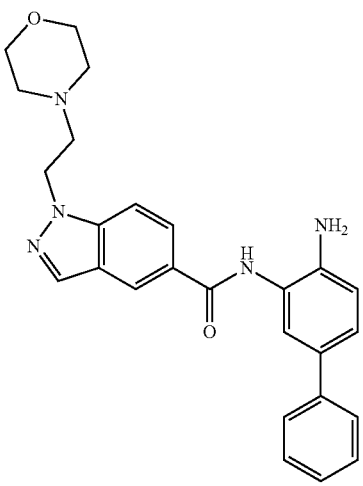

-continued
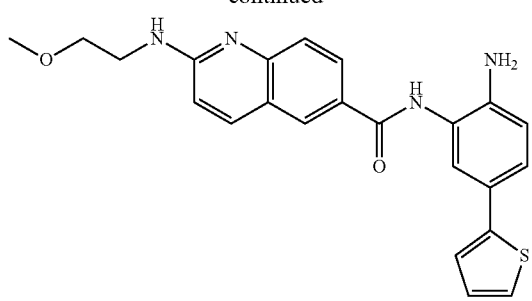
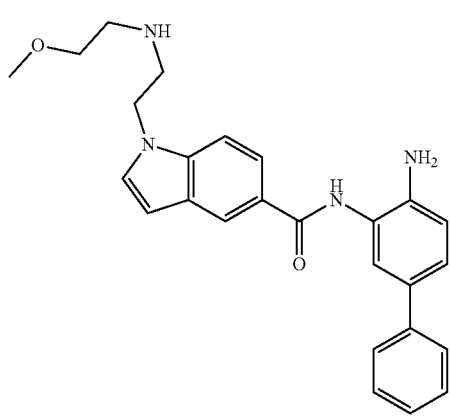
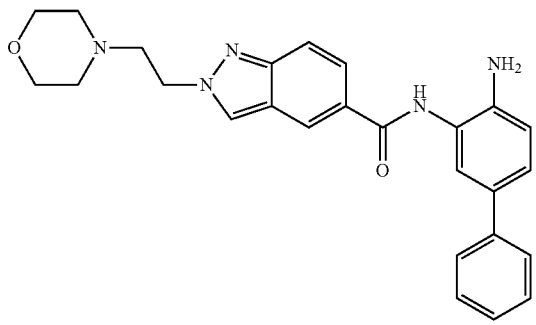
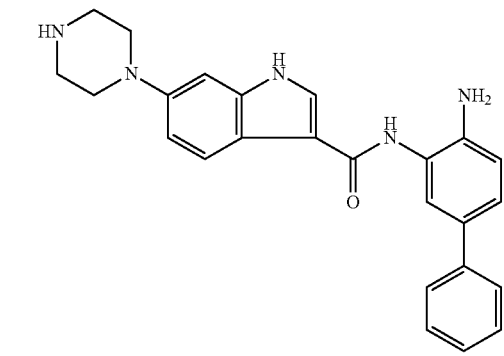
-continued
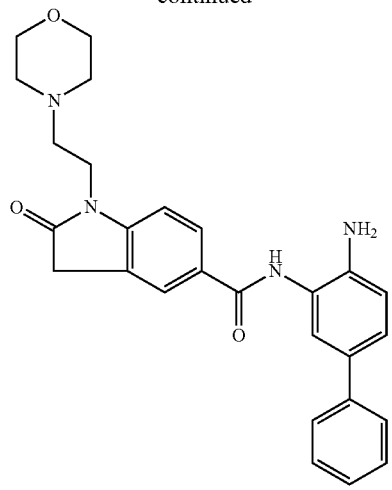
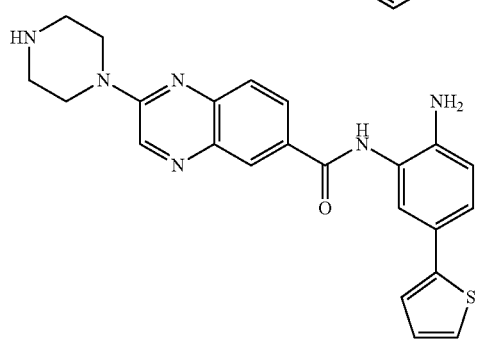
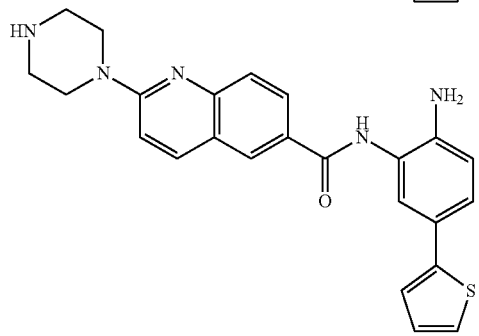
or pharmaceutically acceptable salts thereof.
Representative compounds of the invention include, but are not limited to, the following compounds of Table 1 below.
TABLE 1
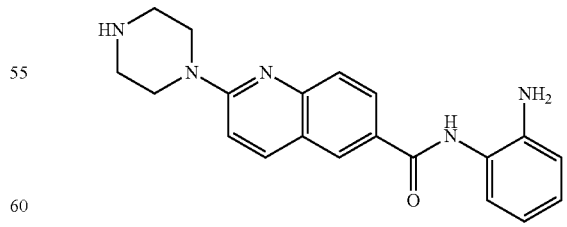
N-(2-aminophenyl)-2-(piperazin-1-yl)quinoline-6-carboxamide
$IC_{50}(nM)$
HDAC1 = >2,000
HDAC2 = 624
HDAC3 = 104

TABLE 1-continued

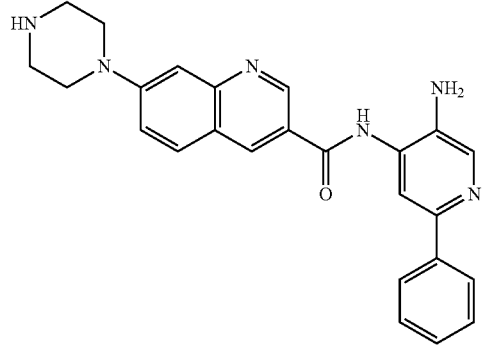

N-(5-amino-2-phenylpyridin-4-yl)-7-
(piperazin-1-yl)quinoline-3-carboxamide
$IC_{50}(nM)$
HDAC1 = 1,233
HDAC2 = 1192
HDAC3 = 1876

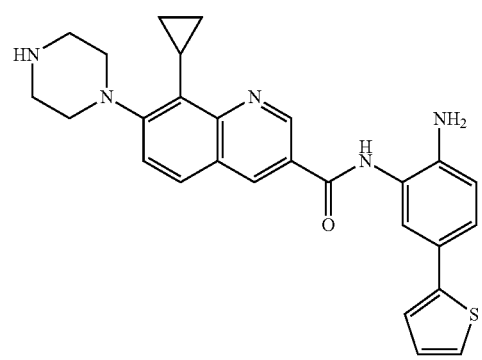

N-(2-amino-5-(thiophen-2-yl)phenyl)-8-
cyclopropyl-7-(piperazin-1-yl)quinoline-3-
carboxamide. Compound 002
$IC_{50}(nM)$
HDAC1 = 3.1
HDAC2 = 14
HDAC3 = 99

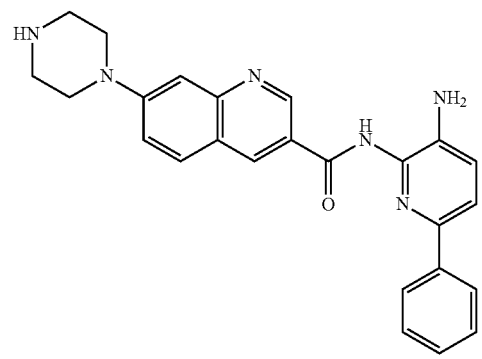 [SMILES: Nc1ccc(-c2ccccc2)nc1NC(=O)c1cnc2cc(N3CCNCC3)ccc2c1]

N-(3-amino-6-phenylpyridin-2-yl)-7-
(piperazin-1-yl)quinoline-3-carboxamide
$IC_{50}(nM)$
HDAC1 = 1,968
HDAC2 = 336
HDAC3 = 798

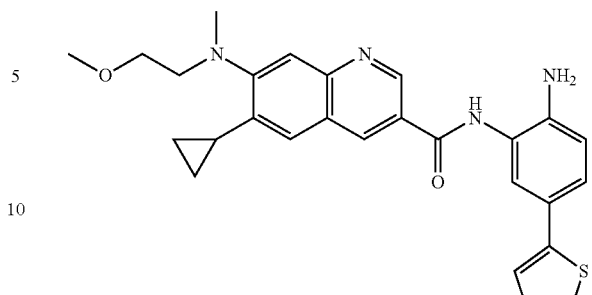

N-(2-amino-5-(thiophen-2-yl)phenyl)-6-
cyclopropyl-7-((2-
methoxyethyl)(methyl)amino)quinoline-3-
carboxamide
$IC_{50}(nM)$
HDAC1 = 944
HDAC2 = 667
HDAC3 = >2,000

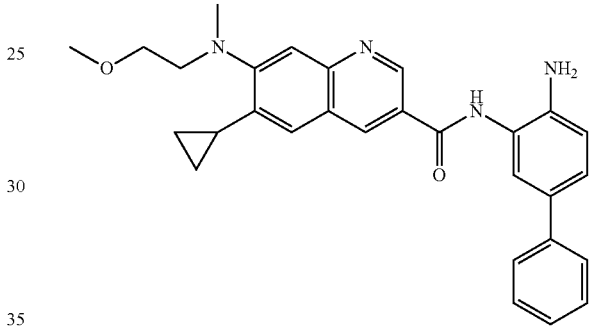

N-(4-amino-[1,1'-biphenyl]-3-yl)-6-
cyclopropyl-7-((2-
methoxyethyl)(methyl)amino)quinoline-3-
carboxamide
$IC_{50}(nM)$
HDAC1 = >2,000
HDAC2 = 1220
HDAC3 = >2,000

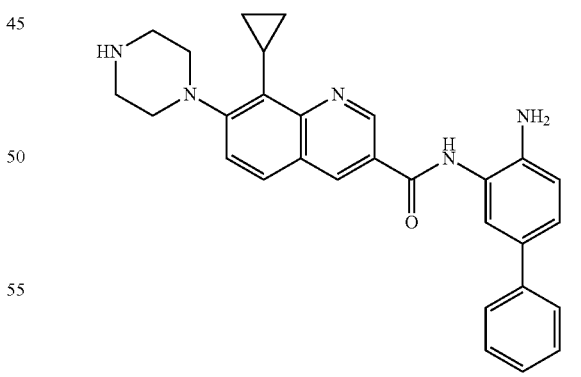

N-(4-amino-[1,1'-biphenyl]-3-yl)-8-
cyclopropyl-7-(piperazin-1-yl)quinoline-3-
carboxamide, Compound 003
$IC_{50}(nM)$
HDAC1 = 7.8
HDAC2 = 15
HDAC3 = 164

TABLE 1-continued

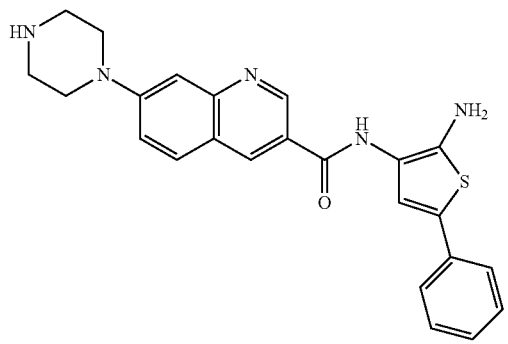 [SMILES: Nc1sc(-c2ccccc2)cc1NC(=O)c1cnc2cc(N3CCNCC3)ccc2c1]

N-(2-amino-5-phenylthiophen-3-yl)-7-
(piperazin-1-yl)quinoline-3-carboxamide
IC$_{50}$(nM)
HDAC1 = 1210
HDAC2 = 193
HDAC3 = 171

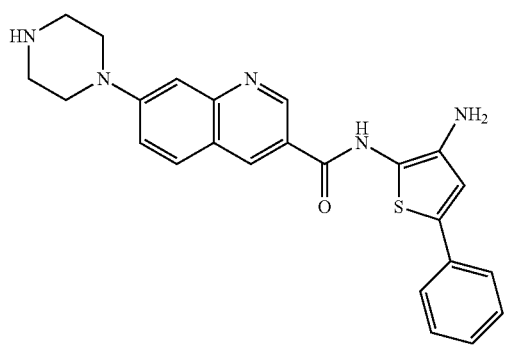 [SMILES: Nc1cc(-c2ccccc2)sc1NC(=O)c1cnc2cc(N3CCNCC3)ccc2c1]

N-(3-amino-5-phenylthiophen-2-yl)-7-
(piperazin-1-yl)quinoline-3-carboxamide
IC$_{50}$(nM)
HDAC1 = >2,000
HDAC2 = >2,000
HDAC3 = >2,000

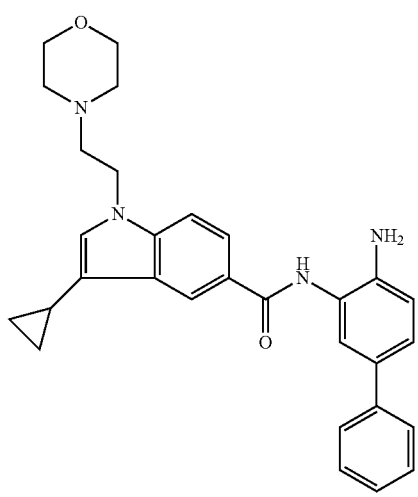 [SMILES: Nc1ccc(-c2ccccc2)cc1NC(=O)c1ccc2c(c1)c(C1CC1)cn2CCN1CCOCC1]

N-(4-amino-[1,1'-biphenyl]-3-yl)-3-
cyclopropyl-1-(2-morpholinoethyl)-1H-
indole-5-carboxamide
IC$_{50}$(nM)
HDAC1 = >2,000
HDAC2 = 681
HDAC3 = 1905

TABLE 1-continued

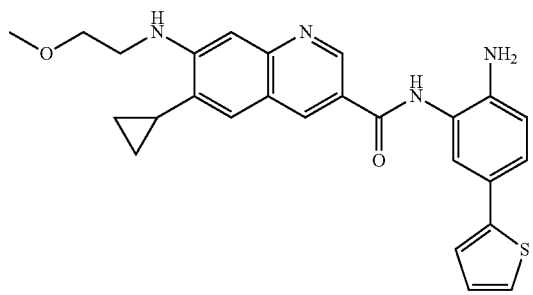 [SMILES: COCCNc1cc2ncc(C(=O)Nc3cc(-c4cccs4)ccc3N)cc2cc1C1CC1]

N-(2-amino-5-(thiophen-2-yl)phenyl)-6-
cyclopropyl-7-((2-
methoxyethyl)amino)quinoline-3-carboxamide
IC$_{50}$(nM)
HDAC1 = 89
HDAC2 = 243
HDAC3 = 1548

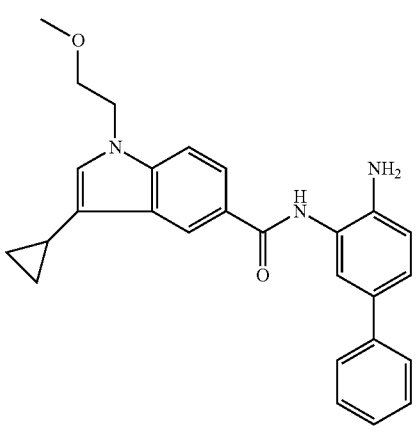 [SMILES: COCCn1cc(C2CC2)c2cc(C(=O)Nc3cc(-c4ccccc4)ccc3N)ccc21]

N-(4-amino-[1,1'-biphenyl]-3-yl)-3-
cyclopropyl-1-(2-methoxyethyl)-1H-indole-5-
carboxamide
IC$_{50}$(nM)
HDAC1 = >2,000
HDAC2 = >2,000
HDAC3 = >2,000

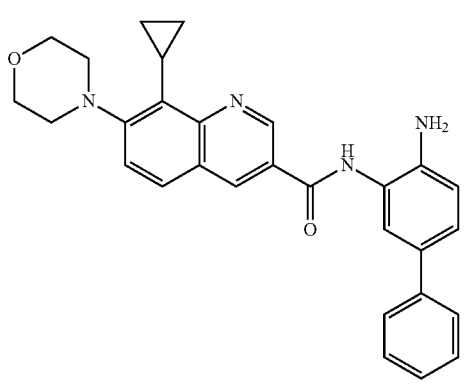 [SMILES: Nc1ccc(-c2ccccc2)cc1NC(=O)c1cnc2c(C3CC3)c(N3CCOCC3)ccc2c1]

N-(4-amino-[1,1'-biphenyl]-3-yl)-8-
cyclopropyl-7-morpholinoquinoline-3-
carboxamide
IC$_{50}$(nM)
HDAC1 = 295
HDAC2 = 799
HDAC3 = >2,000

TABLE 1-continued

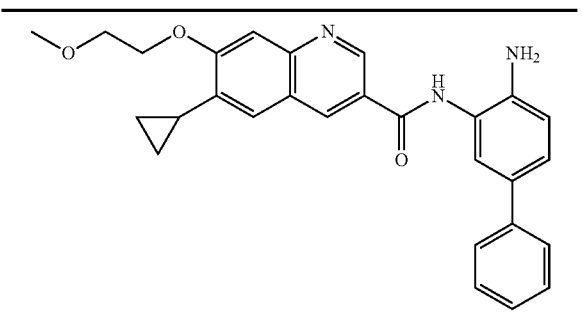

N-(4-amino-[1,1'-biphenyl]-3-yl)-6-
cyclopropyl-7-(2-methoxyethoxy)quinoline-
3-carboxamide
IC$_{50}$(nM)
HDAC1 = >2,000
HDAC2 = 1559
HDAC3 = >2,000

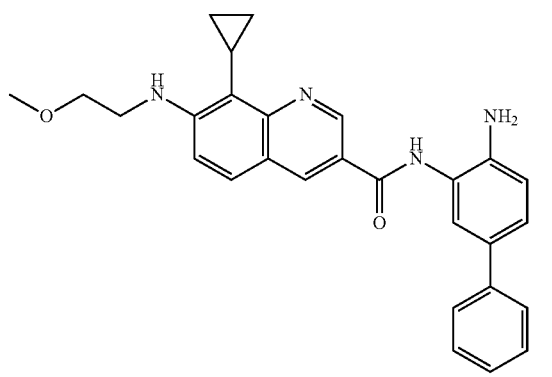 [SMILES: COCCNc1ccc2cc(C(=O)Nc3cc(-c4ccccc4)ccc3N)cnc2c1C1CC1]

N-(4-amino-[1,1'-biphenyl]-3-yl)-8-
cyclopropyl-7-((2-
methoxyethyl)amino)quinoline-3-carboxamide
IC$_{50}$(nM)
HDAC1 = 115
HDAC2 = 301
HDAC3 = >2,000

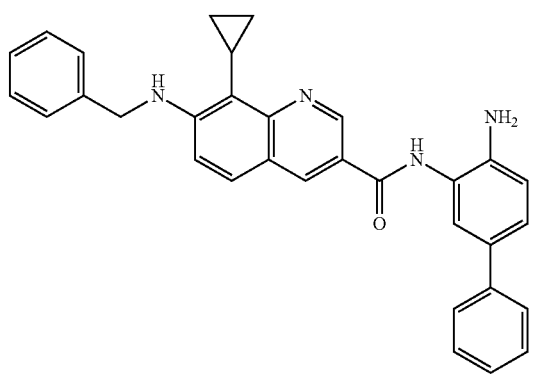 [SMILES: Nc1ccc(-c2ccccc2)cc1NC(=O)c1cnc2c(C3CC3)c(NCc3ccccc3)ccc2c1]

N-(4-amino-[1,1'-biphenyl]-3-yl)-7-
(benzylamino)-8-cyclopropylquinoline-3-
carboxamide
IC$_{50}$(nM)
HDAC1 = 652
HDAC2 = >2,000
HDAC3 = No inhibition TABLE 1-continued

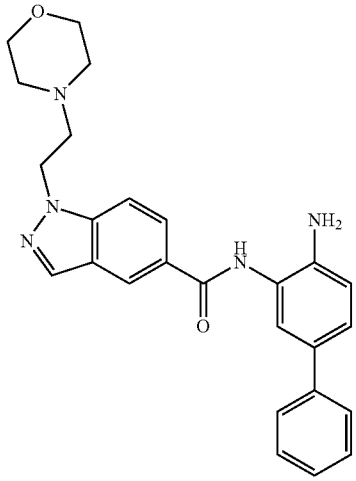 [SMILES: Nc1ccc(-c2ccccc2)cc1NC(=O)c1ccc2c(cnn2CCN2CCOCC2)c1]

N-(4-amino-[1,1'-biphenyl]-3-yl)-1-(2-
morpholinoethyl)-1H-indazole-5-carboxamide
IC$_{50}$(nM)
HDAC1 = 7.4
HDAC2 = 19
HDAC3 = 344

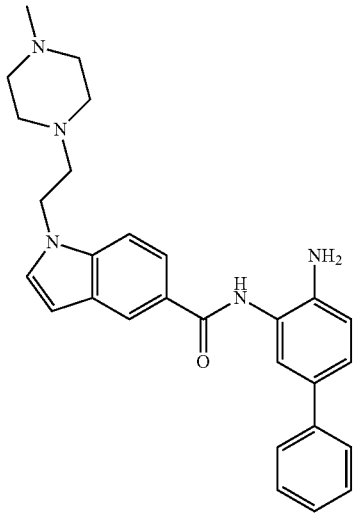 [SMILES: CN1CCN(CCn2ccc3cc(C(=O)Nc4cc(-c5ccccc5)ccc4N)ccc32)CC1]

N-(4-amino-[1,1'-biphenyl]-3-yl)-1-(2-(4-
methylpiperazin-1-yl)ethyl)-1H-indole-5-
carboxamide
IC$_{50}$(nM)
HDAC1 = 7.1
HDAC2 = 11
HDAC3 = 175

TABLE 1-continued

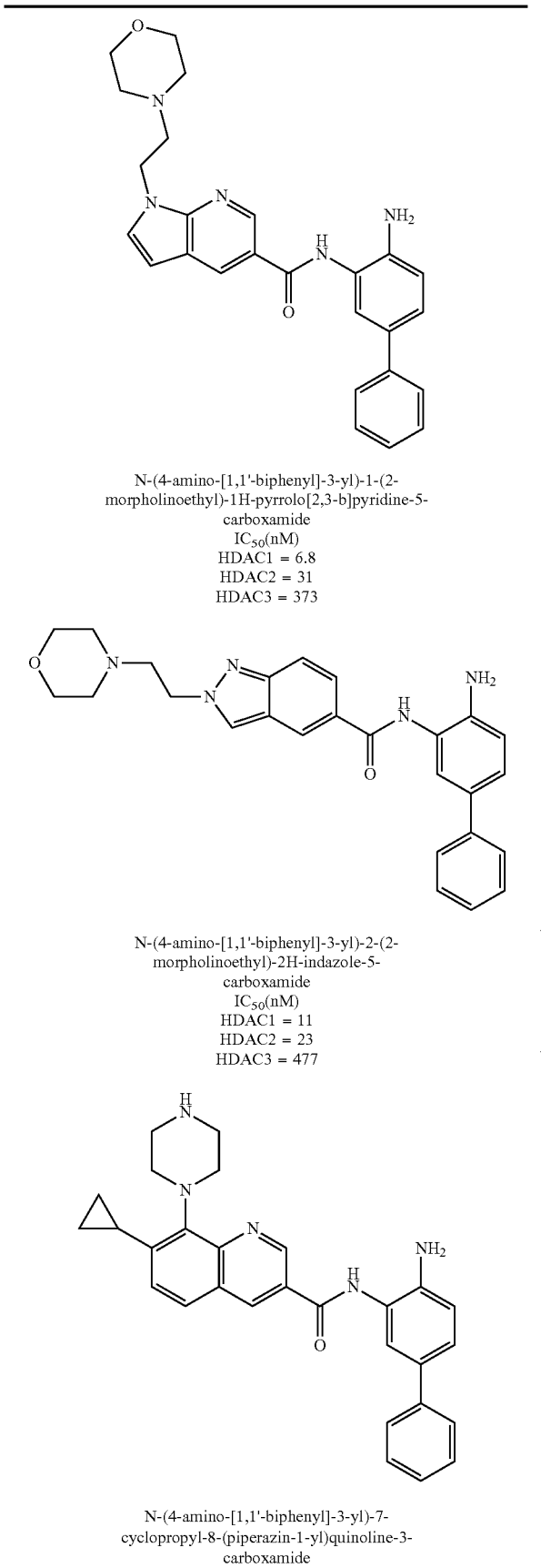

N-(4-amino-[1,1'-biphenyl]-3-yl)-1-(2-morpholinoethyl)-1H-pyrrolo[2,3-b]pyridine-5-carboxamide
IC$_{50}$(nM)
HDAC1 = 6.8
HDAC2 = 31
HDAC3 = 373

N-(4-amino-[1,1'-biphenyl]-3-yl)-2-(2-morpholinoethyl)-2H-indazole-5-carboxamide
IC$_{50}$(nM)
HDAC1 = 11
HDAC2 = 23
HDAC3 = 477

N-(4-amino-[1,1'-biphenyl]-3-yl)-7-cyclopropyl-8-(piperazin-1-yl)quinoline-3-carboxamide TABLE 1-continued IC$_{50}$(nM)
HDAC1 = 103
HDAC2 = 56
HDAC3 = 257

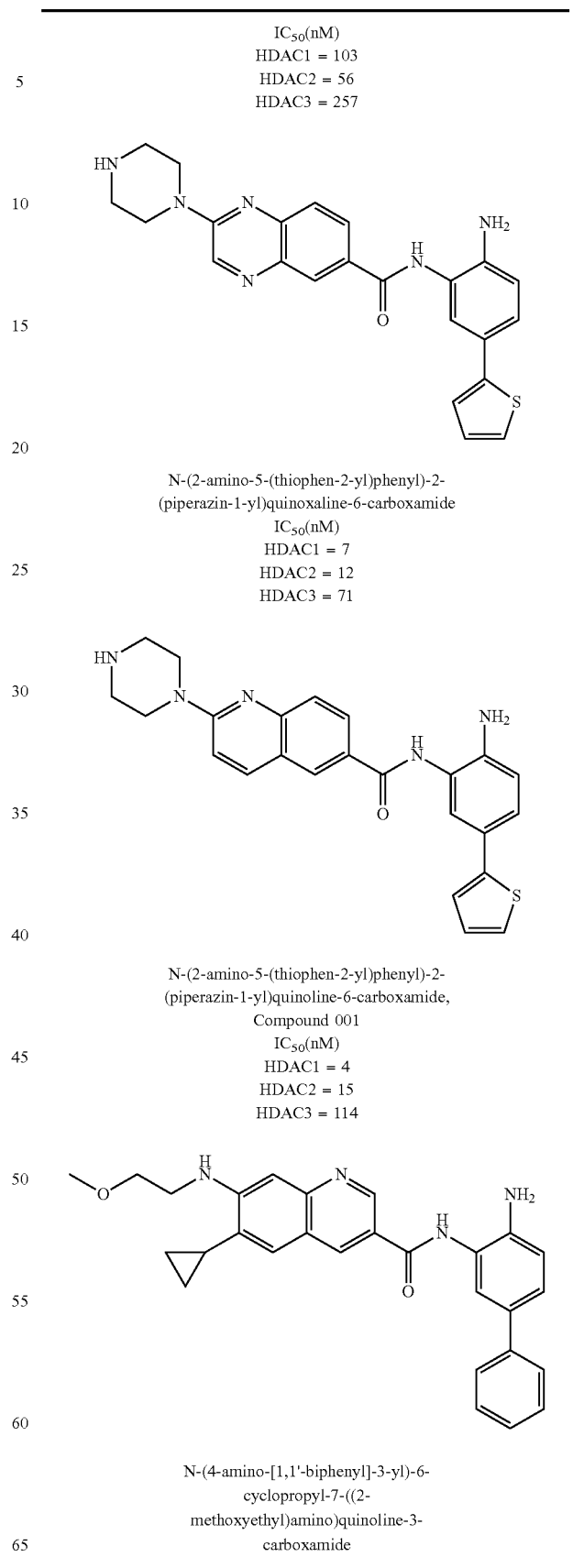

N-(2-amino-5-(thiophen-2-yl)phenyl)-2-(piperazin-1-yl)quinoxaline-6-carboxamide
IC$_{50}$(nM)
HDAC1 = 7
HDAC2 = 12
HDAC3 = 71

N-(2-amino-5-(thiophen-2-yl)phenyl)-2-(piperazin-1-yl)quinoline-6-carboxamide,
Compound 001
IC$_{50}$(nM)
HDAC1 = 4
HDAC2 = 15
HDAC3 = 114

N-(4-amino-[1,1'-biphenyl]-3-yl)-6-cyclopropyl-7-((2-methoxyethyl)amino)quinoline-3-carboxamide TABLE 1-continued

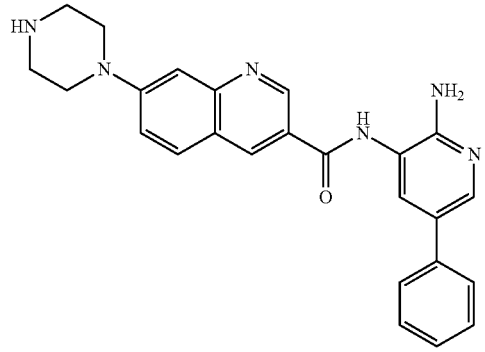

N-(2-amino-5-phenylpyridin-3-yl)-7-(piperazin-1-yl)quinoline-3-carboxamide

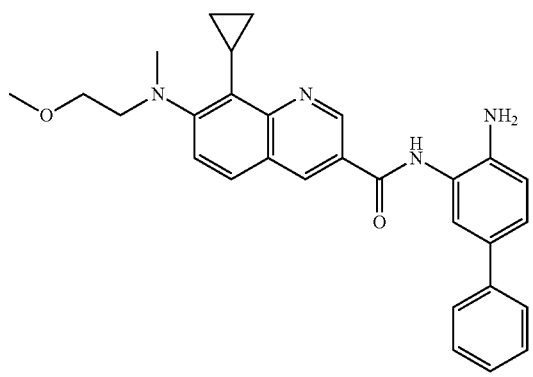 [SMILES: COCCN(C)c1ccc2cc(C(=O)Nc3cc(-c4ccccc4)ccc3N)cnc2c1C1CC1]

N-(4-amino-[1,1'-biphenyl]-3-yl)-8-cyclopropyl-7-((2-methoxyethyl)(methyl)amino)quinoline-3-carboxamide

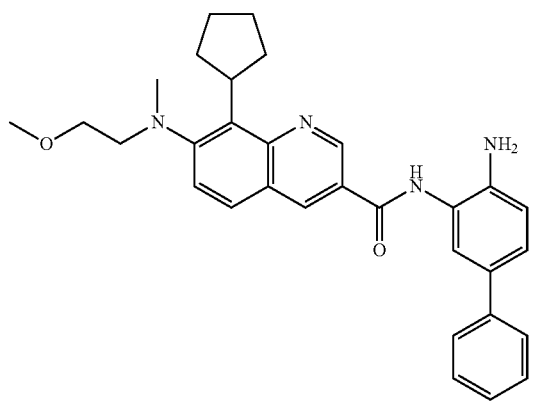 [SMILES: COCCN(C)c1ccc2cc(C(=O)Nc3cc(-c4ccccc4)ccc3N)cnc2c1C1CCCC1]

N-(4-amino-[1,1'-biphenyl]-3-yl)-8-cyclopentyl-7-((2-methoxyethyl)(methyl)amino)quinoline-3-carboxamide TABLE 1-continued

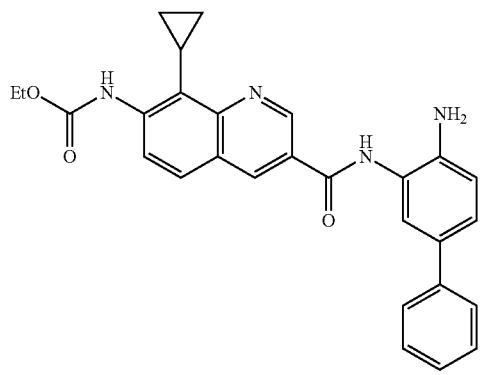 [SMILES: CCOC(=O)Nc1ccc2cc(C(=O)Nc3cc(-c4ccccc4)ccc3N)cnc2c1C1CC1]

ethyl (3-((4-amino-[1,1'-biphenyl]-3-yl)carbamoyl)-8-cyclopropylquinolin-7-yl)carbamate

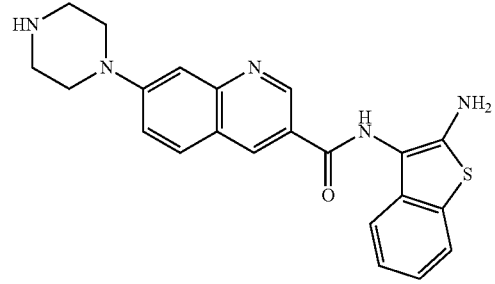 [SMILES: Nc1sc2ccccc2c1NC(=O)c1cnc2cc(N3CCNCC3)ccc2c1]

N-(2-aminobenzo[b]thiophen-3-yl)-7-(piperazin-1-yl)quinoline-3-carboxamide

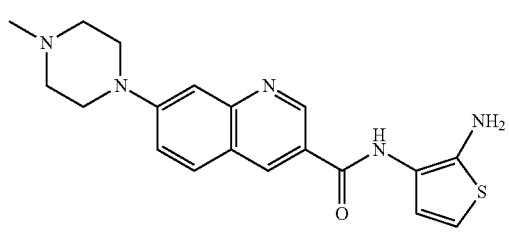 [SMILES: CN1CCN(c2ccc3cc(C(=O)Nc4ccsc4N)cnc3c2)CC1]

N-(2-aminothiophen-3-yl)-7-(4-methylpiperazin-1-yl)quinoline-3-carboxamide

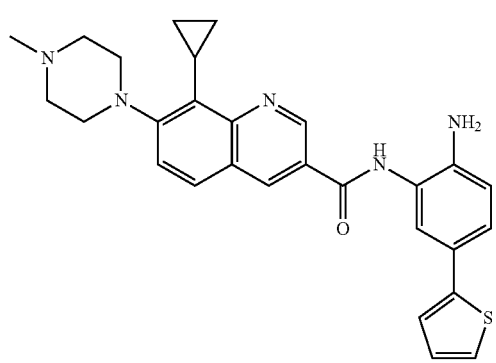 [SMILES: CN1CCN(c2ccc3cc(C(=O)Nc4cc(-c5cccs5)ccc4N)cnc3c2C2CC2)CC1]

N-(2-amino-5-(thiophen-2-yl)phenyl)-8-cyclopropyl-7-(4-methylpiperazin-1-yl)quinoline-3-carboxamide TABLE 1-continued

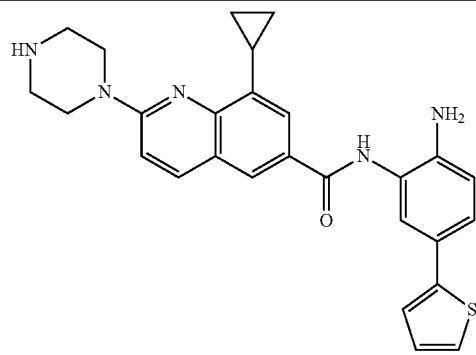

N-(2-amino-5-(thiophen-2-yl)phenyl)-8-cyclopropyl-2-(piperazin-1-yl)quinoline-carboxamide

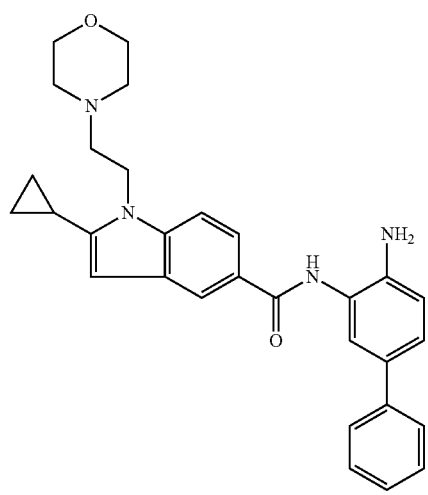 [SMILES: Nc1ccc(-c2ccccc2)cc1NC(=O)c1ccc2c(c1)cc(C1CC1)n2CCN1CCOCC1]

N-(4-amino-[1,1'-biphenyl]-3-yl)-2-cyclopropyl-1-(2-morpholinoethyl)-1H-indole-5-carboxamide
IC$_{50}$(nM)
HDAC1 = 15
HDAC2 = 70
HDAC3 = 689

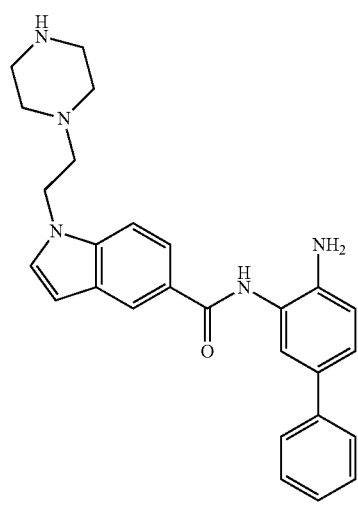

N-(4-amino-[1,1'-biphenyl]-3-yl)-1-(2-(piperazin-1-yl)ethyl)-1H-indole-5-carboxamide TABLE 1-continued

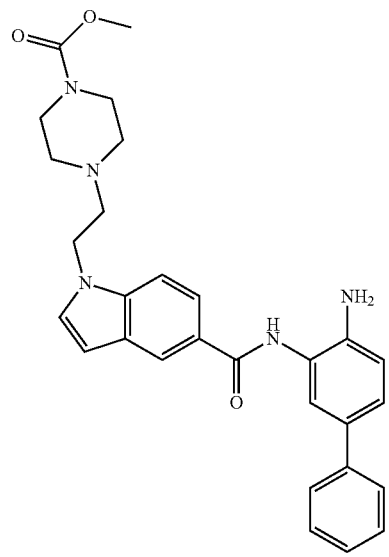 [SMILES: COC(=O)N1CCN(CCn2ccc3cc(C(=O)Nc4cc(-c5ccccc5)ccc4N)ccc32)CC1]

methyl 4-(2-(5-((4-amino-[1,1'-biphenyl]-3-yl)carbamoyl)-1H-indol-1-yl)ethyl)piperazine-1-carboxylate

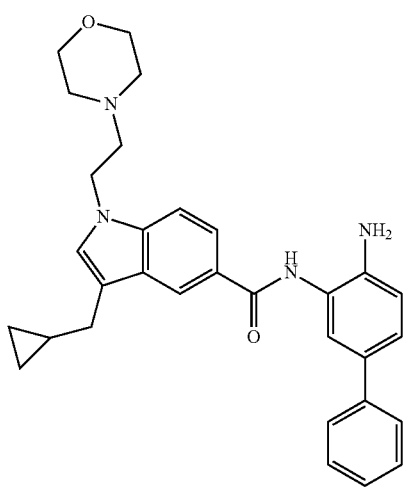 [SMILES: Nc1ccc(-c2ccccc2)cc1NC(=O)c1ccc2c(c1)c(CC1CC1)cn2CCN1CCOCC1]

N-(4-amino-[1,1'-biphenyl]-3-yl)-3-(cyclopropylmethyl)-1-(2-morpholinoethyl)-1H-indole-5-carboxamide

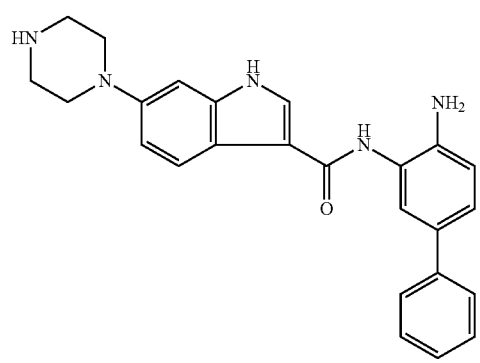 [SMILES: Nc1ccc(-c2ccccc2)cc1NC(=O)c1c[nH]c2cc(N3CCNCC3)ccc12]

N-(4-amino-[1,1'-biphenyl]-3-yl)-6-(piperazin-1-yl)-1H-indole-3-carboxamide

TABLE 1-continued

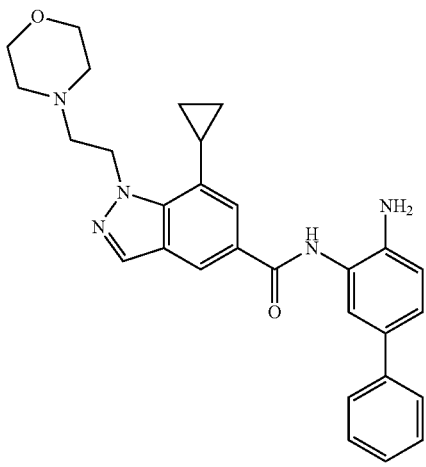 [SMILES: Nc1ccc(-c2ccccc2)cc1NC(=O)c1cc(C2CC2)c2c(cnn2CCN2CCOCC2)c1]

N-(4-amino-[1,1'-biphenyl]-3-yl)-7-
cyclopropyl-1-(2-morpholinoethyl)-1H-
indazole-5-carboxamide

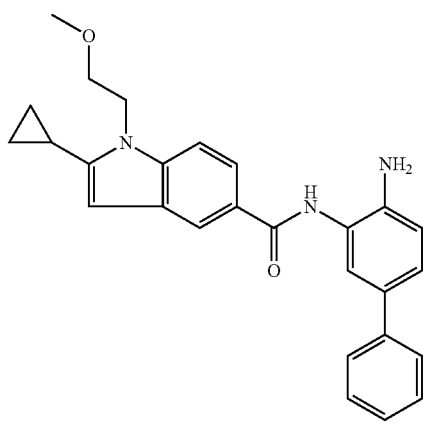 [SMILES: COCCn1c(C2CC2)cc2cc(C(=O)Nc3cc(-c4ccccc4)ccc3N)ccc21]

N-(4-amino-[1,1'-biphenyl]-3-yl)-2-
cyclopropyl-1-(2-methoxyethyl)-1H-indole-5-
carboxamide

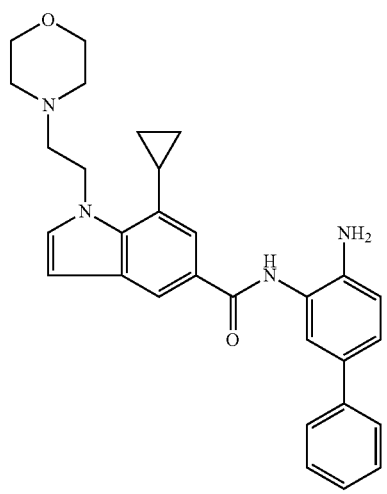 [SMILES: Nc1ccc(-c2ccccc2)cc1NC(=O)c1cc(C2CC2)c2c(ccn2CCN2CCOCC2)c1]

N-(4-amino-[1,1'-biphenyl]-3-yl)-7-
cyclopropyl-1-(2-morpholinoethyl)-1H-
indole-5-carboxamide

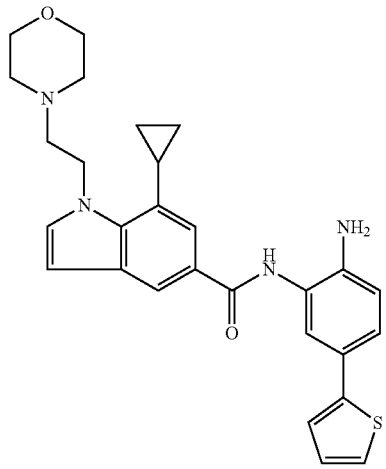 [SMILES: Nc1ccc(-c2cccs2)cc1NC(=O)c1cc(C2CC2)c2c(ccn2CCN2CCOCC2)c1]

N-(2-amino-5-(thiophen-2-yl)phenyl)-7-
cyclopropyl-1-(2-morpholinoethyl)-1H-indole-
5-carboxamide

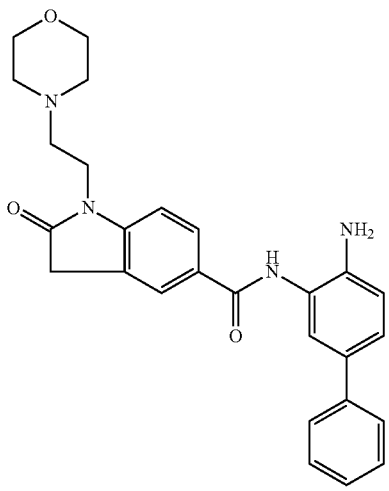 [SMILES: Nc1ccc(-c2ccccc2)cc1NC(=O)c1ccc2c(c1)CC(=O)N2CCN1CCOCC1]

N-(4-amino-[1,1'-biphenyl]-3-yl)-1-(2-
morpholinoethyl)-2-oxoindoline-5-
carboxamide

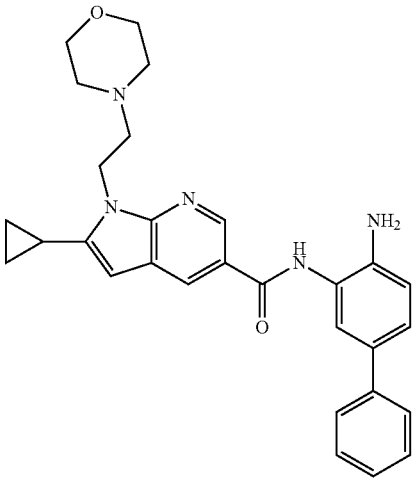 [SMILES: Nc1ccc(-c2ccccc2)cc1NC(=O)c1cnc2c(c1)cc(C1CC1)n2CCN1CCOCC1]

N-(4-amino-[1,1'-biphenyl]-3-yl)-2-
cyclopropyl-1-(2-morpholinoethyl)-1H-
pyrrolo[2,3-b]pyridine-5-carboxamide TABLE 1-continued

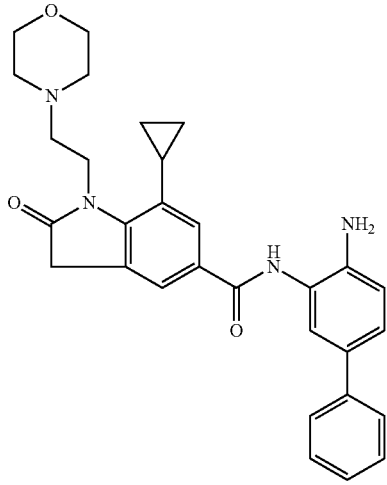 [SMILES: Nc1ccc(-c2ccccc2)cc1NC(=O)c1cc2c(c(C3CC3)c1)N(CCN1CCOCC1)C(=O)C2]

N-(4-amino-[1,1'-biphenyl]-3-yl)-7-cyclopropyl-1-(2-morpholinoethyl)-2-oxoindoline-5-carboxamide

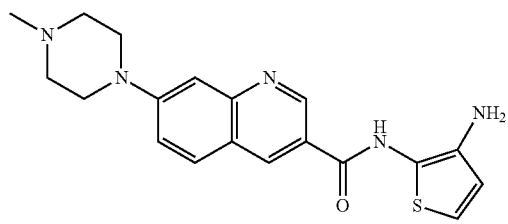 [SMILES: CN1CCN(c2ccc3cc(C(=O)Nc4sccc4N)cnc3c2)CC1]

N-(3-aminothiophen-2-yl)-7-(4-methylpiperazin-1-yl)quinoline-3-carboxamide

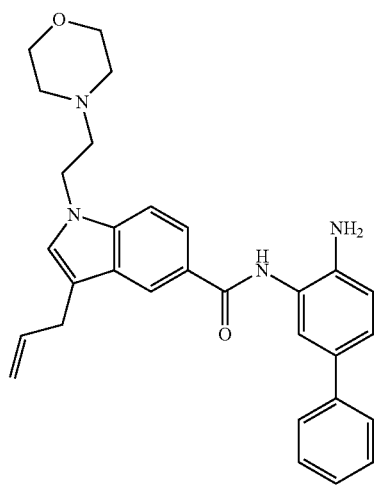 [SMILES: C=CCc1cn(CCN2CCOCC2)c2ccc(C(=O)Nc3cc(-c4ccccc4)ccc3N)cc12]

3-allyl-N-(4-amino-[1,1'-biphenyl]-3-yl)-1-(2-morpholinoethyl)-1H-indole-5-carboxamide TABLE 1-continued

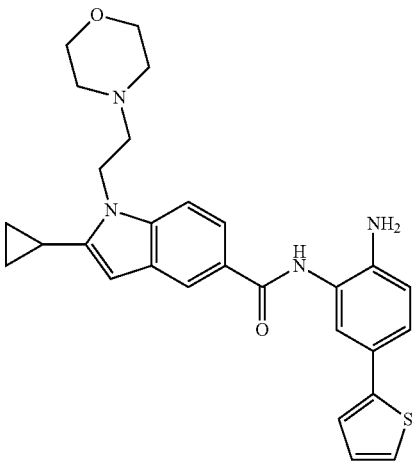 [SMILES: Nc1ccc(-c2cccs2)cc1NC(=O)c1ccc2c(c1)cc(C1CC1)n2CCN1CCOCC1]

N-(2-amino-5-(thiophen-2-yl)phenyl)-2-cyclopropyl-1-(2-morpholinoethyl)-1H-indole-5-carboxamide
IC$_{50}$(nM)
HDAC1 = 6
HDAC2 = 36
HDAC3 = 445

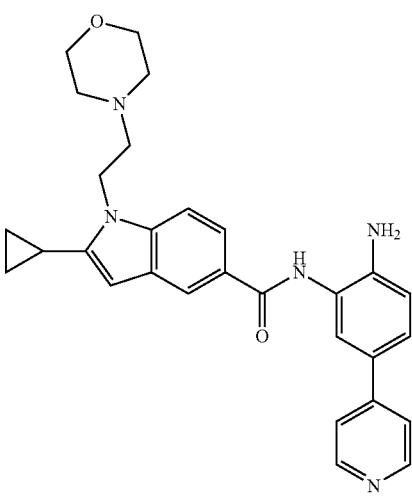 [SMILES: Nc1ccc(-c2ccncc2)cc1NC(=O)c1ccc2c(c1)cc(C1CC1)n2CCN1CCOCC1]

N-(2-amino-5-(pyridin-4-yl)phenyl)-2-cyclopropyl-1-(2-morpholinoethyl)-1H-indole-5-carboxamide, Compound 004
IC$_{50}$(nM)
HDAC1 = 27
HDAC2 = 24
HDAC3 = 247

TABLE 1-continued

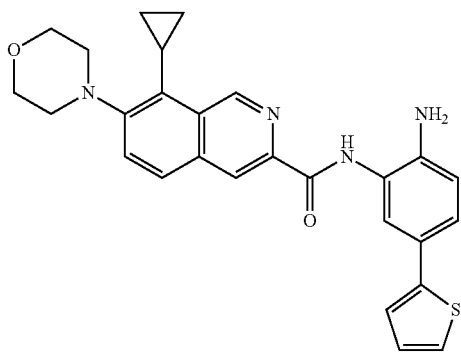 [SMILES: Nc1ccc(-c2cccs2)cc1NC(=O)c1cc2ccc(N3CCOCC3)c(C3CC3)c2cn1]

N-(2-amino-5-(thiophen-2-yl)phenyl)-8-cyclopropyl-7-morpholinoisoquinoline-3-carboxamide

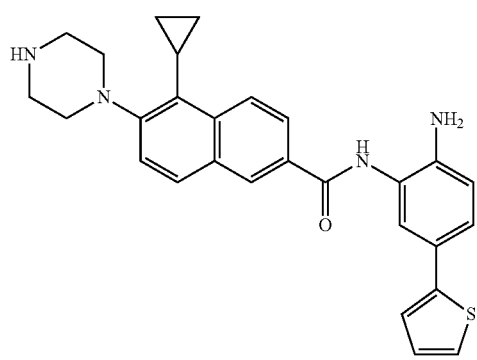

N-(2-amino-5-(thiophen-2-yl)phenyl)-5-cyclopropyl-6-(piperazin-1-yl)-2-naphthamide

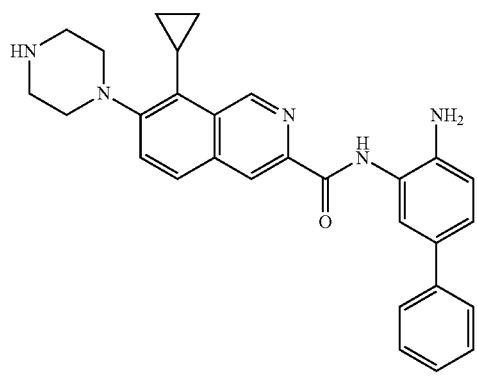 [SMILES: Nc1ccc(-c2ccccc2)cc1NC(=O)c1cc2ccc(N3CCNCC3)c(C3CC3)c2cn1]

N-(4-amino-[1,1'-biphenyl]-3-yl)-8-cyclopropyl-7-(piperazin-1-yl)isoquinoline-3-carboxamide TABLE 1-continued

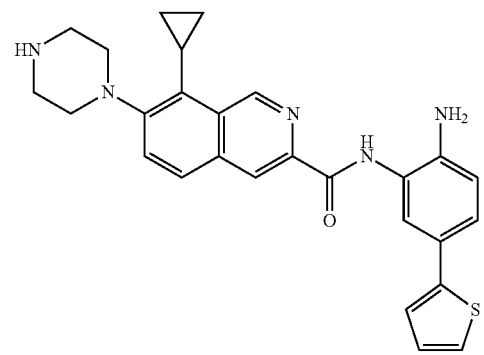 [SMILES: Nc1ccc(-c2cccs2)cc1NC(=O)c1cc2ccc(N3CCNCC3)c(C3CC3)c2cn1]

N-(2-amino-5-(thiophen-2-yl)phenyl)-8-cyclopropyl-7-(piperazin-1-yl)isoquinoline-3-carboxamide

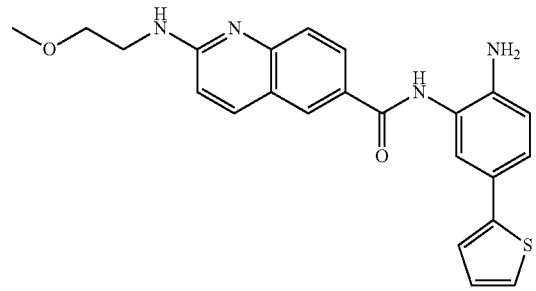 [SMILES: COCCNc1ccc2cc(C(=O)Nc3cc(-c4cccs4)ccc3N)ccc2n1]

N-(2-amino-5-(thiophen-2-yl)phenyl)-2-((2-methoxyethyl)amino)quinoline-6-carboxamide

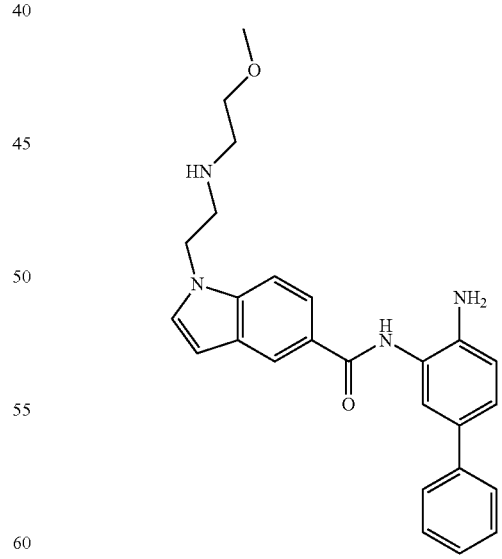

N-(4-amino-[1,1'-biphenyl]-3-yl)-1-(2-((2-methoxyethyl)amino)ethyl)-1H-indole-5-carboxamide

TABLE 1-continued

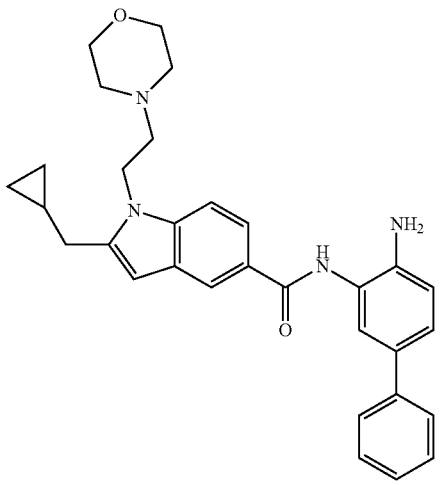 [SMILES: Nc1ccc(-c2ccccc2)cc1NC(=O)c1ccc2c(c1)cc(CC1CC1)n2CCN1CCOCC1]

N-(4-amino-[1,1'-biphenyl]-3-yl)-2-
(cyclopropylmethyl)-1-(2-morpholinoethyl)-
1H-indole-5-carboxamide

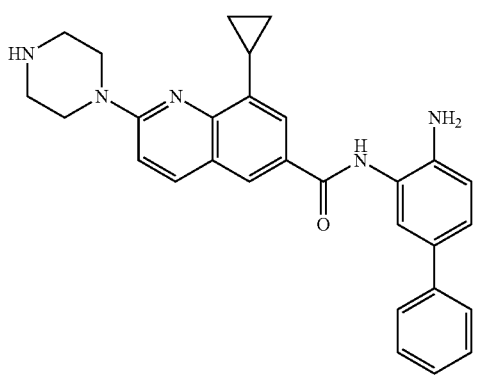 [SMILES: Nc1ccc(-c2ccccc2)cc1NC(=O)c1cc(C2CC2)c2nc(N3CCNCC3)ccc2c1]

N-(4-amino-[1,1'-biphenyl]-3-yl)-8-
cyclopropyl-2-(piperazin-1-yl)quinoline-6-
carboxamide

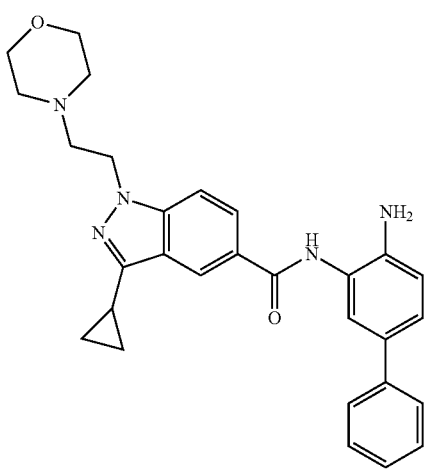 [SMILES: Nc1ccc(-c2ccccc2)cc1NC(=O)c1ccc2c(c1)c(C1CC1)nn2CCN1CCOCC1]

N-(4-amino-[1,1'-biphenyl]-3-yl)-3-
cyclopropyl-1-(2-morpholinoethyl)-1H-
indazole-5-carboxamide or pharmaceutically acceptable salts thereof.

In preferred embodiments, the compounds of the instant invention have one or more of the following properties: the compound is capable of inhibiting at least one histone deacetylase; the compound is capable of inhibiting HDAC1 and/or HDAC2; the compound is a selective HDAC1 and/or HDAC2 inhibitor.

The invention also provides for a pharmaceutical composition comprising a compound of instant invention, or a pharmaceutically acceptable salt thereof, together with a pharmaceutically acceptable carrier.

Another object of the present invention is the use of a compound as described herein (e.g., of any formulae herein) in the manufacture of a medicament for use in the treatment of a disorder or disease herein. Another object of the present invention is the use of a compound as described herein (e.g., of any formulae herein) for use in the treatment of a disorder or disease herein.

In another aspect, the invention provides a method of synthesizing a compound of Formula I, II, III, or any of the compounds presented in Table 1. The synthesis of the compounds of the invention can be found in the Examples below.

Another embodiment is a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3$H, $^2$H, $^{14}$C, $^{13}$C, $^{35}$S, $^{32}$P, $^{125}$I, and $^{131}$I) introduced into the compound. Such compounds are useful for drug metabolism studies and diagnostics, as well as therapeutic applications.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999, and subsequent editions thereof.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxan, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). The compounds of this invention may also be represented in multiple tautomeric forms, in such instances, the invention expressly includes all tautomeric forms of the compounds described herein. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present invention. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods of the Invention

In one aspect, the invention provides a method of selectively inhibiting HDAC1 or HDAC2 over other HDACs in a subject, comprising administering a compound of Formula I, II or any of the compounds presented in Table 1 and pharmaceutically acceptable salts thereof.

In one embodiment, the compound has a selectivity for HDAC1 or HDAC2 of 5 to 1000 fold greater than for other HDACs. In another embodiment, the compound has a selectivity for HDAC1 or HDAC2 when tested in a HDAC enzyme assay of about 5 to 1000 fold greater than for other HDACs. In some embodiments, the compound has a selectivity for HDAC1 over HDAC2. In other embodiments, the compound has a selectivity for HDAC2 over HDAC1. In some embodiments, the compound has a balanced HDAC1 and HDAC2 selectivity. The term "balanced" means that the selectivity for HDAC1 and HDAC2 is approximately equal, i.e., that the selectivities for HDAC1 and HDAC2 are within about ±10% of each other.

In another aspect, the invention provides a method of treating a disease mediated by HDAC1 or HDAC2 in a subject comprising administering to the subject a Formula I, II or any of the compounds presented in Table 1 and pharmaceutically acceptable salts thereof.

In another aspect, the invention provides a method of activating latent HIV in a subject comprising administering to the subject a Formula I, II or any of the compounds presented in Table 1. The same compounds can be used treat HIV infections. In another embodiment, the compounds can be used in combination with one or more anti-retroviral agents for the treatment of HIV infections. In an embodiment, the HIV infection is HIV-1.

Anti-retroviral agents that can be used in combination with the HDAC inhibitors of the instant invention include nucleoside reverse transcriptase inhibitors, non-nucleoside reverse transcriptase inhibitors, protease inhibitors, virus uptake/adsorption inhibitors, virus receptor antagonists, viral fusion inhibitors, viral integrase inhibitors, entry inhibitor, co-receptor antagonist, cyclin dependent kinase inhibitor, and transcription inhibitors or other anti-retroviral agents used in treatment of HIV infection. Preferred antiretroviral agents include efavirenz, indinavir sulfate, and raltegravir potassium.

Inhibition of HDAC1 and 2 is sufficient to derepress fetal globin. In cultured human CD34+ bone marrow cells undergoing erythroid differentiation, these compounds induced a dose dependent increase in fetal hemoglobin expression, with a 2-3-fold induction observed at 1 µM. Cytotoxicity of these compounds was minimal, showing $IC_{50}$ values ranging from 1 to 2 µM. The selective HDAC1 and HDAC2 inhibitors of the present invention have favorable pharmacokinetic profiles. Thus, the compounds are capable of derepressing fetal globin through HDAC inhibition. In a preferred embodiment, the compounds are able to treat sickle-cell disease or beta-thalessemia. Further, the compounds are able to treat a subject suffering from or susceptible to a hemoglobinopathy. Additionally, compounds with a pharmacological profile of increased selectivity towards HDAC2 inhibition versus HDAC1 may be less cytotoxic and minimize effects on differentiation, while still inducing HbG in human CD34+ bone marrow cells.

As discussed above, the present invention provides compounds useful for the treatment of various diseases. In certain embodiments, the compounds of the present invention are useful as inhibitors of histone deacetylases (HDACs) and thus are useful as anti-cancer agents, and thus may be useful in the treatment of cancer, by effecting tumor cell death or inhibiting the growth of tumor cells. The compounds of the invention are capable of inducing apoptosis in cancer cells thereby able to treat a disease such as a cancer or proliferation disease.

In certain embodiments, the cancer is lung cancer, colon and rectal cancer, breast cancer, prostate cancer, liver cancer, pancreatic cancer, brain cancer, kidney cancer, ovarian cancer, stomach cancer, skin cancer, bone cancer, gastric cancer, breast cancer, glioma, gliobastoma, hepatocellular carcinoma, papillary renal carcinoma, head and neck squamous cell carcinoma, leukemia, lymphomas, myelomas, retinoblastoma, cervical cancer, melanoma and/or skin cancer, bladder cancer, uterine cancer, testicular cancer, esophageal cancer, and solid tumors. In some embodiments, the cancer is lung cancer, colon cancer, breast cancer, leukemia, or lymphomas. In a further embodiment, the cancer is non-small cell lung cancer (NSCLC).

In further embodiments, the cancer is a hematologic cancer such as a leukemia or a lymphoma. In a certain embodiment, the lymphoma is Hodgkins lymphoma. In certain embodiments, the inventive compounds are effective anticancer agents, which are active against leukemia cells and thus are useful for the treatment of leukemias, e.g., myeloid, lymphocytic, myelocytic and lymphoblastic leukemias.

In another aspect, the present invention provides for a method of treating a subject suffering from or susceptible to Hodgkins lymphoma comprising administering to a subject in need thereof a therapeutically effective amount of a compound of the instant invention to thereby treat the subject suffering from or susceptible to Hodgkins lymphoma.

In various embodiments, the invention provides a method of treating cancer in a subject further comprising co-administering one or more of a chemotherapeutic agent, radiation agent, hormonal agent, biological agent or an anti-inflammatory agent to the subject. In some embodiments the chemotherapeutic agent is azacitidine, clofarabine, erlotinib, bortezomib, tamoxifen, trastuzumab, raloxifene, doxorubicin, fluorouracil/5-fu, pamidronate disodium, anastrozole, exemestane, cyclophosphamide, epirubicin, letrozole, toremifene, fulvestrant, fluoxymesterone, methotrexate, megastrol acetate, docetaxel, paclitaxel, testolactone, aziridine, vinblastine, capecitabine, goselerin acetate, zoledronic acid, taxol, vinblastine, or vincristine.

In another embodiment, the chemotherapeutic agent is an aromatase inhibitor.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

Also, as discussed above, the compounds of the invention are selective inhibitors of HDAC1 and/or HDAC2 and, as such, are useful in the treatment of disorders modulated by these histone deacetylases (HDACs). For example, compounds of the invention may be useful in the treatment of cancer (e.g., lung cancer, colon cancer, breast cancer, leukemia, or lymphomas, etc.). Accordingly, in yet another aspect, according to the methods of treatment of the present invention, tumor cells are killed, or their growth is inhibited by contacting said tumor cells with an inventive compound or composition, as described herein.

Thus, in another aspect of the invention, methods for the treatment of cancer are provided comprising administering a therapeutically effective amount of an inventive compound (i.e., of any of the formulae herein), as described herein, to a subject in need thereof. In certain embodiments, the subject is identified as in need of such treatment. In certain embodiments, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention a "therapeutically effective amount" of the inventive compound or pharmaceutical composition is that amount effective for killing or inhibiting the growth of tumor cells. The compounds and compositions, according to the method of the present invention, may be administered using any amount and any route of administration effective for killing or inhibiting the growth of tumor cells. Thus, the expression "amount effective to kill or inhibit the growth of tumor cells," as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like.

In certain embodiments, the method involves the administration of a therapeutically effective amount of the compound or a pharmaceutically acceptable derivative thereof to a subject (including, but not limited to a human or animal) in need of it. In certain embodiments, the inventive compounds as useful for the treatment of cancer and other proliferative disorders including, but not limited to lung cancer (e.g. non-small cell lung cancer), colon and rectal cancer, breast cancer, prostate cancer, liver cancer, pancreatic cancer, brain cancer, kidney cancer, ovarian cancer, stomach cancer, skin cancer, bone cancer, gastric cancer, breast cancer, glioma, gliobastoma, hepatocellular carcinoma, papillary renal carcinoma, head and neck squamous cell carcinoma, leukemia (e.g., CML, AML, CLL, ALL), lymphomas (non-Hodgkin's and Hodgkin's), myelomas, retinoblastoma, cervical cancer, melanoma and/or skin cancer, bladder cancer, uterine cancer, testicular cancer, esophageal cancer, and solid tumors.

In certain embodiments, the invention provides a method of treatment of any of the disorders described herein, wherein the subject is a human.

In accordance with the foregoing, the present invention further provides a method for preventing or treating any of the diseases or disorders described above in a subject in need of such treatment, which method comprises administering to said subject a therapeutically effective amount of a compound of the invention or a pharmaceutically acceptable salt thereof. For any of the above uses, the required dosage will vary depending on the mode of administration, the particular condition to be treated and the effect desired.

Pharmaceutical Compositions

In another aspect, the invention provides a pharmaceutical composition comprising any of the compounds of the instant invention (Formula I, II, III or any of the compounds presented in Table 1) or a pharmaceutically acceptable salt, thereof, together with a pharmaceutically acceptable carrier.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

According to the methods of treatment of the present invention, disorders are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention, as used herein, means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight (0.05 to 4.5 mg/m$^2$). An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds of the present invention may range from about 0.1 mg/kg to about 500 mg/kg (about 0.18 mg/m$^2$ to about 900 mg/m$^2$), alternatively from about 1 to about 50 mg/kg (about 1.8 to about 90 mg/m$^2$). In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims. Definitions of variables in the structures in schemes herein are commensurate with those of corresponding positions in the formulae delineated herein.

Example 1: Synthesis of N-(2-aminophenyl)-2-(piperazin-1-yl)quinoline-6-carboxamide

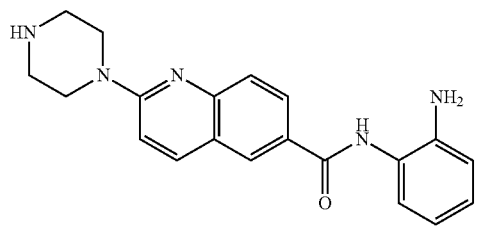 [SMILES: Nc1ccccc1NC(=O)c1ccc2nc(N3CCNCC3)ccc2c1]

Reaction Scheme

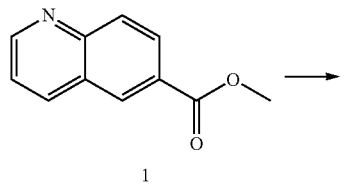

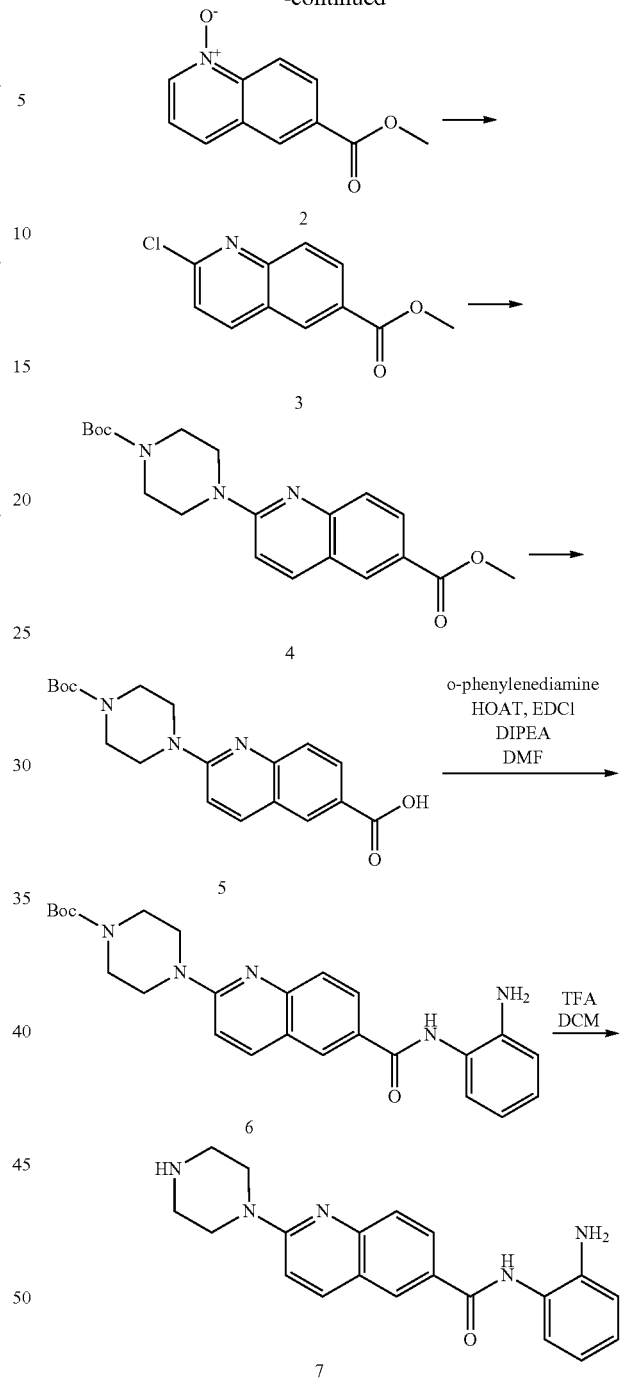

Experimental Procedure

Step 1: A mixture of compound 1 (10 g, 0.53 mol) and m-CPBA (18.4 g, 0.106 mol) in DCM (50 ml) was stirred at r.t. overnight. Aq. NaHCO$_3$ (40 ml, saturated) was added to the reaction mixture and stirred for 30 min. The organic layer was separated, dried, filtered and concentrated to obtain a residue, which was re-crystallized by EA (5 ml) to afford compound 2 (8.7 g, 80%) as a light yellow solid.

Step 2: To a solution of compound 2 (4.0 g, 0.020) and DMF (8 ml) in DCM was added SOCl$_2$ (8 ml) slowly at 0° C. and stirred at r.t. for 5 h. The resulting mixture was concentrated to obtain a residue, and DCM (50 ml) with Aq.

NaHCO₃ (saturated, 20 ml) was added and stirred for 30 min. The organic layer was separated and concentrated to obtain a residue, which was purified by silica gel chromatography to afford compound 3 (1.3 g, 30%) as a white solid.

Step 3: A mixture of compound 3 (10 g, 0.045 mol), CuI (10 g, 0.53 mol), N-boc-piperazine (25 g, 0.135 mol) and K₂CO₃ (18.6 g, 0.135 mol) in DMSO (120 ml) was stirred at 100° C. for overnight. Upon completion as monitored by TLC (thin-layer chromatography), 300 ml of EA (ethyl acetate) was added, followed by filtration (underlay 15 cm diatomite). Concentration of the mixture yielded a residue, to which water (300 ml) and Aq. Citric acid (saturated, 30 ml) were added. Stirring at r.t. for 30 min., followed by filtration yielded compound 4 (18 g, ~100%) as a yellow solid to be used in the next step without purification.

Step 4: A mixture of compound 4 (18 g, crude) and 2M NaOH (50 ml) in EtOH (100 ml) and THF (100 ml) was stirred at 70° C. for 4 h. TLC was used to monitor the reaction to completion. The reaction mixture was concentrated to a residue, to which water (300 ml) and aq. sat. citric acid (40 ml) were added. Subsequent filtration yielded compound 5 (14.5 g, 91% over two step) as a yellow solid.

Step 5: A mixture of compound 5 (100 mg, 0.3 mmol), benzene-1,2-diamine (130 mg, 1.2 mmol), HOAT (150 mg, 1.1 mmol), EDCI (200 mg, 1.1 mmol), DIPEA (300 mg, 2.3 mmol) and 4 A (20 g) in DMF (40 ml) was stirred at 55° C. for overnight. Put into some H₂O and extracted with EA (20 ml×3), separated, dried and concentrated to get a crude product Purified by Prep-TLC, get the desired product 6 (115 mg, 80%).

Step 6: A mixture of compound 6 (110 mg 0.25 mmol) and TFA (5 ml) in 10 ml DCM was stirred at r.t. for 2 h. Evaporation of the solvent yielded crude product which was purified by HPLC to afford the white product, compound 7 (11 mg, 13%). ¹H NMR (500 MHz, DMSO) δ 9.69 (s, 1H), 8.38 (s, 1H), 8.29 (s, 1H), 8.11 (dd, J=21.5, 8.9 Hz, 2H), 7.59 (d, J=H), 7.29 (d, J=9.2 Hz, 1H), 7.20 (d, J=7.5 Hz, 1H), 6.97 (t, J=7.6 Hz, 1H), 6.79 (d, J=7.6 Hz, 1H 8.8 Hz, 1), 6.61 (t, J=7.4 Hz, 1H), 4.91 (s, 2H), 3.72 (s, 4H), 2.87 (s, 4H). LCMS: m/z=348 (M+H)⁺

Example 2: Synthesis of N-(5-amino-2-phenylpyridin-4-yl)-7-(piperazin-1-yl)quinoline-3-carboxamide

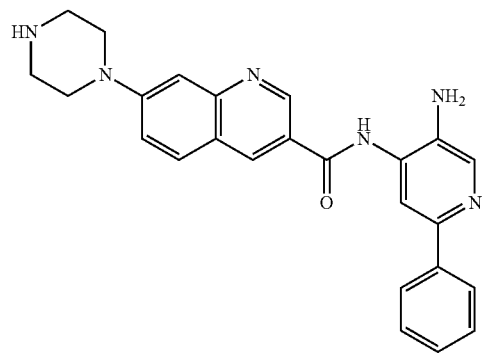 [SMILES: Nc1cnc(-c2ccccc2)cc1NC(=O)c1cnc2cc(N3CCNCC3)ccc2c1]

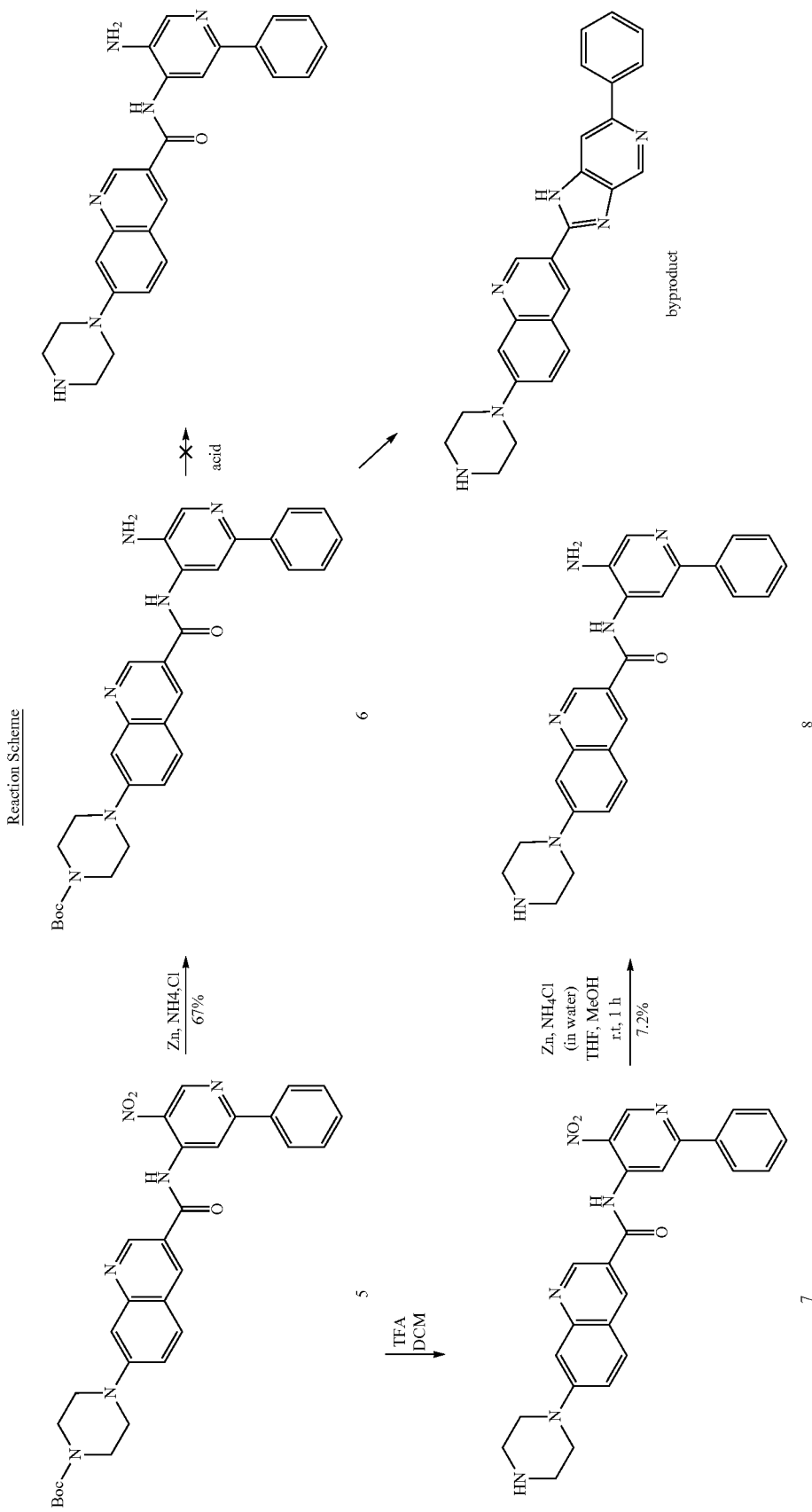

Experimental Procedure

Step 1: Compound 7 was prepared according to the procedure as described in Example 1, compound 7.

Step 2: To a mixture of compound 7 (100 mg, 0.22 mmol) in THF (2 ml) and MeOH (2 ml), was added Zn (114 mg, 1.76 mmol) followed by aqueous NH$_4$Cl (93 mg, 1.76 mmol). The reaction mixture was stirred at room temperature for 20 min., and extracted with EA (2×15 nil). The combined organic layers were purified by Prep-HPLC to afford the desired product, compound 8 (7 mg, 7.2%). $^1$H NMR (500 MHz, DMSO) δ 10.10-9.88 (m, 1H), 9.23 (d, J=2.2 Hz, 1H), 8.78 (d, J=2.1 Hz, 1H), 8.21 (s, 1H), 8.03 (s, 1H), 7.93 (dd, J=5.3, 4.0 Hz, 3H), 7.60-7.52 (m, 1H), 7.43 (t, J=7.7 Hz, 2H), 7.36-7.23 (m, 2H), 5.42 (s, 2H), 3.34 (s, 4H), 2.89 (d, J=4.6 Hz, 4H). LCMS: m/z=425 (M+H)$^+$ Example 3: Synthesis of N-(2-amino-5-(thiophen-2-yl)phenyl)-8-cyclopropyl-7-(piperazin-1-yl)quinoline-3-carboxamide, Compound 002

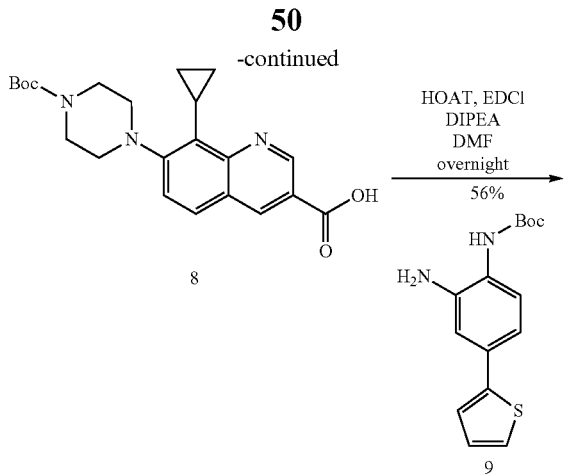

Reaction Scheme

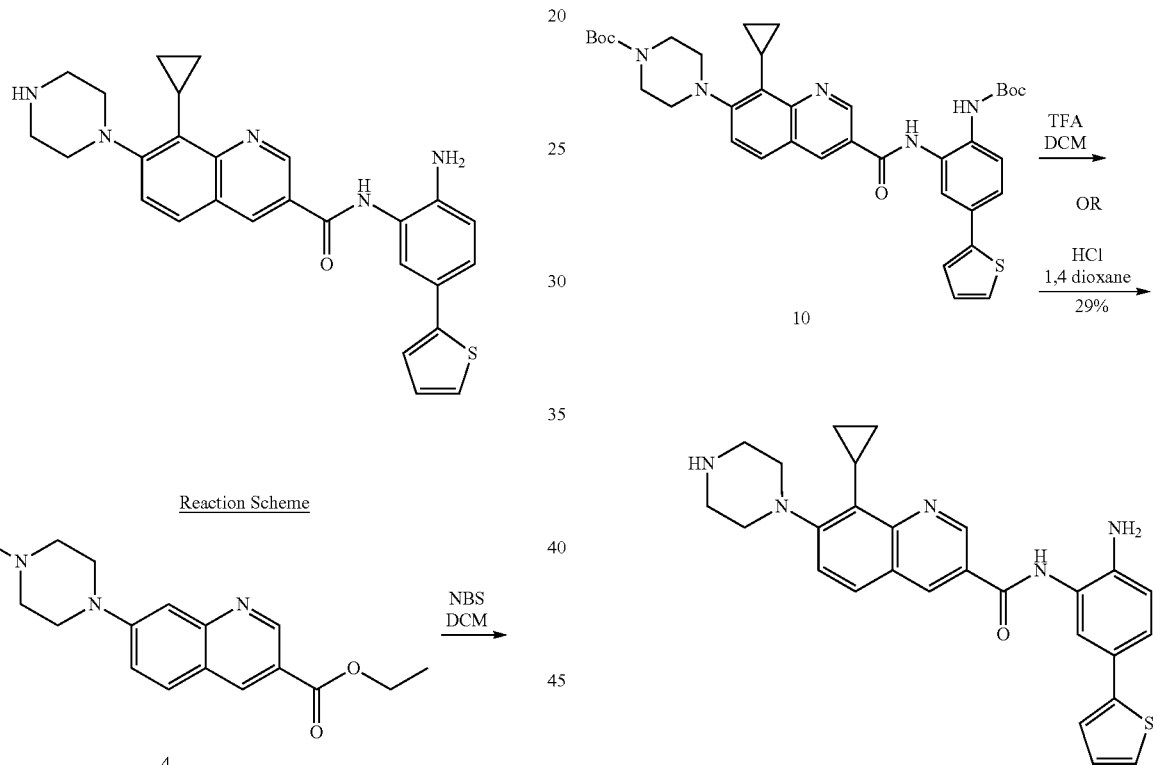

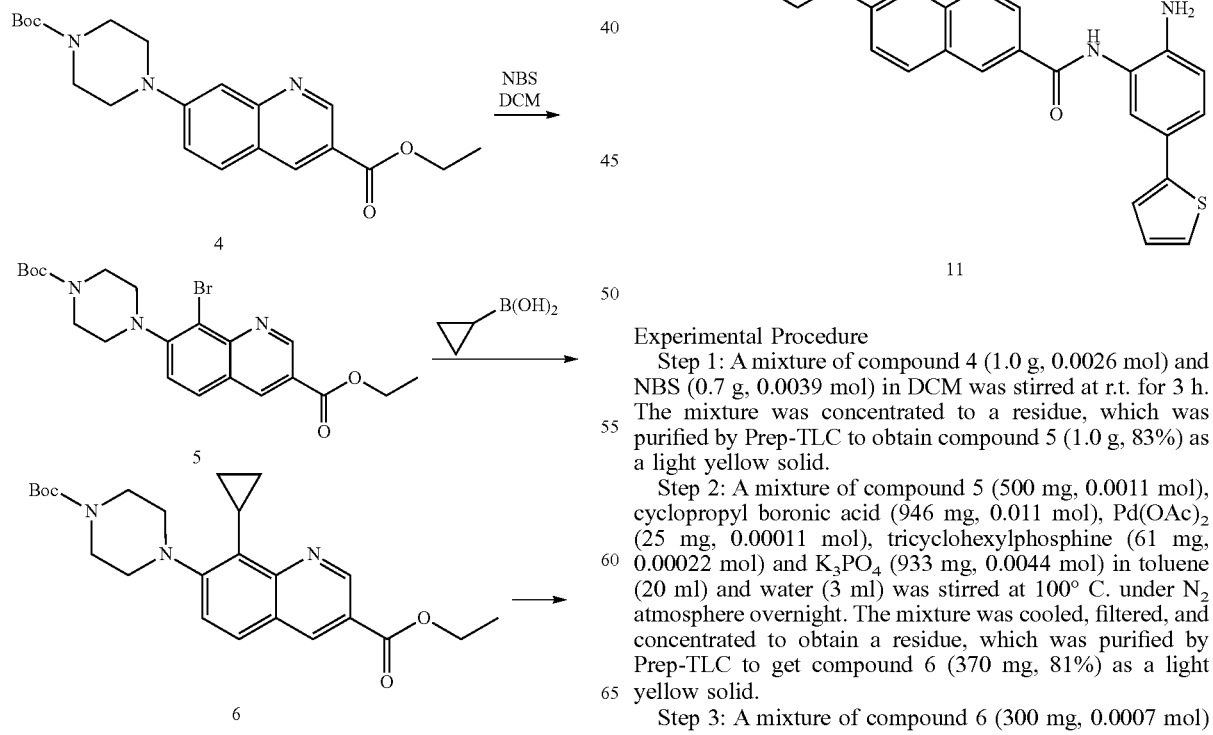

Experimental Procedure

Step 1: A mixture of compound 4 (1.0 g, 0.0026 mol) and NBS (0.7 g, 0.0039 mol) in DCM was stirred at r.t. for 3 h. The mixture was concentrated to a residue, which was purified by Prep-TLC to obtain compound 5 (1.0 g, 83%) as a light yellow solid.

Step 2: A mixture of compound 5 (500 mg, 0.0011 mol), cyclopropyl boronic acid (946 mg, 0.011 mol), Pd(OAc)$_2$ (25 mg, 0.00011 mol), tricyclohexylphosphine (61 mg, 0.00022 mol) and K$_3$PO$_4$ (933 mg, 0.0044 mol) in toluene (20 ml) and water (3 ml) was stirred at 100° C. under N$_2$ atmosphere overnight. The mixture was cooled, filtered, and concentrated to obtain a residue, which was purified by Prep-TLC to get compound 6 (370 mg, 81%) as a light yellow solid.

Step 3: A mixture of compound 6 (300 mg, 0.0007 mol) and NaOH (2M, 5 mL) in EtOH (15 ml) and THF (15 ml)

was stirred at 60° C. for 5 h. The mixture was concentrated to obtain a residue, to which was added aq. sat. citric acid (10 mL) and extracted with EA (25 ml×2). The organic layers were separated, dried, filtered and concentrated to obtain compound 8 (195 mg, 70%) as a light yellow solid.

Step 4: A mixture of compound 8 (120 mg, 0.0003 mol), tert-butyl 2-amino-4-(thiophen-2-yl)phenylcarbamate (88 mg, 0.0003 mol), HOAT (61 mg, 0.00045 mol), EDCI (115 mg, 0.0006 mol), and DIPEA (155 mg, 0.0012 mol) in DMF (5 ml) was stirred at 55° C. for overnight. Water (20 ml) was added to the mixture, and extracted with EA (25 ml×2). The organic layers were separated, dried, filtered, and concentrated to get a residue, which was purified by Prep-TLC to afford compound 10 (170 mg, 84%) as a yellow solid.

Step 5: To a solution of compound 10 (100 mg, 0.00015 mol) in DCM (3 ml) was added TFA (1.5 ml) and stirred at r.t. for 1 h. The mixture was concentrated to obtain a residue, which was purified by Prep-HPLC to afford compound 11 (40 mg, 57%) as a light yellow solid. $^1$H NMR (500 MHz, DMSO) δ 9.94 (s, 1H), 9.32 (s, 1H), 8.86-8.75 (m, 1H), 8.33-8.25 (m, 1H), 7.94-7.84 (m, 1H), 7.53 (s, 1H), 7.50-7.44 (m, 1H), 7.36 (d, J=4.4 Hz, 1H), 7.34-7.30 (m, 1H), 7.26 (d, J=3.0 Hz, 1H), 7.06 (d, J=1.3 Hz, 1H), 6.83 (d, J=8.3 Hz, 1H), 5.25 (s, 2H), 3.20 (s, 4H), 3.04 (s, 4H), 2.39-2.34 (m, 1H), 1.19 (d, J=3.7 Hz, 2H), 1.10 (d, J=7.0 Hz, 2H). LCMS: m/z=470 (M+H)$^+$ Example 4: Synthesis of N-(3-amino-6-phenylpyridin-2-yl)-7-(piperazin-1-yl)quinoline-3-carboxamide

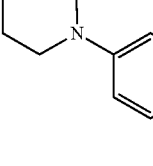

Reaction Scheme

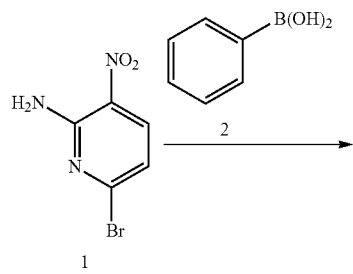

Experimental Procedure

Step 1: To a solution of compound 1 (2.5 g, 14.5 mmol) in DME (8 ml), EtOH (4 ml), and H$_2$O (4 ml) was added compound 2 (3.54 g, 29 mmol), Pd(PPh$_3$)$_4$ (335 mg, 0.29 mmol), and Na$_2$CO$_3$ (2.3 g, 21.7 mmol) under a nitrogen atmosphere. The reaction mixture was microwaved at 100° C. for 0.5 h, and extracted with EA (2×30 ml). The organic layers were combined and purified by gel chromatography (PE:EA=4:1) to afford the desired product of compound 3 (1.74 g, 56%).

Step 2: To compound 3 (132 mg, 0.62 mmol) in Py (4 ml) was added compound 4 (220 mg, 0.62 mmol), at 0° C. POCl$_3$ (1 ml) was added dropwise, and the reaction mixture was stirred at r.t. overnight. Upon completion, the reaction was quenched with ice-water, and extracted with EA (2×10 ml). The organic layers were combined and purified by gel chromatography (PE:EA=1:1) to afford the desired product of compound 5 (140 mg, 41%).

Step 3: Compound 6 was prepared according to the procedure as described in Example 1, compound 7.

Step 4: Compound 7 was prepared according to the procedure as described in Example 2, compound 8. $^1$H NMR (500 MHz, DMSO) δ 10.57 (s, 1H), 9.27 (s, 1H), 8.82 (s, 1H), 7.96 (d, J=7.7 Hz, 2H), 7.90 (d, J=9.0 Hz, 1H), 7.71 (s, 1H), 7.54 (d, J=9.0 Hz, 1H), 7.41 (s, 2H), 7.29 (s, 3H), 5.26 (s, 2H), 3.34 (s, 3H), 2.91 (s, 3H). LCMS: m/z=425 (M+H)$^+$ Example 5: Synthesis of N-(2-amino-5-phenylpyridin-3-yl)-7-(piperazin-1-yl)quinoline-3-carboxamide

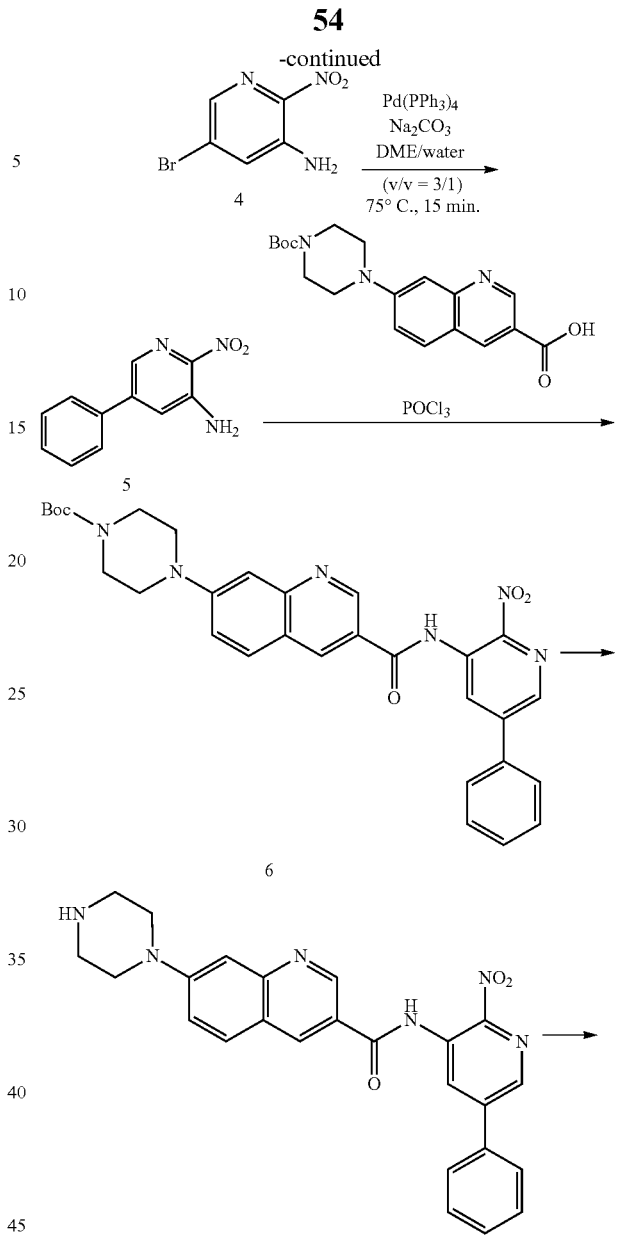

Reaction Scheme

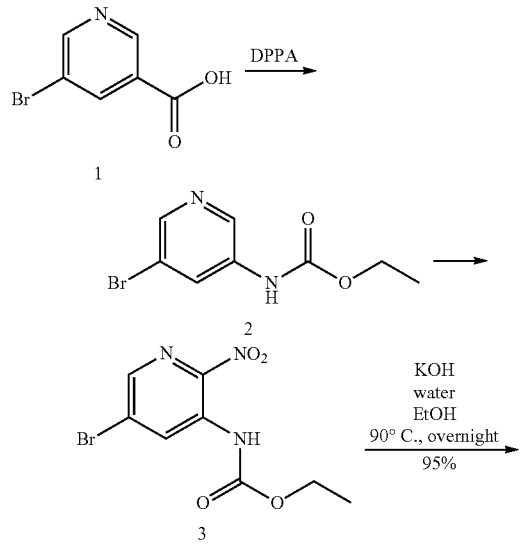

Experimental Procedure

Step 1: To a solution of compound 1 (15.0 g, 74.0 mmol) in ethanol (200 ml) was added DPPA (16.0 ml, 74.0 mmol) followed by triethylamine (10.9 ml, 77.0 mmol). The reaction mixture was then refluxed overnight. After cooling, a half amount of solvent was removed by evaporation. The remaining ethanol solution was extracted with EA. The organic layer was washed with NaHCO₃ (aq.) and brine, dried over Na₂SO₄, and concentrated. The residue was purified by silica gel chromatography to give compound 2 (3.0 g, 17%) as a white solid.

Step 2: To a mixture of concentrated H₂SO₄ (2.0 ml) and HNO₃ (0.5 nil), compound 2 (2.0 g, 8.2 mmol) was added portion-wise at 0° C. After stirring at 0° C. for 5 min., the mixture was stirred at r.t. overnight. The mixture was poured into ice-water then basified with aqueous NH₄OH. The mixture was extracted with ethyl acetate. The organic layer was washed with aqueous NH₄OH and brine, dried over Na₂SO₄, and concentrated. The residue was purified by silica gel chromatography to give compound 3 (1.5 g, 64%) as a white solid.

Step 3: To a solution of compound 3 (1.5 g, 5.2 mmol) in THF (10 ml) was added KOH (582 mg, 10.4 mmol) in water (5.0 ml) and stirred at 90° C. overnight. Water was added to the mixture resulting in a precipitate that was collected by filtration, washed with water, and then dried under reduced pressure to give compound 4 (1.1 g, 95%)

Step 4: Compound 5 (600 mg, 70%) as a brown solid, was obtained through Suzuki cross-coupling reactions of compound 4 (860 mg, 4.0 mmol) and phenylboronic acid in the presence of Pd(PPh3)4 and Na₂CO₃.

Step 5: Compound 6 (600 mg, 70%) as a brown solid, was obtained through condensation of compound 5 with 7-(4-(tert-butoxycarbonyl)piperazin-1-yl)quinoline-3-carboxylic acid (273 mg, 1.3 mmol) in the presence of POCl₃.

Step 6: Compound 7 (36 mg, 28%) as a yellow solid, was obtained through Boc deprotection of compound 6 (160 mg, 0.33 mmol) with TFA in DCM.

Step 7: Compound 8 (13 mg, 28%) as a yellow solid, was obtained through reduction of 7 (36 mg, 0.06 mmol) with Zn/NH₄Cl. ¹H NMR (500 MHz, DMSO) δ 9.88 (s, 1H), 9.24 (d, J=2.2 Hz, 1H), 8.78 (d, J=1.9 Hz, 1H), 8.24 (d, J=2.3 Hz, 1H), 7.93 (dd, J=17.5, 5.7 Hz, 2H), 7.61 (d, J=7.3 Hz, 2H), 7.57-7.50 (m, 1H), 7.43 (t, J=7.8 Hz, 2H), 7.28 (d, J=21.2 Hz, 2H), 6.09 (s, 2H), 3.33 (s, 4H), 2.96-2.78 (m, 4H). LCMS: m/z=425 (M+H)⁺

Example 6: Synthesis of N-(2-amino-5-phenylthiophen-3-yl)-7-(piperazin-1-yl)quinoline-3-carboxamide Reaction Scheme

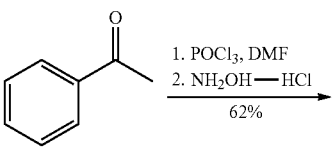

1

Ref: *JMC*, 2006, 6425-6428

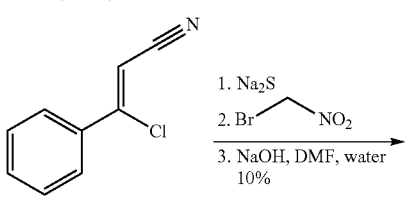

2

Ref. *Tetrahedron*, 2008, 3232-3235

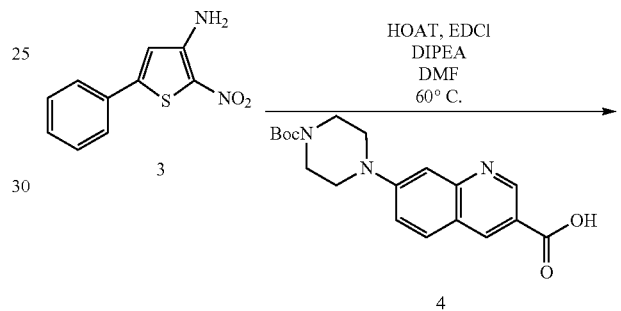

3

4

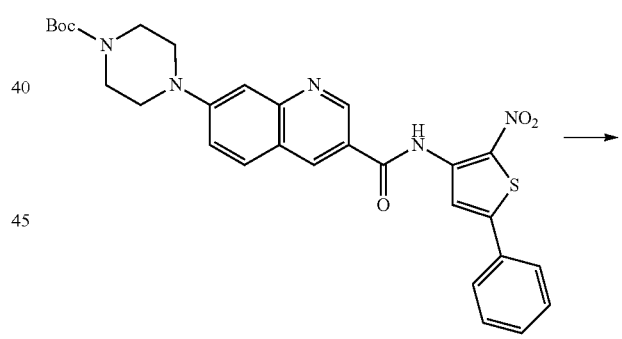

5

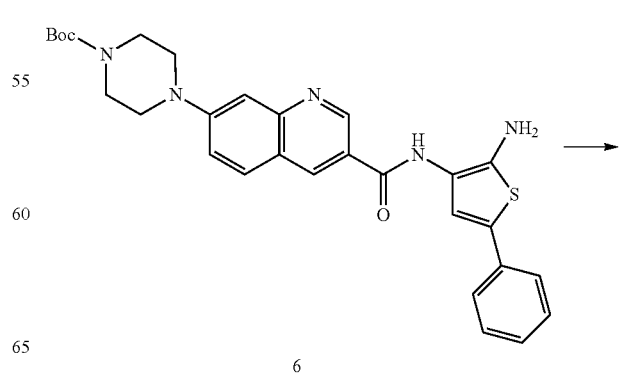

6

-continued

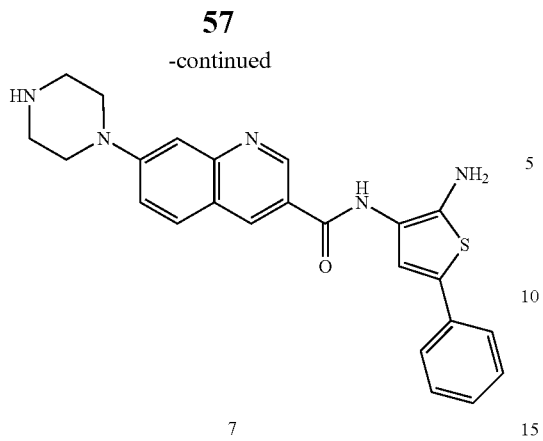

7

Experimental Procedure

Step 1: To DMF (13 ml) cooled with ice, was added POCl₃ (1.56 ml, 16.66 mmol) drop-wise over 15 mm. Then, compound 1 (1.0 g, 8.3 mmol) was added drop-wise while maintaining a temperature between 45-55° C. The reaction mixture was then stirred at r.t. for 30 min. after which 0.5 ml of NH₂OH—HCl (2.3 g, 33.32 mmol) in dry DMF (10 ml) was added. The reaction mixture was then stirred at 70-80° C. for 5 mm, followed by addition of the remaining NH₂OH—HCl in DMF. At this point the temperature was allowed to rise to r.t., and the reaction mixture was stirred overnight. The reaction was quenched through dilution with ice-water and extracted with DCM (2×30 ml). The combined organic layers were purified by gel chromatography (PE: EA=50:1) to afford the desired product of compound 2 (788 mg, 62%).

Step 2: To a solution of Na₂S.9H₂O (5.95 g, 24.8 mmol) in H₂O (2 ml) was added DMF (10 ml) at 55° C. and the resulting solution was stirred for 30 min. before drop-wise addition of compound 2 (3.68 g, 22.6 mmol) in DMF (5 ml). The reaction continued to stir for 90 min. at which point BrCH₂NO₂ (3.14 g, 22.6 mmol) in DMF (5 ml) was added at r.t. The reaction was then stirred at 55° C. for 90 mM. NaOH (904 mg, 5N) was added and the reaction was stirred for an additional hour. The reaction mixture was then extracted with EA (2×30 ml). The organic layers were combined and subsequent crystallization from EA yielded the desired product of compound 3 (546 mg, 10%).

Step 3: Compound 5 was prepared according to the procedure, as described in Example 3, compound 10.

Step 4: Compound 6 was prepared according to the procedure, as described in Example 2, compound 8.

Step 5: Compound 7 was prepared according to the procedure, as described in Example 1, compound 7. ¹H NMR (500 MHz, DMSO) δ 9.94 (s, 1H), 9.22 (d, J=2.1 Hz, 1H), 8.72 (d, J=1.9 Hz, 1H), 7.89 (s, 1H), 7.58-7.50 (m, 1H), 7.43 (d, J=7.4 Hz, 2H), 7.33 (t, J=7.8 Hz, 2H), 7.26 (d, J=13.7 Hz, 2H), 7.15 (s, 1H), 5.59 (s, 2H), 3.32 (s, 4H), 2.99-2.76 (m, 4H). LCMS: m/z=430 (M+H)⁺

Example 7: Synthesis of N-(2-amino-5-(thiophen-2-yl)phenyl)-6-cyclopropyl-7-((2-methoxyethyl)(methyl)amino)quinoline-3-carboxamide (11) and N-(4-amino-[1,1'-biphenyl]-3-yl)-6-cyclopropyl-7-((2-methoxyethyl)(methyl)amino)quinoline-3-carboxamide (12)

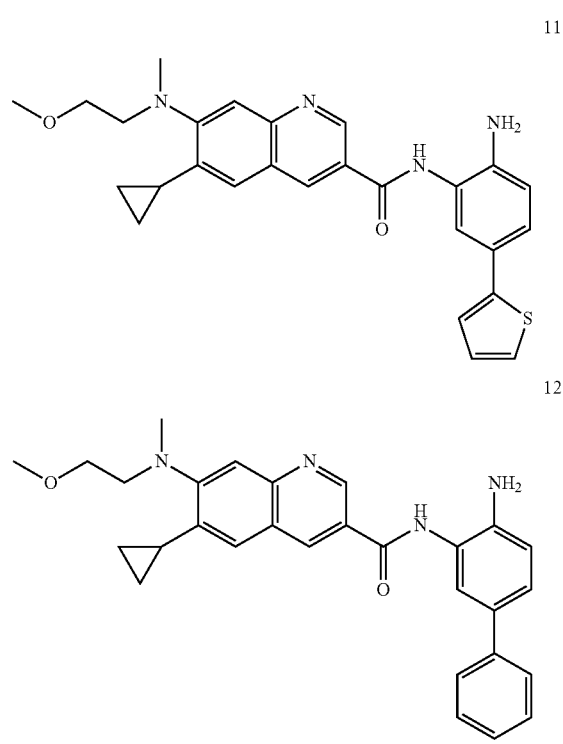

Reaction Scheme

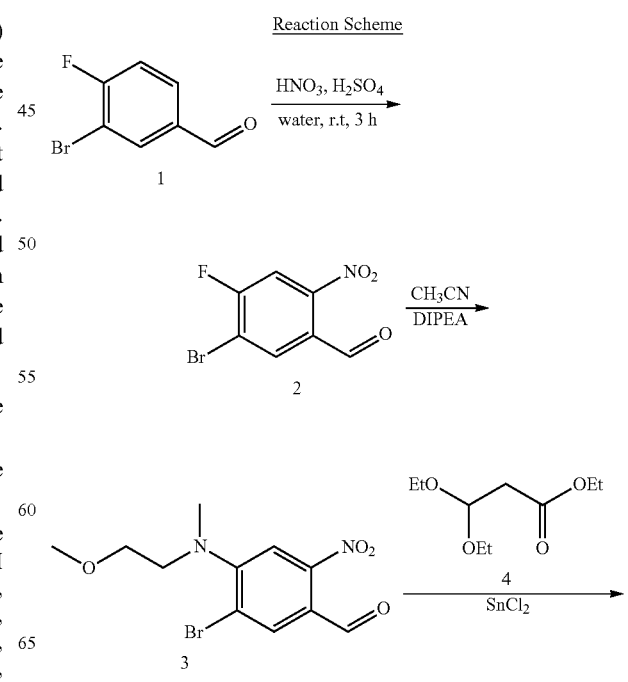

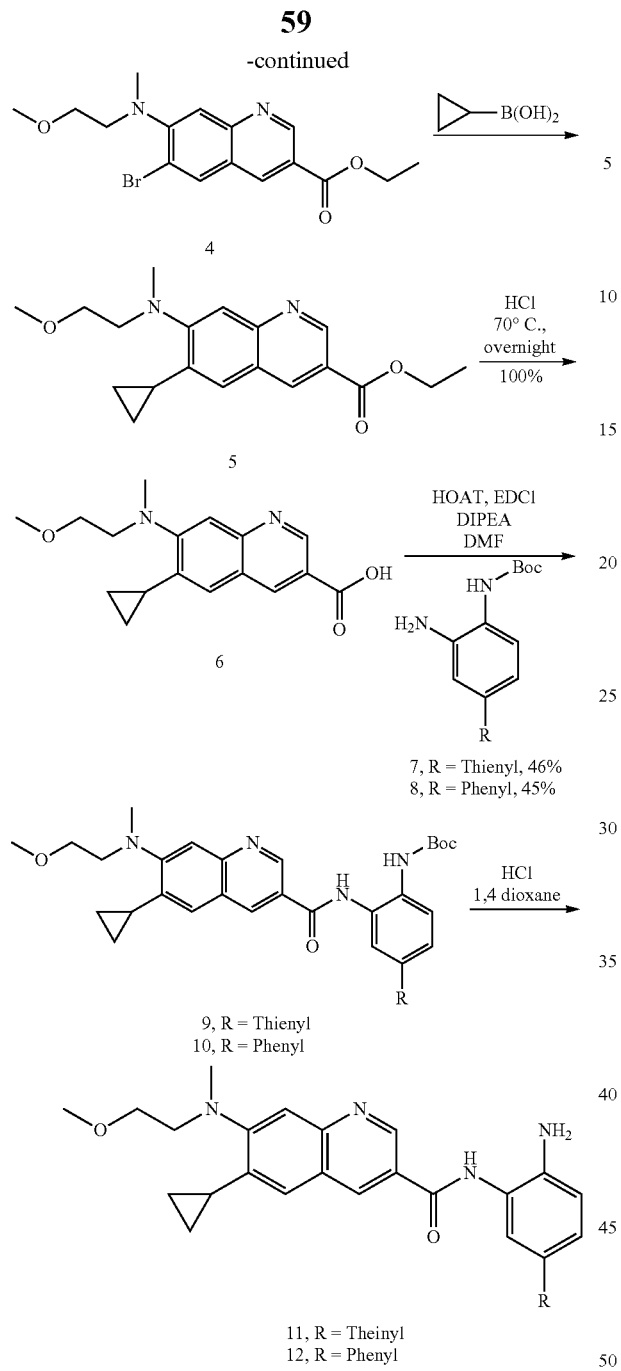

7, R = Thienyl, 46%
8, R = Phenyl, 45%

9, R = Thienyl
10, R = Phenyl

11, R = Theinyl
12, R = Phenyl

Experimental Procedure

Step 1: To a solution of compound 1 (5.0 g, 0.0246 mol) in conc. $H_2SO_4$ (30 ml) was added fuming nitric acid (10 ml) slowly at 0° C. The resulting solution was stirred at r.t. overnight. The reaction was quickly added to ice water (100 ml), extracted with EA (40 ml×2). The organic layers were combined and concentrated to yield a residue, which was purified by silica gel chromatography to obtain compound 2 (3.6 g, 65%) as a yellow solid.

Step 2: A mixture of compound 2 (3.0 g, 0.0121 mol), 2-methoxy-N-methylethanamine (4.3 g, 0.0484 mol) and DIPEA (6.2 g, 0.0484 mol) in acetonitrile (20 ml) was stirred at 80° C. overnight. The mixture was concentrated to give a residue, which was purified by silica gel chromatography to afford compound 3 (1.8 g, 47%) as a yellow oil.

Step 3: A mixture of compound 3 (1 g, 0.0032 mol), $SnCl_2$ (1.8 g, 0.0096 mol) and ethyl 3,3-diethoxypropanoate (1.8 g, 0.0096 mol) in EtOH (20 ml) was stirred at 90° C. overnight. The mixture was concentrated to give a residue, to which was added EA (50 ml) and aq. sat. $NaHCO_3$ (5 ml). The resulting solution was stirred for 30 min., filtered, dried, and concentrated resulting in a residue, which was re-crystallized by PE to yield compound 4 (500 mg, 43%).

Step 4: Compound 5 was prepared according to the procedure, as described in Example 3, compound 6.

Step 5: A solution of compound 5 (328 mg, 0.001 mol) in conc. HCl (5 ml) and water (5 ml) was stirred at 70° C. overnight. The mixture was concentrated to yield compound 6 (300 mg, 100%) as a yellow solid.

Step 6: Compounds 9 and 10 were prepared according to the procedure, as described in Example 1, compound 6.

Step 7: Compound 11 was prepared according to the procedure, as described in Example 1, compound 7. $^1$H NMR (500 MHz, DMSO) δ 9.91 (s, 1H), 9.24 (s, 1H), 8.76 (s, 1H), 7.52 (d, J=5.3 Hz, 3H), 7.41-7.21 (m, 3H), 7.09-7.02 (m, 1H), 6.85-6.80 (m, 1H), 5.24 (s, 2H), 3.61 (t, J=5.7 Hz, 2H), 3.41 (t, J=5.8 Hz, 2H), 3.25 (s, 3H), 2.97 (s, 3H), 2.29 (s, 1H), 1.13 (d, J=7.2 Hz, 2H), 0.91 (d, J=4.2 Hz, 2H). LCMS: m/z=473 (M+H)$^+$ Compound 12 was prepared according to the procedure, as described in Example 1, compound 7. $^1$H NMR (500 MHz, DMSO) δ 9.93 (s, 1H), 9.25 (s, 1H), 8.76 (s, 1H), 7.57 (d, J=8.5 Hz, 3H), 7.52 (d, J=5.0 Hz, 2H), 7.44-7.32 (m, 3H), 7.25 (t, J=7.4 Hz, 1H), 6.88 (d, J=8.3 Hz, 1H), 5.19 (s, 2H), 3.61 (d, J=5.7 Hz, 2H), 3.41 (t, J=5.8 Hz, 2H), 3.25 (s, 3H), 2.97 (s, 3H), 2.29 (s, 1H), 1.13 (s, 2H), 0.91 (d, J=4.0 Hz, 2H). LCMS: m/z=467 (M+H)$^+$ Example 8: Synthesis of N-(3-amino-5-phenylthiophen-2-yl)-7-(piperazin-1-yl)quinoline-3-carboxamide

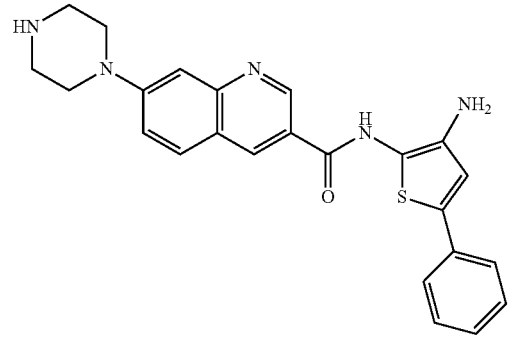

Reaction Scheme

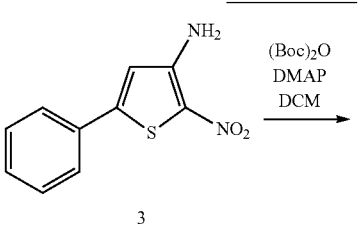

3

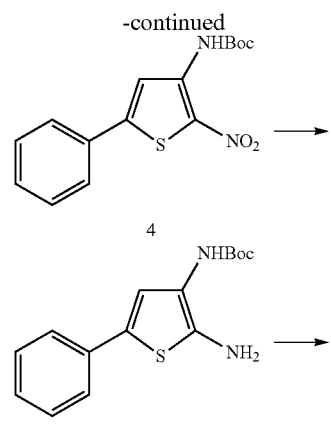

4

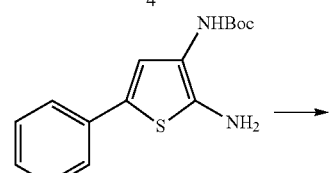

5

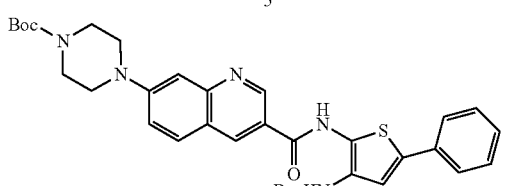

6

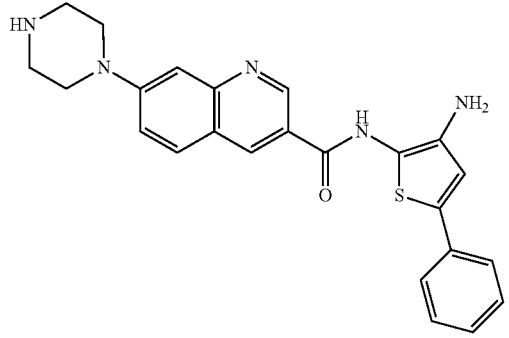 [SMILES: Nc1cc(-c2ccccc2)sc1NC(=O)c1cnc2cc(N3CCNCC3)ccc2c1]

7

Experimental Procedure

Step 1: To a solution of compound 3 (520 mg, 2.36 mmol) in THF, (15 ml) was added (Boc)$_2$O (772 mg, 3.54 mmol) at 0° C. NaH (489 mg, 4.72 mmol) was added, and the reaction was stirred for 4 hours, quenched with H$_2$O, and extracted with EA (2×30 ml). The combined organic layers were purified by gel chromatography (PE:EA=20:1) to afford the desired product of compound 4 (500 mg, 66%).

Step 2: To a solution of compound 4 (100 mg, 0.31 mmol) in EtOH (10 ml), was added Zn (150 mg, 2.5 mmol) and HOAc (150 mg, 2.5 mmol). The reaction was stirred at 65° C. for 10 min. and extracted with EA (2×10 ml). The combined the organic layers were washed with aqueous NaCl, dried by anhydrous Na$_2$SO$_4$, and concentrated to yield the desired product of compound 5 (90 mg, 100%).

Step 3: Compound 6 was prepared according to the procedure as described in Example 3, compound 10.

Step 4: Compound 6 was prepared according to the procedure as described in Example 1, compound 7. $^1$H NMR (500 MHz, DMSO) δ 10.34 (s, 1H), 9.23 (d, J=2.1 Hz, 1H), 8.75 (d, J=1.9 Hz, 1H), 8.33-8.16 (m, 1H), 7.95 (d, J=9.1 Hz, 1H), 7.58-7.51 (m, 3H), 7.38 (t, J=7.7 Hz, 2H), 7.30 (s, 1H), 7.26 (d, J=7.3 Hz, 1H), 6.94 (s, 1H), 3.44 (d, J=5.2 Hz, 4H), 3.06-3.01 (m, 4H). LCMS: m/z=430 (M+H)$^+$ Example 9: Synthesis of N-(4-amino-[1,1'-biphenyl]-3-yl)-8-cyclopropyl-7-(piperazin-1-yl)quinoline-3-carboxamide, Compound 003

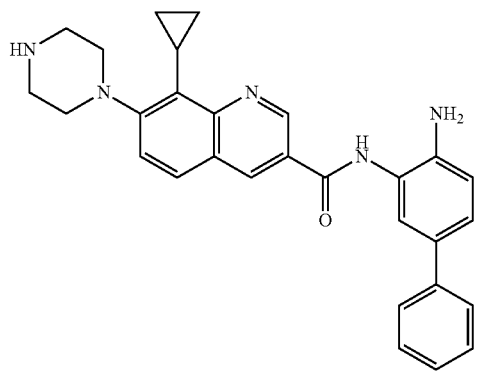 [SMILES: Nc1ccc(-c2ccccc2)cc1NC(=O)c1cnc2c(C3CC3)c(N3CCNCC3)ccc2c1]

Reaction Scheme

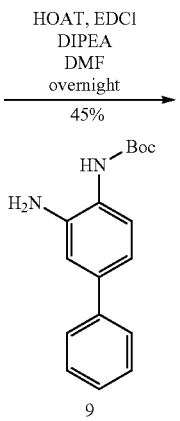

8

9

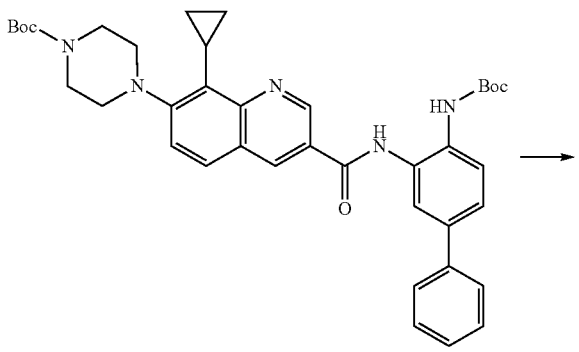

10

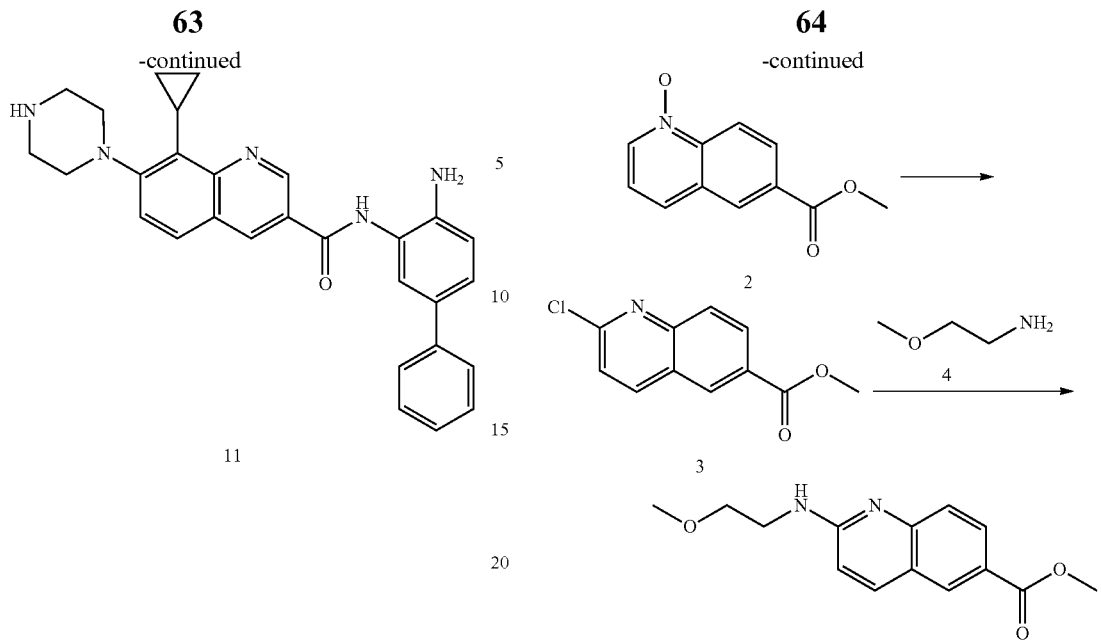

Experimental Procedure

Step 1: Compound 10 was prepared according to the procedure as described in Example 1, compound 6.

Step 2: Compound 6 was prepared according to the procedure, as described in Example 1, compound 7. $^1$H NMR (500 MHz, DMSO) δ 9.92 (s, 1H), 9.31 (d, J=1.9 Hz, 1H), 8.81 (s, 1H), 7.87 (d, J=8.9 Hz, 1H), 7.57 (d, J=8.8 Hz, 3H), 7.47 (d, J=8.9 Hz, 1H), 7.43-7.32 (m, 3H), 7.25 (t, J=7.3 Hz, 1H), 6.89 (d, J=8.4 Hz, 1H), 5.20 (s, 2H), 3.11 (s, 4H), 2.93 (d, J=4.3 Hz, 4H), 2.41-2.34 (m, 1H), 1.19 (dd, J=5.7, 3.5 Hz, 2H), 1.12-1.03 (m, 2H). LCMS: m/z=464 (M+H)$^+$

Example 10: Synthesis of N-(2-amino-5-(thiophen-2-yl)phenyl)-2-((2-methoxyethyl)amino)quinoline-6-carboxamide

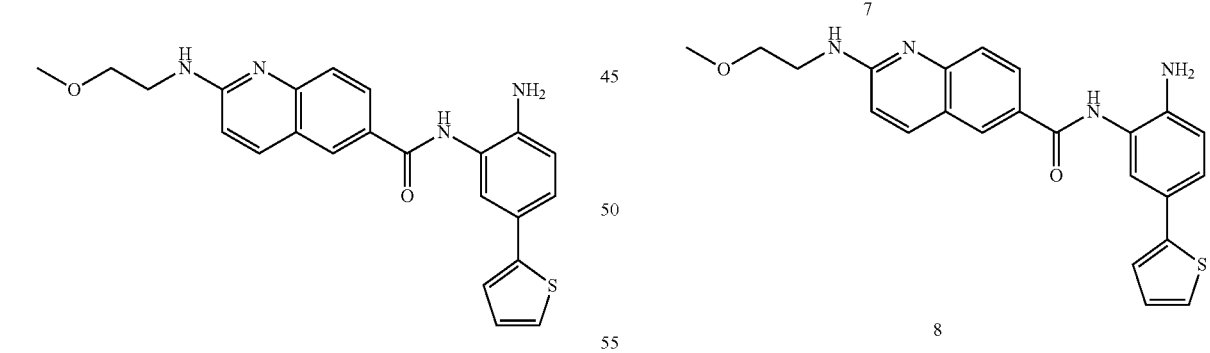

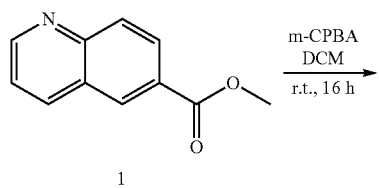

Experimental Procedure

Step 1: A mixture of compound 1 (10 g, 0.53 mol) and m-CPBA (18.4 g, 0.106 mol) in DCM (50 ml) was stirred at r.t. overnight. Aq. NaHCO$_3$ (40 ml, saturated) was added to the reaction mixture and stirred for 30 min. The organic layer was separated, dried, filtered and concentrated to obtain a residue, which was re-crystallized by EA (5 ml) to afford compound 2 (8.7 g, 80%) as a light yellow solid.

Step 2: To a solution of compound 2 (4.0 g, 0.020) and DMF (8 ml) in DCM was added SOCl$_2$ (8 ml) slowly at 0° C. and stirred at r.t. for 5 h. The resulting mixture was concentrated to obtain a residue, and DCM (50 ml) with Aq. NaHCO₃ (saturated, 20 ml) was added and stirred for 30 min. The organic layer was separated and concentrated to obtain a residue, which was purified by silica gel chromatography to afford compound 3 (1.3 g, 30%) as a white solid.

Step 3: A mixture of compound 3 (10 g, 0.045 mol), CuI (10 g, 0.53 mol), amine (10 g, 0.135 mol) and K₂CO₃ (18.6 g, 0.135 mol) in DMSO (120 ml) was stirred at 100° C. for overnight. Upon completion as monitored by TLC (thin-layer chromatography), 300 ml of EA (ethyl acetate) was added, followed by filtration (underlay 15 cm diatomite). Concentration of the mixture yielded a residue, to which water (300 ml) and aq. citric acid (saturated, 30 ml) were added. Stirring at r.t. for 30 min., followed by filtration yielded compound 4 (18 g, ~100%) as a yellow solid to be used in the next step without purification.

Step 4: A mixture of compound 4 (18 g, crude) and 2M NaOH (50 ml) in EtOH (100 mL) and THF (100 ml) was stirred at 70° C. for 4 h. TLC was used to monitor the reaction to completion. The reaction mixture was concentrated to a residue, to which water (300 mL) and aq. sat. citric acid (40 ml) were added. Subsequent filtration yielded compound 5 (14.5 g, 91% over two step) as a yellow solid.

Step 5: A mixture of compound 5 (100 mg, 0.3 mmol), compound 6 (81.2 mg, 1.2 mmol), HOAT (150 mg, 1.1 mmol), EDCI (200 mg, 1.1 mmol), DIPEA (300 mg, 2.3 mmol) and 4 A (20 g) in DMF (40 mL) was stirred at 55° C. for overnight. Put into some H₂O and extracted with EA (20 ml×3), separated, dried and concentrated to get a crude product Purified by Prep-TLC, get the desired product 7 (95.1 mg, 54%).

Step 6: Compound 8 was prepared according to the procedure, as described in Example 1, compound 6. ¹H NMR (500 MHz, DMSO) δ 9.73 (s, 1H), 8.34 (d, J=1.8 Hz, 1H), 8.06 (dd, J=8.7, 1.9 Hz, 1H), 7.95 (d, J=9.0 Hz, 1H), 7.53 (dd, J=18.2, 5.3 Hz, 2H), 7.42-7.33 (m, 2H), 7.30 (dd, J=8.3, 2.1 Hz, 1H), 7.25 (d, J=3.4 Hz, 1H), 7.05 (dd, J=5.0, 3.7 Hz, 1H), 6.89 (d, J=9.0 Hz, 1H), 6.82 (d, J=8.3 Hz, 1H), 5.16 (s, 2H), 3.61 (t, J=5.2 Hz, 2H), 3.55 (t, J=5.4 Hz, 2H), 3.31 (s, 3H). LCMS: m/z=419 (M+H)⁺

Example 11: Synthesis of N-(4-amino-[1,1'-biphenyl]-3-yl)-6-cyclopropyl-7-((2-methoxyethyl)amino)quinoline-3-carboxamide

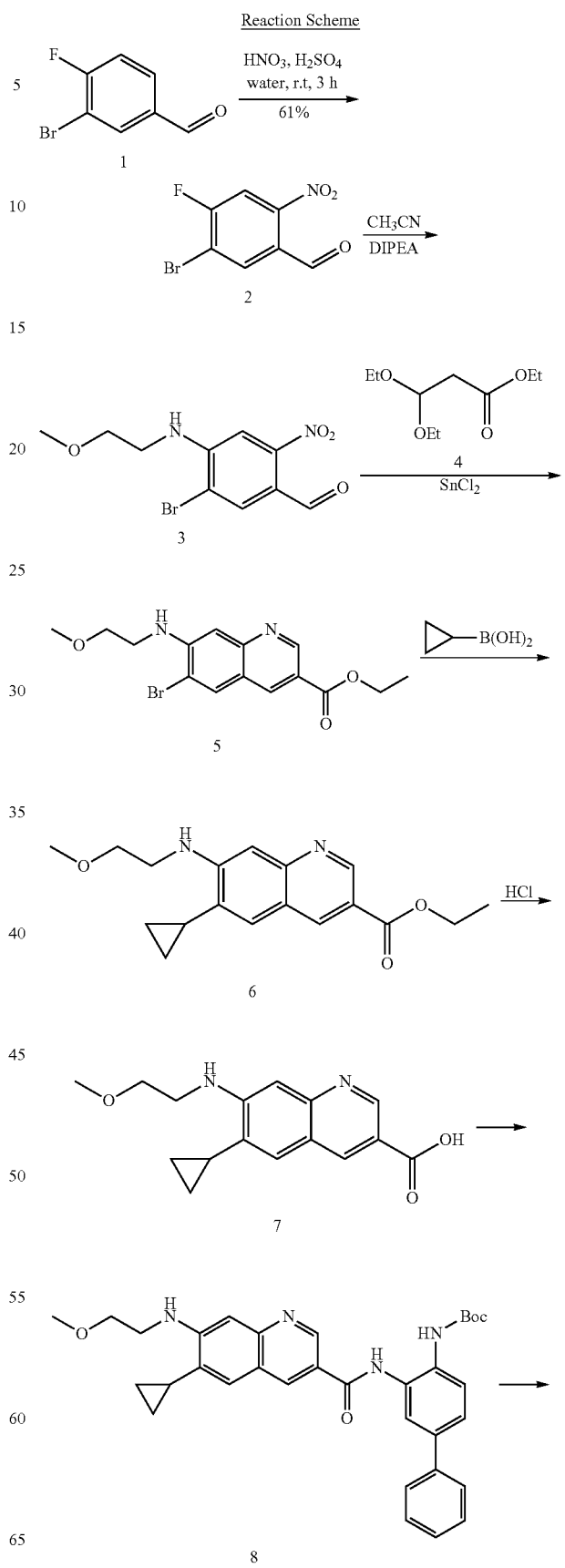

Reaction Scheme

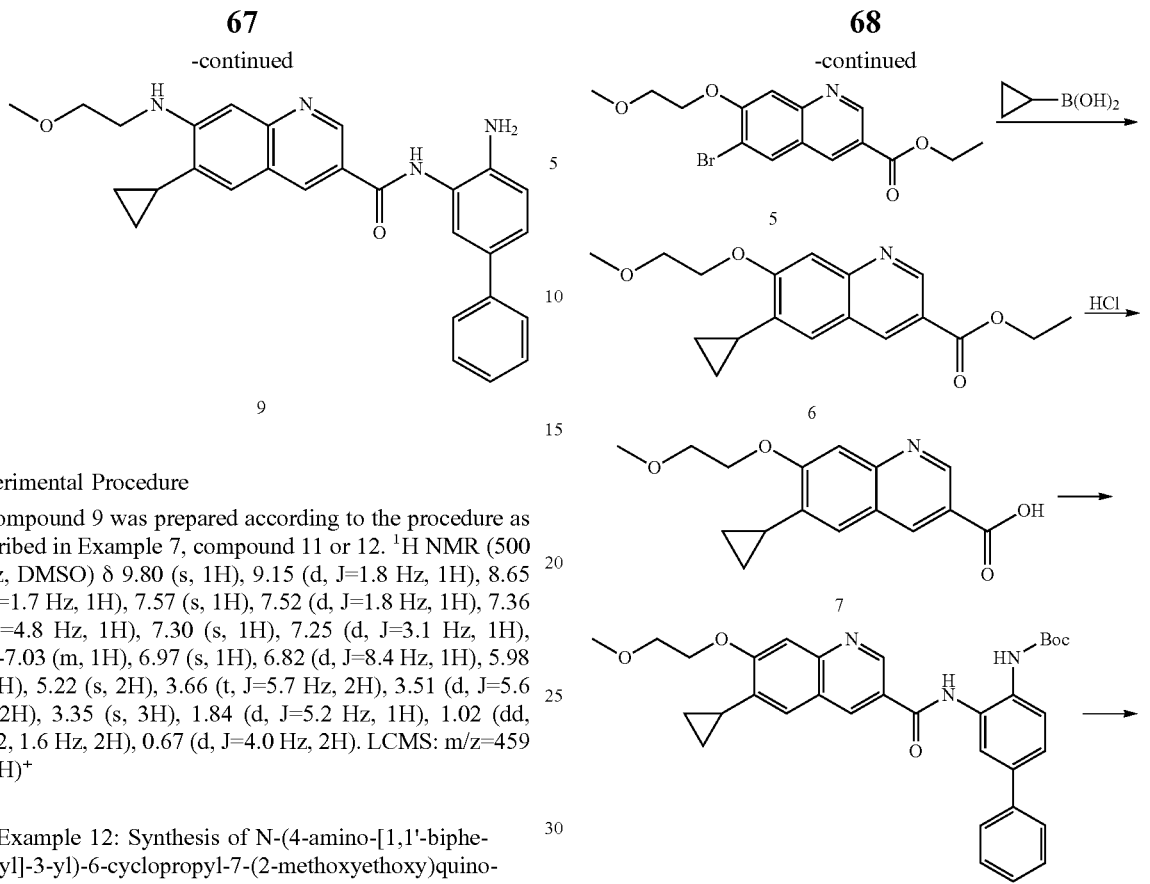

Experimental Procedure

Compound 9 was prepared according to the procedure as described in Example 7, compound 11 or 12. $^1$H NMR (500 MHz, DMSO) δ 9.80 (s, 1H), 9.15 (d, J=1.8 Hz, 1H), 8.65 (d, J=1.7 Hz, 1H), 7.57 (s, 1H), 7.52 (d, J=1.8 Hz, 1H), 7.36 (d, J=4.8 Hz, 1H), 7.30 (s, 1H), 7.25 (d, J=3.1 Hz, 1H), 7.08-7.03 (m, 1H), 6.97 (s, 1H), 6.82 (d, J=8.4 Hz, 1H), 5.98 (s, 1H), 5.22 (s, 2H), 3.66 (t, J=5.7 Hz, 2H), 3.51 (d, J=5.6 Hz, 2H), 3.35 (s, 3H), 1.84 (d, J=5.2 Hz, 1H), 1.02 (dd, J=8.2, 1.6 Hz, 2H), 0.67 (d, J=4.0 Hz, 2H). LCMS: m/z=459 (M+H)$^+$ Example 12: Synthesis of N-(4-amino-[1,1'-biphenyl]-3-yl)-6-cyclopropyl-7-(2-methoxyethoxy)quinoline-3-carboxamide

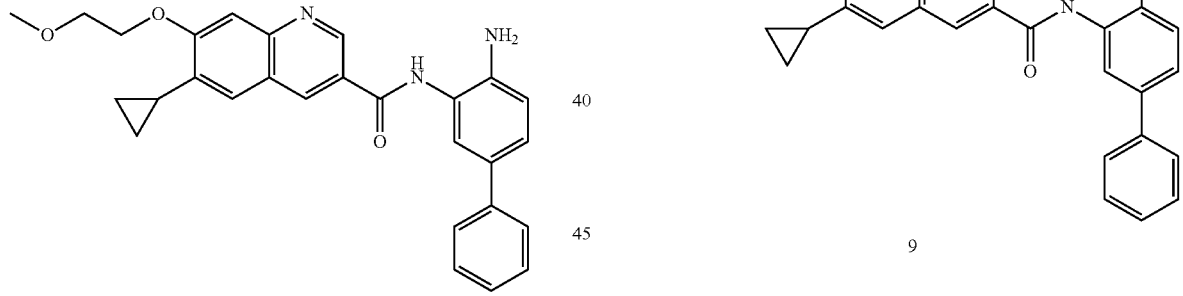

Reaction Scheme

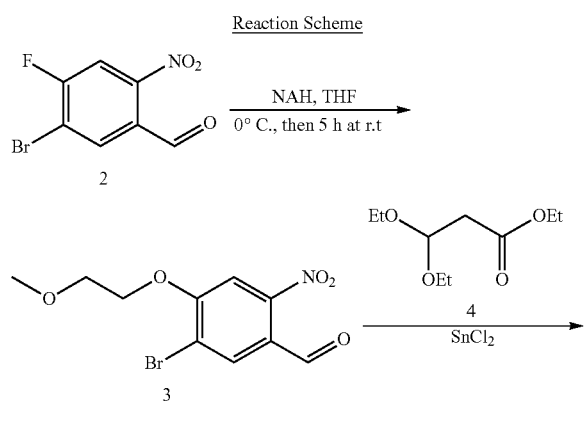

Experimental Procedure

Step 1: 2-methoxyethanol was dissolved in THF followed by addition of NaH at 0° C. After stirring at 0° C. for 20 min., compound 2 was added and the mixture was stirred at r.t. for 5 h. The mixture was concentrated and quenched with ice water. The mixture was extracted with ethyl acetate. The organic layers were combined, washed with brine, dried over Na$_2$SO$_4$, and concentrated. The resulting residue was purified by silica gel chromatography to give compound 3 (1.2 g, 34%) as a white solid.

Compound 9 was prepared according to the procedure as described in Example 11, compound 9. $^1$H NMR (500 MHz, DMSO) δ 9.94 (s, 1H), 9.27 (s, 1H), 8.79 (s, 1H), 7.62-7.54 (m, 4H), 7.46 (s, 1H), 7.43-7.32 (m, 3H), 7.25 (t, J=7.3 Hz, 1H), 6.88 (d, J=8.4 Hz, 1H), 5.20 (s, 2H), 4.51-4.23 (m, 2H), 3.96-3.73 (m, 2H), 3.39 (s, 3H), 2.37-2.18 (m, 1H), 1.05 (d, J=8.4 Hz, 2H), 0.84 (d, J=4.3 Hz, 2H). LCMS: m/z=454 (M+H)$^+$ Example 13: Synthesis of N-(4-amino-[1,1'-biphenyl]-3-yl)-3-cyclopropyl-1-(2-morpholinoethyl)-1H-indole-5-carboxamide

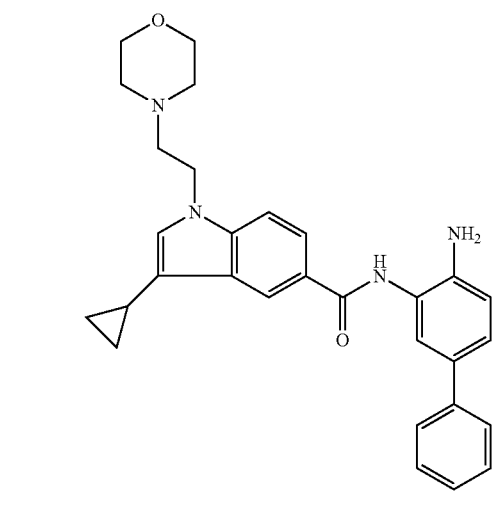 [SMILES: Nc1ccc(-c2ccccc2)cc1NC(=O)c1ccc2c(c1)c(C1CC1)cn2CCN1CCOCC1]

Reaction Scheme

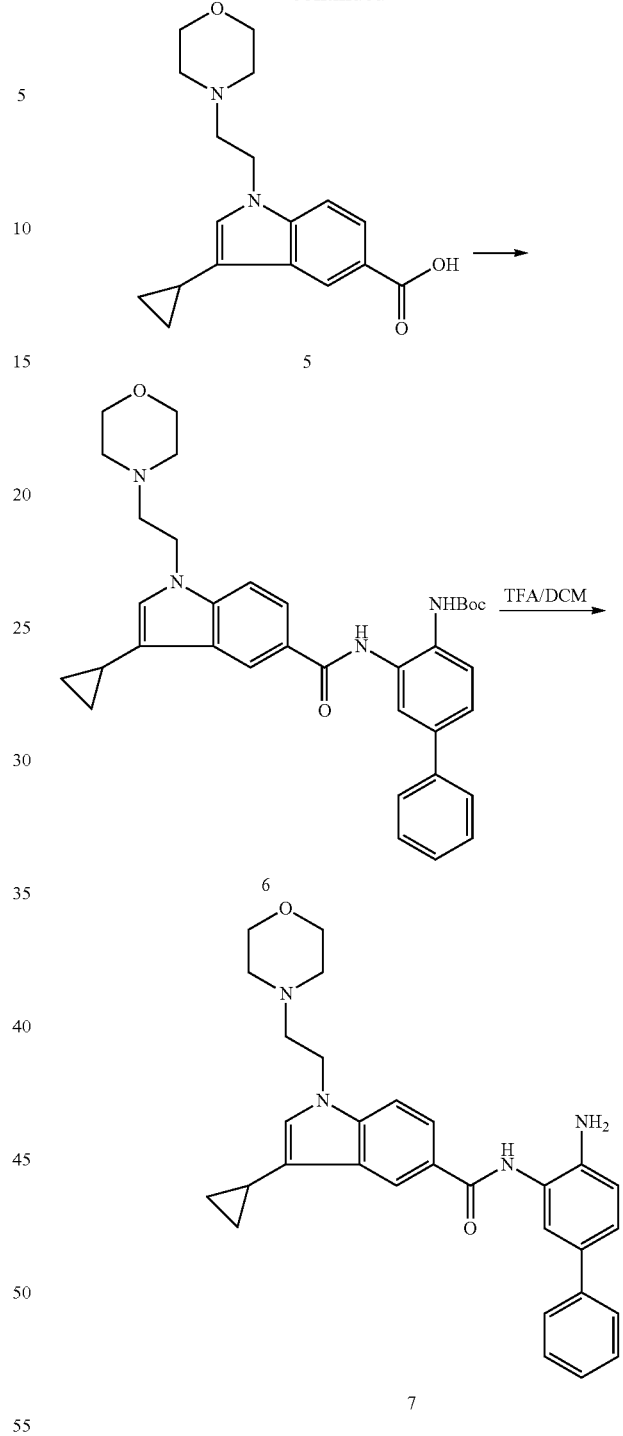

Experimental Procedure

Step 1: To a solution of compound 1 (500 mg, 1.97 mmol) in DMSO was added compound 2 (563 mg, 3.94 mmol) and KOH (220 mg, 3.94 mmol). The resulting reaction mixture was stirred at 45° C. for 4 h, quenched with H$_2$O, and extracted with EA (2×25 ml). The combined organic layers were purified by gel chromatography to yield the desired product, compound 3 (600 mg, 83%).

Step 2: Compound 4 was prepared according to the procedure as described in Example 3, compound 6.

Step 3: Compound 5 was prepared according to the procedure as described in Example 3, compound 8.

Step 4: Compound 6 was prepared according to the procedure as described in Example 3, compound 10.

Step 5: Compound 7 was prepared according to the procedure as described in Example 3, compound 11. $^1$H NMR (500 MHz, DMSO) δ 9.71 (s, 1H), 8.36 (s, 1H), 7.81 (d, J=8.6 Hz, 1H), 7.56 (dd, J=15.0, 10.5 Hz, 4H), 7.40 (t, J=7.7 Hz, 2H), 7.36-7.30 (m, 1H), 7.25 (s, 1H), 7.19 (s, 1H), 6.89 (d, J=8.3 Hz, 1H), 5.06 (s, 2H), 4.24 (s, 2H), 3.59-3.48 (m, 4H), 2.64 (s, 2H), 2.41 (s, 4H), 2.00 (s, 1H), 0.91 (dd, J=8.2, 1.8 Hz, 2H), 0.64 (d, J=3.6 Hz, 2H). LCMS: m/z=481 (M+H)$^+$ Example 14: Synthesis of N-(4-amino-[1,1'-biphenyl]-3-yl)-3-cyclopropyl-1-(2-methoxyethyl)-1H-indole-5-carboxamide

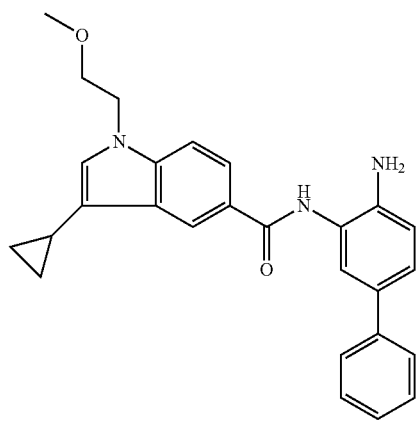 [SMILES: COCCn1cc(C2CC2)c2cc(C(=O)Nc3cc(-c4ccccc4)ccc3N)ccc21]

Reaction Scheme

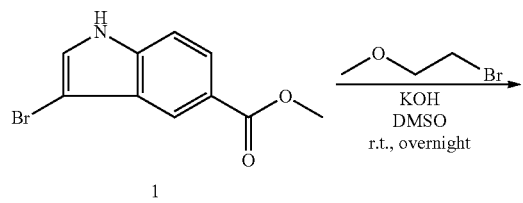

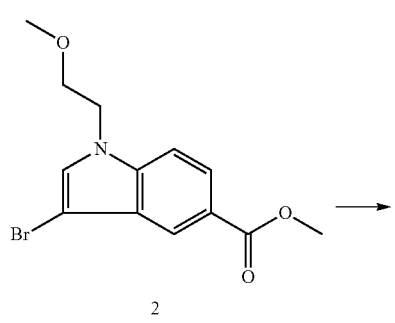

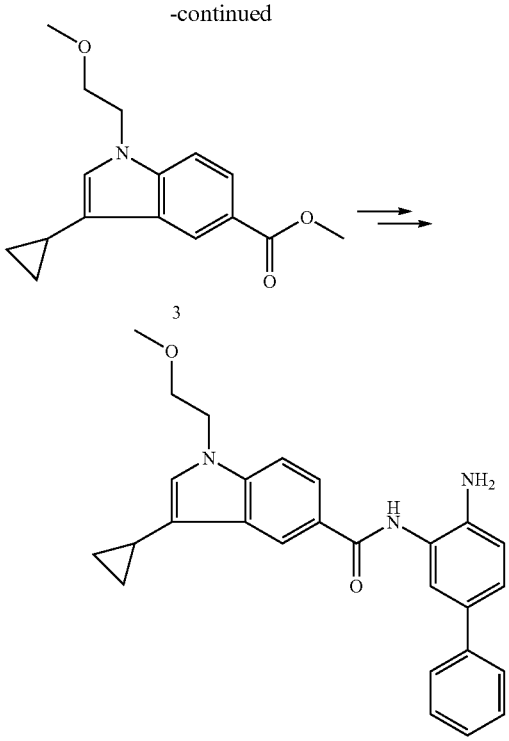

Experimental Procedure

Compound 4 was prepared according to the procedure as described in Example 13, compound 7. $^1$H NMR (500 MHz, DMSO) δ 9.72 (s, 1H), 8.36 (s, 1H), 7.81 (d, J=8.6 Hz, 1H), 7.57 (dd, J=10.3, 4.7 Hz, 3H), 7.52 (d, J=8.7 Hz, 1H), 7.40 (t, J=7.7 Hz, 2H), 7.33 (dd, J=8.3, 2.1 Hz, 1H), 7.25 (t, J=7.3 Hz, 1H), 7.15 (s, 1H), 6.89 (d, J=8.3 Hz, 1H), 5.06 (s, 2H), 4.29 (d, J=5.2 Hz, 2H), 3.64 (t, J=5.3 Hz, 2H), 3.21 (s, 3H), 2.00 (s, 1H), 0.91 (dd, J=8.3, 1.9 Hz, 2H), 0.72-0.58 (m, 2H). LCMS: m/z=426 (M+H)$^+$ Example 15: Synthesis of N-(4-amino-[1,1'-biphenyl]-3-yl)-7-cyclopropyl-8-(piperazin-1-yl)quinoline-3-carboxamide

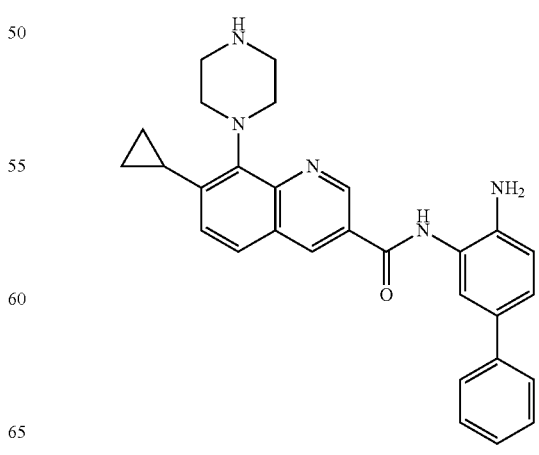

Reaction Scheme

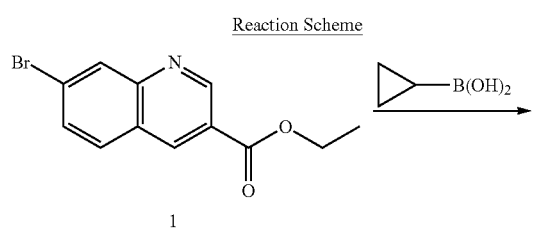
1

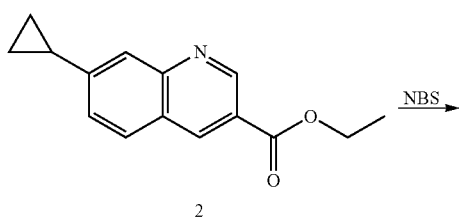
2

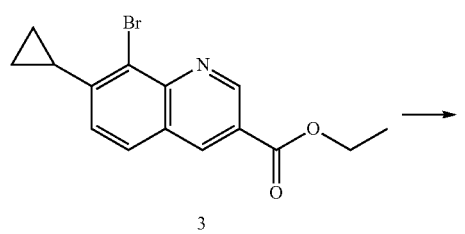
3

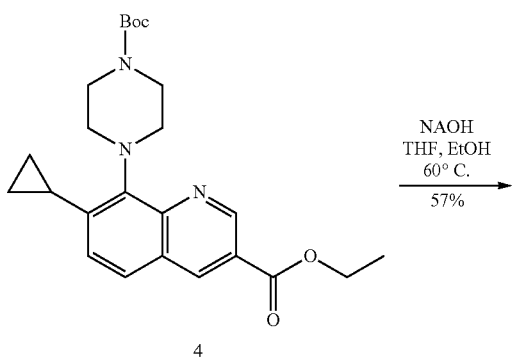
4

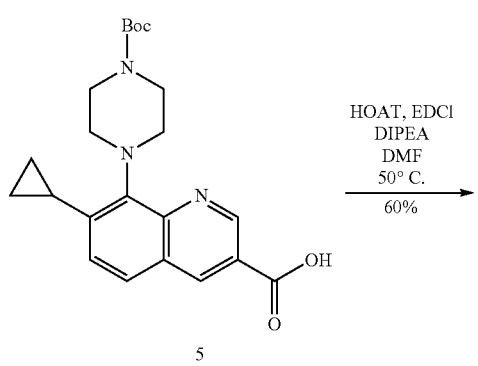
5

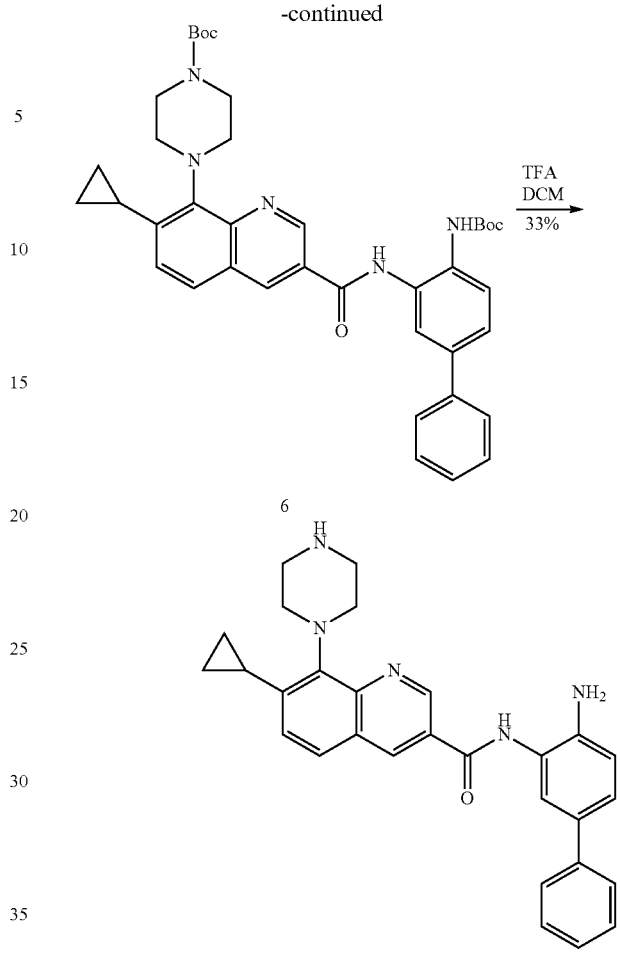

Ref: *Chemistry of Heterocyclic Compounds*, 1988, p. 892-897

Experimental Procedure

Step 1: Compound 2 was prepared according to the procedure as described in Example 3, compound 6.

Step 2: To a solution of compound 2 (1.2 g, 5 mmol) in 16 ml 98% $H_2SO_4/H_2O$ (5:3) was added NBS (866 mg, 5 mmol). The reaction mixture was stirred at r.t. for 2 h and extracted with DCM (20 ml). The organic layer was dried and concentrated to give a crude product, which was purified by silica gel column to yield the desired product 3 (517 mg, 32.5%).

Step 3: Compound 4 was prepared according to the procedure as described in Example 1, compound 4.

Step 4: Compound 5 was prepared according to the procedure as described in Example 1, compound 5.

Step 5: Compound 6 was prepared according to the procedure as described in Example 3, compound 10.

Step 6: Compound 7 was prepared according to the procedure as described in Example 3, compound 11. $^1$H NMR (500 MHz, DMSO) δ 9.35 (s, 1H), 8.92 (s, 1H), 8.43 (s, 1H), 7.84 (d, J=8.6 Hz, 1H), 7.63-7.54 (m, 3H), 7.45-7.33 (m, 3H), 7.25 (t, J=7.4 Hz, 1H), 7.12 (d, J=8.6 Hz, 1H), 6.90 (d, J=8.3 Hz, 1H), 3.10 (s, 4H), 2.93 (s, 1H), 2.51 (s, 4H), 1.11 (d, J=8.7 Hz, 2H), 0.83 (d, J=4.8 Hz, 2H). LCMS: m/z=464 (M+H)$^+$

Example 16: Synthesis of N-(4-amino-[1,1'-biphenyl]-3-yl)-1-(2-((2-methoxyethyl)amino)ethyl)-1H-indole-5-carboxamide
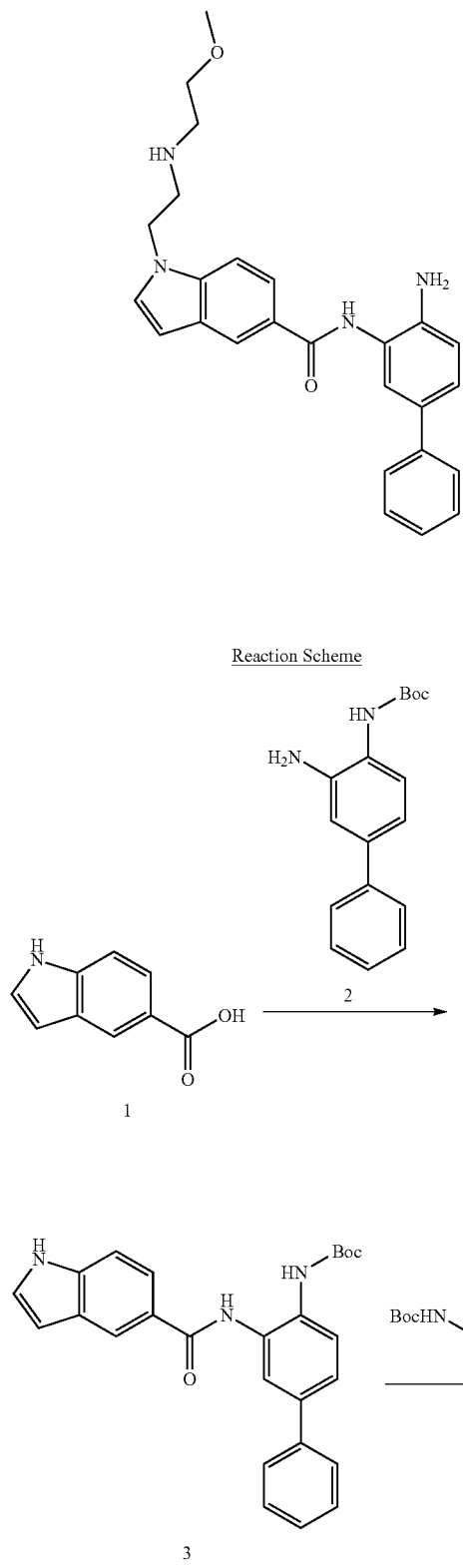
Reaction Scheme
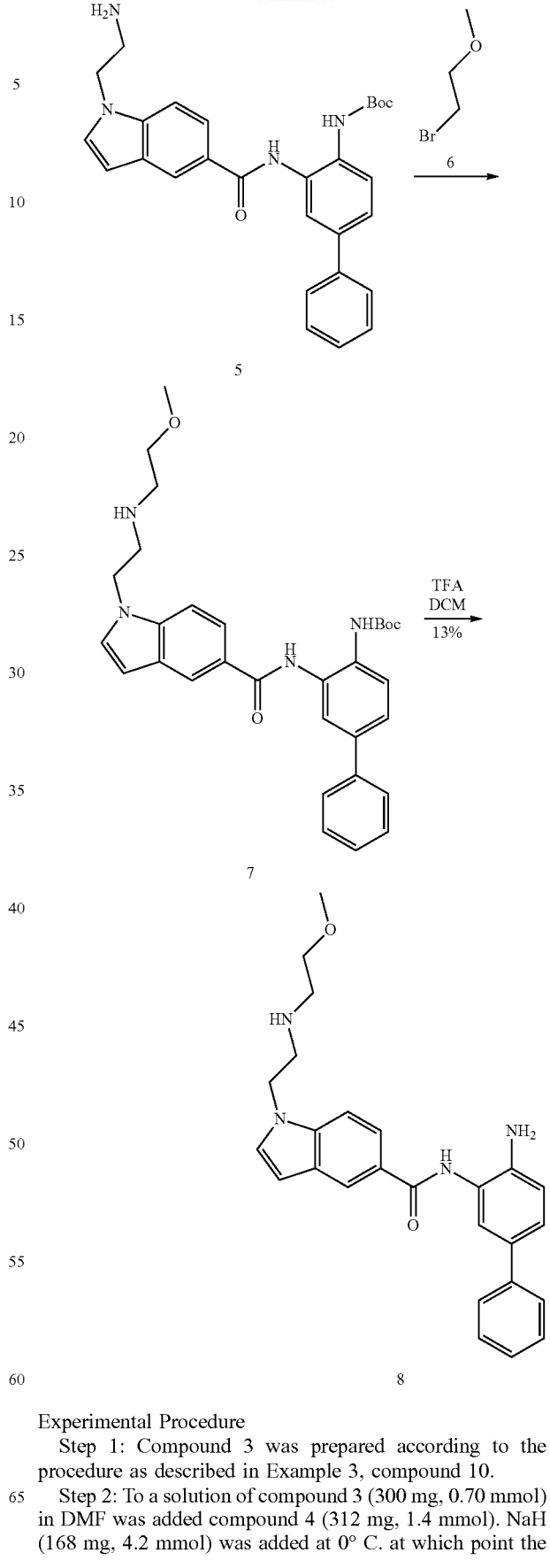
Experimental Procedure
Step 1: Compound 3 was prepared according to the procedure as described in Example 3, compound 10.
Step 2: To a solution of compound 3 (300 mg, 0.70 mmol) in DMF was added compound 4 (312 mg, 1.4 mmol). NaH (168 mg, 4.2 mmol) was added at 0° C. at which point the reaction mixture was warmed to r.t and stirred overnight. The reaction was quenched with H₂O, extracted with EA (2×20 ml) and the combined organic layers were purified by gel chromatography (DCM:MeOH=20:1) to afford the desired product of compound 5 (80 mg, 17%).

Step 3: To a solution of compound 5 (70 mg, 0.15 mmol) in CH₃CN was added K₂CO₃ (21 mg, 0.15 mmol) and compound 6 (21 mg, 0.15 mmol), at 60° C. was stirred overnight, extracted with EA (2×15 ml), combined the organic layer, purified by prep-TLC (PE:EA=1:1) to afford the desired product of compound 7 (39 mg, 49%).

Step 4: Compound 8 was prepared according to the procedure as described in Example 3, compound 11. ¹H NMR (500 MHz, DMSO) δ 9.65 (s, 1H), 8.30 (s, 1H), 7.81 (d, J=8.1 Hz, 1H), 7.63-7.53 (m, 4H), 7.49 (s, 1H), 7.40 (t, J=7.7 Hz, 2H), 7.32 (dd, J=8.3, 2.0 Hz, 1H), 7.24 (s, 1H), 6.88 (d, J=8.3 Hz, 1H), 6.58 (d, J=2.7 Hz, 1H), 5.07 (s, 2H), 4.29 (s, 2H), 3.30 (s, 2H), 3.21 (s, 3H), 2.92 (s, 2H), 2.64 (s, 2H). LCMS: m/z=429 (M+H)⁺

Example 17: Synthesis of 3-allyl-N-(4-amino-[1,1'-biphenyl]-3-yl)-1-(2-morpholinoethyl)-1H-indole-5-carboxamide

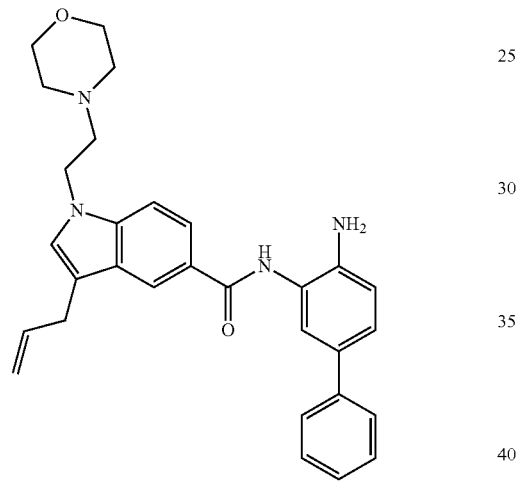

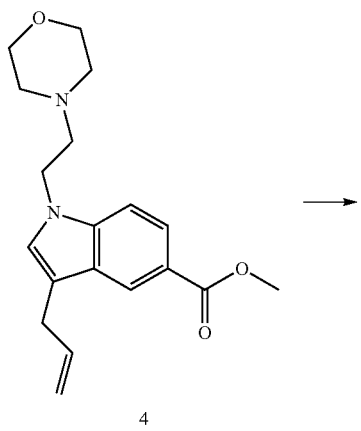

Reaction Scheme

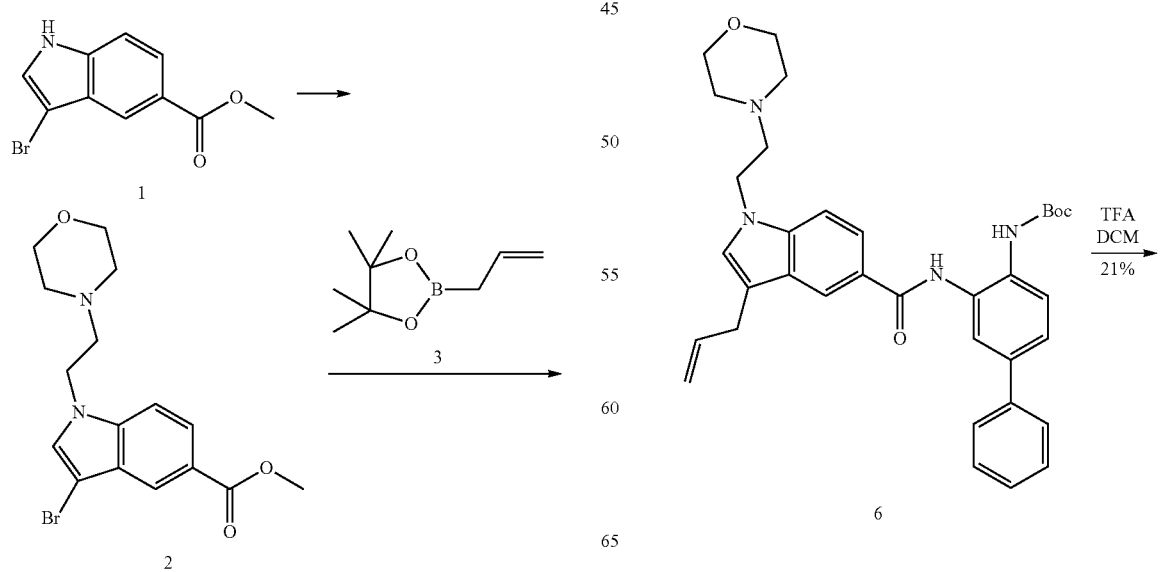

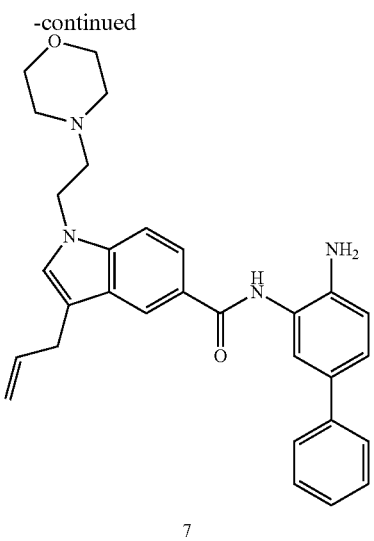

Experimental Procedure

Step 1: Compound 2 was prepared according to the procedure as described in Example 14, compound 3.

Step 2: To a solution of compound 2 (517 mg, 1.42 mmol) in DMSO was added compound 3 (483 mg, 2.84 mmol), CsF (437 mg, 2.84 mmol), and Pd(PPh$_3$)$_2$Cl$_2$ (28 mg, 0.04 mmol) under a N$_2$ atmosphere. The reaction was stirred overnight at 100° C. The reaction mixture was extracted with EA (2×25 ml) and the combined organic layers were purified by gel chromatography (PE:EA=4:1) to yield the desired product, compound 4 (293 mg, 63%).

Step 3: Compound 5 was prepared according to the procedure as described in Example 3, compound 8.

Step 4: Compound 6 was prepared according to the procedure as described in Example 3, compound 10.

Step 5: Compound 7 was prepared according to the procedure as described in Example 3, compound 11. $^1$H NMR (500 MHz, DMSO) δ 9.67 (s, 1H), 8.27 (s, 1H), 7.82 (d, J=8.5 Hz, 1H), 7.56 (t, J=9.1 Hz, 4H), 7.33 (ddd, J=38.7, 17.0, 7.4 Hz, 5H), 6.89 (d, J=8.3 Hz, 1H), 6.09 (d, J=6.8 Hz, 1H), 5.10 (dd, J=45.0, 11.9 Hz, 4H), 4.29 (t, J=6.3 Hz, 2H), 3.53 (s, 6H), 2.66 (t, J=6.4 Hz, 2H), 2.42 (s, 4H). LCMS: m/z=481 (M+H)$^+$ Example 18: Synthesis of ethyl (3-((4-amino-[1,1'-biphenyl]-3-yl)carbamoyl)-8-cyclopropylquinolin-7-yl)carbamate

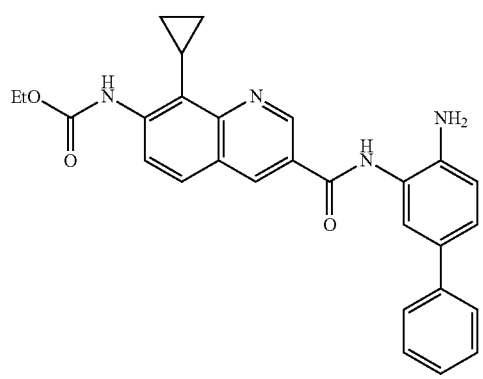 [SMILES: CCOC(=O)Nc1ccc2cc(C(=O)Nc3cc(-c4ccccc4)ccc3N)cnc2c1C1CC1]

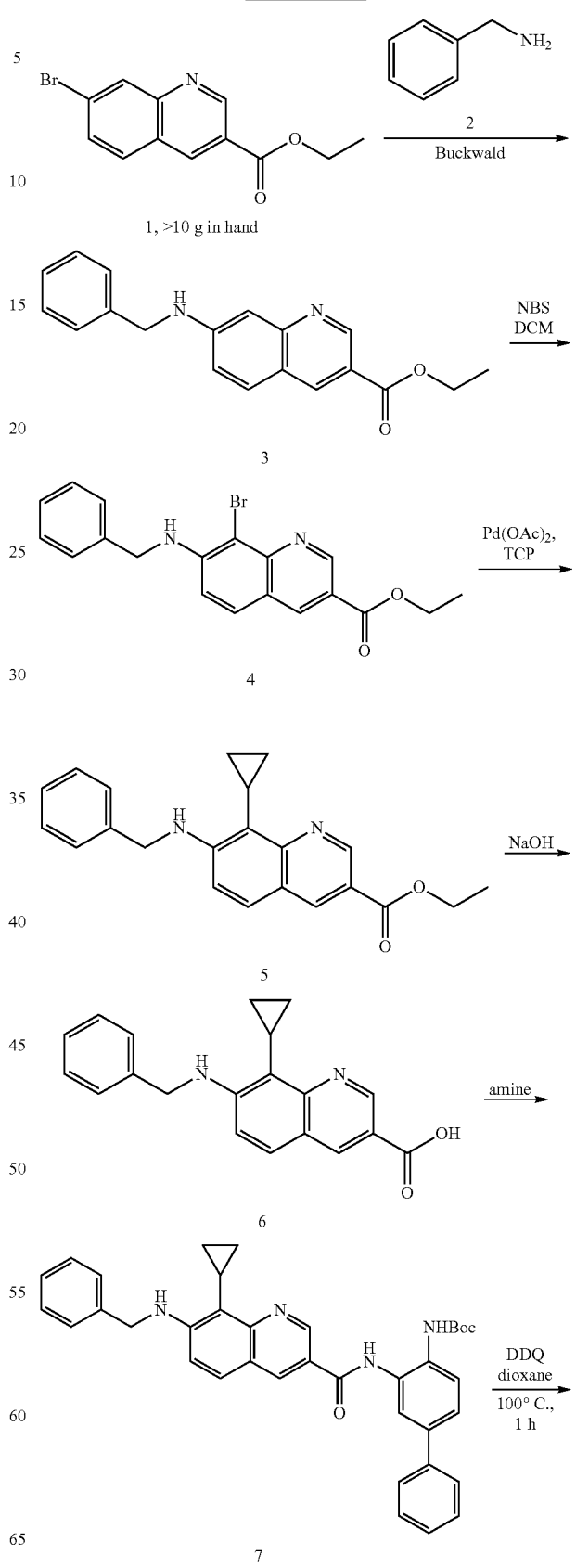

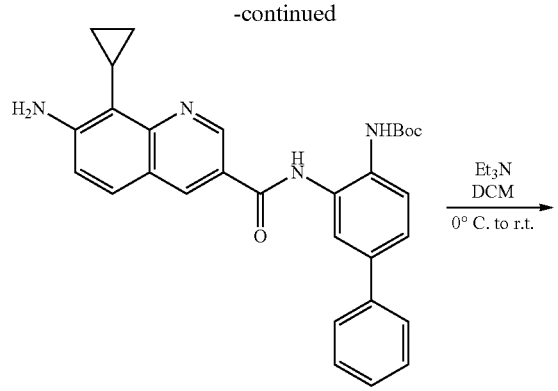

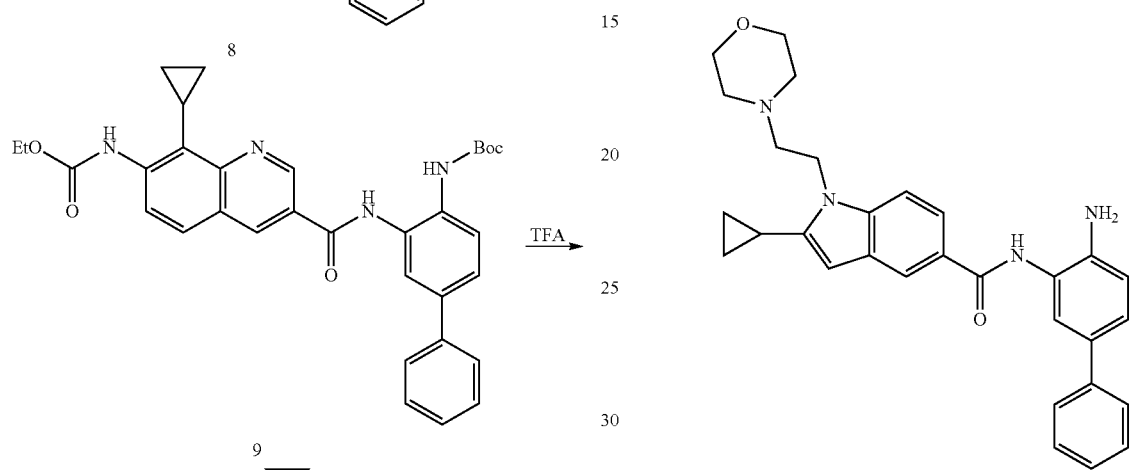

NMR (500 MHz, DMSO) δ 10.08 (s, 1H), 9.39 (s, 1H), 9.30 (s, 1H), 8.93 (s, 1H), 7.96 (d, J=8.9 Hz, 1H), 7.86-7.78 (m, 1H), 7.64-7.57 (m, 3H), 7.41 (dd, J=13.0, 5.2 Hz, 3H), 7.26 (t, J=7.3 Hz, 1H), 6.95 (d, J=8.3 Hz, 1H), 4.19 (d, J=7.1 Hz, 2H), 2.15 (s, 1H), 1.29 (t, J=7.1 Hz, 3H), 1.12 (dd, J=8.5, 2.0 Hz, 2H), 0.81 (d, J=4.0 Hz, 2H). LCMS: m/z=467 (M+H)+

Example 19: Synthesis of N-(4-amino-[1,1'-biphenyl]-3-yl)-2-cyclopropyl-1-(2-morpholinoethyl)-1H-indole-5-carboxamide Reaction Scheme

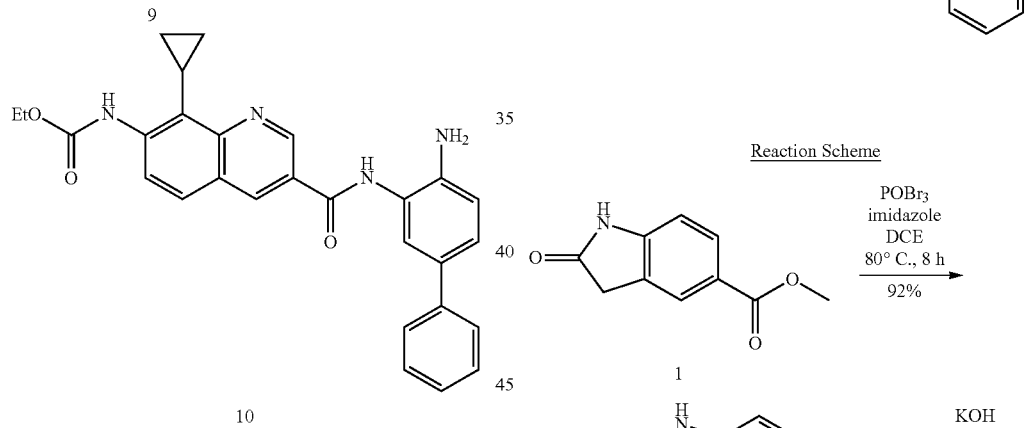

Experimental Procedure

Step 1: Compound 7 was prepared according to the procedure as described in Example 3, compound 10.

Step 2: To a solution of compound 7 (140 mg, 0.24 mmol) in dioxane was added DDQ (54 mg, 0.48 mmol). The reaction mixture was stirred for 1 hour at 100° C., quenched with sat. citric acid, and adjusted to a pH of 9 through addition of NaHCO₃. The resulting solution was extracted with EA (2×20 ml) and the combined organic layers were concentrated. Crystallization from EA and PE (3:1) afforded the desired product, compound 8 (65 mg, 55%).

Step 3: To a solution of compound 8 (65 mg, 0.13 mmol) in DCM at 0° C. was added ethyl carbonochloridate (142 mg, 1.3 mmol) and Et₃N (141 mg. 14.3 mmol). The reaction was stirred at r.t. overnight, quenched with aqeous NaHCO₃ and extracted with EA (2×15 ml). The organic layers were combined and concentrated to afford the desired product, compound 9 (60 mg, 82%).

Step 4: Compound 10 was prepared according to the procedure as described in Example 3, compound 11. ¹H -continued

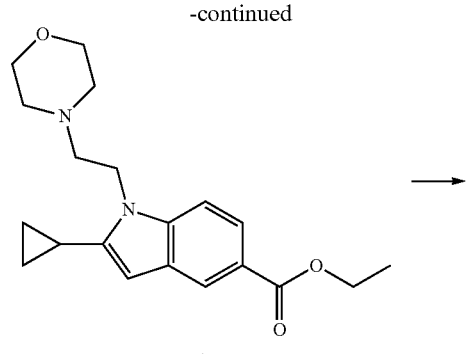

4

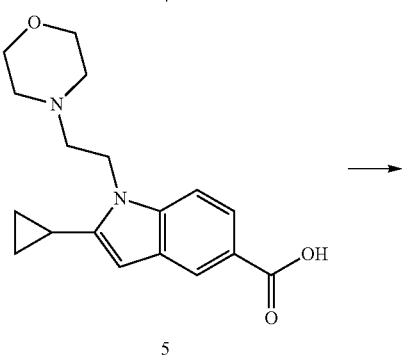

5

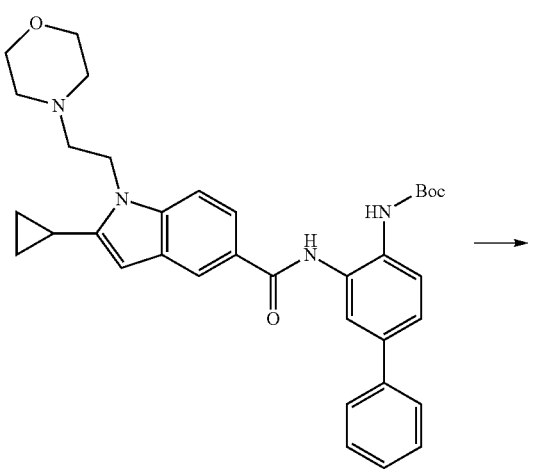

6

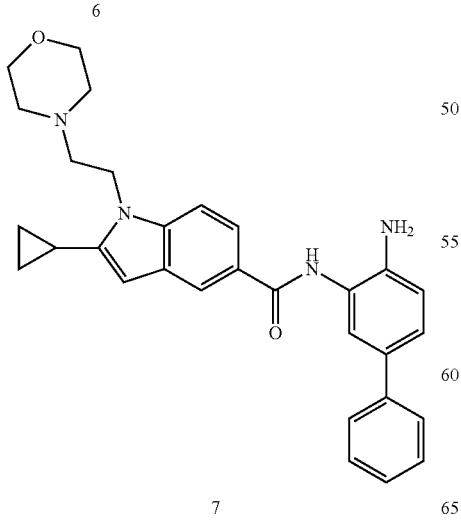

7

Experimental Procedure

Step 1: To a solution of compound 1 (1.0 g, 5.2 mmol) in DCE (50 ml) was added POBr₃ (8.8 g, 31.2 mmol) and imidazole (1.4 g, 20.8 mmol). The reaction was stirred at 80° C. overnight. Water and DCM were added to the reaction, and the organic layer was separated, washed with brine, and dried under reduced pressure to give compound 2 (1.1 g, 84%).

Step 2: Compound 3 was prepared according to the procedure as described in Example 14, compound 3.

Step 3: Compound 4 was prepared according to the procedure as described in Example 3, compound 6.

Step 4: Compound 5 was prepared according to the procedure as described in Example 3, compound 8.

Step 5: Compound 6 was prepared according to the procedure as described in Example 3, compound 10.

Step 6: Compound 7 was prepared according to the procedure as described in Example 3, compound 11. $^{1}$H NMR (400 MHz, DMSO) δ 9.61 (s, 1H), 8.15 (d, J=1.2 Hz, 1H), 7.76 (dd, J=8.6, 1.5 Hz, 1H), 7.56 (dd, J=4.8, 2.5 Hz, 3H), 7.49 (d, J=8.6 Hz, 1H), 7.39 (t, J=7.7 Hz, 2H), 7.31 (dd, J=8.3, 2.2 Hz, 1H), 7.24 (t, J=7.3 Hz, 1H), 6.88 (d, J=8.3 Hz, 1H), 6.23 (s, 1H), 5.05 (s, 2H), 4.43 (t, J=7.0 Hz, 2H), 3.62-3.52 (m, 4H), 2.66 (t, J=6.9 Hz, 2H), 2.47 (d, J=4.3 Hz, 4H), 2.16-2.03 (m, 1H), 1.08-0.96 (m, 2H), 0.75 (q, J=5.9 Hz, 2H). LCMS: m/z=481.3 (M+H)⁺.

Example 20: Synthesis of N-(4-amino-[1,1'-biphenyl]-3-yl)-2-cyclopropyl-1-(2-methoxyethyl)-1H-indole-5-carboxamide

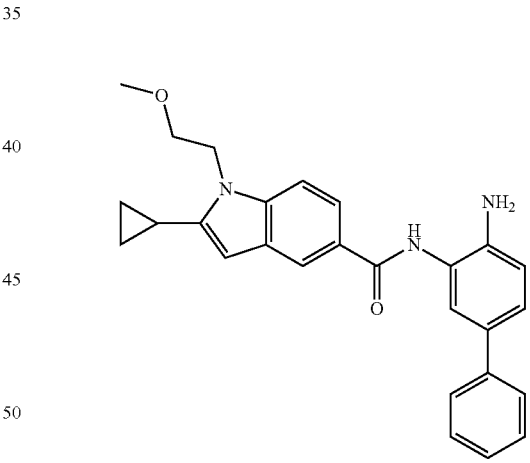

Reaction Scheme

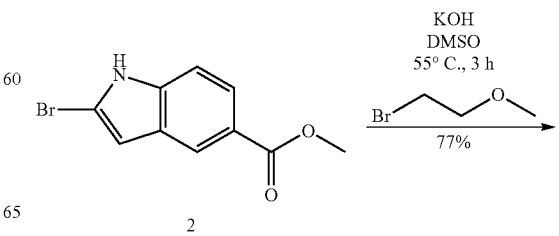

-continued
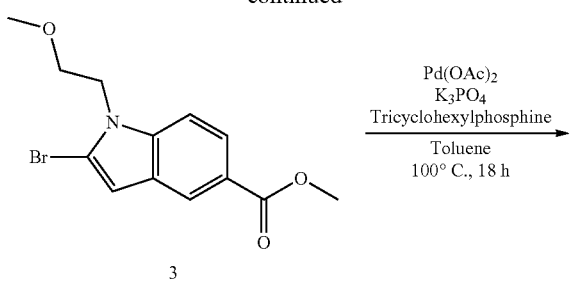
Experimental Procedure
Compound 7 was prepared according to the procedure as described in Example 19, compound 7. $^1$H NMR (500 MHz, DMSO) δ 9.63 (s, 1H), 8.16 (d, J=0.9 Hz, 1H), 7.76 (dd, J=8.6, 1.4 Hz, 1H), 7.57 (dd, J=4.6, 2.4 Hz, 3H), 7.51 (d, J=8.6 Hz, 1H), 7.39 (t, J=7.7 Hz, 2H), 7.32 (dd, J=8.3, 2.1 Hz, 1H), 7.24 (t, J=7.3 Hz, 1H), 6.88 (d, J=8.3 Hz, 1H), 6.23 (s, 1H), 5.06 (s, 2H), 4.49 (t, J=5.4 Hz, 2H), 3.69 (t, J=5.5 Hz, 2H), 3.21 (d, J=6.8 Hz, 3H), 2.11-2.03 (m, 1H), 1.05-0.96 (m, 2H), 0.80-0.67 (m, 2H). LCMS: m/z=426 (M+H)$^+$
Example 21: Synthesis of N-(4-amino-[1,1'-biphenyl]-3-yl)-1-(2-(piperazin-1-yl)ethyl)-1H-indole-5-carboxamide
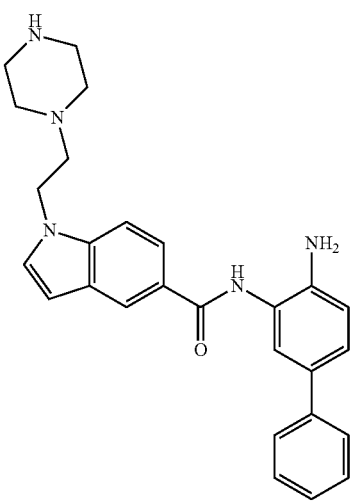 [SMILES: Nc1ccc(-c2ccccc2)cc1NC(=O)c1ccc2c(ccn2CCN2CCNCC2)c1]
Reaction Scheme
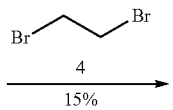
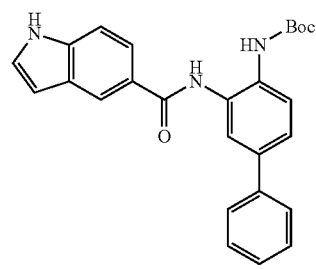
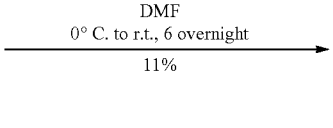

-continued

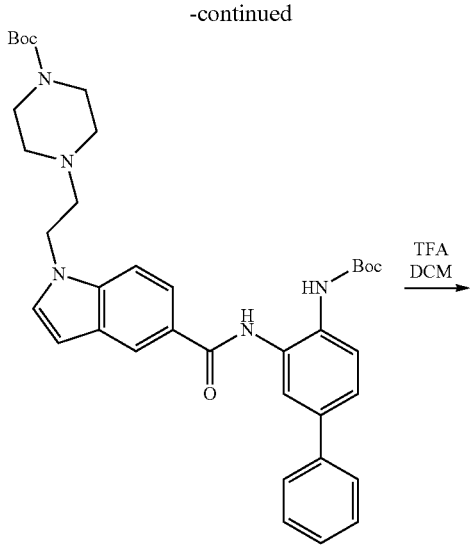

5

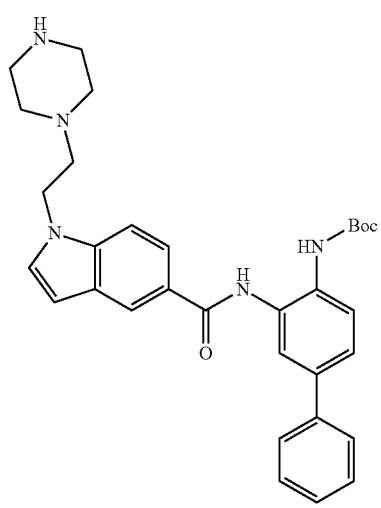

7

Experimental Procedure

Step 1: Compound 5 was prepared according to the procedure as described in Example 17, compound 5.

Step 2: Compound 7 was prepared according to the procedure as described in Example 3, compound 11. ¹H NMR (500 MHz, DMSO) δ 9.66 (s, 1H), 8.30 (s, 1H), 7.82 (d, J=8.7 Hz, 1H), 7.56 (ddd, J=21.0, 19.7, 5.9 Hz, 5H), 7.40 (t, J=7.7 Hz, 2H), 7.32 (dd, J=8.3, 2.1 Hz, 1H), 7.25 (t, J=7.3 Hz, 1H), 6.89 (d, J=8.3 Hz, 1H), 6.59 (d, J=3.0 Hz, 1H), 5.07 (s, 2H), 4.34 (t, J=6.2 Hz, 2H), 2.95 (s, 4H), 2.73 (t, J=6.3 Hz, 2H), 2.57 (s, 4H). LCMS: m/z=440 (M+H)⁺

Example 22: Synthesis of N-(2-aminobenzo[b]thiophen-3-yl)-7-(piperazin-1-yl)quinoline-3-carboxamide

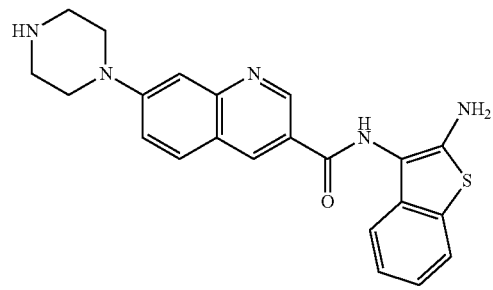 [SMILES: Nc1sc2ccccc2c1NC(=O)c1cnc2cc(N3CCNCC3)ccc2c1]

Reaction Scheme

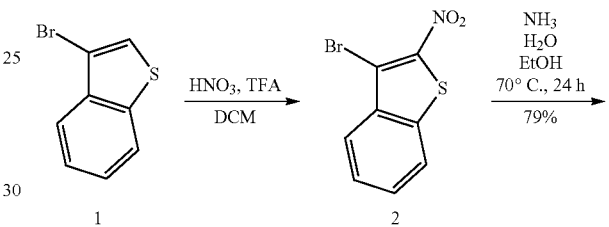

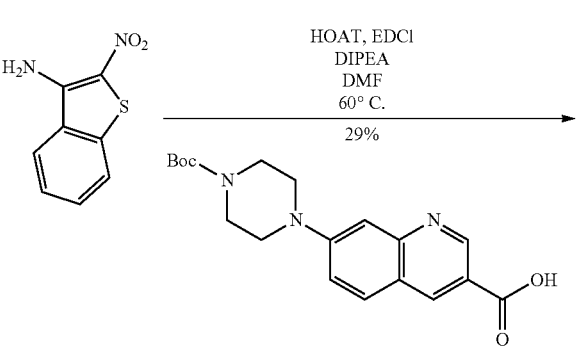

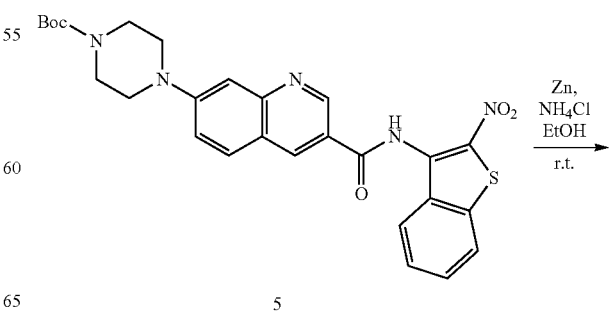

5

Example 23: Synthesis of N-(2-amino-5-(thiophen-2-yl)phenyl)-8-cyclopropyl-7-(4-methylpiperazin-1-yl)quinoline-3-carboxamide

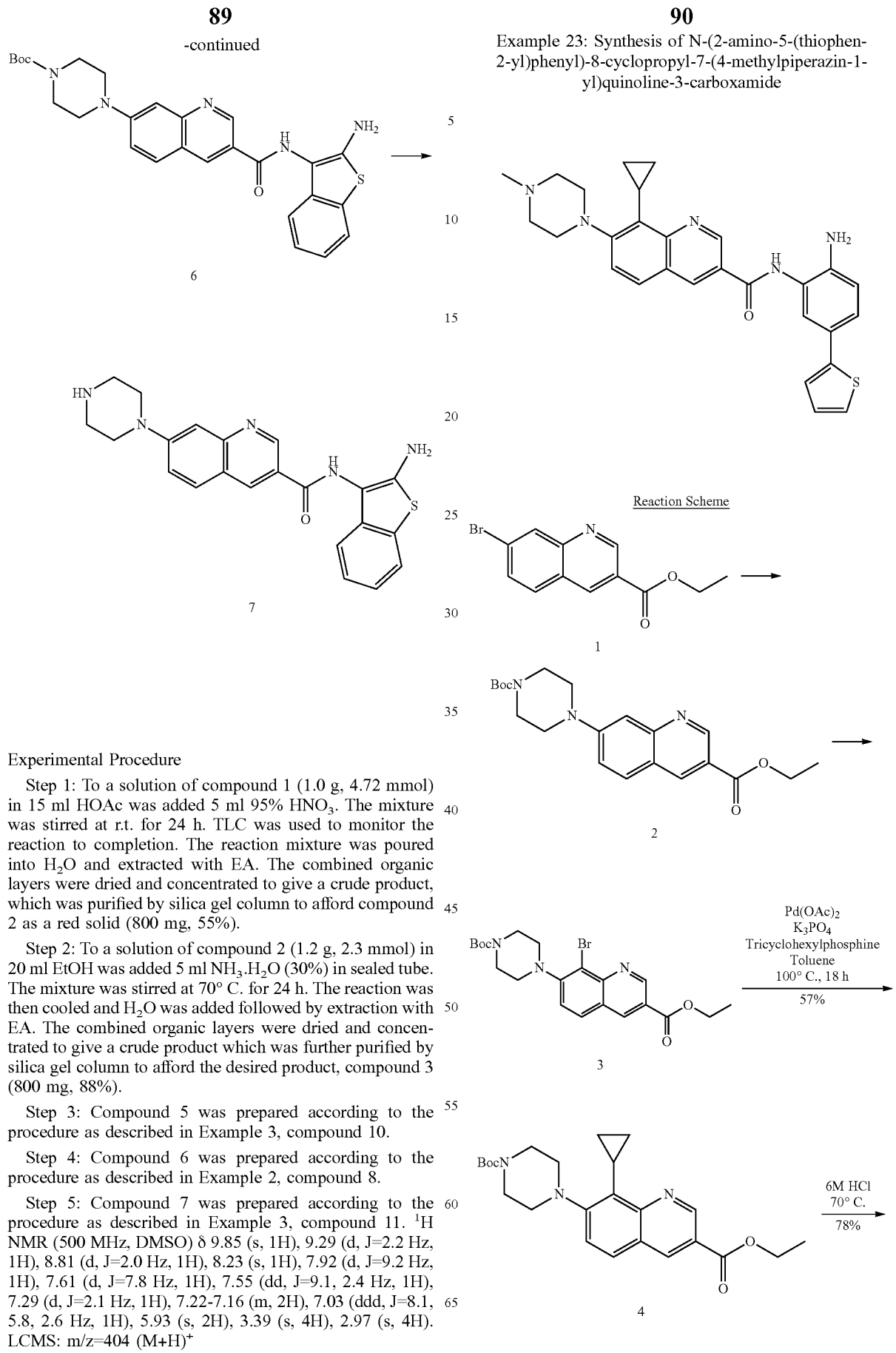

Experimental Procedure

Step 1: To a solution of compound 1 (1.0 g, 4.72 mmol) in 15 ml HOAc was added 5 ml 95% HNO₃. The mixture was stirred at r.t. for 24 h. TLC was used to monitor the reaction to completion. The reaction mixture was poured into H₂O and extracted with EA. The combined organic layers were dried and concentrated to give a crude product, which was purified by silica gel column to afford compound 2 as a red solid (800 mg, 55%).

Step 2: To a solution of compound 2 (1.2 g, 2.3 mmol) in 20 ml EtOH was added 5 ml NH₃.H₂O (30%) in sealed tube. The mixture was stirred at 70° C. for 24 h. The reaction was then cooled and H₂O was added followed by extraction with EA. The combined organic layers were dried and concentrated to give a crude product which was further purified by silica gel column to afford the desired product, compound 3 (800 mg, 88%).

Step 3: Compound 5 was prepared according to the procedure as described in Example 3, compound 10.

Step 4: Compound 6 was prepared according to the procedure as described in Example 2, compound 8.

Step 5: Compound 7 was prepared according to the procedure as described in Example 3, compound 11. $^1$H NMR (500 MHz, DMSO) δ 9.85 (s, 1H), 9.29 (d, J=2.2 Hz, 1H), 8.81 (d, J=2.0 Hz, 1H), 8.23 (s, 1H), 7.92 (d, J=9.2 Hz, 1H), 7.61 (d, J=7.8 Hz, 1H), 7.55 (dd, J=9.1, 2.4 Hz, 1H), 7.29 (d, J=2.1 Hz, 1H), 7.22-7.16 (m, 2H), 7.03 (ddd, J=8.1, 5.8, 2.6 Hz, 1H), 5.93 (s, 2H), 3.39 (s, 4H), 2.97 (s, 4H). LCMS: m/z=404 (M+H)⁺

-continued

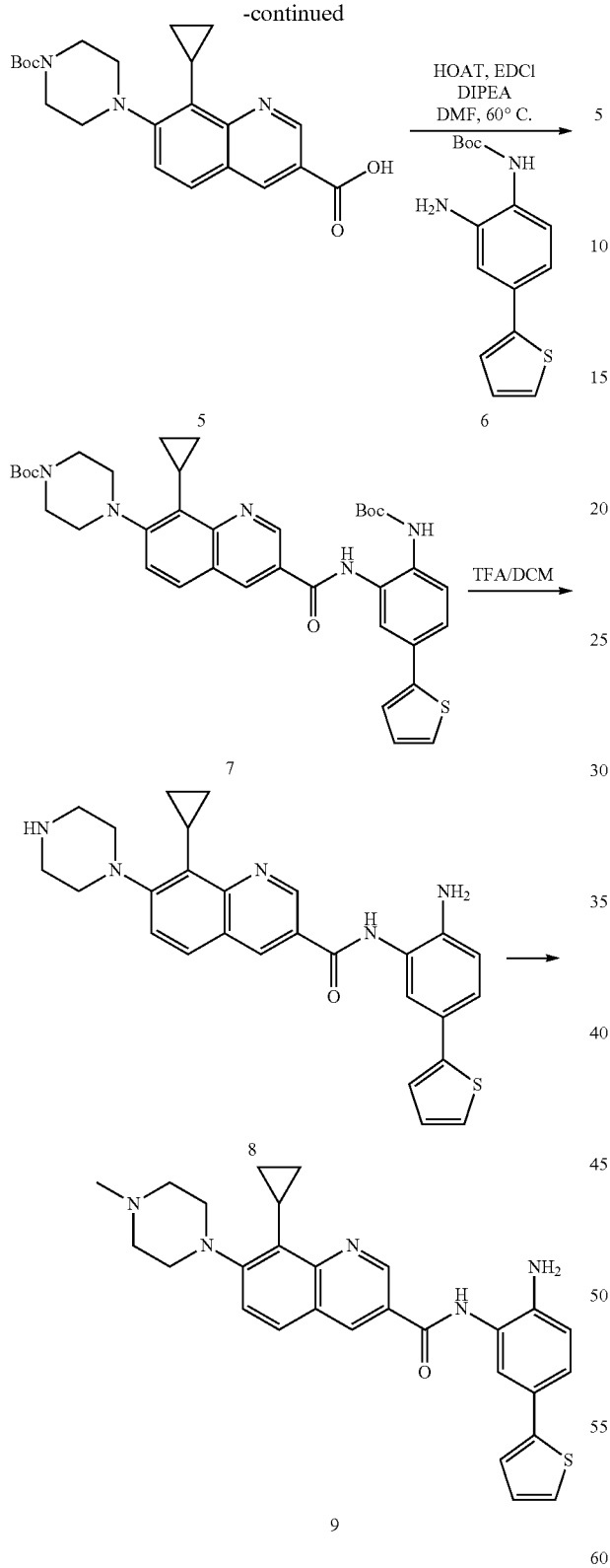

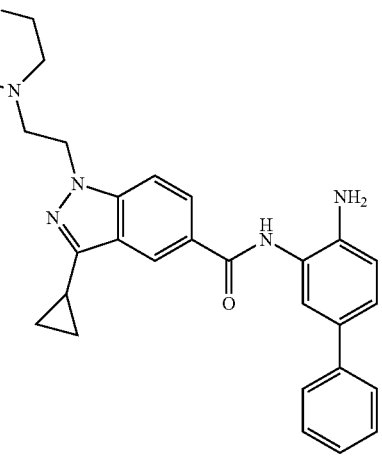

ml). The combined organic layers were purified by Prep-HPLC to afford the desired product, compound 9 (7 mg, 23%).

Example 24: Synthesis of N-(4-amino-[1,1'-biphenyl]-3-yl)-3-cyclopropyl-1-(2-morpholinoethyl)-1H-indazole-5-carboxamide

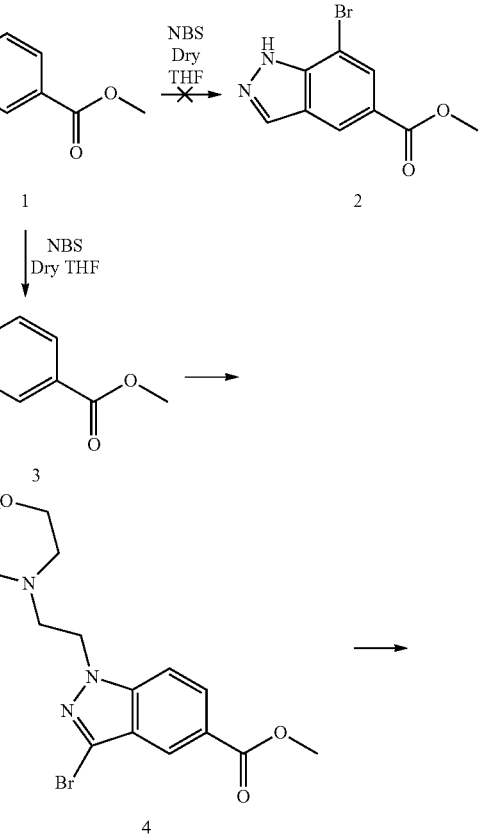

Experimental Procedure

Step 1: Compound 8 was prepared according to the procedure as described in Example 3, compound 11.

Step 7: To a solution of compound 8 (30 mg, 0.064 mmol) in THF was added Et$_3$N (26 mg, 0.28 mmol), and iodomethane (20 mg, 0.14 mmol). The reaction was stirred at r.t. for 1 hour, quenched with H$_2$O, and extracted with EA (2×15

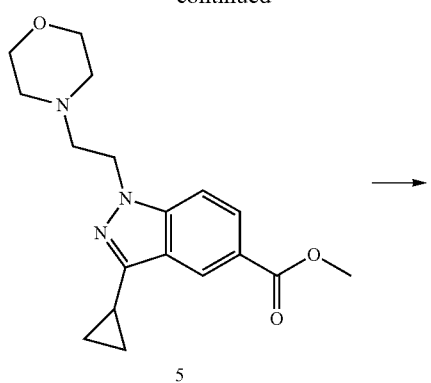

5

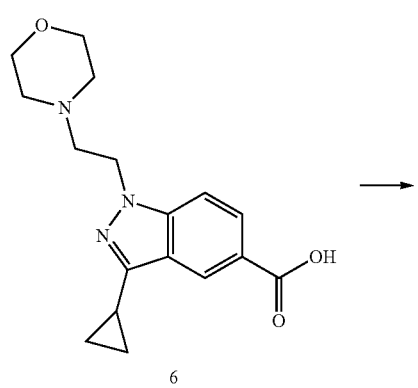

6

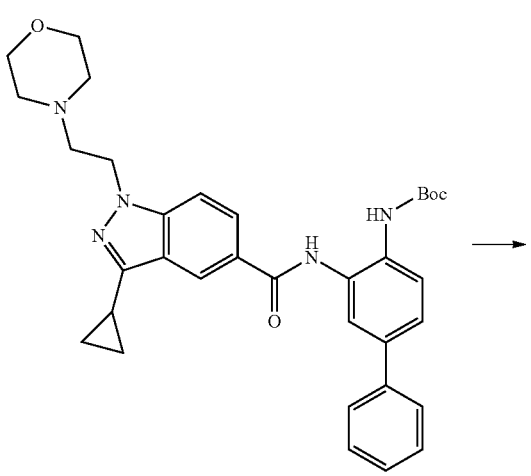

7

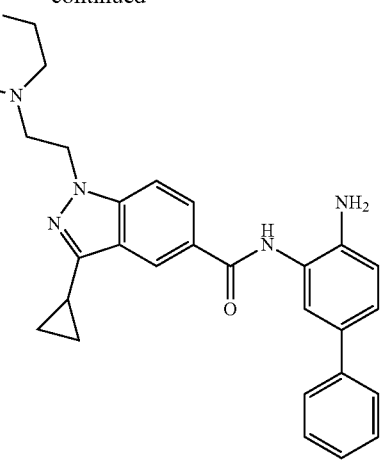

8

Experimental Procedure

Step 1: A mixture of compound 1 (1.7 g, 0.01 mol) and NBS (2.1 g, 0.012 mol) in THF (10 ml) was stirred at r.t. overnight. The mixture was concentrated to yield a residue, to which was added DCM (5 ml). After stirring for 30 min, the solution was filtered to yield compound 2 (1.9 g, 80%) as a light yellow solid.

Step 2: A mixture of compound 2 (1.0 g, 0.004 mol), 4-(2-chloroethyl)morpholine (1.2 g, 0.008 mol) and $Cs_2CO_3$ (2.5 g, 0.016 mol) in DMSO (10 ml) was stirred at r.t. overnight. Water (20 ml) was added to the reaction mixture, and then extracted with EA (50 ml×2). The organic layers were combined, dried and concentrated to a residue, which was re-crystallized by PE (10 ml) to afford compound 3 (500 mg, 70%) as a light yellow solid.

Step 3: Compound 8 was prepared according to the procedure as described in Example 1, compound 7. $^1$H NMR (500 MHz, DMSO) δ 9.80 (s, 1H), 8.52 (s, 1H), 7.99 (s, 1H), 7.69 (d, J=8.8 Hz, 1H), 7.56 (dd, J=12.8, 4.7 Hz, 3H), 7.40 (t, J=7.7 Hz, 2H), 7.34 (dd, J=8.3, 2.2 Hz, 1H), 7.25 (d, J=7.3 Hz, 1H), 6.89 (d, J=8.3 Hz, 1H), 5.12 (s, 2H), 4.47 (s, 2H), 3.51 (s, 4H), 2.74 (s, 2H), 2.43 (s, 2H), 2.35 (s, 1H), 1.13-0.95 (m, 4H). LCMS: m/z=482 (M+H)$^+$ A similar reaction scheme is presented in US Patent Publication No. US 2005/130960.

Example 25: Synthesis of N-(2-amino-5-(thiophen-2-yl)phenyl)-2-cyclopropyl-1-(2-morpholinoethyl)-1H-indole-5-carboxamide

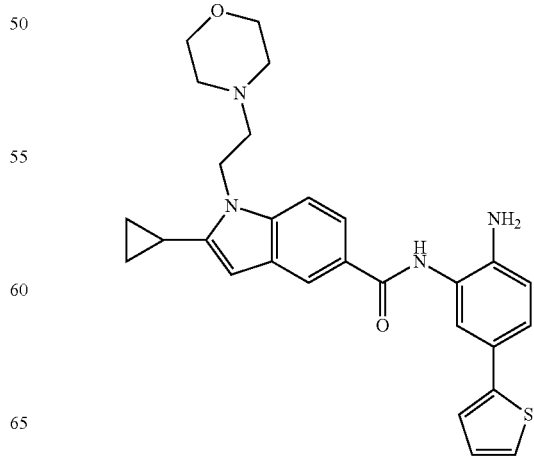

Reaction Scheme

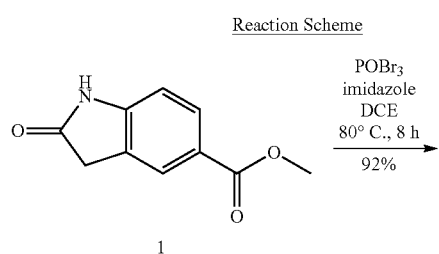

1

POBr₃
imidazole
DCE
80° C., 8 h
92%

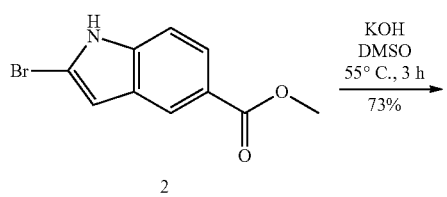

2

KOH
DMSO
55° C., 3 h
73%

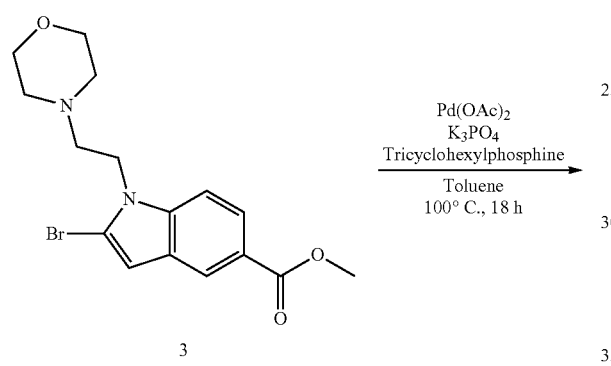

3

Pd(OAc)₂
K₃PO₄
Tricyclohexylphosphine
Toluene
100° C., 18 h

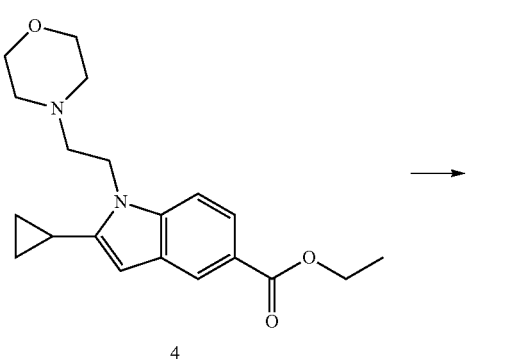

4

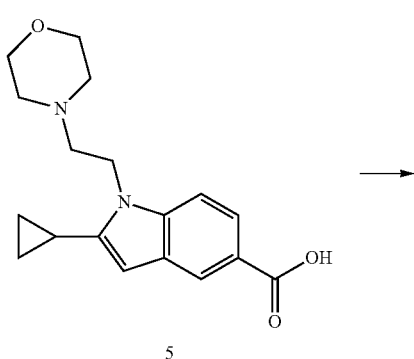

5

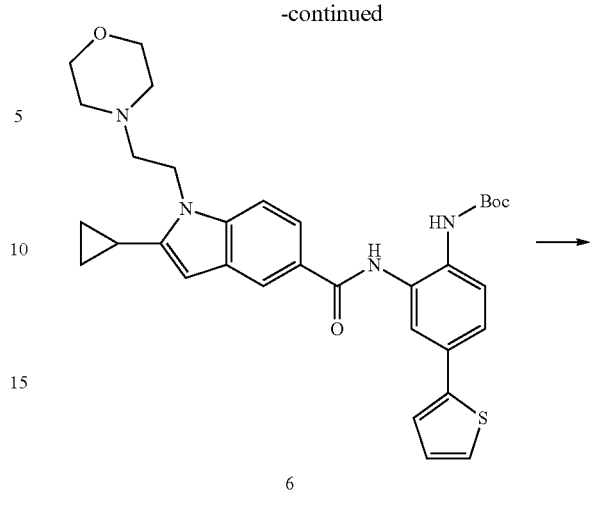

6

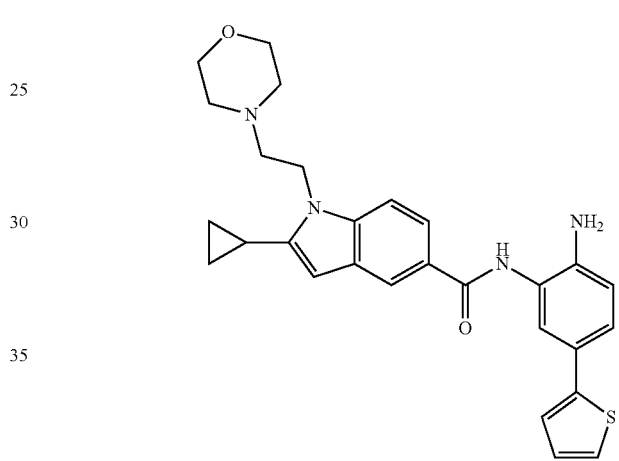

7

Experimental Procedure

Step 1: Compound 2 was prepared according to the procedure as described in Example 20, compound 2.

Step 2: Compound 3 was prepared according to the procedure as described in Example 14, compound 3.

Step 3: Compound 4 was prepared according to the procedure as described in Example 3, compound 6.

Step 4: Compound 5 was prepared according to the procedure as described in Example 3, compound 8.

Step 5: Compound 6 was prepared according to the procedure as described in Example 3, compound 10.

Step 6: Compound 7 was prepared according to the procedure as described in Example 3, compound 11. ¹H NMR (500 MHz, DMSO) δ 9.63 (s, 1H), 8.16 (s, 1H), 7.79-7.73 (m, 1H), 7.51 (d, J=2.1 Hz, 2H), 7.36 (d, J=5.1 Hz, 1H), 7.29 (dd, J=8.3, 2.1 Hz, 1H), 7.25 (d, J=3.5 Hz, 1H), 7.05 (dd, J=5.0, 3.6 Hz, 1H), 6.82 (d, J=8.3 Hz, 1H), 6.24 (s, 1H), 5.12 (s, 2H), 4.43 (s, 2H), 3.57 (s, 5H), 2.77-2.58 (m, 2H), 2.09 (s, 1H), 1.02 (d, J=8.0 Hz, 2H), 0.76 (d, J=4.4 Hz, 2H). LCMS: m/z=487.2 (M+H)+.

Example 26: Synthesis of N-(2-amino-5-(pyridin-4-yl)phenyl)-2-cyclopropyl-1-(2-morpholinoethyl)-1H-indole-5-carboxamide, Compound 004
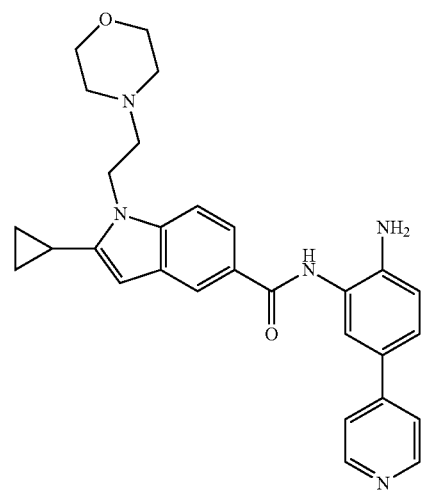 [SMILES: Nc1ccc(-c2ccncc2)cc1NC(=O)c1ccc2c(c1)cc(C1CC1)n2CCN1CCOCC1]
Reaction Scheme
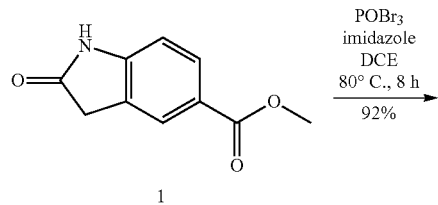
1
POBr₃
imidazole
DCE
80° C., 8 h
92%
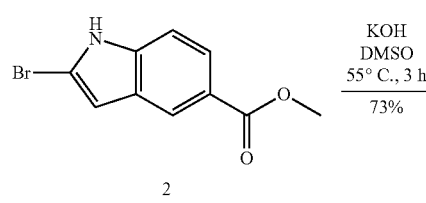
2
KOH
DMSO
55° C., 3 h
73%
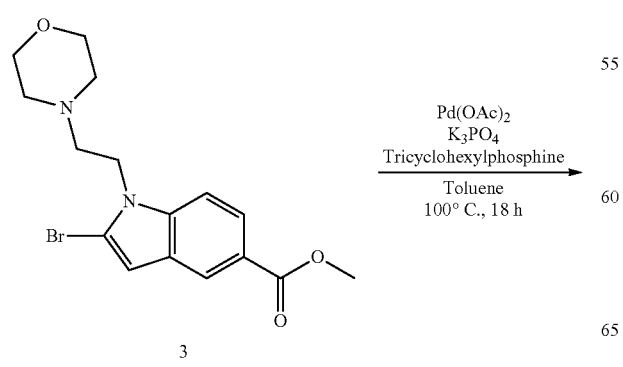
3
Pd(OAc)₂
K₃PO₄
Tricyclohexylphosphine
Toluene
100° C., 18 h
-continued
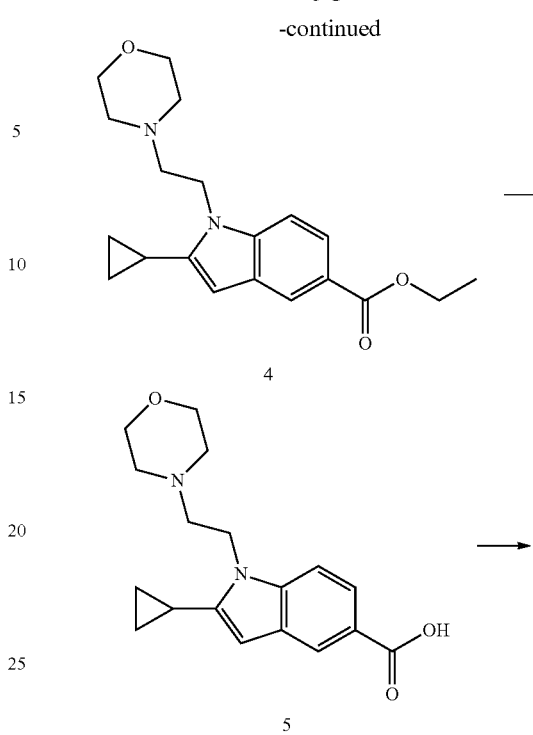
4
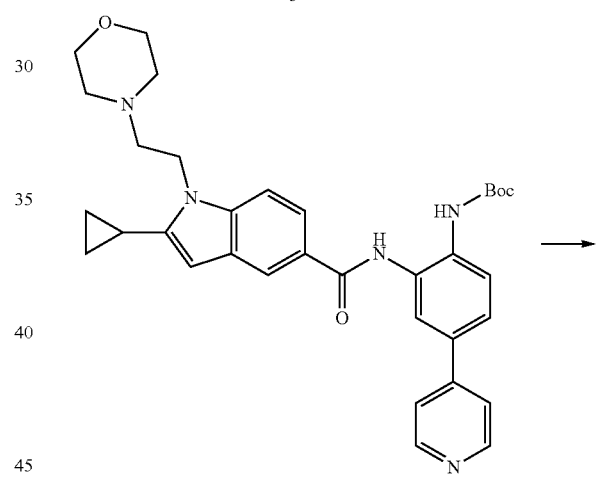
5
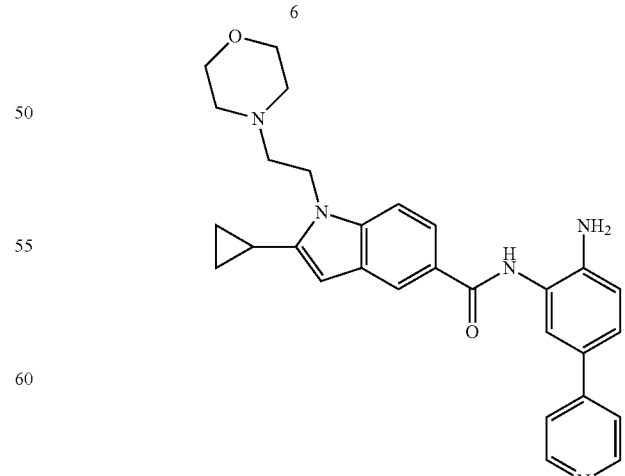
6
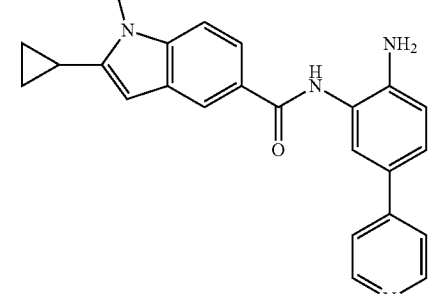
7

Experimental Procedure

Step 1: Compound 2 was prepared according to the procedure as described in Example 20, compound 2.

Step 2: Compound 3 was prepared according to the procedure as described in Example 14, compound 3.

Step 3: Compound 4 was prepared according to the procedure as described in Example 3, compound 6.

Step 4: Compound 5 was prepared according to the procedure as described in Example 3, compound 8.

Step 5: Compound 6 was prepared according to the procedure as described in Example 3, compound 10.

Step 6: Compound 7 was prepared according to the procedure as described in Example 3, compound 11. $^1$H NMR (500 MHz, DMSO) δ 9.68 (s, 1H), 8.62 (s, 2H), 8.21 (s, 1H), 7.99-7.77 (m, 4H), 7.67 (dd, J=8.5, 2.0 Hz, 1H), 7.58 (d, J=8.6 Hz, 1H), 6.93 (d, J=8.5 Hz, 1H), 6.29 (s, 1H), 4.81-4.54 (m, 2H), 3.81 (s, 4H), 3.21 (d, J=40.1 Hz, 6H), 2.11 (t, J=5.0 Hz, 1H), 1.14-1.00 (m, 2H), 0.88-0.71 (m, 2H). LCMS: m/z=482.2 (M+H)+.

Example 27: Synthesis of N-(2-amino-5-(thiophen-2-yl)phenyl)-2-(piperazin-1-yl)quinoline-6-carboxamide, Compound 001

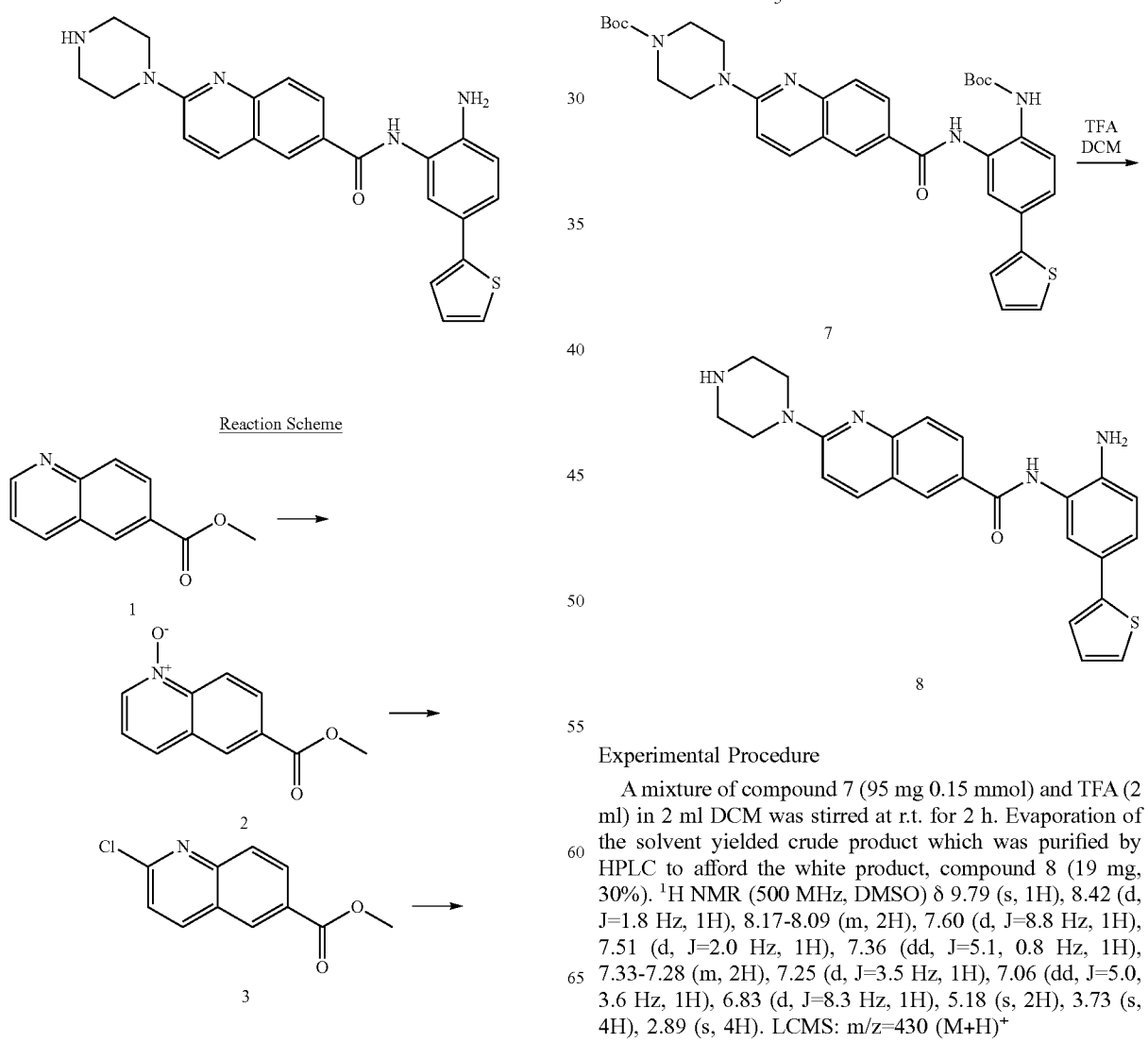

Experimental Procedure

A mixture of compound 7 (95 mg 0.15 mmol) and TFA (2 ml) in 2 ml DCM was stirred at r.t. for 2 h. Evaporation of the solvent yielded crude product which was purified by HPLC to afford the white product, compound 8 (19 mg, 30%). $^1$H NMR (500 MHz, DMSO) δ 9.79 (s, 1H), 8.42 (d, J=1.8 Hz, 1H), 8.17-8.09 (m, 2H), 7.60 (d, J=8.8 Hz, 1H), 7.51 (d, J=2.0 Hz, 1H), 7.36 (dd, J=5.1, 0.8 Hz, 1H), 7.33-7.28 (m, 2H), 7.25 (d, J=3.5 Hz, 1H), 7.06 (dd, J=5.0, 3.6 Hz, 1H), 6.83 (d, J=8.3 Hz, 1H), 5.18 (s, 2H), 3.73 (s, 4H), 2.89 (s, 4H). LCMS: m/z=430 (M+H)$^+$ Example 28: Synthesis of N-(4-amino-[1,1'-biphenyl]-3-yl)-2-cyclopropyl-1-(2-morpholinoethyl)-1H-pyrrolo[2,3-b]pyridine-5-carboxamide

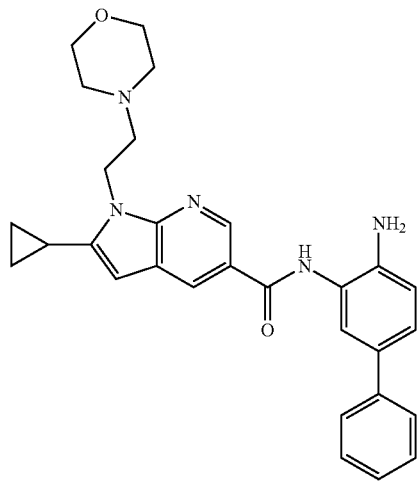 [SMILES: Nc1ccc(-c2ccccc2)cc1NC(=O)c1cnc2c(c1)cc(C1CC1)n2CCN1CCOCC1]

Reaction Scheme

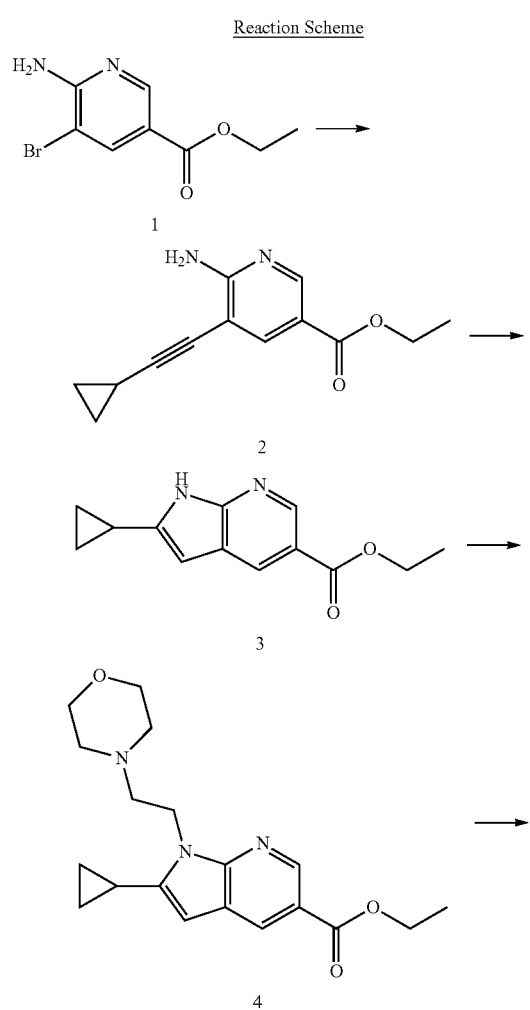

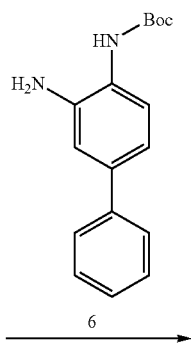

Step 1: A mixture of compound 1 (2.4 g, 0.01 mol), ethynylcyclopropane (6.6 g, 0.1 mol), (dppf)2PdCl2 (1.6 g, 0.002 mol), CuI (750 mg, 0.004 mol) and NEt3 (3.03 g, 0.03 mol) in THF (100 ml) was stirred at 80° C. under $N_2$ atmosphereovernight. The mixture was cooled, filtered, and concentrated to obtain a residue, which was purified by silica gel column to give compound 2 (2.1 g, 90%) as a light yellow solid.

Step 2: A mixture of compound 2 (2.3 g, 0.01 mol), Kt-BuO (3.4 g, 0.03 mol), in DMF (50 ml) was stirred at 80° C. under overnight. The mixture was concentrated to a residue, to which was added brine (100 ml), extracted with EA (200 ml), and washed with water (50 ml). the resulting organic layers were combined, dried and concentrated to give compound 3 (1.8 g, 80%) as a light yellow solid.

Step 3: A mixture of compound 3 (2.3 g, 0.01 mol), 4-(2-chloroethyl)morpholine (3.0 g, 0.02 mol) and $Cs_2CO_3$ in DMF (50 ml) was stirred at r.t. overnight. The mixture was poured into water (100 ml), extracted with EA (200 ml), and washed with water (50 ml). The resulting organic layers were separated, dried, and concentrated to give compound 4 (2.4 g, 70%) as a light yellow solid.

Step 4: A mixture of compound 4 (1.7 g, 0.005 mol) in 4M HCl (50 ml) was stirred at 80° C. overnight. The mixture was concentrated to give compound 5 (1.5 g, 95%) as a light yellow solid.

Step 5: A mixture of compound 5 (315 mg, 1 mmol), compound 6 (284 mg, 1 mmol), HOAT (300 mg, 2.2 mmol), EDCI (400 mg, 2.2 mmol), DMAP (268 mg, 2.2 mmol) in DMF (20 mL) was stirred at 55° C. overnight. The reaction mixture was added to $H_2O$ and extracted with EA (20 ml×3). The resulting organic layers were combined, dried and concentrated to give the crude product which was purified by Prep-TLC to yield compound 7 (290 mg, 50%) as light yellow solid.

Step 6: A mixture of compound 7 (116 mg 0.2 mmol) and TFA (5 mL) in 5 mL DCM was stirred at r.t. for 2 h. The mixture was concentrated to a residue, which was purified by HPLC to afford compound 8 (38 mg, 40%) as light yellow solid. $^1$H NMR (500 MHz, DMSO) δ 9.75 (s, 1H), 8.81 (s, 1H), 8.44 (s, 1H), 7.57 (d, J=8.0 Hz, 3H), 7.39 (t, J=7.7 Hz, 2H), 7.33 (dd, J=8.3, 2.0 Hz, 1H), 7.24 (t, J=7.3 Hz, 1H), 6.87 (d, J=8.3 Hz, 1H), 6.26 (s, 1H), 5.14 (s, 2H), 4.53 (t, J=6.9 Hz, 2H), 3.54 (s, 4H), 2.72 (t, J=6.9 Hz, 2H), 2.49-2.44 (m, 4H), 2.15 (d, J=5.0 Hz, 1H), 1.06 (d, J=4.1 Hz, 2H), 0.81 (d, J=3.5 Hz, 2H). LCMS: m/z=482 (M+H)$^+$.

Example 29: Synthesis N-(2-amino-5-(thiophen-2-yl)phenyl)-8-cyclopropyl-7-morpholinoisoquinoline-3-carboxamide

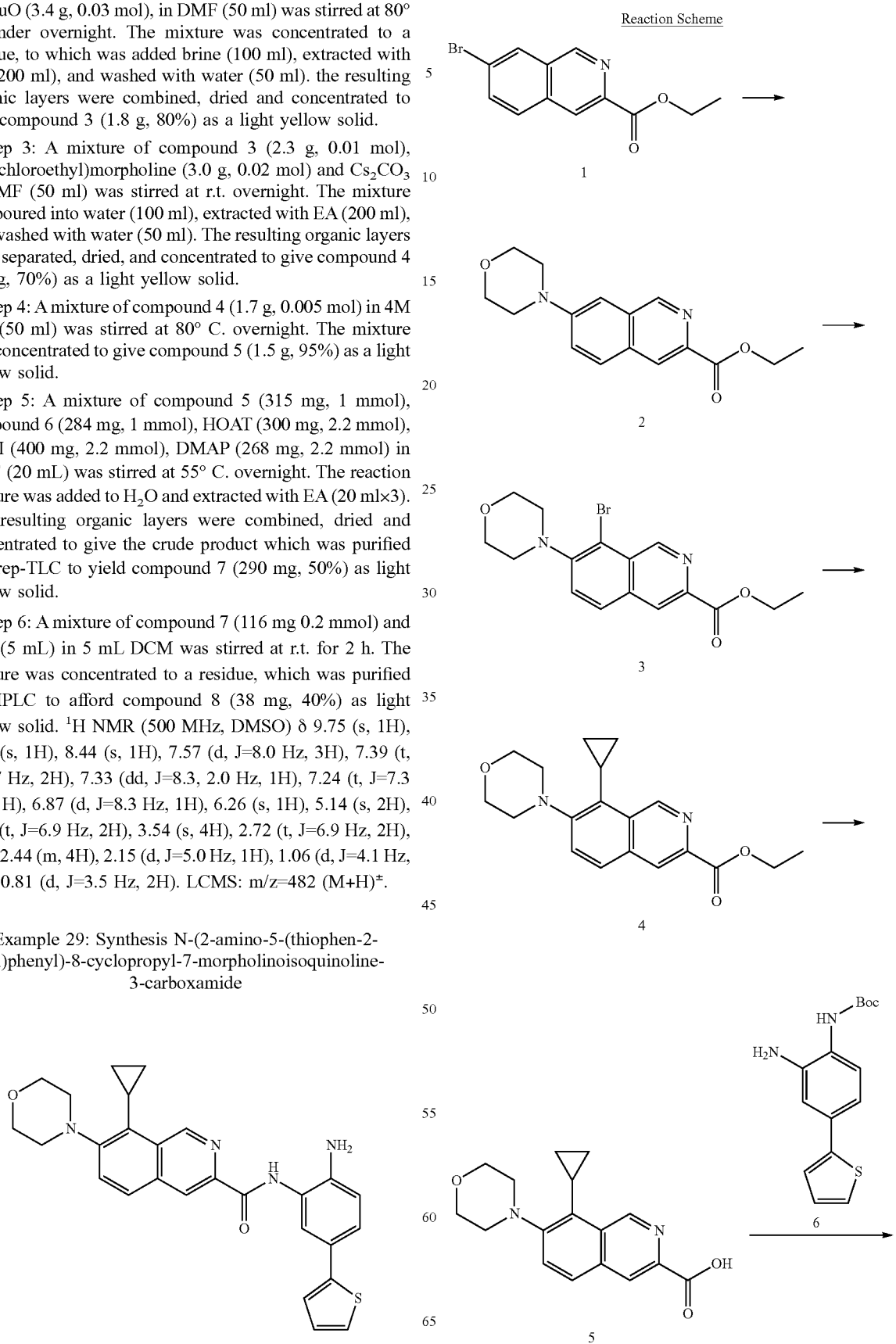

Reaction Scheme

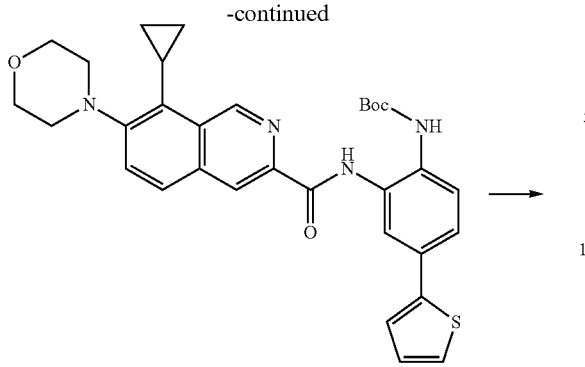

7

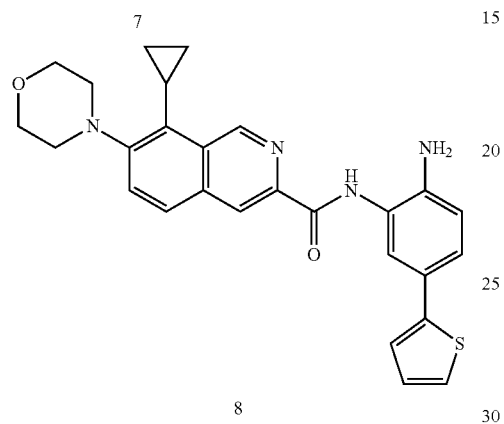

8

Step 1: A mixture of compound 1 (2.8 g, 0.01 mol), morpholine (2.6 g, 0.03 mol), Pd$_2$(dba)$_3$, (916 mg, 0.001 mol), RuPhos (467 mg, 0.001 mol) and Cs$_2$CO$_3$ (9.8 g, 0.03 mol) in toluene (150 ml) was stirred at 95° C. under N$_2$ atmosphere overnight. The mixture was cooled, filtered, and concentrated to obtain a residue, which was purified by silica gel column to give compound 2 (1.9 g, 65%) as a light yellow solid.

Step 2: A solution of compound 2 (1.8 g, 0.005 mol) in DCM (30 ml) was added NBS (885 mg, 0.005 mol) at 0° C. and stirred for 1 h. The mixture was added to H$_2$O (10 ml) and stirred for 30 min. the resulting organic layer was separated, dried, and concentrated to give compound 3 (1.3 g, 70%) as a light yellow solid for use in the next step without purification.

Step 3: A mixture of compound 3 (1.1 g, 0.003 mol), cyclopropyl boronic acid (2.2 g, 0.025 mol), Pd(OAc)$_2$ (56 mg, 0.00025 mol), tricyclohexylphosphine (70 mg, 0.00025 mol) and K$_3$PO$_4$ (1.6 g, 0.0075 mol) in toluene (100 ml) and water (20 ml) was stirred at 100° C. under N$_2$ atmosphere overnight. The mixture was cooled, filtered, and concentrated to obtain a residue, which was purified by silica gel column to give compound 4 (636 mg, 65%) as a light yellow solid.

Step 4: A solution of compound 4 (652 g, 2 mmol) in EtOH (20 ml) and THF (20 ml) was added 2M NaOH (10 ml) and stirred at 60° C. for 3 h. The mixture was concentrated to get a residue, which was purified by flash column to give compound 5 (536 mg, 90%) as a light yellow solid.

Step 5: A mixture of compound 5 (298 mg, 1 mmol), compound 6 (290 mg, 1 mmol), HOAT (150 mg, 1.1 mmol), EDCI (200 mg, 1.1 mmol), DIPEA (300 mg, 2.3 mmol) in DMF (40 ml) was stirred at 55° C. overnight. The reaction mixture was then added to H$_2$O and extracted with EA (20 ml×3), separated, dried, and concentrated to give a crude product purified by Prep-TLC to give the desired product, compound 7 (256 mg, 45%) as a light yellow solid.

Step 6: A mixture of compound 7 (114 mg 0.2 mmol) and TFA (5 ml) in 5 ml DCM was stirred at r.t. for 2 h. The mixture was concentrated to a residue, which was purified by HPLC to afford compound 8 (37 mg, 40%) as light yellow solid. $^1$H NMR (400 MHz, DMSO) δ 10.37 (s, 1H), 9.87 (s, 1H), 8.55 (s, 1H), 8.06 (d, J=8.9 Hz, 1H), 7.95 (d, J=2.1 Hz, 1H), 7.63 (d, J=9.0 Hz, 1H), 7.42 (d, J=5.1 Hz, 1H), 7.38-7.29 (m, 2H), 7.09 (dd, J=5.1, 3.6 Hz, 1H), 6.98 (d, J=8.3 Hz, 1H), 3.84 (s, 4H), 3.25 (s, 4H), 2.26 (m, 1H), 1.31 (d, J=4.1 Hz, 2H), 0.79 (d, J=4.1 Hz, 2H). LCMS: m/z=471 (M+H)$^+$.

Example 30: Synthesis of N-(4-amino-[1,1'-biphenyl]-3-yl)-8-cyclopropyl-7-(piperazin-1-yl)isoquinoline-3-carboxamide

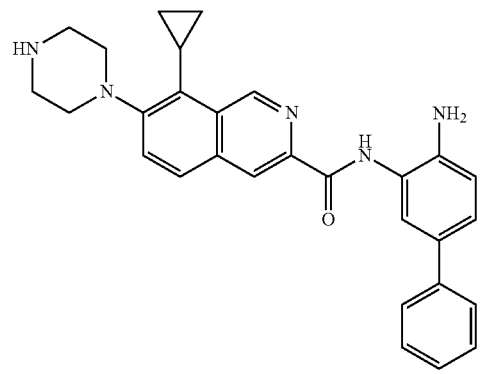 [SMILES: Nc1ccc(-c2ccccc2)cc1NC(=O)c1cc2ccc(N3CCNCC3)c(C3CC3)c2cn1]

Reaction Scheme

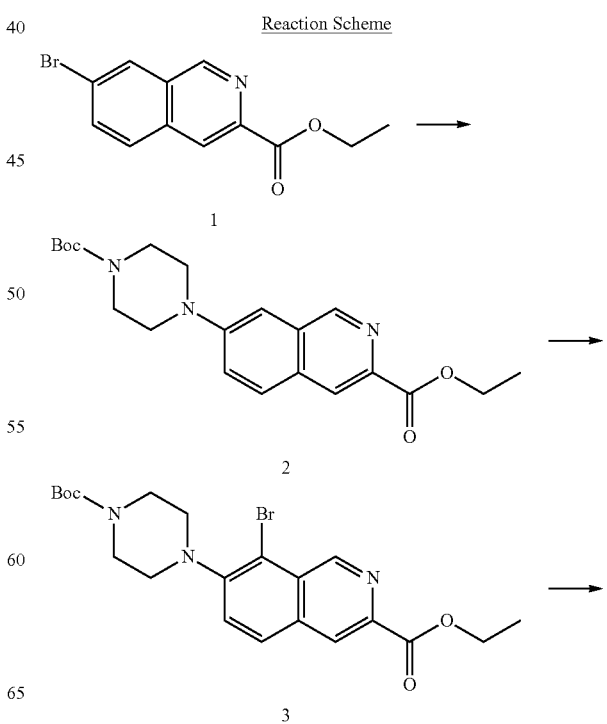

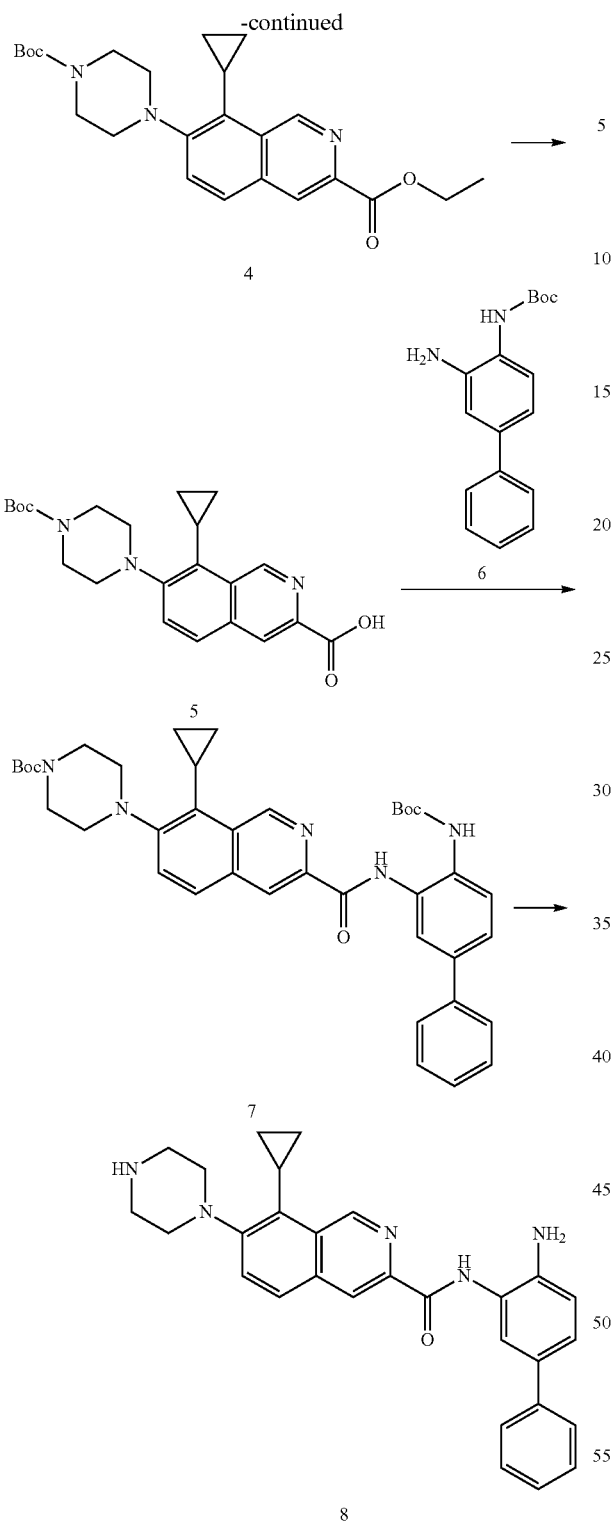

Step 2: A solution of compound 2 (1.9 g, 0.005 mol) in DCM (30 ml) was added NBS (885 mg, 0.005 mol) at 0° C. and stirred for 1 h. The reaction mixture was added to H₂O (10 ml), stirred for 30 min. The resulting organic layer was separated, dried, and concentrated to give compound 3 (1.6 g, 70%) as a light yellow solid to be used in the next step without purification.

Step 3: A mixture of compound 3 (1.2 g, 0.0025 mol), cyclopropyl boronic acid (2.2 g, 0.025 mol), Pd(OAc)₂ (56 mg, 0.00025 mol), tricyclohexylphosphine (70 mg, 0.00025) and K₃PO₄ (1.6 g, 0.0075 mol) in toluene (100 ml) and water (20 ml) was stirred at 100° C. under N₂ atmosphere overnight. The mixture was cooled, filtered, and concentrated to obtain a residue, which was purified by silica gel column to give compound 4 (1.1 g, 80%) as a light yellow solid.

Step 4: A solution of compound 4 (1.1 g, 0.0025 mol) in EtOH (20 ml) and THF (20 ml) was added 2M NaOH (10 ml) and stirred at 60° C. for 3 h. The mixture was concentrated to a residue, to which was added aq.sat.citric acid (10 ml). The mixture eas extracted with EA (150 ml), washed with water (50 ml), and the resulting organic layers were combined, dried and concentrated to give compound 5 (890 g, 90%) as a light yellow solid.

Step 5: A mixture of compound 5 (397 mg, 1 mmol), compound 6 (284 mg, 1.2 mmol), HOAT (150 mg, 1.1 mmol), EDCI (200 mg, 1.1 mmol), DIPEA (300 mg, 2.3 mmol) in DMF (40 ml) was stirred at 55° C. for overnight. The reaction mixture was poured into H₂O and extracted with EA (20 ml×3), separated, dried, and concentrated to give a crude product. Purification by Prep-TLC yielded the desired product, compound 7 (345 mg, 52%) as a light yellow solid.

Step 6: A mixture of compound 7 (132 mg 0.2 mmol) and TFA (5 ml) in 5 ml DCM was stirred at r.t. for 2 h. The mixture was concentrated to a residue, which was purified by HPLC to afford compound 8 (32 mg, 32%) as light yellow solid. ¹H NMR (500 MHz, DMSO) δ 10.28 (s, 1H), 9.87 (s, 1H), 8.54 (s, 1H), 8.05 (d, J=9.0 Hz, 1H), 7.96 (d, J=1.9 Hz, 1H), 7.60 (m, 3H), 7.41 (t, J=7.7 Hz, 2H), 7.35-7.22 (m, 2H), 6.94 (d, J=8.3 Hz, 1H), 5.11 (s, 2H), 3.33 (s, 4H), 3.08 (s, 4H), 2.25 (s, 1H), 1.30 (d, J=4.2 Hz, 2H), 0.77 (d, J=4.2 Hz, 2H). LCMS: m/z=464 (M+H)⁺

Example 31: Synthesis N-(2-amino-5-(thiophen-2-yl)phenyl)-8-cyclopropyl-7-(piperazin-1-yl)isolquinoline-3-carboxamide

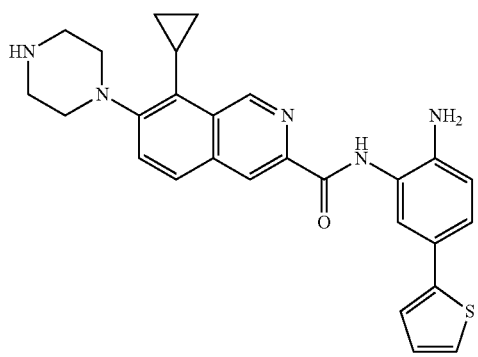 [SMILES: Nc1ccc(-c2cccs2)cc1NC(=O)c1cc2ccc(N3CCNCC3)c(C3CC3)c2cn1]

Step 1: A mixture of compound 1 (2.8 g, 0.01 mol), tert-butyl piperazine-1-carboxylate (6.6 g, 0.03 mol), Pd₂(dba)₃ (916 mg, 0.001 mol), RuPhos (467 mg, 0.001 mol) and Cs₂CO₃ (9.8 g, 0.03 mol) in tolune (150 mL) was stirred at 95° C. under N₂ atmosphere for overnight. The mixture was cooled, filtered, and concentrated to obtain a residue, which was purified by silica gel column to give compound 2 (3.3 g, 87%) as a light yellow solid.

4H), 2.24 (t, J=5.7 Hz, 1H), 1.29 (d, J=8.2 Hz, 2H), 0.76 (d, J=4.1 Hz, 2H). LCMS: m/z=470 (M+H)+

Example 32: Synthesis of N-(4-amino-[1,1'-biphenyl]-3-yl)-8-cyclopropyl-7-morpholinoquinoline-3-carboxamide

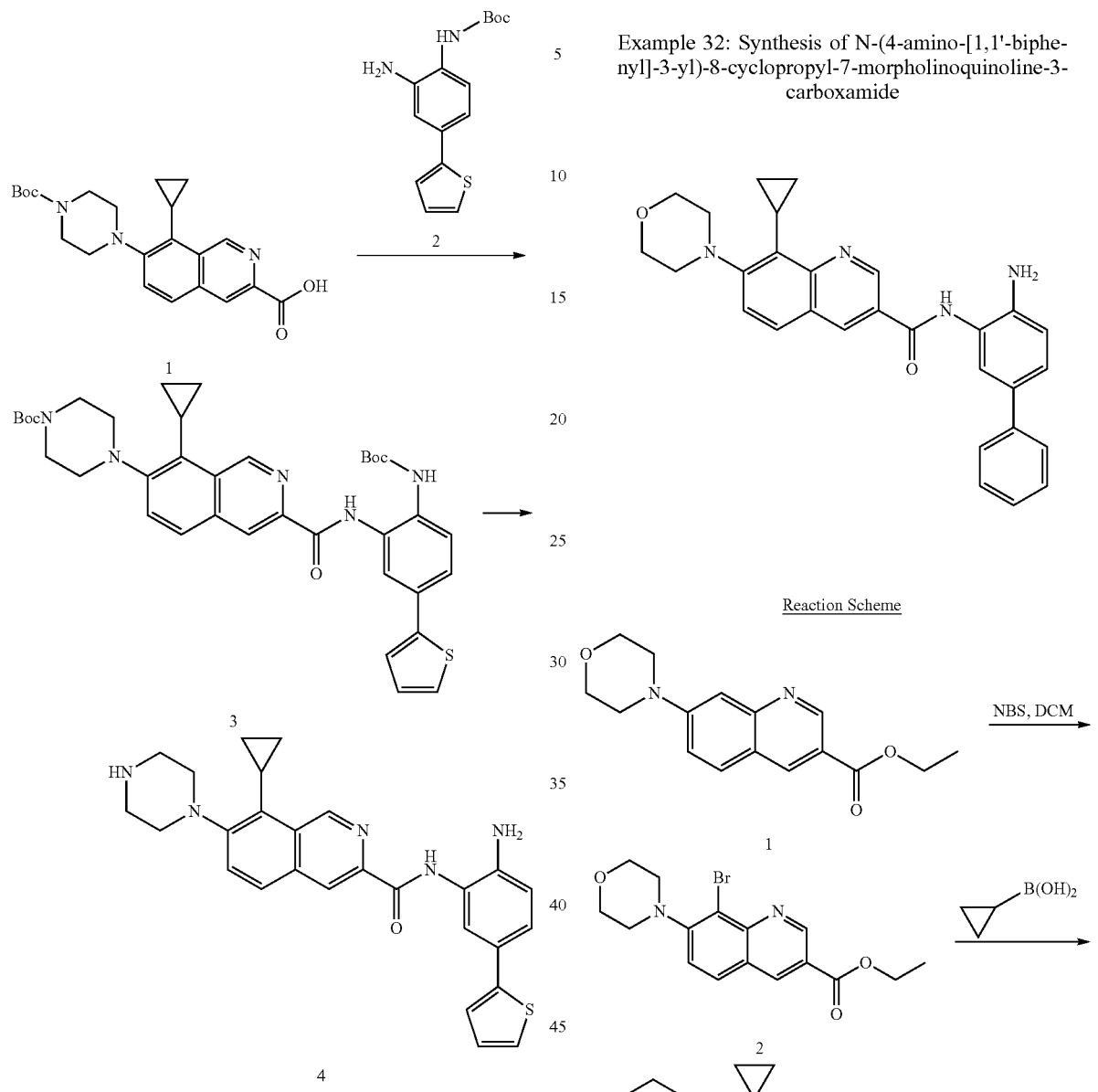

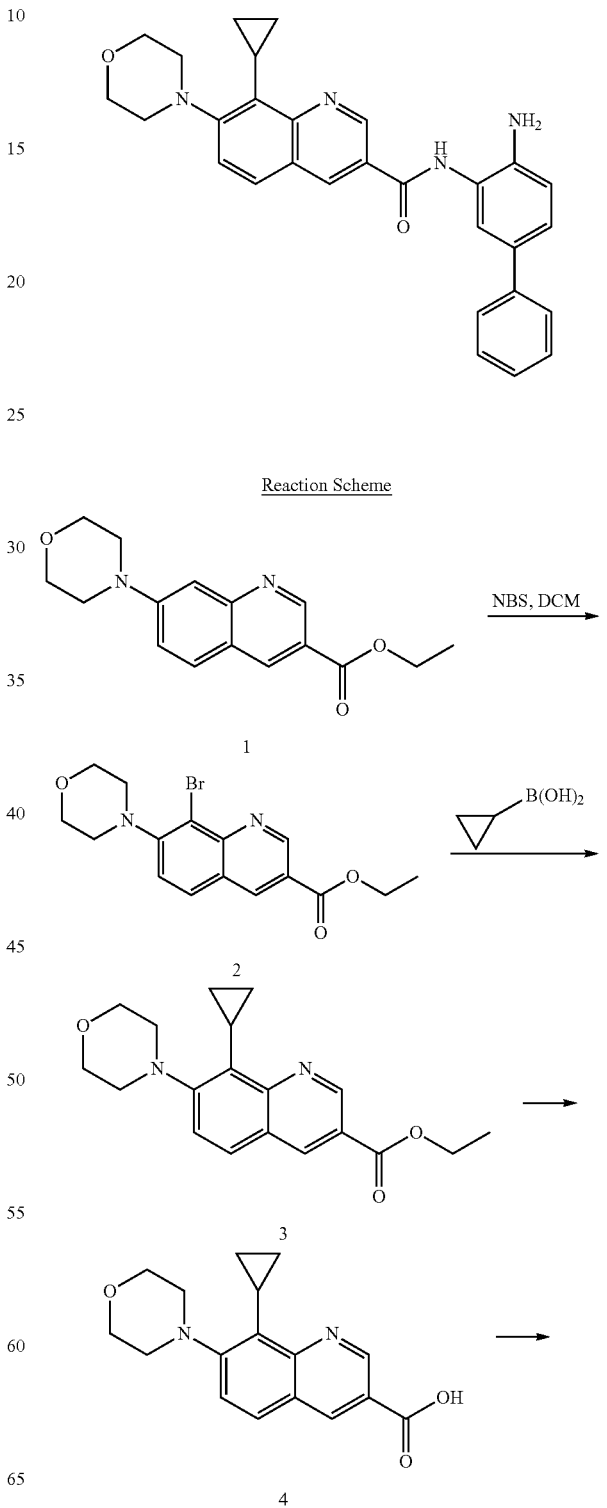

Step 1: A mixture of compound 1 (397 mg, 1 mmol), compound 2 (290 mg, 1.2 mmol), HOAT (150 mg, 1.1 mmol), EDCI (200 mg, 1.1 mmol), DIPEA (300 mg, 2.3 mmol) in DMF (40 ml) was stirred at 55° C. for overnight. The reaction mixture was poured into H$_2$O and extracted with EA (20 ml×3), separated, dried, and concentrated to give a crude product. Purification by Prep-TLC yielded the desired product, compound 7 (375 mg, 56%) as a light yellow solid.

Step 2: A mixture of compound 3 (167 mg, 0.25 mmol) and TFA (5 ml) in 5 ml DCM was stirred at r.t. for 2 h. The mixture was concentrated to a residue, which was purified by HPLC to afford compound 4 (47 mg, 40%) as light yellow solid. $^1$H NMR (500 MHz, DMSO) δ 10.25 (s, 1H), 9.85 (s, 1H), 8.52 (s, 1H), 8.02 (d, J=9.0 Hz, 1H), 7.95 (d, J=2.0 Hz, 1H), 7.60 (d, J=9.0 Hz, 1H), 7.38 (d, J=4.3 Hz, 1H), 7.32-7.24 (m, 2H), 7.07 (dd, J=5.0, 3.6 Hz, 1H), 6.88 (d, J=8.3 Hz, 1H), 5.16 (s, 2H), 3.16 (s, 4H), 3.00-2.88 (m,

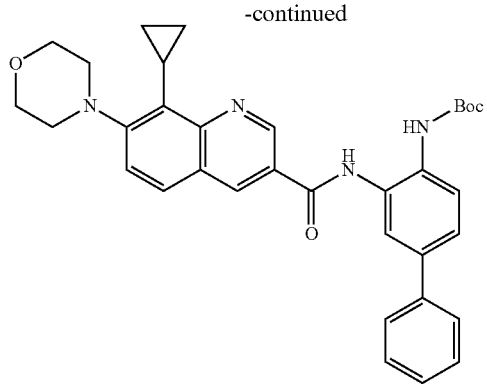

5

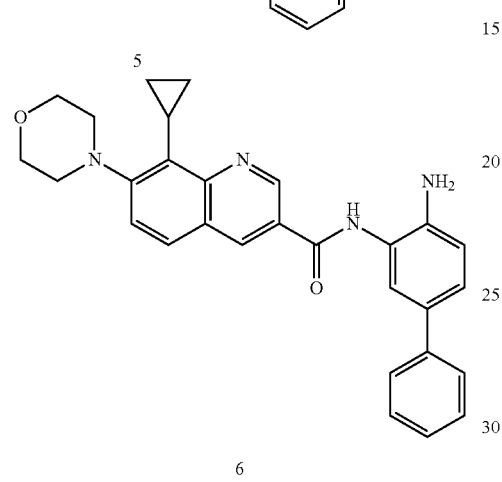

6

Step 1: To a solution of compound 1 (600 mg, 2.1 mmol) in DCM (25 ml) was added NBS (485 mg, 2.7 mmol) at 0° C. The reaction solution was then stirred at r.t. for 2 h. andquenched with sat. NaHCO₃, washed with water, brine, dried and concentrated to get a residue, which was purified by column (PE/EA=4/1) to give compound 2 (600 mg, 73%) as a yellow oil.

Step 2: A mixture of compound 2 (440 mg, 1.2 mmol), cyclopropylboronic acid (310 mg, 3.6 mmol), Pd(OAc)₂ (27 mg, 0.12 mmol), tricyclohexylphosphine (34 mg, 0.12 mmol), K₃PO₄ (763 mg, 3.6 mmol), toluene (8 ml) and H₂O (4 ml) was heated to 100° C. and stirred overnight under N₂ atmosphere. The reaction was filtered and concentrated to give a residue, which was purified by column (PE/EA=3/1) to give compound 3 (220 mg, 59%) as a yellow oil.

Step 3: A mixture of compound 3 (200 mg, 0.61 mmol) and HCl (2.0 M in H₂O, 5 ml) was heated to 100° C. and stirred overnight. The mixture was concentrated to give compound 4 (200 mg, crude) as a light yellow solid.

Step 4: A mixture of compound 4 (200 mg, 0.67 mmol), EDCI (257 mg, 1.34 mmol), HOAT (182 mg, 1.34 mmol), DIPEA (1.0 ml), and DMF (5 ml) was stirred at r.t. for 10 min. The amine (152 mg, 0.54 mmol) was then added, and the mixture was heated to 60° C. and stirred overnight. H₂O was added to the reaction mixture and the resulting precipitate was collected to afford compound 5 (210 mg, 69%) as a yellow oil.

Step 5: To a solution of compound 5 (100 mg, 0.33 mmol) in dioxane (4 ml) was added HCl (4.0 ml, 4.0 M in dioxane) at 0° C., and then the reaction solution was stirred at r.t. overnight. The mixture was concentrated to a residue, which was purified by prep-HPLC to afford compound 6 (37 mg, 45%) as yellow solid. ¹H NMR (500 MHz, DMSO) δ 9.94 (s, 1H), 9.34 (s, 1H), 8.83 (s, 1H), 7.90 (d, J=8.9 Hz, 1H), 7.64-7.53 (m, 3H), 7.49 (d, J=8.9 Hz, 1H), 7.44-7.31 (m, 3H), 7.25 (t, J=7.3 Hz, 1H), 6.89 (d, J=8.3 Hz, 1H), 5.21 (s, 2H), 3.84 (d, J=3.7 Hz, 4H), 3.20 (s, 4H), 2.36 (dd, J=12.8, 7.0 Hz, 1H), 1.14 (dd, J=34.8, 5.9 Hz, 4H). LCMS: m/z=465 (M+H)⁺

Example 33: Synthesis of N-(4-amino-[1,1'-biphenyl]-3-yl)-1-(2-morpholinoethyl)-1H-indazole-5-carboxamide

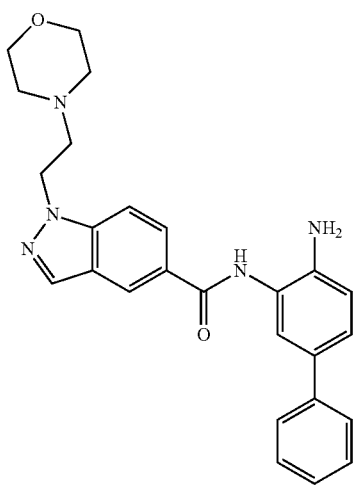 [SMILES: Nc1ccc(-c2ccccc2)cc1NC(=O)c1ccc2c(cnn2CCN2CCOCC2)c1]

Reaction Scheme

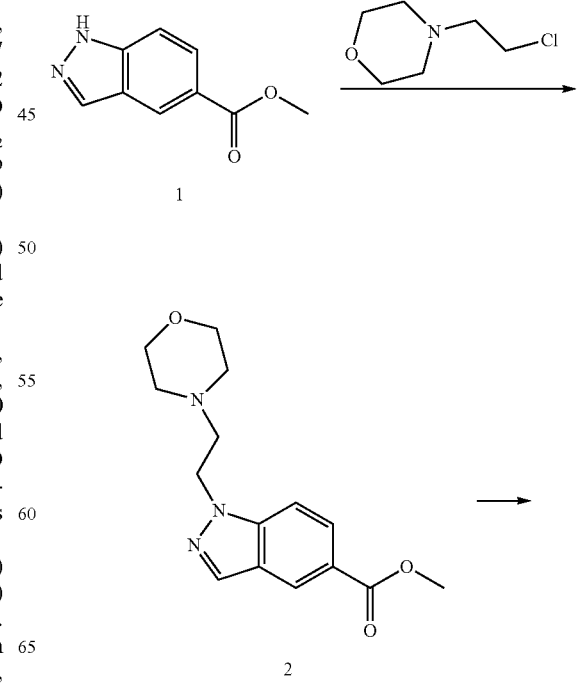

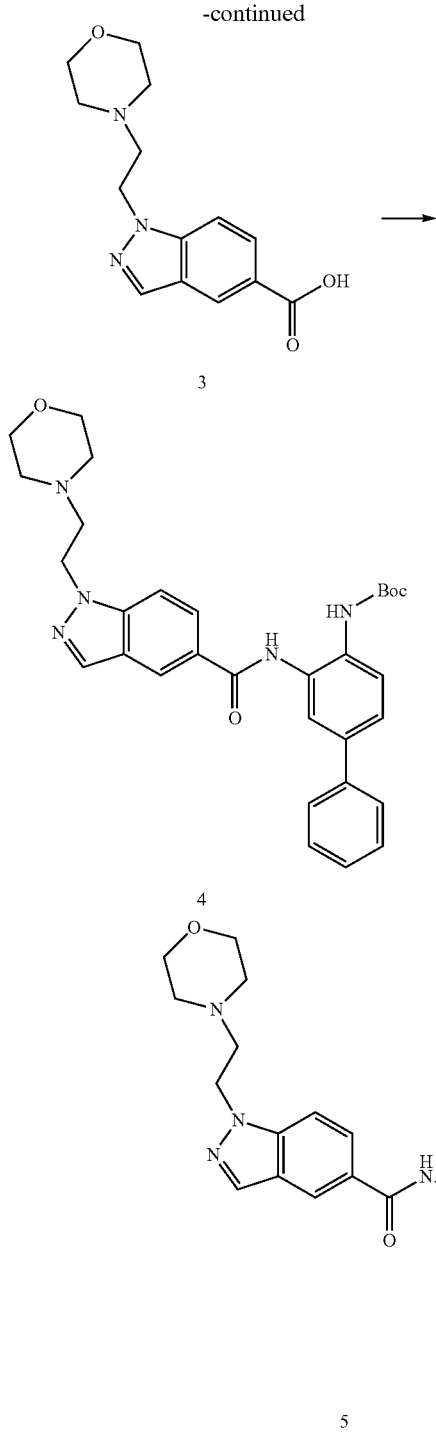

Step 3: A mixture of compound 3 (150 mg, 0.54 mmol), EDCI (207 mg, 1.08 mmol), HOAT (147 mg, 1.08 mmol), DIPEA (1.0 ml) and DMF (5 ml) was stirred at r.t. for 10 min. The amine (125 mg, 0.44 mmol) was added, and then the mixture was heated to 60° C. and stirred overnight. H$_2$O was added to the reaction mixture and the precipitate was collected to afford compound 4 (120 mg, 34%) as a brown solid.

Step 4: To a solution of compound 4 (100 mg, 0.18 mmol) in DCM (5 ml) was added TFA (1.0 ml) at 0° C., and the reaction solution was stirred at r.t. for 45 mins. The reaction mixture was concentrated to a residue, which was purified by prep-HPLC to afford compound 5 (40 mg, 41%) as a white solid. $^1$H NMR (500 MHz, DMSO) δ 9.77 (s, 1H), 8.50 (s, 1H), 8.25 (s, 1H), 8.02 (d, J=8.9 Hz, 1H), 7.80 (d, J=8.8 Hz, 1H), 7.57 (d, J=7.9 Hz, 3H), 7.40 (t, J=7.7 Hz, 2H), 7.34 (dd, J=8.3, 1.9 Hz, 1H), 7.24 (t, J=7.3 Hz, 1H), 6.88 (d, J=8.3 Hz, 1H), 5.11 (s, 2H), 4.58 (t, J=6.4 Hz, 2H), 3.54-3.42 (m, 4H), 2.79 (t, J=6.4 Hz, 2H), 2.42 (s, 4H). LCMS: m/z=442 (M+H)$^+$ Example 34: Synthesis of N-(4-amino-[1,1'-biphenyl]-3-yl)-2-(2-morpholinoethyl)-2H-indazole-5-carboxamide

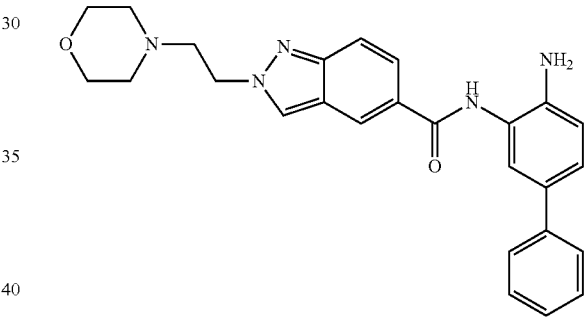

Reaction Scheme

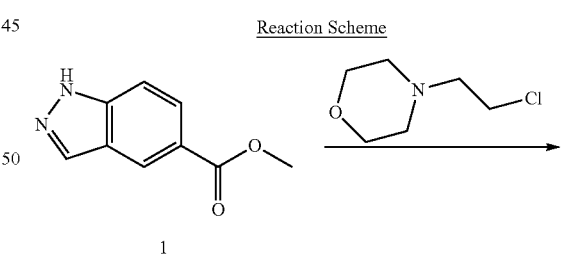

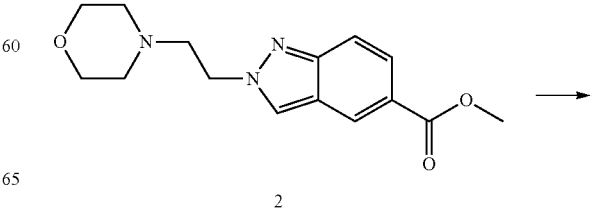

Step 1: A mixture of 1 (591 mg, 3.366 mmol), 4-(2-chloroethyl)morpholine (1.0 mg, 6.72 mmol), KOH (376 mg, 6.72 mmol) in DMSO (10 ml) was stirred at 25° C. overnight. The mixture was extracted with EA. The combined organic layers were washed with water and brine, dried, and concentrated to give a residue, which was purified by column (PE/EA=1/1) to give compound 2 (600 mg, 78%) as a white solid.

Step 2: A mixture of compound 2 (400 mg, 1.38 mmol) and HCl (2.0 M in H$_2$O, 10 ml) was heated to 100° C. and stirred overnight. The mixture was concentrated to give compound 3 (370 mg, 95%) as a white solid.

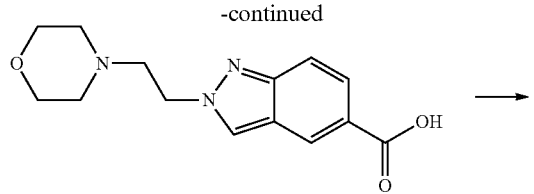

3

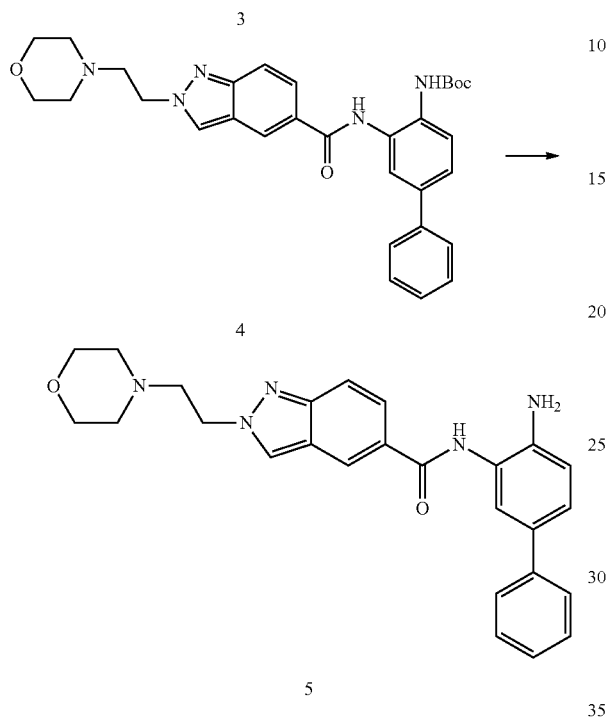

Step 1: A mixture of compound 1 (591 mg, 3.366 mmol), 4-(2-chloroethyl)morpholine (1.0 mg, 6.72 mmol), KOH (376 mg, 6.72 mmol) in DMSO (10 ml) was stirred at 25° C. overnight. The mixture was extracted with EA. The resulting combined organic layers were washed with water and brine, dried, and concentrated to a residue, which was purified by column chromatography (PE/EA=1/1) to give compound 2 (246 mg, 19%) as a white solid.

Step 2: A mixture of compound 2 (400 mg, 1.38 mmol) and HCl (2.0 M in H$_2$O, 10 ml) was heated to 100° C. for overnight. The mixture was concentrated to give compound 3 (370 mg, 95%) as a white solid.

Step 3: A mixture of compound 3 (150 mg, 0.54 mmol), EDCI (207 mg, 1.08 mmol), HOAT (147 mg, 1.08 mmol), DIPEA (1.0 ml) and DMF (5 ml) was stirred at r.t. for 10 min. The amine (125 mg, 0.44 mmol) was added, and then the mixture was heated to 60° C. and stirred overnight. Water was added to the mixture and the precipitate was collected to afford compound 4 (120 mg, 34%) as a brown solid.

Step 4: To a solution of compound 4 (100 mg, 0.18 mmol) in DCM (5 ml) was added TFA (1.0 ml) at 0° C. The reaction solution was warmed to r.t. and stirred for 45 mins. The mixture was concentrated to a residue, which was purified by prep-HPLC to afford compound 5 (40 mg, 41%) as a white solid. $^1$H NMR (500 MHz, DMSO) δ 9.72 (s, 1H), 8.63 (s, 1H), 8.50 (s, 1H), 7.83 (d, J=9.2 Hz, 1H), 7.68 (d, J=9.0 Hz, 1H), 7.57 (d, J=7.6 Hz, 3H), 7.40 (t, J=7.6 Hz, 2H), 7.33 (dd, J=8.3, 1.9 Hz, 1H), 7.24 (t, J=7.2 Hz, 1H), 6.88 (d, J=8.3 Hz, 1H), 5.10 (s, 2H), 4.59 (t, J=6.3 Hz, 2H), 3.59-3.45 (m, 4H), 2.88 (t, J=6.4 Hz, 2H), 2.44 (s, 4H). LCMS: m/z=442 (M+H)$^+$ Example 35: Synthesis of N-(4-amino-[1,1'-biphenyl]-3-yl)-1-(2-morpholinoethyl)-2-oxoindoline-5-carboxamide

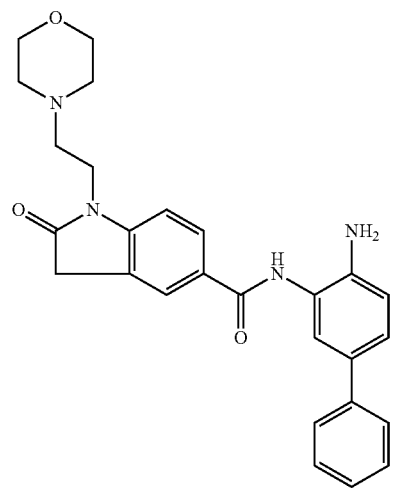 [SMILES: Nc1ccc(-c2ccccc2)cc1NC(=O)c1ccc2c(c1)CC(=O)N2CCN1CCOCC1]

Reaction Scheme

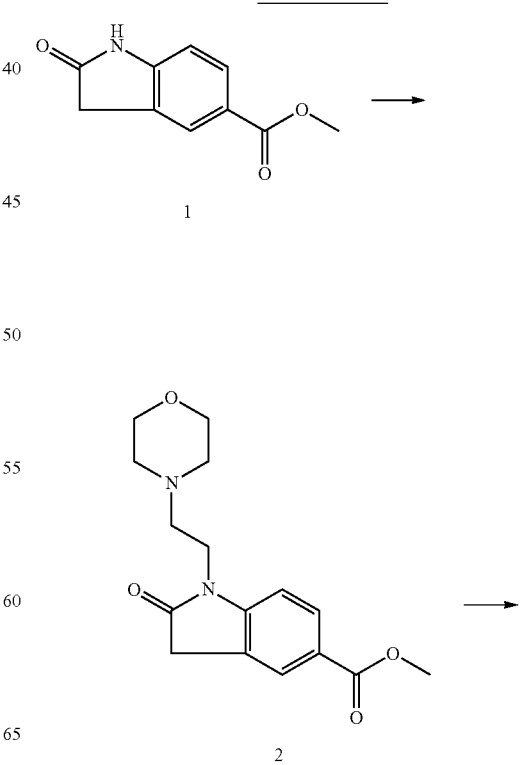

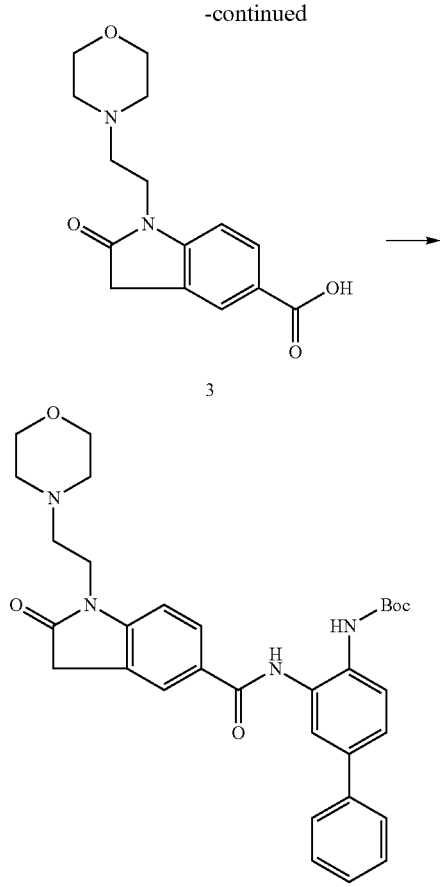

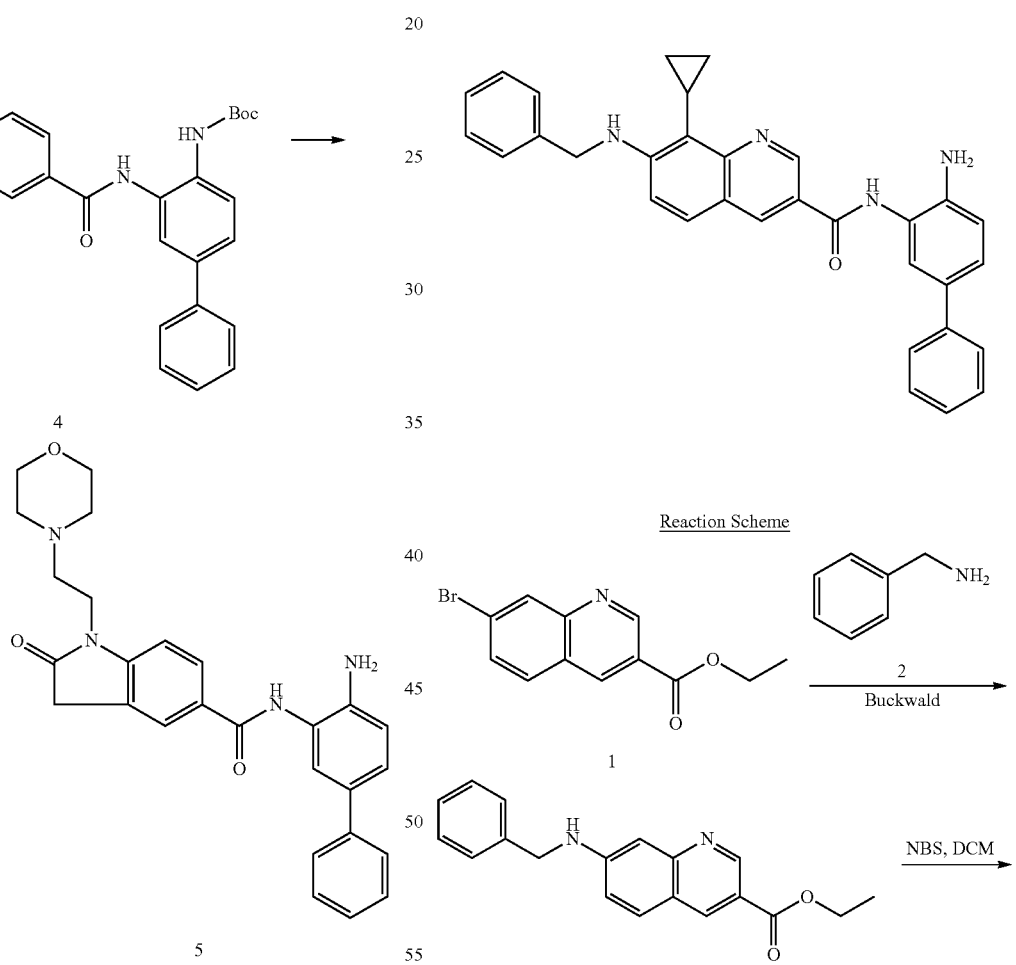

DIPEA (1.0 ml) and DCM (5 ml) was stirred at r.t. for 10 min. The amine-R1 (50 mg, 0.17 mmol) was added, and the resulting mixture was stirred at r.t. overnight. The mixture was concentrated and purified by Prep-HPLC to afford compound 4 (35 mg, 37%) as a white solid.

Step 4: To a solution of compound 4 (35 mg, 0.06 mmol) in DCM (2 ml) was added TFA (0.4 ml) at 0° C. The reaction solution was then warmed to r.t. and stirred for 45 min. The reaction mixture was concentrated to afford compound 5 (28 mg, 98%) as brown solid. $^1$H NMR (500 MHz, DMSO) δ 9.81 (s, 1H), 8.05 (d, J=8.1 Hz, 1H), 8.00 (s, 1H), 7.56 (dd, J=14.9, 4.6 Hz, 2H), 7.47-7.34 (m, 2H), 7.27 (t, J=8.1 Hz, 1H), 6.96 (d, J=8.3 Hz, 1H), 4.14 (t, J=6.2 Hz, 2H), 4.02 (s, 2H), 3.66 (d, J=28.0 Hz, 4H), 3.45 (s, 2H), 3.18 (d, J=14.5 Hz, 2H). LCMS: m/z=457 (M+H)$^+$ Example 36: Synthesis of N-(4-amino-[1,1'-biphenyl]-3-yl)-7-(benzylamino)-8-cyclopropyliquinoline-3-carboxamide Step 1: To a solution of compound 1 (100 mg, 0.52 mmol) in AcN (3 ml) was added K$_2$CO$_3$ (108 mg, 0.78 mmol) at 85° C. followed by stirring for 5 hours. The reaction mixture was concentrated and purified by gel chromatography (PE: EA=3:1) to afford compound 2 (30 mg, 19%).

Step 2: A mixture of compound 2 (560 mg, 1.84 mmol) and HCl (2.0 M in H$_2$O, 10 ml) was heated to 100° C. for overnight. The mixture was concentrated to give compound 3 (500 mg, 94%) as a light yellow solid.

Step 3: A mixture of compound 3 (50 mg, 0.17 mmol), EDCI (70 mg, 0.34 mmol), HOAT (50 mg, 0.34 mmol),

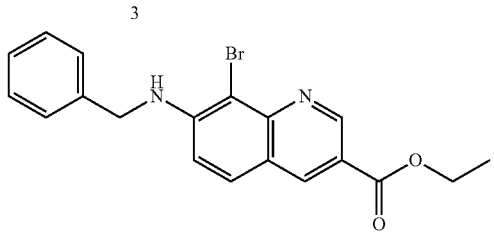

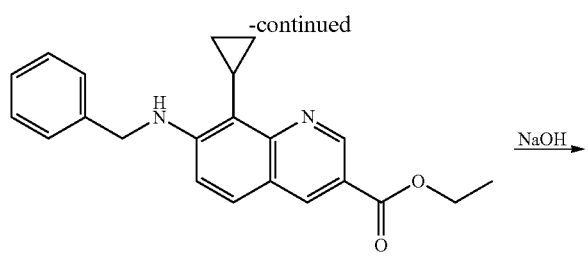
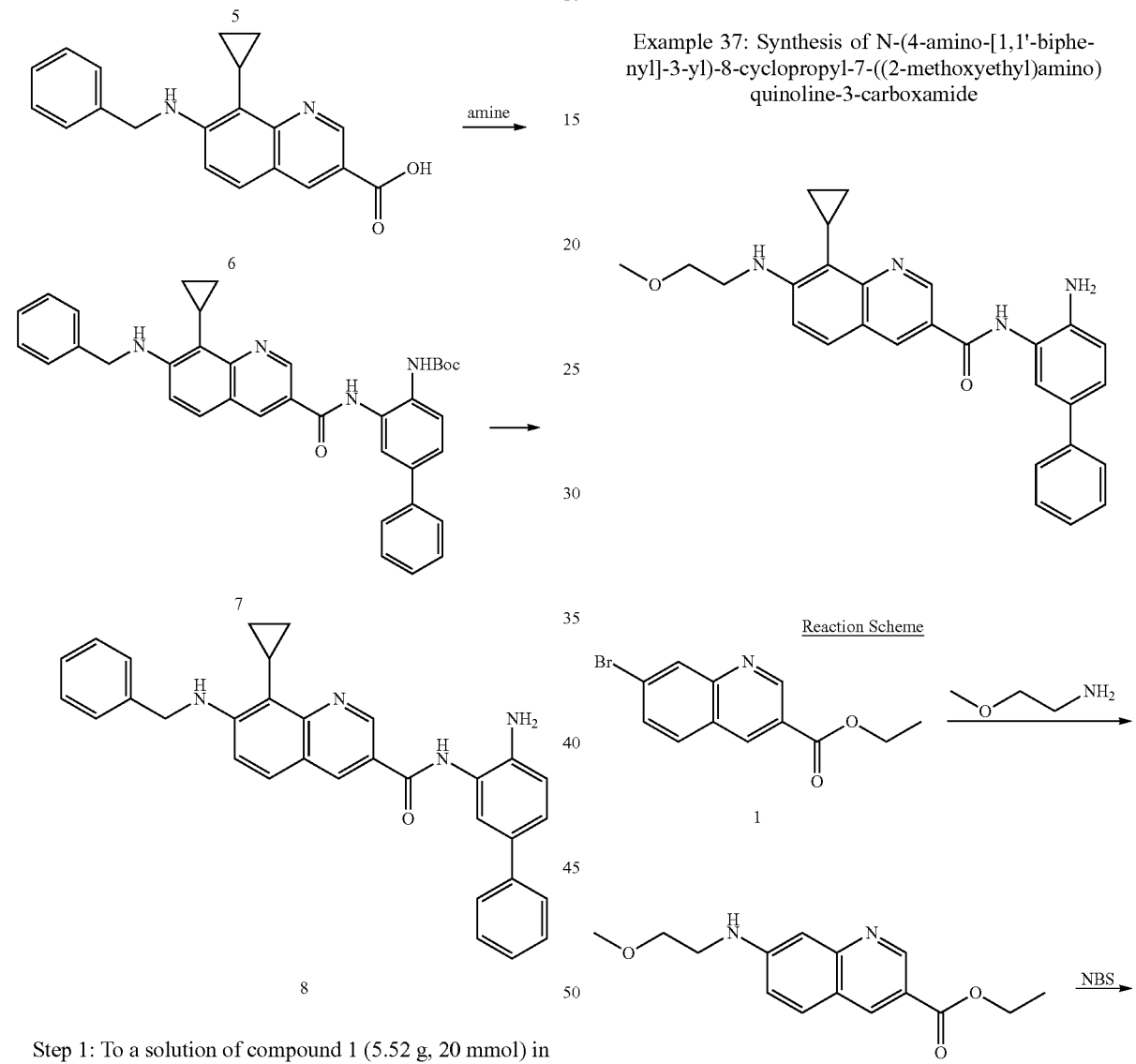

Step 6: Compound 8 was prepared according to the procedure as described in Example 1, compound 6. $^1$H NMR (500 MHz, DMSO) δ 9.79 (s, 1H), 9.24 (s, 1H), 8.64 (d, J=2.0 Hz, 1H), 7.71 (d, J=9.0 Hz, 1H), 7.56 (d, J=7.1 Hz, 3H), 7.40 (dd, J=13.6, 7.5 Hz, 4H), 7.34 (t, J=7.5 Hz, 3H), 7.28-7.20 (m, 2H), 7.08 (d, J=9.0 Hz, 1H), 6.88 (d, J=8.3 Hz, 1H), 6.62 (t, J=6.3 Hz, 1H), 5.15 (s, 2H), 4.65 (d, J=6.1 Hz, 2H), 3.29 (s, 2H), 1.74 (d, J=5.7 Hz, 1H), 1.25 (t, J=7.1 Hz, 2H), 0.73 (d, J=4.1 Hz, 2H). LCMS: m/z=485 (M+H)$^+$ Example 37: Synthesis of N-(4-amino-[1,1'-biphenyl]-3-yl)-8-cyclopropyl-7-((2-methoxyethyl)amino)quinoline-3-carboxamide

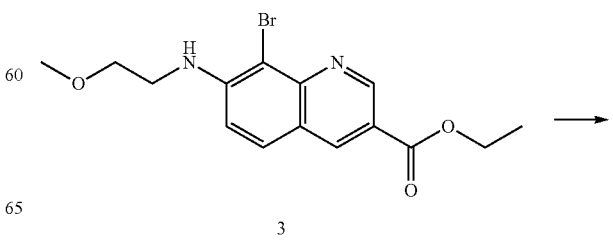

Step 1: To a solution of compound 1 (5.52 g, 20 mmol) in toluene (40 ml) was added compound 2 (4.3 g. 40 mmol), RuPhos (930 mg, 2 mmol), Pd$_2$(dba)$_3$ (575 mg, 1 mmol), under N$_2$. The reaction mixture was heated to 100° C. and stirred overnight. Then, the reaction mixture was extracted with EA (2×50 ml), and the combined organic layers were washed with aqueous NaCl, dried by Na$_2$SO$_4$, and concentrated to give compound 3 (4.28 g, 70%).

Step 2: Compound 4 was prepared according to the procedure as described in Example 32, compound 2.

Step 3: Compound 5 was prepared according to the procedure as described in Example 32, compound 3.

Step 4: Compound 6 was prepared according to the procedure as described in Example 32, compound 4.

Step 5: Compound 7 was prepared according to the procedure as described in Example 32, compound 5.

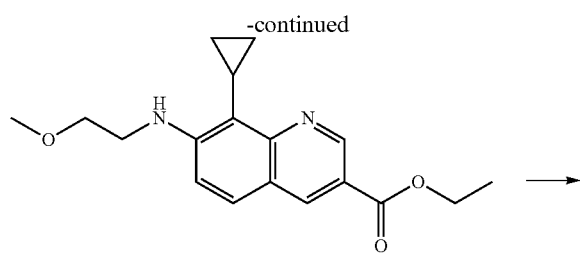

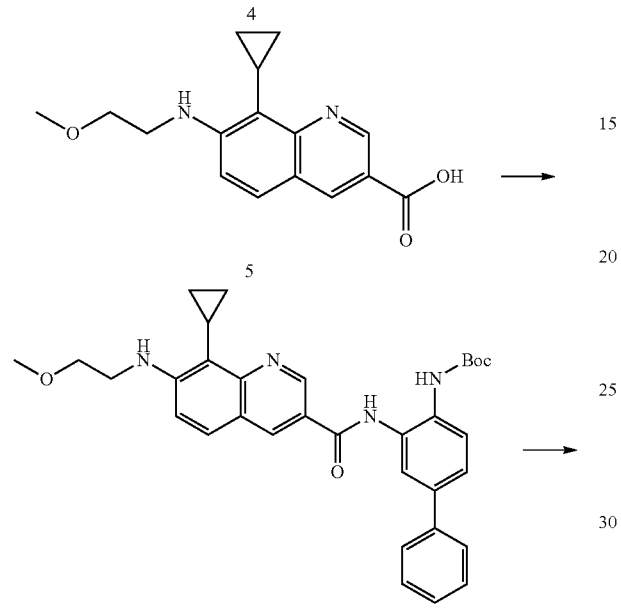

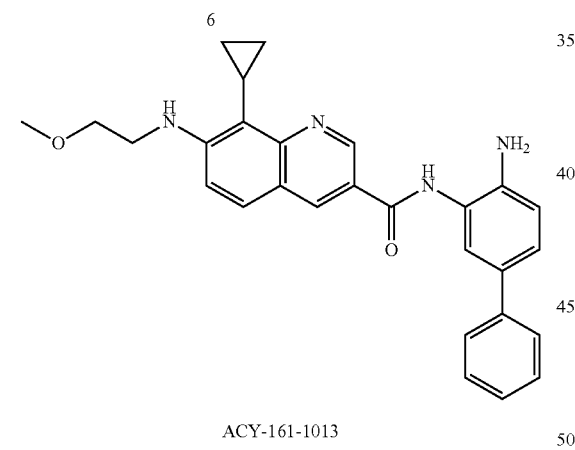

ACY-161-1013

Experimental Procedure

Step 1: To a solution of compound 1 (2 g, 7.17 mmol) in Dioxane (20 ml) was added 2-methoxyethanamine (806 mg, 10.75 mmol) and DIPEA (1.85 g, 14.34 mmol). The reaction mixture was stirred 100° C. for 6 hours, poured into H$_2$O, filtered, and dried to give compound 2 (1.37 g, 70%).

Step 2: Compound 3 was prepared according to the procedure as described in Example 32, compound 2.

Step 3: Compound 4 was prepared according to the procedure as described in Example 32, compound 3.

Step 4: Compound 5 was prepared according to the procedure as described in Example 32, compound 4.

Step 5: Compound 6 was prepared according to the procedure as described in Example 32, compound 5.

Step 6: Compound 7 was prepared according to the procedure as described in Example 32, compound 6. $^1$H NMR (500 MHz, DMSO) δ 9.85 (s, 1H), 9.24 (s, 1H), 8.76 (s, 1H), 7.86 (d, J=8.7 Hz, 1H), 7.57 (d, J=7.7 Hz, 3H), 7.46-7.17 (m, 6H), 6.89 (d, J=8.3 Hz, 1H), 6.45 (m, 1H), 5.19 (s, 1H), 3.58 (dd, J=17.0, 4.8 Hz, 5H), 1.67 (t, J=5.6 Hz, 1H), 1.20 (d, J=7.6 Hz, 2H), 0.64 (d, J=4.3 Hz, 2H). LCMS: m/z=453 (M+H)$^+$

Example 38: Synthesis of N-(4-amino-[1,1'-biphenyl]-3-yl)-1-(2-(4-methylpiperazin-1-yl)ethyl)-1H-indole-5-carboxamide

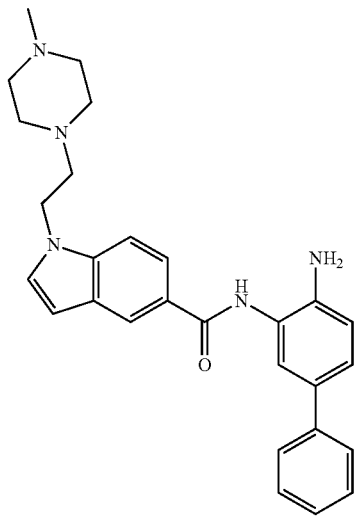 [SMILES: CN1CCN(CCn2ccc3cc(C(=O)Nc4cc(-c5ccccc5)ccc4N)ccc32)CC1]

Reaction Scheme

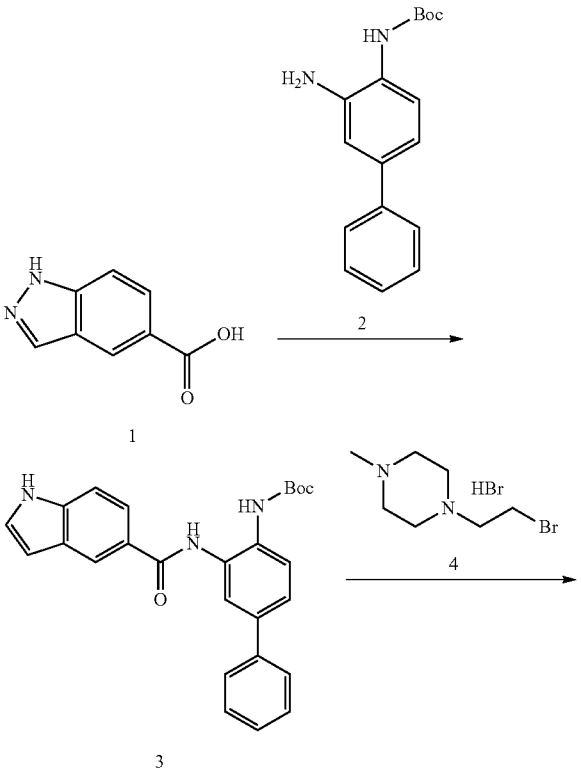

123
-continued

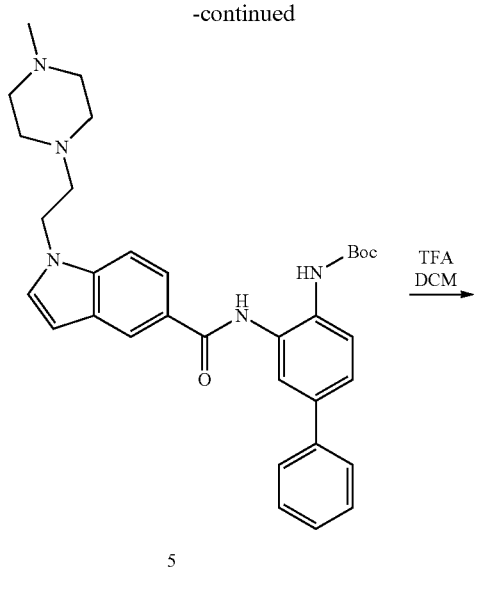

5

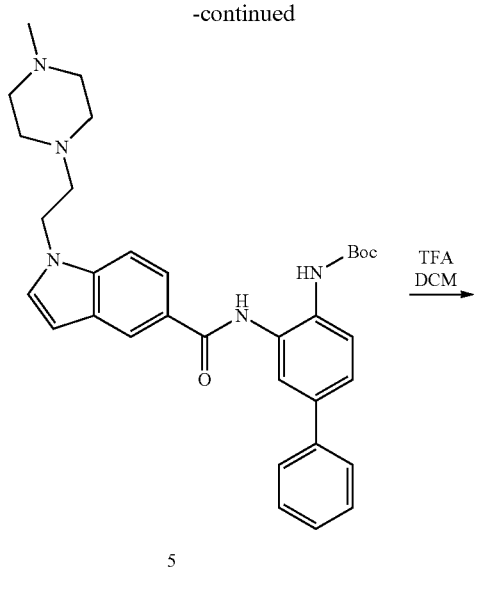

6

Step 1: Compound 3 was prepared according to the procedure as described in Example 1, compound 5.

Step 2: To a solution of compound 3 (240 mg, 0.55 mmol) in DMF was added compound 4 (300 mg, 0.82 mmol). NaH (133 mg, 5.5 mmol) was added at 0° C. at which point the reaction mixture was warmed to r.t and stirred overnight. The reaction was quenched with H$_2$O, extracted with EA (2×20 ml) and the combined organic layers were purified by gel chromatography (DCM:MeOH=20:1) to afford the desired product, compound 5 (190 mg, 62%).

Step 3: Compound 6 was prepared according to the procedure as described in Example 33, compound 6. $^1$H NMR (500 MHz, DMSO) δ 9.65 (s, 1H), 8.29 (s, 1H), 7.81 (d, J=8.6 Hz, 1H), 7.58 (t, J=9.3 Hz, 4H), 7.50 (d, J=2.5 Hz, 1H), 7.40 (t, J=7.6 Hz, 2H), 7.32 (d, J=8.3 Hz, 1H), 7.24 (t, J=7.1 Hz, 1H), 6.88 (d, J=8.3 Hz, 1H), 6.57 (s, 1H), 5.06 (d, J=11.8 Hz, 2H), 4.32 (t, J=6.2 Hz, 2H), 2.67 (t, J=6.3 Hz, 2H), 2.43 (s, 4H), 2.27 (s, 4H), 2.13 (s, 3H). LCMS: m/z=454 (M+H)$^+$

124

Example 39: Synthesis of methyl 4-(2-(5-((4-amino-[1,1'-biphenyl]-3-yl)carbamoyl)-1H-indol-1-yl)ethyl)piperazine-1-carboxylate

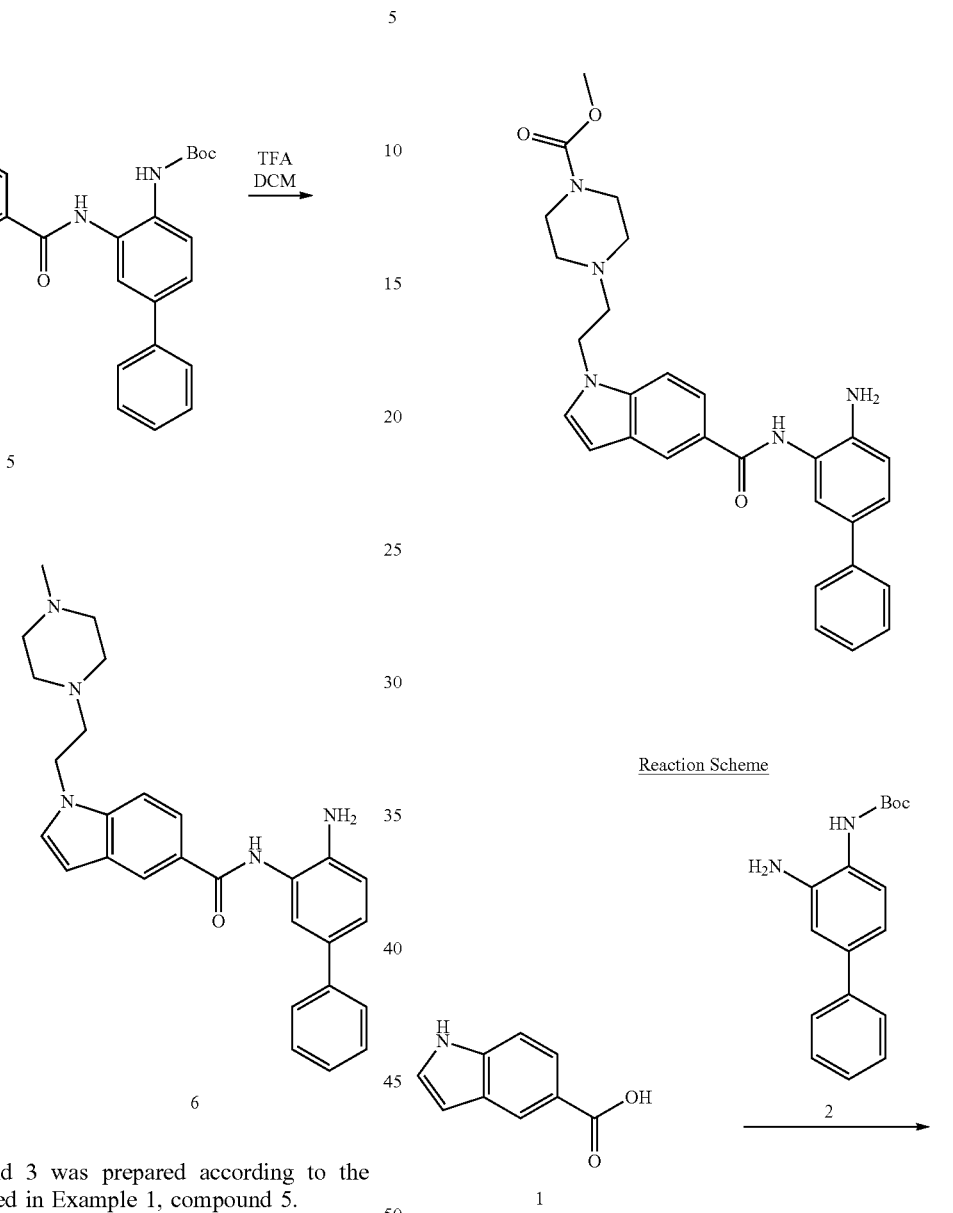

Reaction Scheme

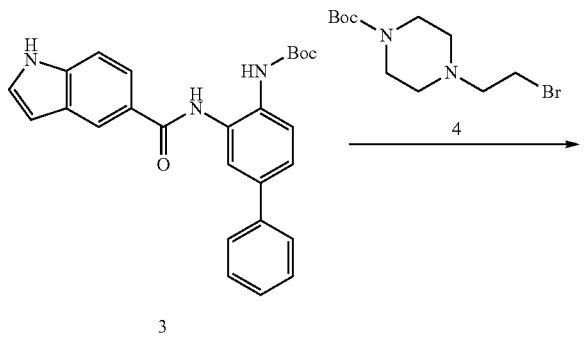

-continued

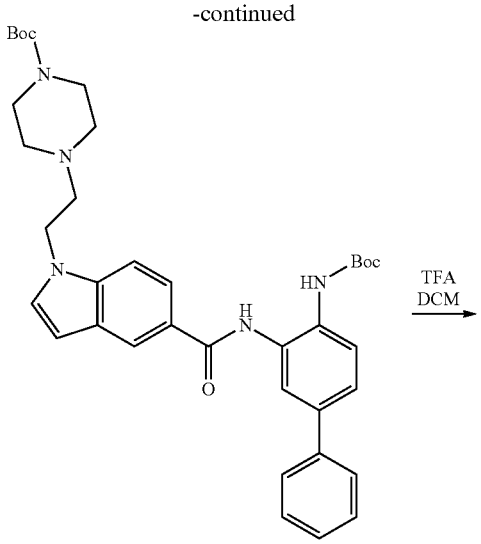

5

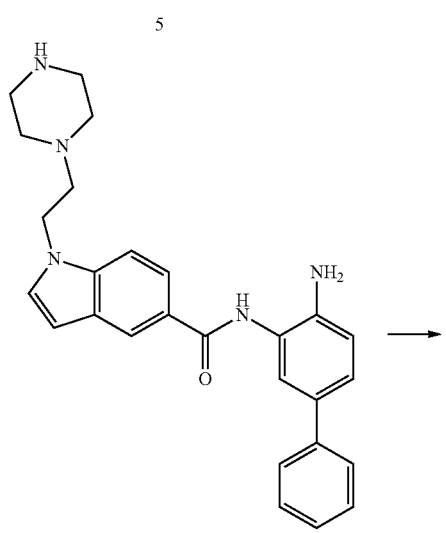

6

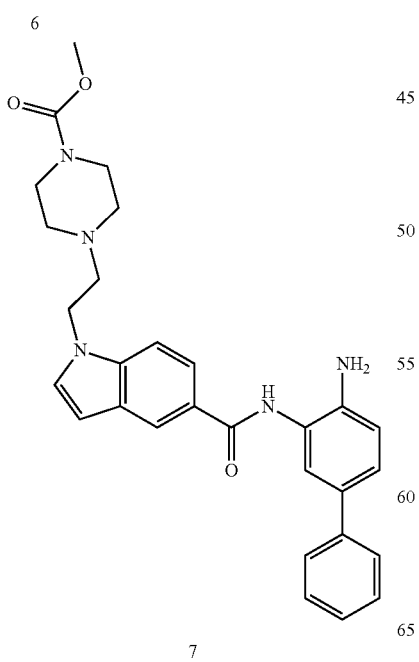

7

Step 1: Compound 3 was prepared according to the procedure as described in Example 32, compound 5.

Step 2: To a solution of compound 3 (240 mg, 0.55 mmol) in DMF was added compound 4 (300 mg, 0.82 mmol). NaH (133 mg, 5.5 mmol) was added at 0° C. at which point the reaction mixture was warmed to r.t. and stirred overnight. The reaction was quenched with $H_2O$, extracted with EA (2×20 ml) and the combined organic layers were purified by gel chromatography (DCM:MeOH=20:1) to afford the desired product, compound 5 (190 mg, 62%).

Step 3: Compound 6 was prepared according to the procedure as described in Example 32, compound 6.

Step 4: To a solution of compound 6 (40 mg, 0.091 mmol) in THF was added DIPEA (17 mg, 0.136 mmol) followed by methyl carbonochloridate (10.3 mg, 0.109 mmol) at 0° C. The reaction mixture was quenched with $NaHCO_3$, extracted with EA (2×10 ml) and the combined organic layers were purified by Pre-TLC (DCM:MeOH=20:1) to afford the desired product, compound 7 (24 mg, 53%). $^1$H NMR (500 MHz, DMSO) δ 9.65 (s, 1H), 8.29 (s, 1H), 7.81 (d, J=8.5 Hz, 1H), 7.63-7.49 (m, 5H), 7.40 (t, J=7.6 Hz, 2H), 7.32 (d, J=8.3 Hz, 1H), 7.24 (t, J=7.2 Hz, 1H), 6.88 (d, J=8.3 Hz, 1H), 6.58 (d, J=2.8 Hz, 1H), 5.08 (s, 2H), 4.35 (t, J=6.3 Hz, 2H), 4.03 (q, J=7.1 Hz, 1H), 3.58 (s, 3H), 2.71 (t, J=6.4 Hz, 2H), 2.42 (s, 4H), 1.99 (s, 2H). LCMS: m/z=498 (M+H)$^+$ Example 40: Synthesis of N-(2-amino-5-(thiophen-2-yl)phenyl)-7-cyclopropyl-1-(2-morpholinoethyl)-1H-indole-5-carboxamide

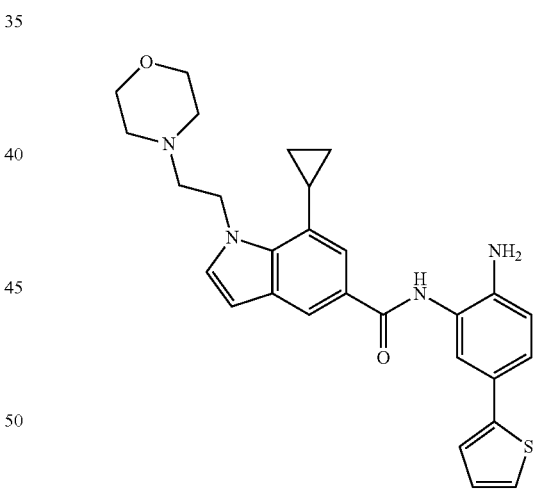

Reaction Scheme

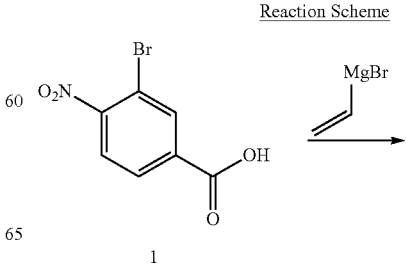

1

-continued

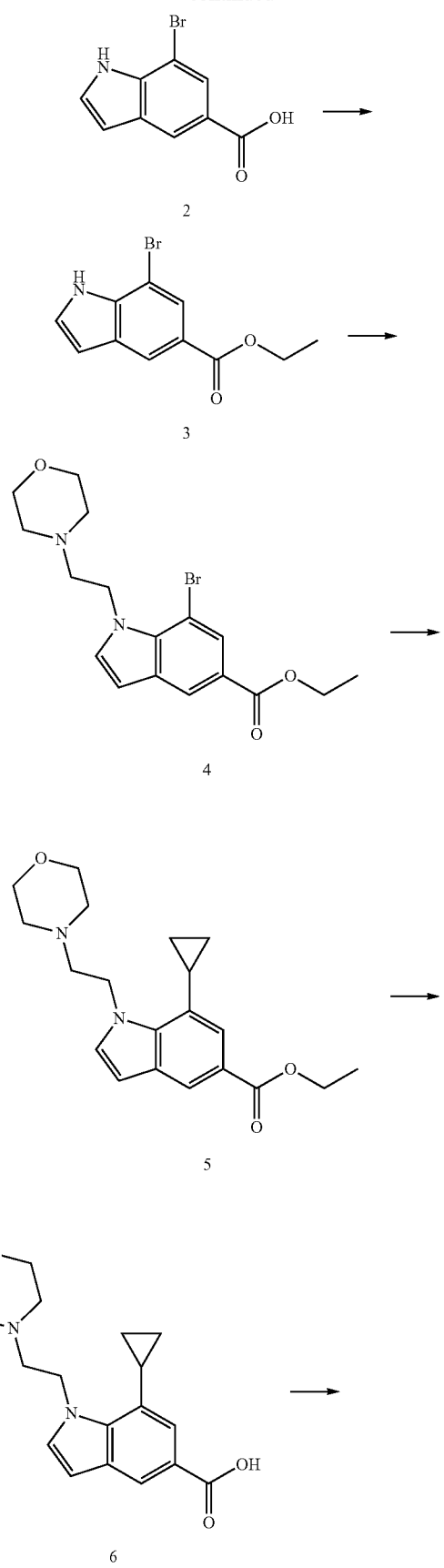

-continued

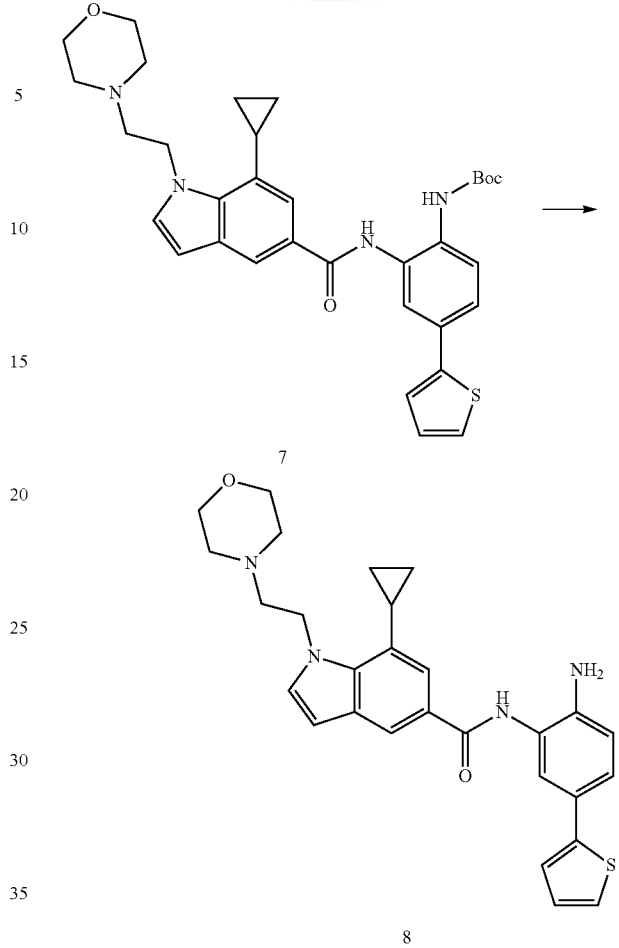

Step 1: To a solution of compound 1 (250 mg, 1.0 mmol) in dry THF (5 ml) was added vinylmagnesium bromide (3.5 ml, 3.5 mmol) at −78° C. and the reaction mixture was stirred for 2 h. The reaction was quenched with NH₄Cl, extracted with EA (2×20 ml), and the combined organic layers were purified by gel chromatography (PE:EA=1:1) to afford the desired product, compound 2 (172 mg, 72%).

Step 2: To a solution of compound 2 (1.6 g, 6.7 mmol) in dry EtOH (20 ml) was added SOCl₂ (3.0 ml) and the reaction was stirred at r.t. overnight. The reaction was then concentrated and purified by gel chromatography (PE:EA=2:1) to afford the desired product, compound 3 (520 mg, 30%).

Step 3: To a solution of compound 3 (520 mg, 1.95 mmol) in DMSO was added 4-(2-chloroethyl)morpholine (418 mg, 2.92 mmol) followed by KOH (218 mg, 3.9 mmol). The reaction mixture was stirred for 2 hours at 5° C. The reaction was then quenched with H₂O, extracted with EA (2×20 ml) and the combined organic layers were purified by gel chromatography (PE:EA=5:1) to afford the desired product, compound 4 (420 mg, 57%).

Step 4: Compound 5 was prepared according to the procedure as described in Example 32, compound 3.

Step 5: Compound 6 was prepared according to the procedure as described in Example 32, compound 4.

Step 6: To a solution of compound 6 (90 mg, 0.286 mmol) in DMF (4 ml) was added tert-butyl 2-amino-4-(thiophen-2-yl)phenylcarbamate (75 mg, 0.26 mmol), EDCI (110 mg, 0.572 mmol), and DMAP (53 mg, 0.429). The reaction mixture was stirred at r.t. overnight. The reaction was then quenched with H₂O, extracted with EA (2×20 ml), and the combined organic layers were purified by gel chromatography (PE:EA=3:1) to afford the desired product, compound 7 (140 mg, 85%).

Step 7: Compound 7 was prepared according to the procedure as described in Example 33, compound 6.

Example 41: Synthesis of N-(2-amino-5-(thiophen-2-yl)phenyl)-2-(piperazin-1-yl) quinoxaline-6-carboxamide

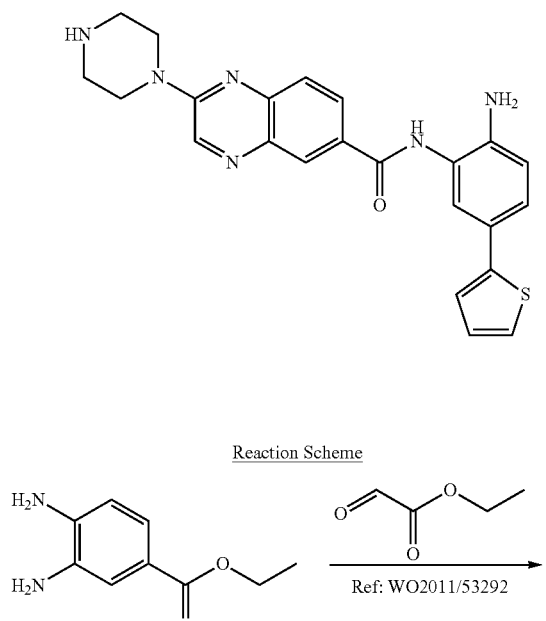

Reaction Scheme

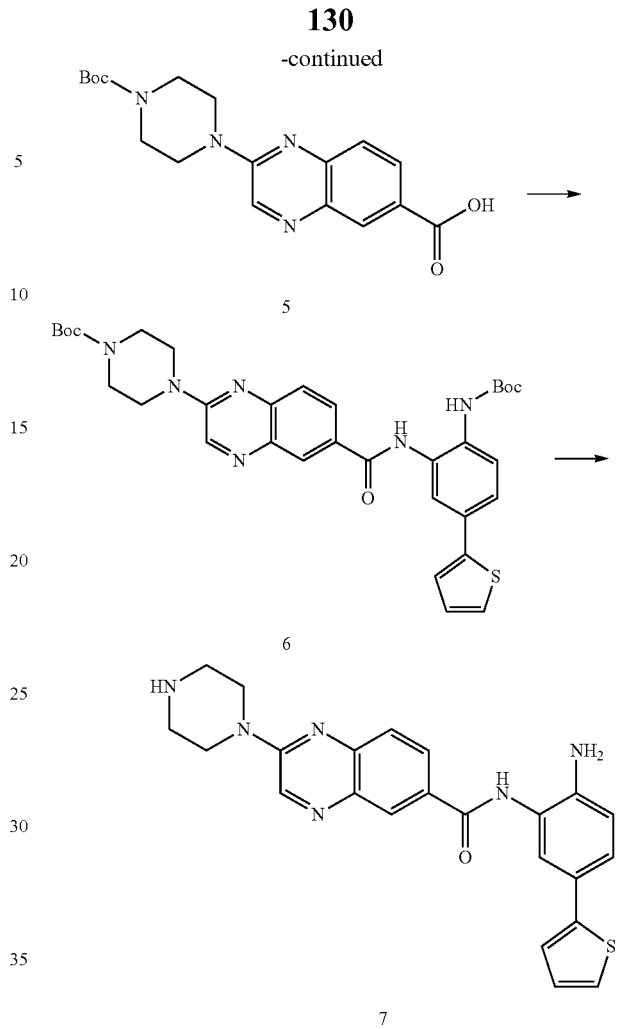

Step 1: To a solution of compound 1 (1.2 g, 6.67 mmol) in dry EtOH (15 ml) was added ethyl 2-oxoacetate (816 mg, 8.0 mmol). The reaction was stirred at reflux for 4 hours, cooled to r.t., and crystalized from EtOH to afford the desired product, compound 2 (1.3 g, 89%).

Step 2: A solution of compound 2 (1.3 g, 5.96 mmol) in POCl₃ (10 ml) was refluxed for 1 hour, concentrated, and extracted with EA (2×20 ml). The resulting organic layers were dried with Na₂SO₄ and concentrated to afford the desired product, compound 3 (1.4 g, 100%).

Step 3: To a solution of compound 3 (1.4 g, 5.9 mmol) in Dioxane (15 ml) was added DIPEA (1.14 g, 8.85 mmol) and tert-butyl piperazine-1-carboxylate (1.31 g, 7.08 mmol). The reaction mixture was stirred at 100° C. overnight, concentrated, and extracted with EA (2×20 ml). The combined organic layers were washed with aqueous NaCl, dried by Na₂SO₄, and concentrated to afford the desired product of compound 4 (1.6 g, 70%).

Step 4: Compound 6 was prepared according to the procedure as described in Example 32, compound 4.

Step 5: Compound 7 was prepared according to the procedure as described in Example 32, compound 5.

Step 6: Compound 8 was prepared according to the procedure as described in Example 32, compound 6. $^1$H NMR (500 MHz, DMSO) δ 9.85 (s, 1H), 8.76 (s, 1H), 8.34 (s, 1H), 7.96-8.02 (m, 2H), 7.57 (d, J=7.7 Hz, 1H), 7.46-7.17 (m, 3H), 6.89 (d, J=8.3 Hz, 1H), 5.21 (s, 2H), 4.05-4.01 (m, 4H), 3.25-3.22 (m, 4H). LCMS: m/z=431 (M+H)⁺

Example 42: N-(2-amino-5-(thiophen-2-yl)phenyl)-8-cyclopropyl-2-(piperazin-1-yl)quinoline-6-carboxamide
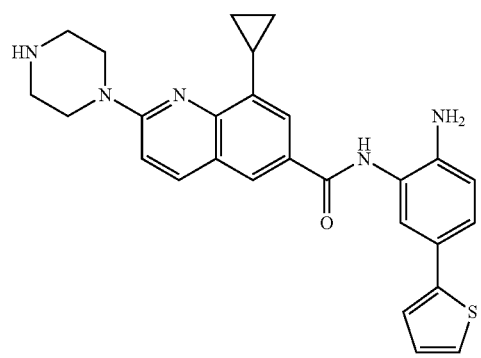 [SMILES: Nc1ccc(-c2cccs2)cc1NC(=O)c1cc(C2CC2)c2nc(N3CCNCC3)ccc2c1]
Reaction Scheme
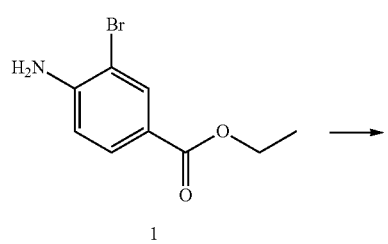
1
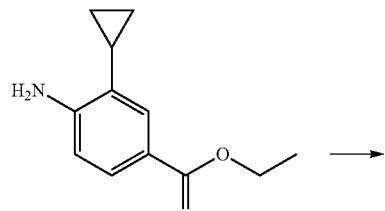
2
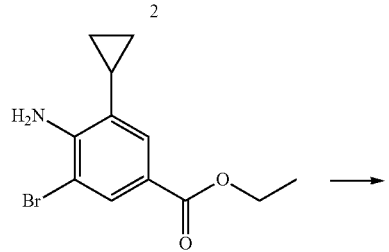
3
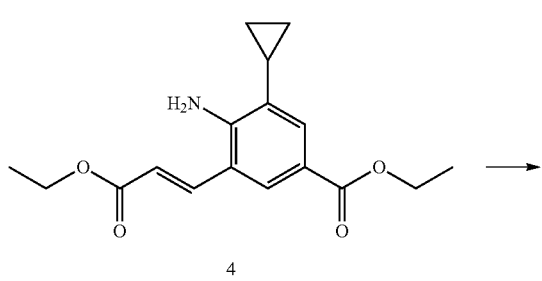
4
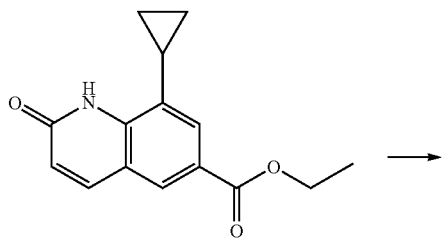
5
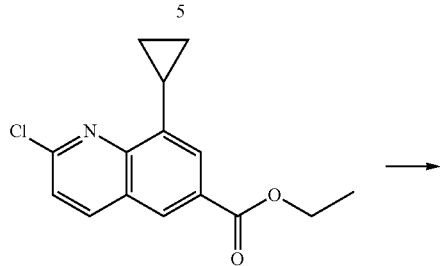
6
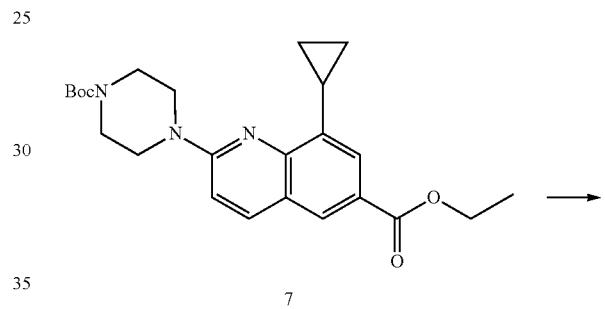
7
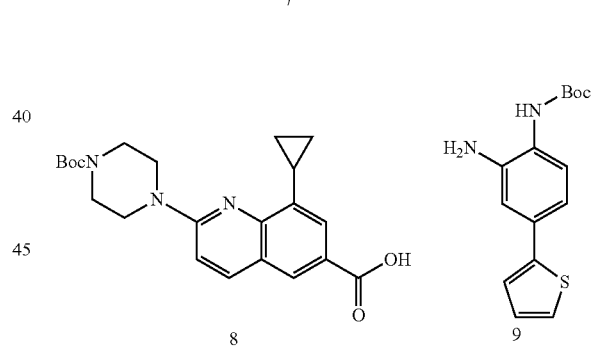
8
9
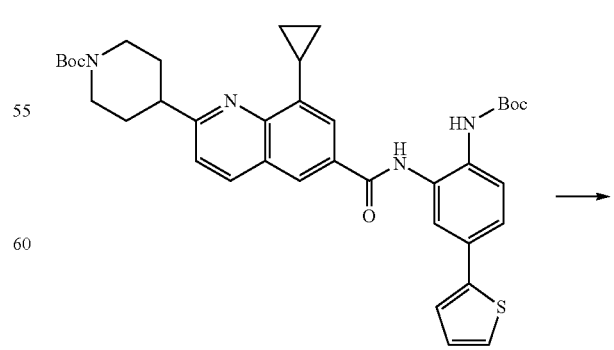
10

-continued

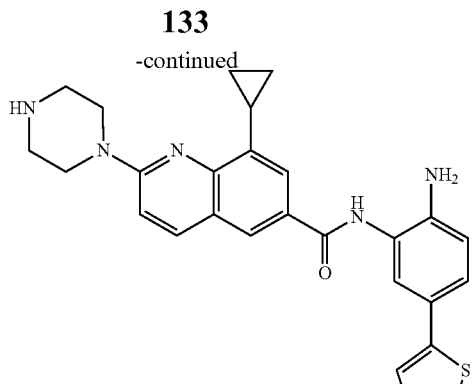

11

Step 1: A mixture of compound 1 (4.84 g, 0.02 mol), cyclopropyl boronic acid (5.16 g, 0.06 mol), Pd(OAc)$_2$ (448 mg, 0.002 mol), tricyclohexylphosphine (560 mg, 0.002 mol) and K$_3$PO$_4$ (12.6 g, 0.06 mol) in toluene (100 mL) and water (20 mL) was stirred at 100° C. under N$_2$ overnight. The mixture was cooled, filtered, and concentrated to obtain a residue, which was purified by silica gel column to give compound 2 (3.47 g, 85%) as a light yellow solid.

Step 2: A mixture of compound 2 (3.08 g, 0.015 mol) and NBS (3.19 g, 0.018 mol) in DCM was stirred at r.t. overnight. The mixture was concentrated to a residue, which was purified by silica gel column to obtain compound 3 (3.18 g, 75%) as a light yellow solid.

Step 3: A mixture of compound 3 (2.8 g, 0.01 mol), Pd(PPh$_3$)$_4$Cl$_2$ (1.2 g, 0.001 mol), ethyl acrylate (10.0 g, 0.1 mol) and KAcO (7.6 g, 0.1 mol) in toluene (100 mL) was stirred at 100° C. under N$_2$ overnight. The mixture was cooled, filtered, and concentrated to obtain a residue, which was purified by silica gel column to give compound 4 (1.4 g, 47%) as a light yellow solid.

Step 4: A mixture of compound 4 (1.5 g, 0.005 mol) and con.H$_2$SO$_4$ (10 mol) in EtOH (100 ml) was stirred at 90° C. for 2 days. The mixture was concentrated and filtered to obtain compound 5 (1.2 g, 94%) as a light yellow solid.

Step 5: To a solution of compound 5 (1.3 g, 0.005 mol) and DMF (3 ml) in DCM (30 ml) was added SOCl$_2$ (3 mL). The reaction was stirred for 5 h at 0° C. The reaction mixture was concentrated to obtain a residue, to which was added DCM (100 ml) and aq.sat.NaHCO$_3$ (20 ml) followed by stirring for 30 min. The organic layer was separated, dried, and concentrated to give compound 6 (1.3 g, 93%) as a light yellow solid.

Step 6: A mixture of compound 6 (1.4 g, 0.005 mol), tert-butyl piperazine-1-carboxylate (2.8 g, 0.015 mol), and CuI (950 mg, 0.005 mol) in DMSO (15 ml) was stirred at 100° C. overnight. The mixture was filtered and EA (200 ml) and water (100 ml) were added to the filtrate. The resulting mixture was stirred for 30 min., and the organic layer was separated, dried, and concentrated to give compound 7 (2.0 g, 93%) as a light yellow solid.

Step 7: To a solution of compound 7 (2.1 g, 0.005 mol) in EtOH (20 ml) and THF (20 ml) was added 2M NaOH (10 ml). The reaction mixture was stirred at 60° C. for 3 h. The mixture was subsequently concentrated to a residue, to which was added aq.sat.citric acid (10 ml). The resulting mixture was extracted with EA (150 ml) and washed with water (50 ml). The organic layer was separated, dried, and concentrated to give compound 8 (1.9 g, 96%) as a light yellow solid.

Step 8: A mixture of compound 8 (397 mg, 1 mmol), compound 9 (290 mg, 1 mmol), HOAT (300 mg, 2.2 mmol), EDCI (400 mg, 2.2 mmol), and DIPEA (600 mg, 4.6 mmol) in DMF (20 ml) was stirred at 55° C. overnight. The reaction mixture was added to H$_2$O and extracted with EA (20 ml×3), separated, dried, and concentrated to give the crude product. Purification by Prep-TLC yielded the desired product, compound 10 (361 mg, 54%).

Step 9: A mixture of compound 10 (334 mg 1 mmol) and TFA (5 ml) in 5 ml DCM was stirred at r.t. for 2 h. The mixture was concentrated to a residue, which was purified by HPLC to afford a white product, compound 11. (150 mg, 32%). $^1$H NMR (500 MHz, DMSO) δ 9.80 (s, 2H), 8.22 (s, 1H), 8.18 (d, J=9.2 Hz, 1H), 7.61 (s, 1H), 7.46 (s, 1H), 7.39-7.29 (m, 3H), 7.26 (d, J=2.9 Hz, 1H), 7.06 (dd, J=5.0, 3.7 Hz, 1H), 6.83 (d, J=8.3 Hz, 1H), 5.17 (s, 2H), 3.85 (s, 4H), 3.06 (s, 4H), 3.05-2.97 (m, 1H), 1.12-1.02 (m, 2H), 0.92 (d, J=4.3 Hz, 2H). LCMS: m/z=470 (M+H)$^+$ Example 43: Synthesis of N-(4-amino-[1,1'-biphenyl]-3-yl)-7-cyclopropyl-1-(2-morpholinoethyl)-1H-indazole-5-carboxamide

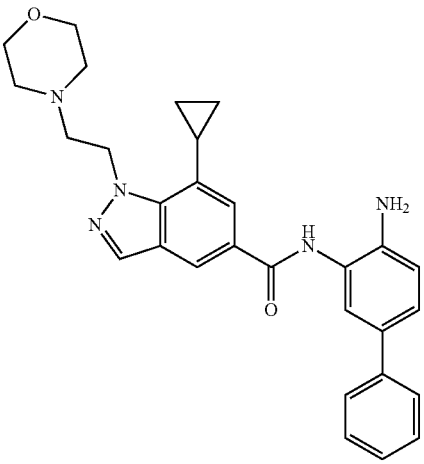 [SMILES: Nc1ccc(-c2ccccc2)cc1NC(=O)c1cc(C2CC2)c2c(cnn2CCN2CCOCC2)c1]

Reaction Scheme

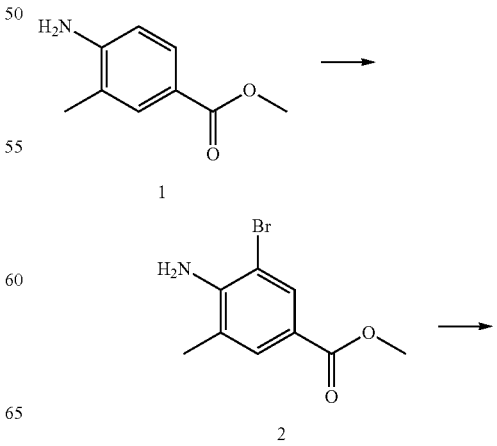

-continued

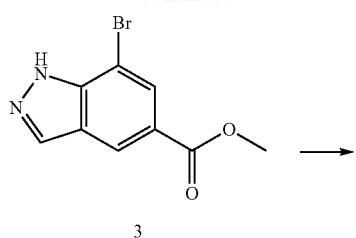

3

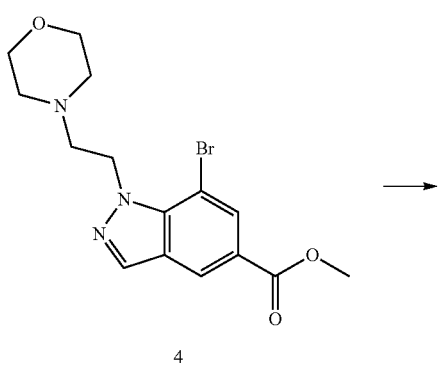

4

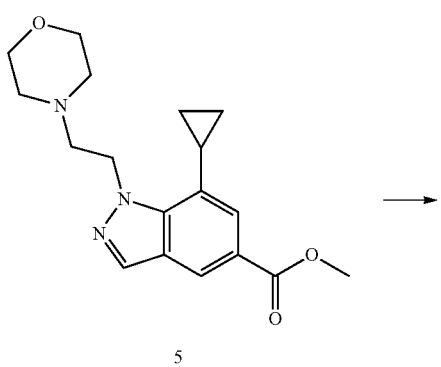

5

6

-continued

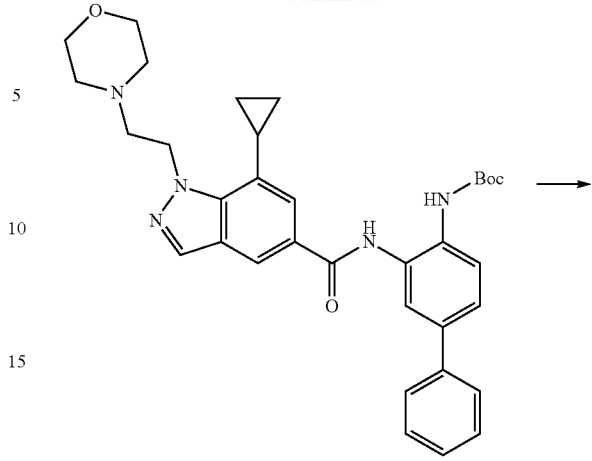

7

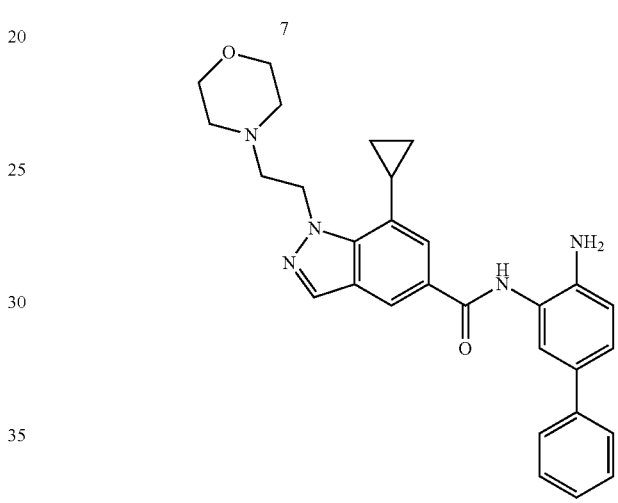

8

Experimental Procedure

Step 1: A mixture of compound 1 (429 mg, 0.0026 mol) and NBS (0.7 g, 0.0039 mol) in DCM was stirred at r.t. for 3 h. The mixture was concentrated to a residue, which was purified by Prep-TLC to obtain compound 2 (522 mg, 83%) as a light yellow solid.

Step 2: To a mixture of compound 2 (2.2 g, 9.1 mmol) in HOAc (40 ml) was added a solution of $NaNO_2$ (6.27 g, 9.1 mmol) in $H_2O$ (9 ml) dropwise. The mixture was stirred at ambient temperature for five h. and then concentrated in vacuo. The resulting solid was triturated with ethyl acetate (40 ml) and filtered. The filtrate was concentrated to afford compound 3 (575 mg, 25%).

Step 3: Compound 4 was prepared according to the procedure as described in Example 40, compound 4.

Step 4: Compound 5 was prepared according to the procedure as described in Example 40, compound 5.

Step 5: Compound 6 was prepared according to the procedure as described in Example 40, compound 6.

Step 6: Compound 7 was prepared according to the procedure as described in Example 40, compound 7.

Step 7: Compound 8 was prepared according to the procedure as described in Example 40, compound 8. $^1$H NMR (500 MHz, DMSO+D2O) δ 8.35 (s, 1H), 8.31 (s, 1H), 7.75 (s, 1H), 7.59 (d, J=7.6 Hz, 2H), 7.51 (s, 1H), 7.46-7.35 (m, 4H), 7.28 (t, J=7.3 Hz, 1H), 6.94 (d, J=8.3 Hz, 1H), 5.02

(t, J=6.9 Hz, 2H), 3.64 (s, 4H), 3.04 (s, 2H), 2.68 (s, 4H), 2.55 (s, 2H), 2.48 (s, 1H), 1.13 (d, J=8.1 Hz, 2H), 0.95 (d, J=4.1 Hz, 2H). LCMS: m/z=482 (M+H)+

Example 44: Synthesis of N-(2-amino-5-(thiophen-2-yl)phenyl)-5-cyclopropyl-6-(piperazin-1-yl)-2-naphthamide

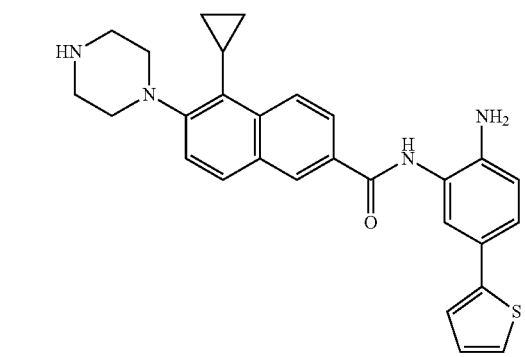 [SMILES: Nc1ccc(-c2cccs2)cc1NC(=O)c1ccc2c(C3CC3)c(N3CCNCC3)ccc2c1]

Reaction Scheme

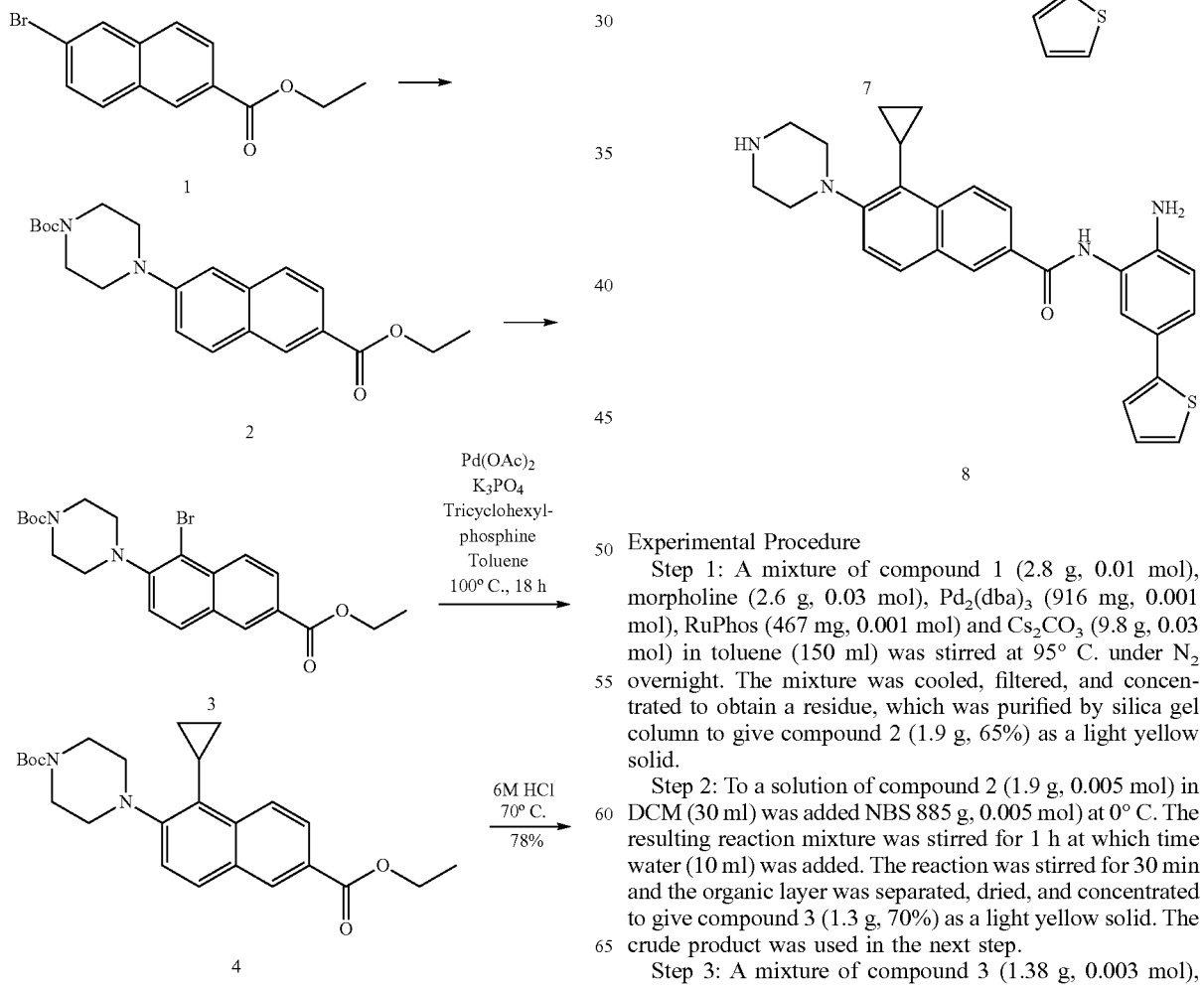

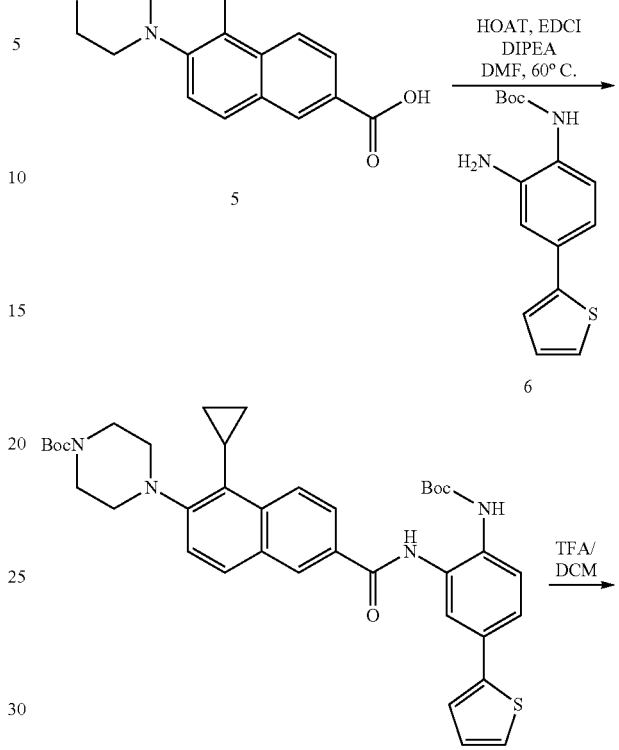

Experimental Procedure

Step 1: A mixture of compound 1 (2.8 g, 0.01 mol), morpholine (2.6 g, 0.03 mol), Pd$_2$(dba)$_3$ (916 mg, 0.001 mol), RuPhos (467 mg, 0.001 mol) and Cs$_2$CO$_3$ (9.8 g, 0.03 mol) in toluene (150 ml) was stirred at 95° C. under N$_2$ overnight. The mixture was cooled, filtered, and concentrated to obtain a residue, which was purified by silica gel column to give compound 2 (1.9 g, 65%) as a light yellow solid.

Step 2: To a solution of compound 2 (1.9 g, 0.005 mol) in DCM (30 ml) was added NBS 885 g, 0.005 mol) at 0° C. The resulting reaction mixture was stirred for 1 h at which time water (10 ml) was added. The reaction was stirred for 30 min and the organic layer was separated, dried, and concentrated to give compound 3 (1.3 g, 70%) as a light yellow solid. The crude product was used in the next step.

Step 3: A mixture of compound 3 (1.38 g, 0.003 mol), cyclopropyl boronic acid (2.2 g, 0.025 mol), Pd(OAc)$_2$ (56 mg, 0.00025 mol), tricyclohexylphosphine (70 mg, 0.00025) and $K_3PO_4$ (1.6 g, 0.0075 mol) in toluene (100 ml) and water (20 ml) was stirred at 100° C. under $N_2$ overnight. The mixture was cooled, filtered, and concentrated to obtain a residue, which was purified by silica gel column yielding compound 4 (636 mg, 65%) as a light yellow solid.

Step 4: To a solution of compound 4 (848 mg, 2 mmol) in EtOH (20 ml) and THF (20 ml) was added 2M NaOH (10 ml). The reaction mixture was stirred at 60° C. for 3 h. Then, the mixture was concentrated to a residue, which was purified by flash column to afford compound 5 (536 mg, 90%) as a light yellow solid.

Step 5: A mixture of compound 5 (396 mg, 1 mmol), compound 6 (290 mg, 1 mmol), HOAT (150 mg, 1.1 mmol), EDCI (200 mg, 1.1 mmol), DIPEA (300 mg, 2.3 mmol) in DMF (40 ml) was stirred at 55° C. overnight. The reaction mixture was added to $H_2O$ and extracted with EA (20 ml×3). The combined organic layers were dried and concentrated to give the crude product. Purification by Prep-TLC afforded the desired product, compound 7 (256 mg, 45%) as a light yellow solid.

Step 6: A mixture of compound 7 (133 mg 0.2 mmol) and TFA (5 ml) in 5 ml DCM was stirred at r.t. for 2 h. The mixture was concentrated to a residue, which was purified by HPLC to afford compound 8 (37 mg, 40%) as a light yellow solid. $^1$H NMR (500 MHz, DMSO) δ 9.87 (s, 1H), 8.53 (s, 1H), 8.46 (d, J=8.9 Hz, 1H), 8.31 (s, 1H), 8.05 (d, J=10.2 Hz, 1H), 7.91 (d, J=8.9 Hz, 1H), 7.53 (d, J=1.9 Hz, 1H), 7.41-7.35 (m, 2H), 7.32 (dd, J=8.3, 2.1 Hz, 1H), 7.27 (d, J=2.9 Hz, 1H), 7.07 (dd, J=5.0, 3.7 Hz, 1H), 5.31-5.10 (m, 2H), 3.24 (s, 4H), 3.12 (s, 4H), 2.07 (d, J=5.5 Hz, 1H), 1.25 (d, J=8.2 Hz, 2H), 0.71 (d, J=4.3 Hz, 2H). LCMS: m/z=469 (M+H)$^+$ Example 45: Synthesis of N-(4-amino-[1,1'-biphenyl]-3-yl)-7-cyclopropyl-1-(2-morpholinoethyl)-1H-indole-5-carboxamide

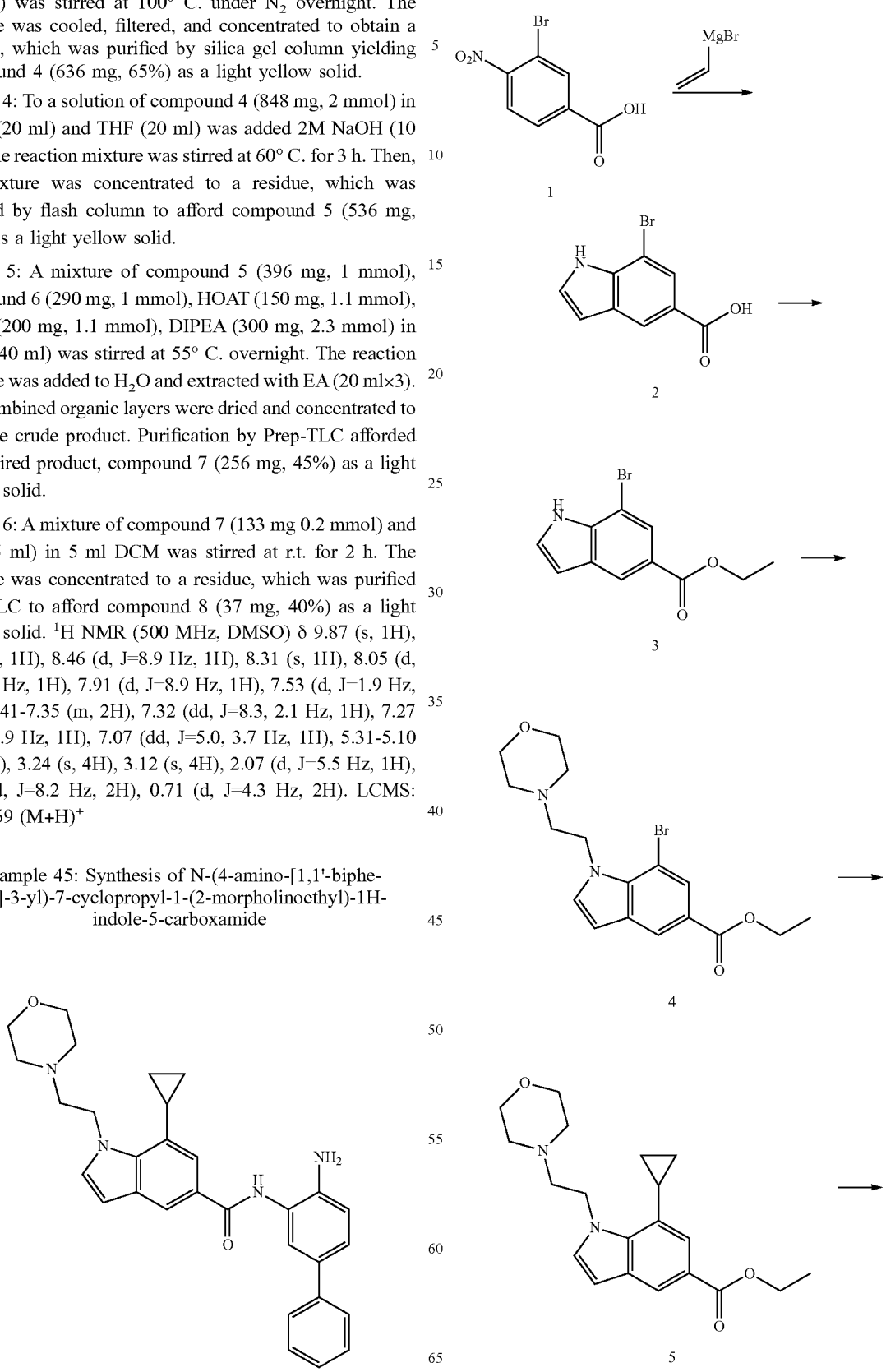

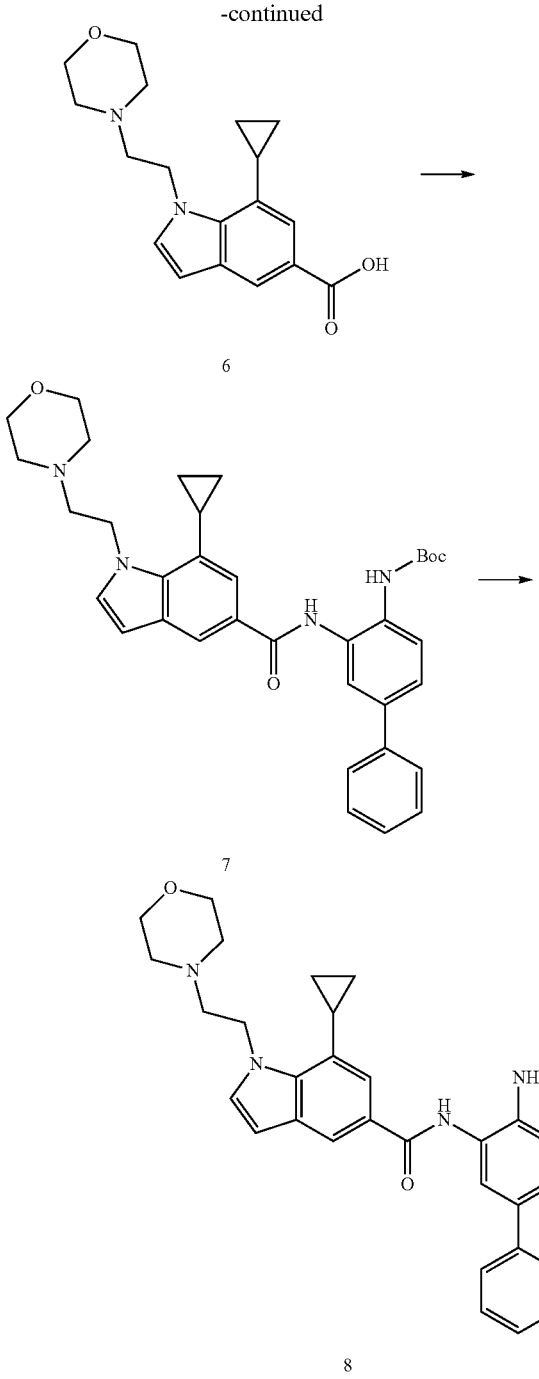

Step 1: To a solution of compound 1 (250 mg, 1.0 mmol) in dry THF (5 ml) was added vinylmagnesium bromide (3.5 ml, 3.5 mmol) at −78° C. The reaction was stirred for 2 hours and then quenched with NH₄Cl. The reaction mixture was extracted with EA (2×20 ml), and the combined organic layers were purified by gel chromatography (PE:EA=1:1) to afford the desired product, compound 2 (172 mg, 72%).

Step 2: To a solution of compound 2 (1.6 g, 6.7 mmol) in dry EtOH (20 ml) was added $SOCl_2$ (3.0 ml) at r.t. The reaction was stirred overnight, concentrated, and purified by gel chromatography (PE:EA=2:1) to afford the desired product, compound 3 (520 mg, 30%).

Step 3: To a solution of compound 3 (520 mg, 1.95 mmol) in DMSO was added 4-(2-chloroethyl)morpholine (418 mg, 2.92 mmol) and KOH (218 mg, 3.9 mmol) at 5° C. The reaction stirred for 2 hours and then quenched with $H_2O$. The reaction mixture was extracted with EA (2×20 ml) and the combined organic layers were purified by gel chromatography (PE:EA=5:1) to afford the desired product of compound 4 (420 mg, 57%).

Step 4: Compound 5 was prepared according to the procedure as described in Example 1, compound 3.

Step 5: Compound 6 was prepared according to the procedure as described in Example 1, compound 4.

Step 6: To a solution of compound 6 (90 mg, 0.286 mmol) in DMF (4 ml) was added tert-butyl 2-amino-4-(thiophen-2-yl)phenylcarbamate (75 mg, 0.26 mmol), EDCI (110 mg, 0.572 mmol), and DMAP (53 mg, 0.429 mmol) at r.t. The reaction stirred overnight and subsequently quenched with $H_2O$. The reaction mixture was extracted with EA (2×20 ml) and the combined organic layers were purified by gel chromatography (PE:EA=3:1) to afford the desired product, compound 7 (140 mg, 85%).

Step 7: Compound 7 was prepared according to the procedure as described in Example 41, compound 8. $^1$H NMR (500 MHz, DMSO) δ 9.67 (s, 1H), 8.14 (s, 1H), 7.59-7.51 (m, 4H), 7.46 (d, J=3.2 Hz, 1H), 7.40 (t, J=7.7 Hz, 2H), 7.33 (dd, J=8.3, 2.1 Hz, 1H), 7.24 (t, J=7.3 Hz, 1H), 6.88 (d, J=8.3 Hz, 1H), 6.59 (s, 1H), 5.06 (s, 2H), 4.76 (s, 2H), 3.57 (s, 4H), 2.71 (s, 2H), 2.47-2.32 (m, 5H), 1.04 (d, J=8.0 Hz, 2H), 0.93 (d, J=4.2 Hz, 2H). LCMS: m/z=481 (M+H)⁺

Example 46: HDAC Enzyme Assays

Compounds for testing were diluted in DMSO to 50 fold the final concentration and a ten point three fold dilution series was made. The compounds were diluted in assay buffer (50 mM HEPES, pH 7.4, 100 mM KCl, 0.001% Tween-20, 0.05% BSA, 201.1M tris(2-carboxyethyl)phosphine) to 6 fold their final concentration. The HDAC enzymes (purchased from BPS Biosciences) were diluted to 1.5 fold their final concentration in assay buffer and pre-incubated with the compounds for 24 hours prior to addition of the substrate.

The substrate tripeptide substrate 3 (synthesized in house) for each enzyme was equal to the Km as determined by a substrate titration curve. The enzyme and substrate concentrations used are given in Table 2. The substrates were diluted in assay buffer at 6× their final concentration with 0.3 µM sequencing grade trypsin (Sigma). The substrate/trypsin mix was added to the enzyme/compound mix, the plate was shaken for 60 seconds and placed into a Spectramax M5 microtiter plate reader. The development of fluorescence was monitored for 30 min and the linear rate of the reaction was calculated. The IC$_{50}$ was determined using Graph Pad Prism by a four parameter curve fit. The IC$_{50}$ values obtained for the compounds of this invention are found in Table 1.

TABLE 2

| | Enzyme concentration | Substrate concentration |
|---|---|---|
| HDAC1 | 3.5 ng/µl | 3.8 µM |
| HDAC2 | 0.2 ng/µl | 2.3 µM |
| HDAC3 | 0.08 ng/µl | 3.9 µM |

Example 47: CD34+ Globin Switching Assay

CD34+ cells isolated from human bone marrow were cultured in vitro using two distinct sets of culture conditions.

Figure 1B:
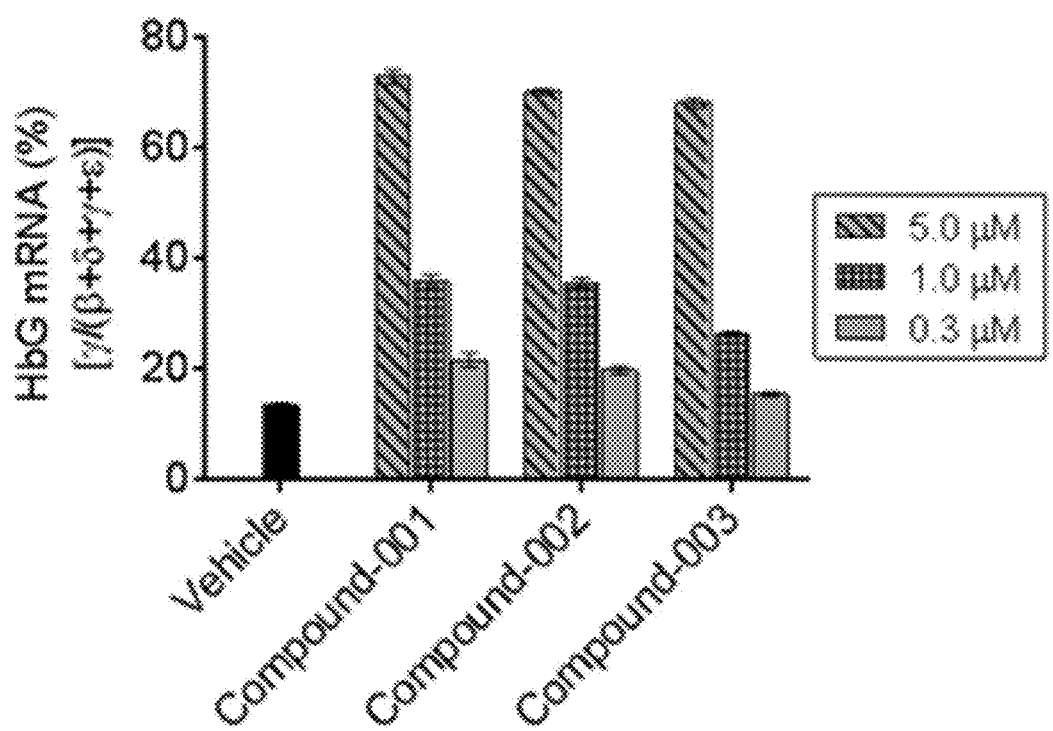
FIG. 1B is a graph that shows the results of an experiment in which cells from CS2 were differentiated in the presence of vehicle (DMSO) or 5, 1, or 0.3 µM of Compound 001, Compound 002, or Compound 003. Globin mRNA levels were determined at day 3 of differentiation.
Figure 1C:
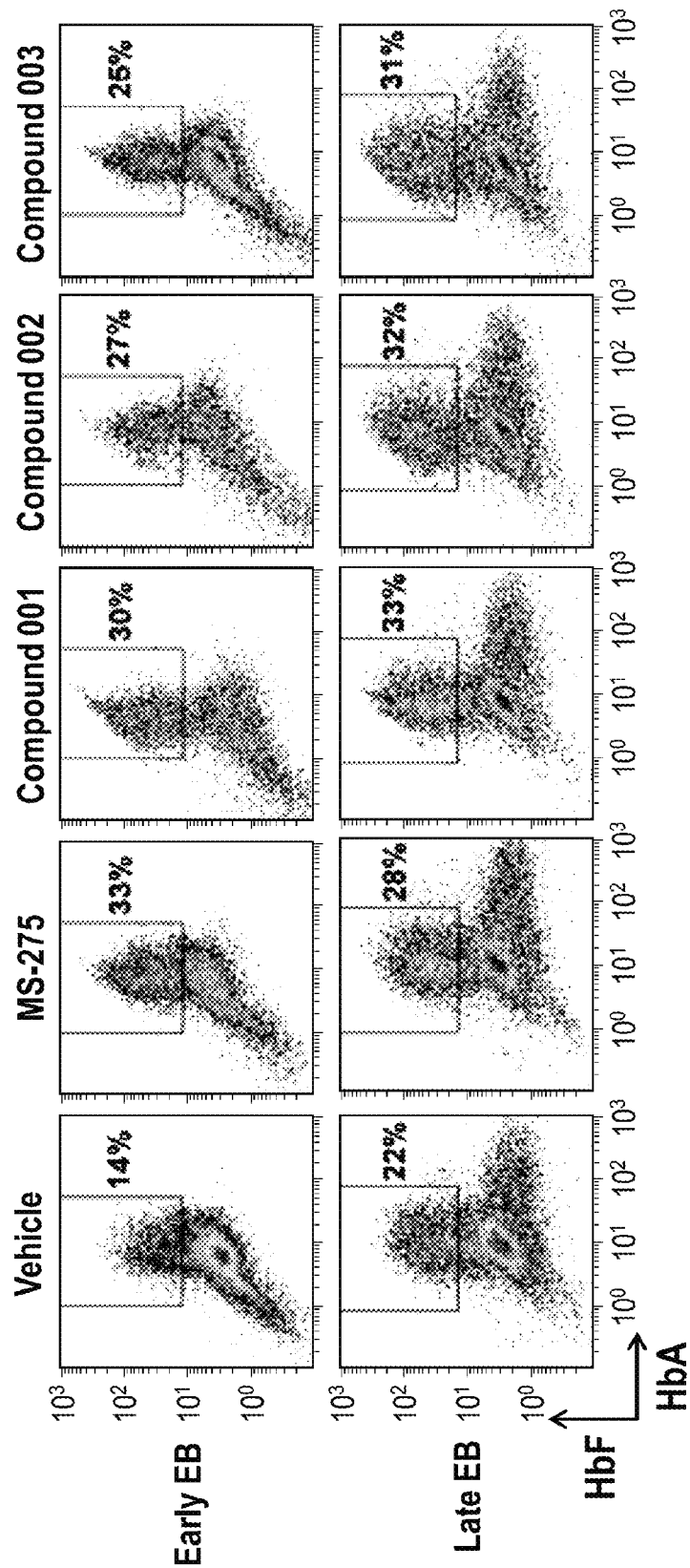
FIG. 1C, upper row, is a graph that shows the results of an experiment in which cells from CS1 were differentiated in the presence of vehicle (DMSO), or 1 µM each of MS-275 (entinostat), Compound 001, Compound 002, or Compound 003. Hemoglobin protein levels within each cell were determined at day 5 of differentiation.

Culture system 1 (CS1), described by Xu J et al. (*Science* 2011 Nov. 18; 334(6058):993-6), consists of a 7 day expansion phase in media that supports hematopoietic progenitor cells followed by a differentiation phase of 4 to 8 days in media that induces development of erythroid lineage cells. Culture system 2 (CS2), described by Bradner J E (*Proc Natl Acad Sci* USA. 2010 Jul. 13; 107(28):12617-22), consists of a 7 day expansion phase in media that supports differentiation of cells towards the erythroid lineage followed by a differentiation phase for 3 days where erythroid cell development continues. After 3 to 5 days in differentiation media CS1 cells are primarily early erythroblasts (EB), while CS2 cells are primarily late EB. mRNA levels were determine by quantitative real time PCR using primer/probe sets designed to adult major β-globin (β), adult minor β-globin (δ), feta β-like globin (HbG, γ), and embryonic β-like globin (ε). Protein levels were determined by flow cytometry using fluorescent antibodies against fetal hemoglobin (HbF) or adult hemoglobin (HbA). In the experiment shown in FIG. 1A, cells from CS1 were differentiated in the presence of vehicle (DMSO), 30 µM hydroxyurea, 1 µM MS-275 (entinostat), or 1 µM Compound 001. Globin mRNA levels were determined in cells at day 0, 3, 5, and 8 of differentiation. In the experiment shown in FIG. 1B, cells from CS2 were differentiated in the presence of vehicle (DMSO) or 5, 1, or 0.3 µM of Compound 001, Compound 002, or Compound 003. Globin mRNA levels were determined at day 3 of differentiation. In the experiment shown in FIG. 1C, upper row, cells from CS1 were differentiated in the presence of vehicle (DMSO), or 1 µM each of MS-275 (entinostat), Compound 001, Compound 002, or Compound 003. Hemoglobin protein levels within each cell were determined at day 5 of differentiation. In the experiment shown in FIG. 1C, lower row; cells from CS2 were differentiated for 2 days in the presence of vehicle (DMSO), or 1 µM each of MS-275 (entinostat), Compound 001, Compound 002, or Compound 003. After 2 days, media was exchanged and cells were differentiated for an additional 2 days in the absence of compound. Hemoglobin protein levels within each cell were determined at day 4 of differentiation. The results of these experiments are shown in FIGS. 1A, 1B, and 1C.

Example 48: Pharmacological Inhibition of Histone Deacetylase (HDAC) 1, 2 or 3 have Distinct Effects on Cellular Viability, Erythroid Differentiation, and Fetal Globin (HbG) Induction The goal of this example was to investigate the effects of selective inhibitors of HDAC1, 2, or 3 on cytotoxicity, erythroid differentiation, and HbG induction in cultured human CD34+ bone marrow cells.

To investigate whether HDAC1 or HDAC2 was the preferred therapeutic target, two compounds were used. Compound 001 is an HDAC1/2 selective compound biased towards HDAC1 with $IC_{50}$ values of 4, 15, and 114 nM for HDAC1, 2, and 3, respectively. In contrast, Compound 004 showed balanced HDAC1 and HDAC2 selectivity with $IC_{50}$ values of 27, 24, and 247 nM for HDAC1, 2, and 3, respectively. Treatment of cells for 6 days with 1 µM of Compound 001 or Compound 004 resulted in a 3-fold increase in the percentage of HbG relative to other beta-like globin transcripts. However, it was found that Compound 001 treatment resulted in an approximately 3-fold decrease in cell viability after 6 days of treatment, while Compound 004 treatment resulted in a minimal reduction (1.2-fold) in cell viability. Decreased cell viability observed with Compound 001 was associated with a reduction of cells positive for the erythroid differentiation markers CD71 and glycophorinA. This result is consistent with the Mx-Cre mouse model where $HDAC1^{KO}$; $HDAC2^{het}$ had reduced numbers of erythrocytes, thrombocytes, and total bone marrow cells, while the $HDAC1^{het}$; $HDAC2^{KO}$ was unaffected (Wilting RH, EMBO Journal, 2010).

These results suggest that compounds with a pharmacological profile of increased selectivity towards HDAC2 inhibition versus HDAC1 may be less cytotoxic and minimize effects on differentiation, while still inducing HbG in human CD34+ bone marrow cells.

Example 49: Mechanistic Insights into Fetal Hemoglobin (HbF) Induction Through Chemical Inhibition of Histone Deacetylase 1 and 2 (HDAC1/2)

The mechanism through which HDAC1/2 inhibition leads to activation of HbG remains largely unknown. In this example, Compound 001 was used to investigate changes in gene expression and chromatin organization that result from inhibition of HDAC1/2.

Gene expression profiling was performed on cells treated with Compound 001 (n=3) or vehicle (n=3) using Affymetrix PrimeView GeneChips. Treatment of early erythroblasts (CD71+, GlyA−) resulted in the up and down regulation of 1294 and 681 probe sets, respectively. In comparison, treatment of late erythroblasts (CD71+, GlyA+) resulted in a total of 255 probe set changes. This finding is consistent with follow-up experiments demonstrating that Compound 001 is unable to induce HbG in cells positive for both CD71 and GlyA. Taken together, these results suggest that erythroblasts become less responsive to HDAC inhibition as they mature. Gene set enrichment analysis using public domain data revealed that genes up- or down-regulated by HDAC1/2 shRNA knockdown are significantly over represented in the list of genes induced or repressed by Compound 001, respectively, suggesting pharmacologic inhibition of HDAC1/2 recapitulates genetic ablation. Significant enrichment in other gene sets involving targets linked to HbG regulation, including lysine-specific demethylase 1 (LSD1) (Shi L, Nature Medicine, 2012) were identified.

GeneChip and quantitative real-time PCR time course experiments show that Compound 001 treatment leads to a decrease in Bcl11A (2-fold) and Sox6 (10-fold) mRNA, known repressors of fetal globin synthesis, and an increase in Klf2 (2-fold) and Gata2 (8-fold) mRNA, proposed fetal globin activators. This result is consistent with work by others that show Gata2 is suppressed, in part, by the NuRD complex (Hong W, EMBO Journal, 2005) and that Gata2 binding at the HbG promoter leads to increased levels of HbG expression (Zhu X, PLoS One, 2012). Interestingly, Gata2 induction preceded Sox6 suppression in Compound 001 treated cells and the Sox6 promoter contains 8 canonical WGATAR binding sites and one Gata2-specific binding motif, raising the possibility suppression of Sox6 by Compound 001 is mediated by Gata2 induction. To investigate these possibilities, chromatin immunoprecipitation coupled with next generation sequencing (ChIP-seq) was performed for HDAC1, HDAC2, Gata2, and the HDAC2-specific histone modification H3K56 in Compound 001 and vehicle treated cells. ChIP-seq data, both by itself and in combination with gene expression data, will provide further insight into the mechanism through which HDAC1/2 regulates HbF synthesis.

INCORPORATION BY REFERENCE

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed is:

1. A compound of Formula I:

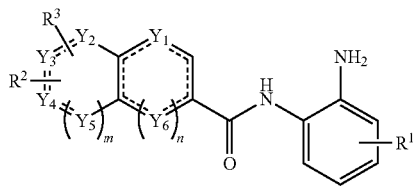

or a pharmaceutically acceptable salt thereof,
wherein
$Y_1$ is $CR^7$ or $NR^7$;
$Y_2$, $Y_3$, $Y_4$, $Y_5$, and $Y_6$ are each independently CH, $CH_2$, N, or C(O), wherein at least one of $Y_2$, $Y_3$, $Y_4$, and $Y_5$ are CH;
$R^1$ is mono-, bi-, or tri-cyclic aryl or heteroaryl, wherein the mono-, bi-, or tri-cyclic aryl or heteroaryl is optionally substituted;
$R^2$ and $R^3$ are each independently selected from $C_{2-6}$-alkenyl, $C_{2-6}$-alkynyl, $C_{3-6}$-cycloalkyl, $C_{1-6}$-alkyl-$C_{3-6}$-cycloalkyl, heterocycloalkyl, $C_{1-6}$-alkyl-heterocycloalkyl, $NR^4R^5$, O—$C_{1-6}$-alkyl-$OR^6$, $C_{1-6}$-alkyl-$OR^6$, aryl, C(O)N(H)-heteroaryl, C(O)-heteroaryl, C(O)-heterocycloalkyl, C(O)-aryl, C(O)—$C_{1-6}$-alkyl, $CO_2$—$C_{1-6}$-alkyl, or C(O)—$C_{1-6}$-alkyl-heterocycloalkyl, wherein the cycloalkyl, heterocycloalkyl, aryl, or heteroaryl is optionally substituted;
$R^4$ is H, $C_{1-6}$-alkyl, or $C_{1-6}$-alkyl-$OR^6$;
$R^5$ is $CO_2R^6$, $C_1$-$C_6$-alkyl-aryl, or $C_{1-6}$-alkyl-$OR^6$;
$R^6$ is H or $C_{1-6}$-alkyl;
$R^7$ is null, H, $C_{1-6}$-alkyl, $C_{3-6}$-cycloalkyl, $C_{1-6}$-alkyl-$C_{3-6}$-cycloalkyl, heterocycloalkyl, or $C_{1-6}$-alkyl-heterocycloalkyl;
a ---- line denotes an optionally double bond;
m is 0 or 1; and
n is 0 or 1, provided at least one of m or n is 1.

2. The compound of claim 1, or a pharmaceutically acceptable salt thereof,
wherein
$R^1$ is mono-, bi-, or tri-cyclic aryl or heteroaryl, wherein the mono-, bi-, or tri-cyclic aryl or heteroaryl is optionally substituted with halo, $C_{1-4}$-alkyl, $CO_2R^6$, $C(O)R^6$, or $C_{1-6}$-alkyl-$OR^6$;
$R^2$ and $R^3$ are each independently selected from $C_{2-6}$-alkenyl, $C_{2-6}$-alkynyl, $C_{3-6}$-cycloalkyl, $C_{1-6}$-alkyl-$C_{3-6}$-cycloalkyl, heterocycloalkyl, $C_{1-6}$-alkyl-heterocycloalkyl, $NR^4R^5$, O—$C_{1-6}$-alkyl-$OR^6$, $C_{1-6}$-alkyl-$OR^6$, aryl, heteroaryl, C(O)N(H)-heteroaryl, C(O)-heteroaryl, C(O)-heterocycloalkyl, C(O)-aryl, C(O)—$C_{1-6}$-alkyl, $CO_2$—$C_{1-6}$-alkyl, and C(O)—$C_{1-6}$-alkyl-heterocycloalkyl, wherein the cycloalkyl, heterocycloalkyl, aryl, or heteroaryl is optionally substituted with $C_{1-4}$-alkyl, $CO_2R^6$, $C(O)R^6$, or $C_{1-6}$-alkyl-$OR^6$.

3. The compound of claim 1, or a pharmaceutically acceptable salt thereof,
wherein
$R^1$ is monocyclic aryl or heteroaryl, wherein the aryl or heteroaryl is optionally substituted with halo;
$R^2$ and $R^3$ are each independently selected from $C_{2-6}$-alkenyl, $C_{3-6}$-cycloalkyl, $C_{1-6}$-alkyl-$C_{3-6}$-cycloalkyl, heterocycloalkyl, $C_{1-6}$-alkyl-heterocycloalkyl, $NR^4R^5$, O—$C_{1-6}$-alkyl-$OR^6$, or $C_{1-6}$-alkyl-$OR^6$;
$R^4$ is H or $C_{1-6}$-alkyl;
$R^5$ is $CO_2R^6$ or $C_{1-6}$-alkyl-$OR^6$; and
$R^6$ is $C_{1-6}$-alkyl.

4. The compound of claim 1, or a pharmaceutically acceptable salt thereof,
wherein
m is 1; n is 1; $Y_1$ is N; and $Y_2$, $Y_3$, $Y_4$, $Y_5$, and $Y_6$ are each CH;
m is 0; n is 1; $Y_2$ is N; $Y_1$ is $CR^7$; and $Y_3$, $Y_4$, and $Y_6$ are each CH;
m is 0; n is 1; $Y_1$ is $CR^7$; $Y_2$ is N; $Y_3$ is C(O); $Y_4$ is $CH_2$; and $Y_6$ is CH;
m is 1; n is 1; $Y_1$ is $CR^7$; $Y_2$ is N, and $Y_3$, $Y_4$, $Y_5$, and $Y_6$ are each CH;
m is 0; n is 1; $Y_1$ is $CR^7$; $Y_2$ and $Y_3$ are each N; and $Y_4$ and $Y_6$ are each CH;
m is 0; n is 1; $Y_1$ and $Y_2$ are N; $Y_3$, $Y_4$, and $Y_6$ are each CH; or
m is 1; n is 1; and Y1, $Y_2$, $Y_3$, $Y_4$, $Y_5$, and $Y_6$ are each CH.

5. The compound of claim 1, or a pharmaceutically acceptable salt thereof, wherein $R^1$ is phenyl, thienyl, or pyridinyl.

6. The compound of claim 1, or a pharmaceutically acceptable salt thereof, wherein $R^1$ is para to $NH_2$ in the compound of Formula I.

7. The compound of claim 1, or a pharmaceutically acceptable salt thereof, wherein $R^2$ is cyclopropyl, cyclopentyl, $CH_2$-cyclopropyl, $CH_2CH=CH_2$.

8. The compound of claim 1, or a pharmaceutically acceptable salt thereof, wherein $R^3$ is heterocycloalkyl, $C_{1-6}$-alkyl-heterocycloalkyl, O—$C_{1-6}$-alkyl-$OR^6$, or $C_{1-6}$-alkyl-$OR^6$, or $NR^4R^5$.

9. The compound of claim 1 or a pharmaceutically acceptable salt thereof, wherein $R^3$ is morpholinyl, piperazinyl, $CH_2CH_2$-morpholinyl, $CH_2$-morpholinyl, $CH_2CH_2$-piperazinyl, $CH_2$-piperazinyl, $OCH_2CH_2OCH_3$, $OCH_2OCH_3$, $CH_2CH_2OCH_3$, or $NHCO_2CH_2CH_3$.

10. The compound of claim 1, or a pharmaceutically acceptable salt thereof, wherein $R^7$ is H or $C_{3-6}$-cycloalkyl.

11. The compound of claim 1, or a pharmaceutically acceptable salt thereof, wherein $R^7$ is cyclopropyl.

12. The compound claim 1, having the structure of Formula III:

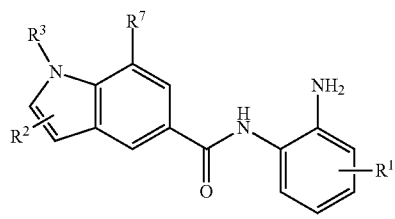
or a pharmaceutically acceptable salt thereof.
13. A compound selected from the group consisting of:
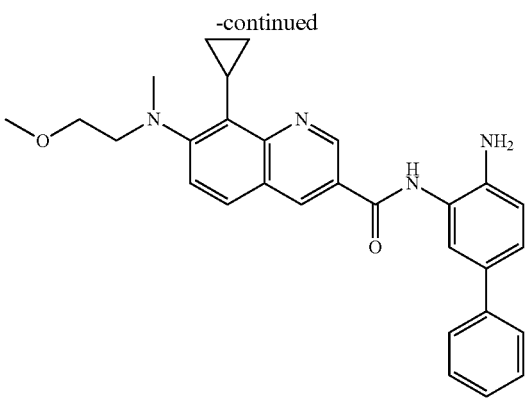
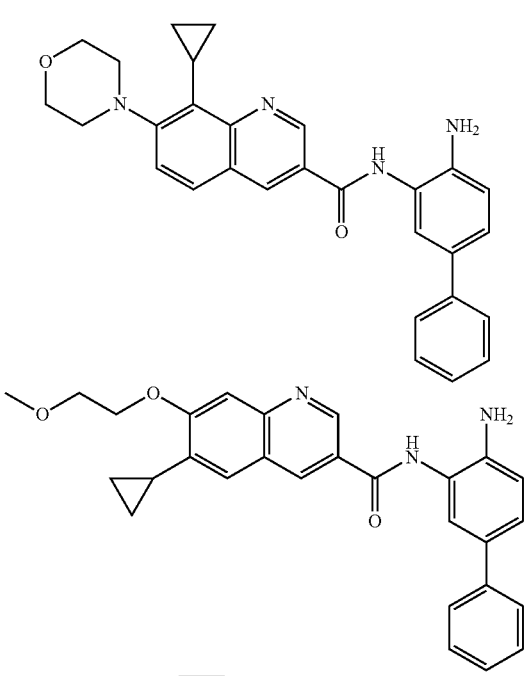
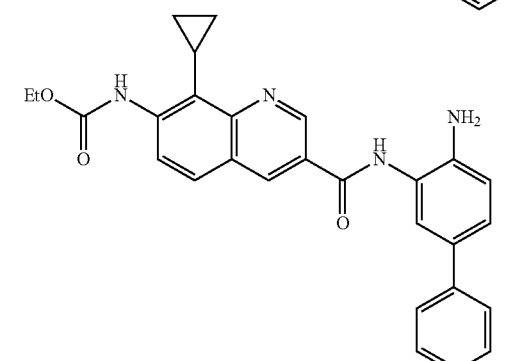
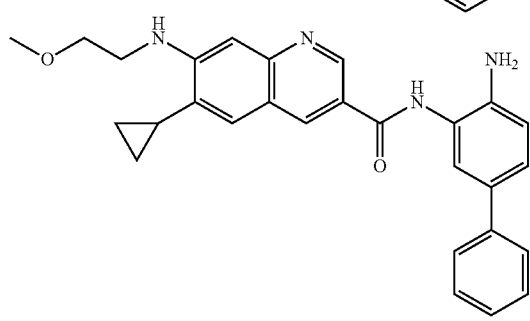
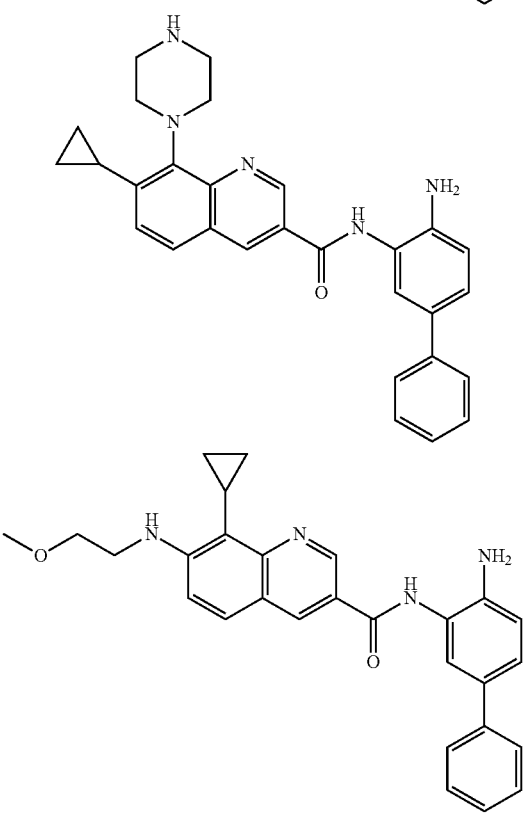
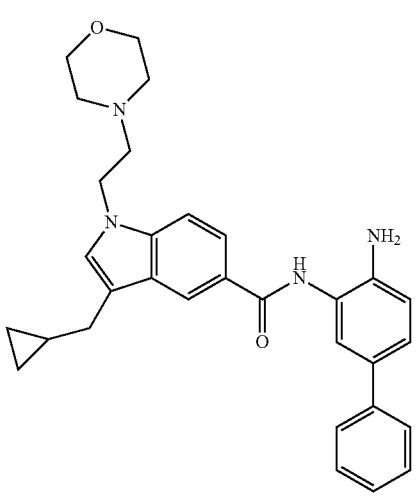

149
-continued
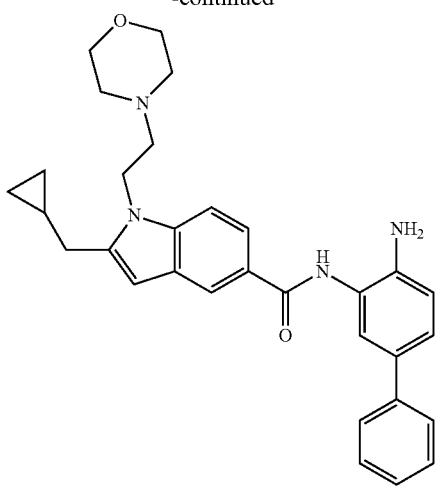
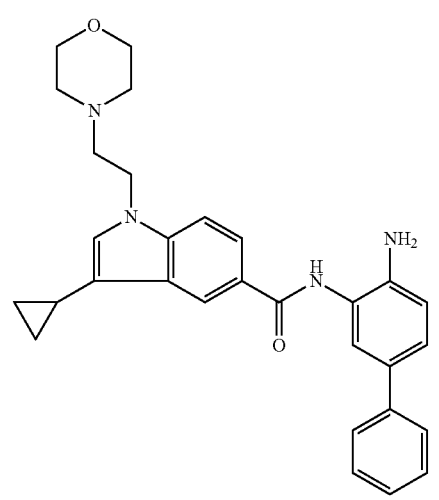
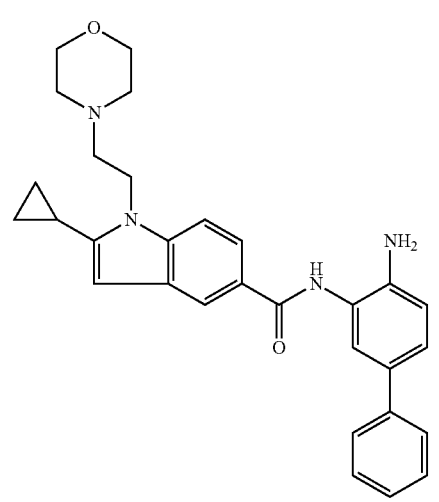
150
-continued
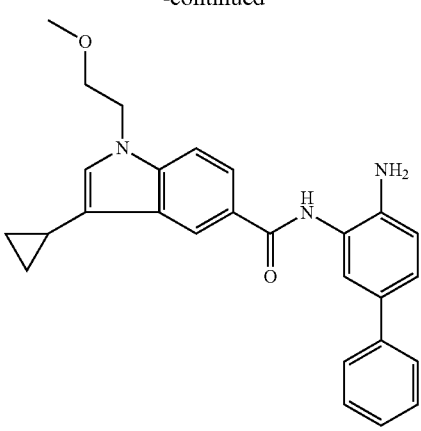
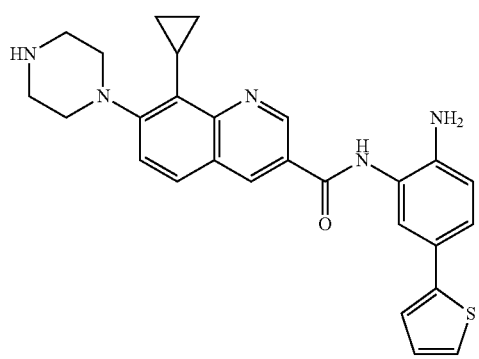
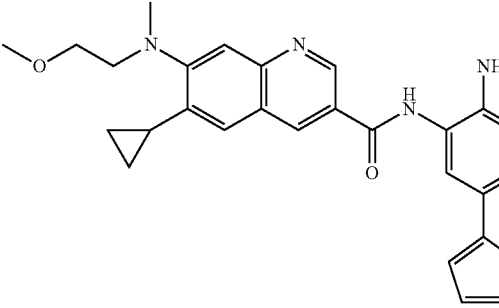
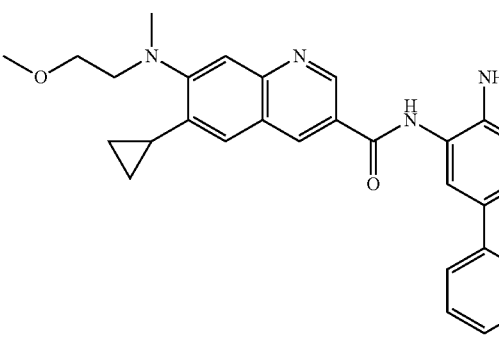

151
-continued
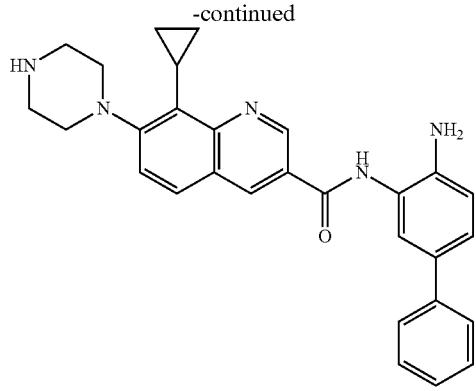
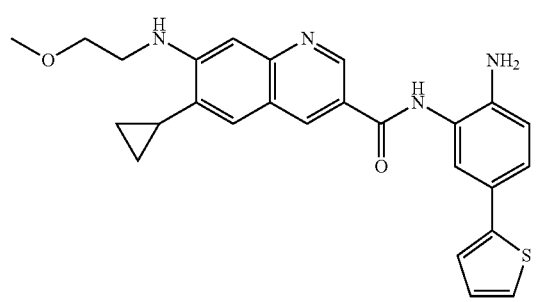
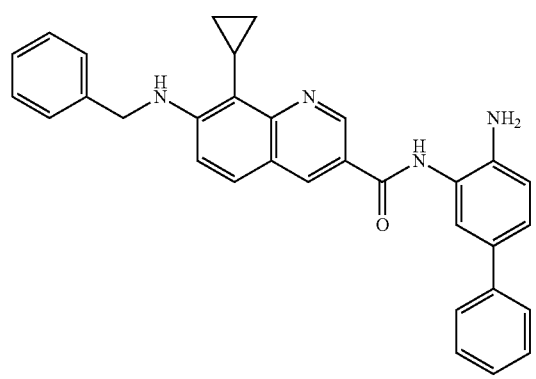
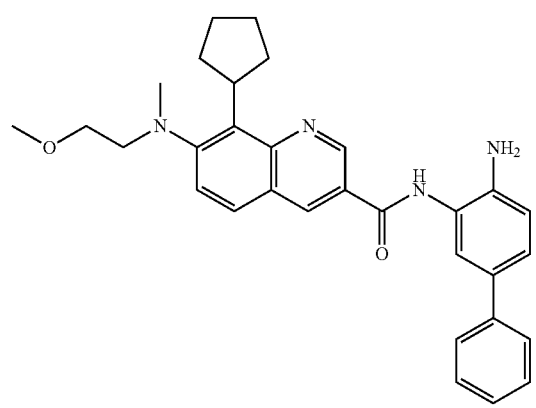
152
-continued
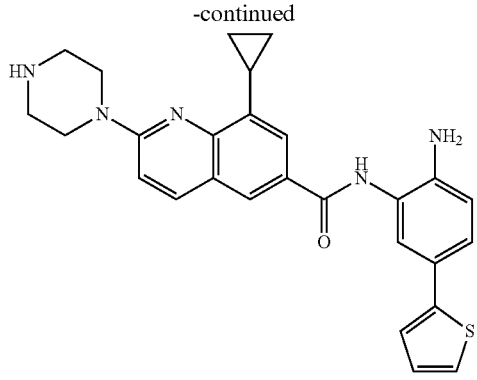
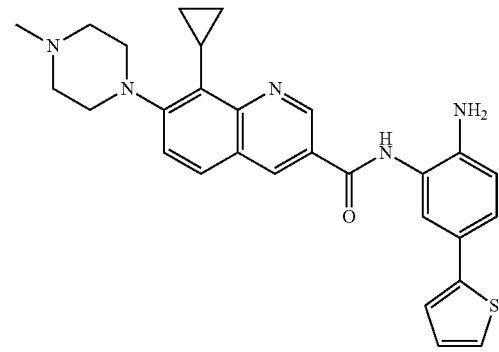
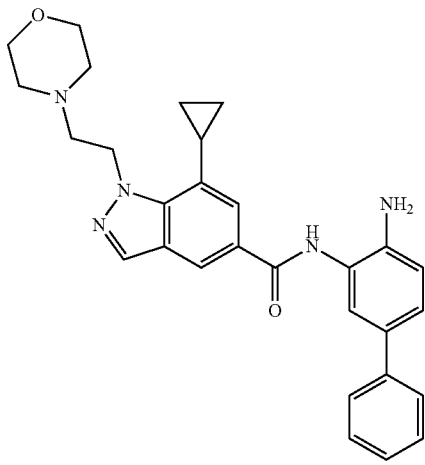
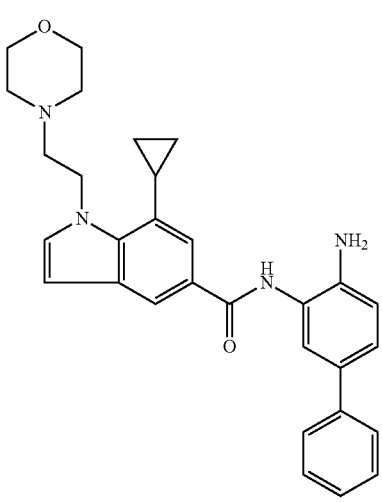

153
-continued
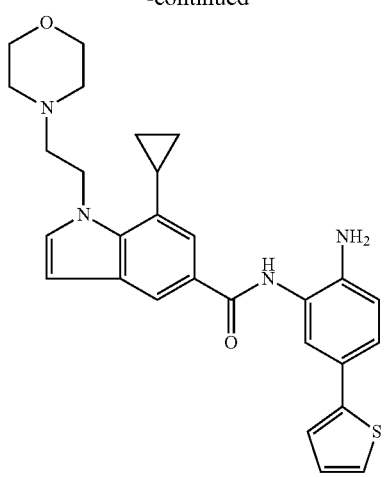
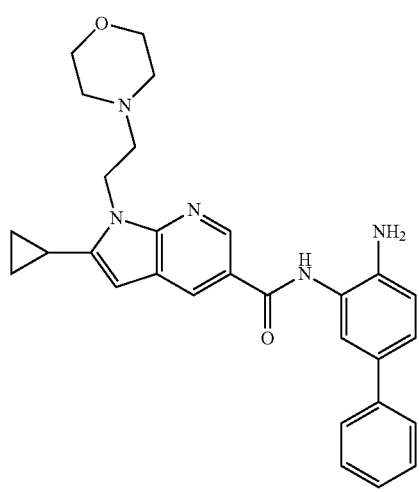
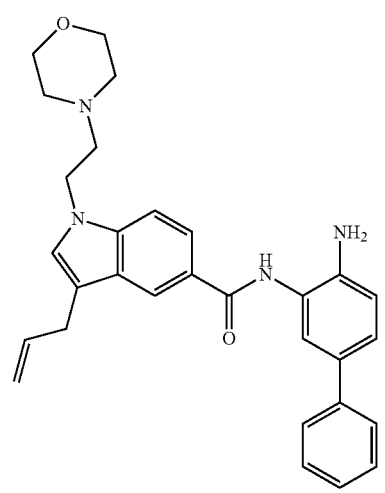
154
-continued
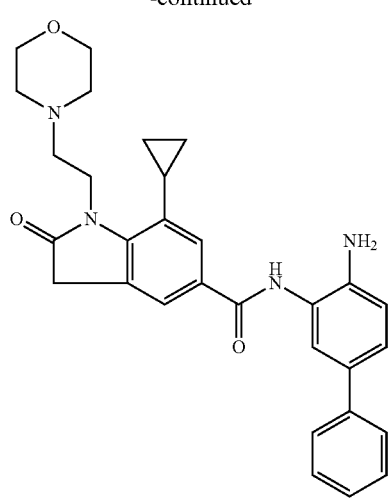
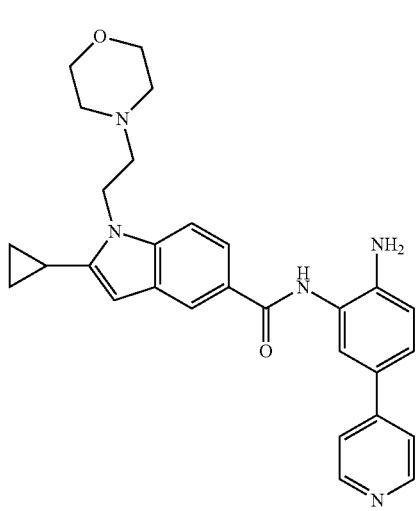

-continued
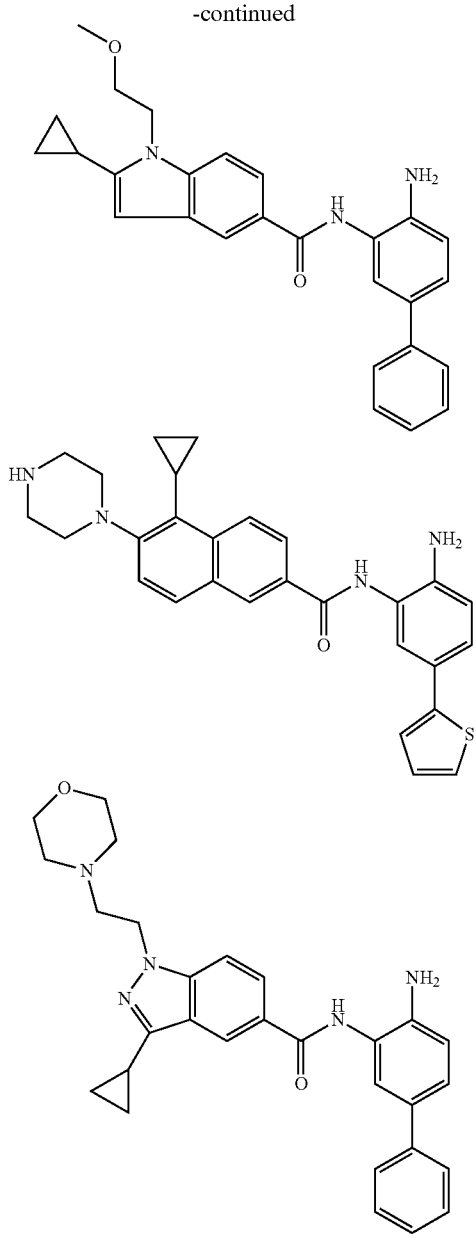
or pharmaceutically acceptable salts thereof.
14. A compound selected from the group consisting of:
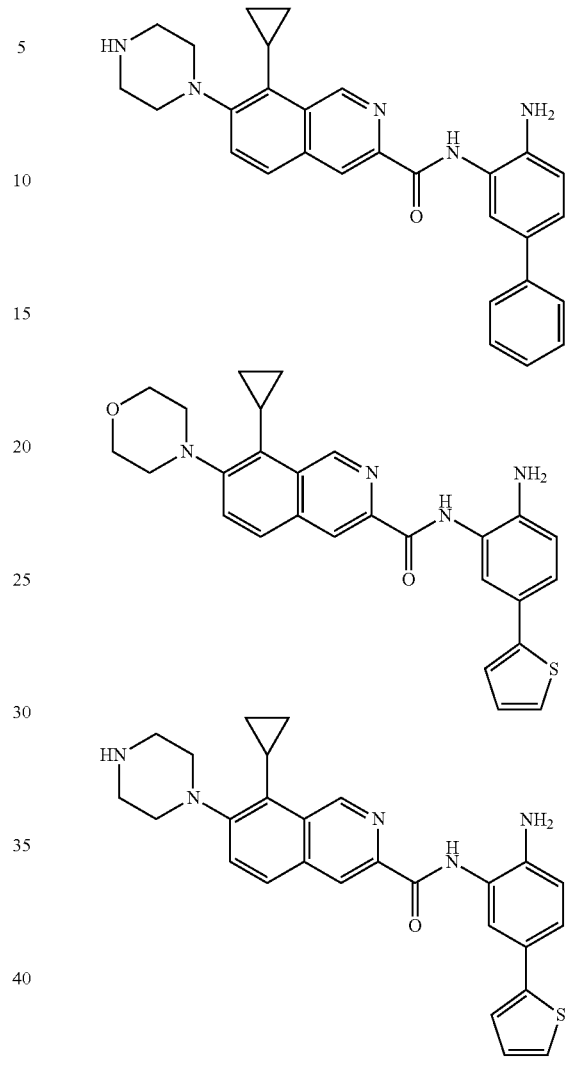
or pharmaceutically acceptable salts thereof.
* * * * *